United States Patent
Nakatsuka et al.

[11] Patent Number: 6,100,260
[45] Date of Patent: Aug. 8, 2000

[54] ISOXAZOLE DERIVATIVES

[75] Inventors: Masashi Nakatsuka; Yoshihide Ueno, both of Osaka; Shin-ichiro Okada, Takatsuki; Fumio Nishikaku, Itami, all of Japan

[73] Assignee: Sumitomo Pharmaceutical Company, Limited, Osaka, Japan

[21] Appl. No.: 09/062,561

[22] Filed: Apr. 20, 1998

Related U.S. Application Data

[60] Provisional application No. 60/048,757, Jun. 3, 1997.

[30] Foreign Application Priority Data

Apr. 21, 1997 [JP] Japan ................................. 9-118871
Dec. 24, 1997 [JP] Japan ................................. 9-367154

[51] Int. Cl.⁷ ..................... A61K 31/535; A61K 31/495; C07D 413/06
[52] U.S. Cl. ..................... 514/236.8; 514/252; 544/137; 544/367
[58] Field of Search ................. 514/236.8, 252; 544/367, 137

[56] References Cited

U.S. PATENT DOCUMENTS 4,293,549  10/1981  Rachlin et al. .
4,914,112   4/1990  Ozato et al. .

FOREIGN PATENT DOCUMENTS

| 0091726 | 10/1983 | European Pat. Off. . |
| 0188333 | 7/1986 | European Pat. Off. . |
| 0248399 | 12/1987 | European Pat. Off. . |
| 2068418 | 8/1971 | France . |
| 2100914 | 3/1972 | France . |
| 2128505 | 10/1972 | France . |
| 2478634 | 9/1981 | France . |
| 2341507 | 2/1975 | Germany . |
| 19624282 | 6/1996 | Germany . |
| 95 14683 | 6/1995 | WIPO . |

OTHER PUBLICATIONS

Patent Abstract of Japan, vol. 004, No. 007, Jan. 19, 1980, (JP 54 144347).
Patent Abstract of Japan, vol. 017, No. 462, Aug. 24, 1993, (JP 05 112564).
C. Nielsen et al., "Synthesis and Hypotensive Activity of N–Alkyl–N –cyano–N –pyridylguanidines", Journal of Medicine Chemistry, vol. 21, No. 8, 1978, pp. 773–781.

*Primary Examiner*—Joseph K. McKane
*Attorney, Agent, or Firm*—Sughrue, Mion, Zinn, Macpeak & Seas, PLLC

[57] ABSTRACT

An isoxazole derivative represented by the formula:

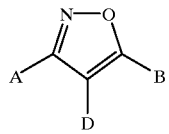

or a pharmaceutically acceptable salt thereof useful as a therapeutic drug for auto-immune diseases and inflammatory diseases.

16 Claims, 1 Drawing Sheet

ISOXAZOLE DERIVATIVES

CROSS-REFERENCE TO RELATED APPLICATION

This application claims the benefit of U.S. Provisional Application No. 60/048,757 filed on Jun. 3, 1997.

BACKGROUND OF THE INVENTION

1. Field of the Invention

The present invention relates to isoxazole derivatives useful as, for example, therapeutic drugs for autoimmune diseases, inflammatory diseases, etc.

2. Description of the Related Art

Acidic nonsteroidal anti-inflammatory drugs or steroidal drugs have been used as therapeutic drugs for inflammatory diseases but are limited in their use because of their side effects. In addition, treatments using such drugs, despite their ability to ameliorate symptoms cannot remove the fundamental cause of the diseases. With the progress of elucidation of the pathophysiology of autoimmune diseases such as rheumatoid arthritis accompanied by serious inflammation, it has been suggested that an immune system disorders are deeply concerned in the onset of inflammation, its progression and maintenance of a chronic state. For these reasons, drugs capable of modifying the diseases by acting on the immune system, such as gold compounds and D-penicillamine have been noted as drugs for causal treatment. They, however, are not always satisfactory because of their side effects and deficiency in lasting efficacy.

On the other hand, isoxazole derivatives having various biological activities have been reported. For example, Japanese Patent Unexamined Publication No. 63-152368 reports aralkyl 5-membered heterocyclic compounds including isoxazole derivatives, as therapeutic drugs for autoimmune diseases, inflammation, allergy, asthma, etc. German Patent No. 2847792 reports quinolylguanidine derivatives including isoxazole derivatives, as anti-inflammatory, analgesic and antipyretic drugs. J. Med. Chem. 21, 773(1978) reports that N-cyano-N'-isoxazolylguanidine derivatives are effective as hypotensive drugs.

Therapeutic drugs for autoimmune diseases should be clearly effective against chronic inflammation which induces tissue destruction. Moreover, it is important for them to have inhibitory effect on an immune system disorders responsible for the diseases, as a drug for radical treatment. In addition, the therapeutic drugs for the diseases should have little adverse side effect because they often require long-term administration.

The present invention is intended to provide a compound useful as a therapeutic or prophylactic drug for autoimmune diseases, inflammatory diseases, etc., which has excellent immunomodulating and anti-choronic-inflammatory effects and has little side effect.

SUMMARY OF THE INVENTION

The present inventors earnestly investigated for solving the above-mentioned problems, and consequently found that isoxazole derivatives have marked immunomodulating and anti-choronic-inflammatory effects and have little side effect, whereby the present invention has been accomplished.

That is, the present invention is as follows.

[1] An isoxazole derivative represented by the formula 1:

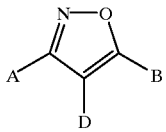

wherein D is a hydrogen atom, a halogen atom, a hydroxyl group, a mercapto group, a nitro group, a cyano group, a carboxyl group, a substituted or unsubstituted amino group, a substituted or unsubstituted hydroxylamino group, a substituted or unsubstituted carbamoyl group, a substituted or unsubstituted sulfamoyl group, a sulfo group, $-R^5$, $-OR^5$, $-CO_2R^6$, $-SR^7$, $-(CO)SR^7$, $-(CS)OR^7$ or $-CS_2R^7$ wherein $R^5$ is a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, a substituted or unsubstituted heterocyclic group, or an acyl group, $R^6$ is a substituted or unsubstituted alkyl group, a substituted or unsubstituted alkenyl group, a substituted or unsubstituted alkynyl group, a substituted or unsubstituted aryl group, or a substituted or unsubstituted heterocyclic group, and $R^7$ is a substituted or unsubstituted alkyl group, or a substituted or unsubstituted aryl group;

one of A and B is a group represented by the formula:

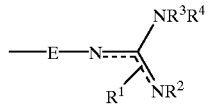

wherein E is a single bond or an alkylene group;

one of the two broken lines represents a double bond together with the solid line, while the other represents a single bond together with the other solid line. $R^1$ is bonded to the nitrogen atom bonded through the single bond represented by the broken line and the solid line; and $R^1$, $R^2$, $R^3$ and $R^4$ are independently a hydrogen atom, a halogen atom, a hydroxyl group, a mercapto group, a nitro group, a cyano group, a carboxyl group, a substituted or unsubstituted amino group, a substituted or unsubstituted hydroxylamino group, a substituted or unsubstituted carbamoyl group, a substituted or unsubstituted sulfamoyl group, a sulfo group, a protecting group for NH group, $-R^5$, $-OR^5$, $-CO_2R^6$, $-SR^7$, $-(CO)SR^7$, $-(CS)OR^7$ or $-CS_2R^7$ wherein $R^5$, $R^6$ and $R^7$ are as defined above, any two of $R^1$, $R^2$, $R^3$ and $R^4$ may be taken together with the nitrogen atom(s) to form a substituted or unsubstituted heterocyclic ring; and the formula: $-NR^3R^4$ may be a group represented by the following formula: $-N=C(NH_2)NR^{43}R^{44}$ wherein $R^{43}$ and $R^{44}$ are as defined in (1) or (2)

(1) each represents independently a hydrogen atom: an alkyl group having 1 to 4 carbon atoms; $-(CH_2)_n-COCH_3$ wherein n represents an integer of 1 to 3; $-(CH_2)_n-CO_2R^{32}$ wherein n is as defined above and $R^{32}$ represents an alkyl group having 1 to 3 carbon atoms; $-(CH_2)_n-CONR^{33}R^{34}$ wherein n is as defined above and $R^{33}$ and $R^{34}$ represent independently hydrogen atoms or alkyl groups having 1 to 3 carbon atoms; $-(CH_2)_m-OR^{35}$ wherein m represents 2 or 3 and $R^{35}$ represents a hydrogen atom, an alkyl group having 1 to 3 carbon atoms or $-(CH_2)_m-OR^{36}$ wherein m is as defined above and $R^{36}$ represents a hydrogen atom or an alkyl group having 1 to 3 carbon atoms; —$(CH_2)_m$—$NR^{37}R^{38}$ wherein m is as defined above and $R^{37}$ and $R^{38}$ represent independently hydrogen atoms or alkyl groups having 1 to 3 carbon atoms, or when taken together with the nitrogen atom, represent pyrrolidine, piperidine, azepane, morpholine or N-methylpiperazine wherein said pyrrolidine, piperidine, azepane, morpholine and N-methylpiperazine may be substituted with one or two methyl groups; a phenyl group; a pyridyl group; a pyrimidinyl group; a pyridazinyl group; a pyrazinyl group; a tetrazolyl group; a benzyl group; a pyridylmethyl group; a pyrimidinylmethyl group; a pyridazinylmethyl group; a pyrazinylmethyl group; a tetrazolylmethyl group; a hydroxyl group; an alkoxy group having 1 to 3 carbon atoms; or —$NR^{39}R^{40}$ wherein $R^{39}$ and $R^{40}$ represent independently hydrogen atoms, alkyl groups having 1 to 3 carbon atoms, phenyl groups or pyridyl groups;

(2) when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from alkyl group, amino group, hydroxyl group, alkoxy group and oxo group; and the other of A and B is a group represented by the formula:
—J—G
wherein G is a substituted or unsubstituted aryl group, or a substituted or unsubstituted heterocyclic group; J is —$C(R^8R^9)$— or —$C(=CR^8R^9)$— wherein $R^8$ and $R^9$ are independently a hydrogen atom, a substituted or unsubstituted lower alkoxy group, or a substituted or unsubstituted lower alkyl group; $R^8$ and $R^9$ may be taken together with the carbon atom to form a substituted or unsubstituted hydrocarbon ring, a substituted or unsubstituted 1,3-dioxane, or a substituted or unsubstituted 1,3-dioxolane, or a pharmaceutically acceptable salt thereof.

[2] An isoxazole derivative or a pharmaceutically acceptable salt thereof according to [1], wherein E is a single bond or a lower alkylene.

[3] An isoxazole derivative or a pharmaceutically acceptable salt thereof according to [1] or [2], wherein D is a hydrogen atom, a nitro group, a cyano group, a carboxyl group, a substituted or unsubstituted amino group, a substituted or unsubstituted hydroxylamino group, a substituted or unsubstituted carbamoyl group, —$R^5$ or —$CO_2R^6$ wherein $R^5$ and $R^6$ are as defined above.

[4] An isoxazole derivative or a pharmaceutically acceptable salt thereof according to [3], wherein D is a hydrogen atom, a carboxyl group, —$R^5$ or —$CO_2R^6$ wherein $R^5$ and $R^6$ are as defined above.

[5] An isoxazole derivative or a pharmaceutically acceptable salt thereof according to any of [1] to [4], wherein $R^1$, $R^2$, $R^3$ and $R^4$ are independently a hydrogen atom, a hydroxyl group, a substituted or unsubstituted amino group, a substituted or unsubstituted hydroxylamino group, a substituted or unsubstituted alkoxy group, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, or a substituted or unsubstituted heterocyclic group; and the formula: —$NR^3R^4$ may be a group represented by the following formula: —$N=C(NH_2)NR^{43}R^{44}$ wherein $R^{43}$ and $R^{44}$ are as defined above; or any two of $R^1$, $R^2$, $R^3$ and $R^4$ may be taken together with the nitrogen atom(s) to form a substituted or unsubstituted heterocyclic ring.

[6] An isoxazole derivative or a pharmaceutically acceptable salt thereof according to [5], wherein $R^1$, $R^2$, $R^3$ and $R^4$ are independently a hydrogen atom, a hydroxyl group, a substituted or unsubstituted amino group, a substituted or unsubstituted hydroxylamino group, a substituted or unsubstituted alkoxy group, a substituted or unsubstituted alkyl group, a substituted or unsubstituted alkenyl group, a substituted or unsubstituted alkynyl group, or a substituted or unsubstituted cycloalkyl group; and the formula: —$NR^3R^4$ may be a group represented by the following formula: —$N=C(NH_2)NR^{43}R^{44}$ wherein $R^{43}$ and $R^{44}$ are as defined above; or any two of $R^1$, $R^2$, $R^3$ and $R^4$ may be taken together with the nitrogen atom(s) to form a substituted or unsubstituted heterocyclic ring.

[7] An isoxazole derivative or a pharmaceutically acceptable salt thereof according to any of [1] to [6], wherein G is a substituted or unsubstituted phenyl group, a substituted or unsubstituted naphthyl group, a substituted or unsubstituted furyl, a substituted or unsubstituted thienyl, a substituted or unsubstituted indolyl, a substituted or unsubstituted isothiazolyl, a substituted or unsubstituted benzothienyl, a substituted or unsubstituted isobenzofuranyl, a substituted or unsubstituted pyrrolyl, a substituted or unsubstituted benzofuryl, a substituted or unsubstituted imidazolyl, a substituted or unsubstituted pyrazolyl, a substituted or unsubstituted isoxazolyl, a substituted or unsubstituted isothiazolyl, a substituted or unsubstituted thiazolyl, a substituted or unsubstituted oxazolyl, a substituted or unsubstituted benzimidazolyl, a substituted or unsubstituted benzothiazolyl, a substituted or unsubstituted benzoxazolyl, a substituted or unsubstituted pyridyl, a substituted or unsubstituted pyrazinyl, a substituted or unsubstituted pyrimidinyl, a substituted or unsubstituted pyridazinyl, a substituted or unsubstituted triazinyl, a substituted or unsubstituted quinolyl, a substituted or unsubstituted isoquinolyl, a substituted or unsubstituted quinazolinyl, a substituted or unsubstituted quinoxalinyl, a substituted or unsubstituted 2,3-dihydrobenzo[1,4]dioxinyl, or a substituted or unsubstituted carbazolyl.

[8] An isoxazole derivative or a pharmaceutically acceptable salt thereof according to [1], which is represented by the formula:

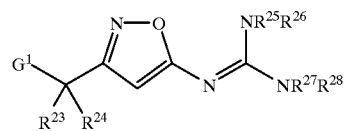

wherein $G^1$ represents phenyl, biphenyl-4-yl, 3-benzoylphenyl, 4-benzoylphenyl, 1H-indol-2-yl, 1H-indol-3-yl, 1-methyl-1H-indol-2-yl, 1-methyl-1H-indol-3-yl, 2,3-dihydrobenzo[1,4]dioxin-6-yl, 1-benzofuran-5-yl, 1-benzofuran-6-yl, quinolyl, isoquinolyl, phen-ylpyridyl, phenylpyrimidinyl, phenylpyridazinyl or phen-ylpyrazinyl wherein said phenyl, biphenyl-4-yl, 3-benzoylphenyl, 4-benzoylphenyl, 1H-indol-2-yl, 1H-indol-3-yl, 1-methyl-1H-indol-2-yl, 1-methyl-1H-indol-3-yl, 2,3-dihydrobenzo[1,4]dioxin-6-yl, 1-benzofuran-5-yl, 1-benzofuran-6-yl, quinolyl, isoquinolyl, phenylpyridyl, phenylpyrimidinyl, phenylpyridazinyl and phenylpyrazinyl may be substituted with one or two groups arbitrarily selected from the group consisting of fluorine atom, chlorine atom, bromine atom, acetyl, cyano, —$CO_2R^{29}$ wherein $R^{29}$ represents an alkyl group having 1 to 3 carbon atoms and —$CONR^{30}R^{31}$ wherein $R^{30}$ and $R^{31}$ represent independently hydrogen atoms or alkyl groups having 1 to 3 carbon atoms;

$R^{23}$ and $R^{24}$ represent independently hydrogen atoms, alkyl groups having 1 to 4 carbon atoms, methoxy or ethoxy, or when taken together, form a methylene group; and the formula: $=C(NR^{25}R^{26})NR^{27}R^{28}$ is as defined in the following (1), (2) or (3):

(1) $R^{25}$ and $R^{26}$ are as defined in the following (a) or (b) and $R^{27}$ and $R^{28}$ are as defined in the following (c) or (d):

(a) each represents independently a hydrogen atom; an alkyl group having 1 to 4 carbon atoms; $-(CH_2)_n-COCH_3$ wherein n is as defined above; $-(CH_2)_n-CO_2R^{32}$ wherein n and $R^{32}$ are as defined above; $-(CH_2)_n-CONR^{33}R^{34}$ wherein n, $R^{33}$ and $R^{34}$ are as defined; $-(CH_2)_m-OR^{35}$ wherein m and $R^{35}$ are as defined above; $-(CH_2)_m-NR^{37}R^{38}$ wherein m, $R^{37}$ and $R^{38}$ are as defined above; a phenyl group; a pyridyl group; a pyrimidinyl group; a pyridazinyl group; a pyrazinyl group; a tetrazolyl group; a benzyl group; a pyridylmethyl group; a pyrimidinylmethyl group; a pyridazinylmethyl group; a pyrazinylmethyl group; a tetrazolylmethyl group; a hydroxyl group; an alkoxy group having 1 to 3 carbon atoms; or $-NR^{39}R^{40}$ wherein $R^{39}$ and $R^{40}$ are as defined above;

(b) when taken together, they form with the nitrogen atom a 5- to 7-membered saturated nitrogen-containing heterocyclic group wherein said 5- to 7-membered saturated nitrogen-containing group may be substituted with one or two substituents independently selected from the group consisting of alkyl group, amino group, hydroxyl group, alkoxy group and oxo group;

(c) each represents independently a hydrogen atom; an alkyl group having 1 to 4 carbon atoms; $-(CH_2)_n-COCH_3$ wherein n is as defined above; $-(CH_2)_n-CO_2R^{32}$ wherein n and $R^{32}$ are as defined above; $-(CH_2)_n-CONR^{33}R^{34}$ wherein n, $R^{33}$ and $R^{34}$ are as defined above; $-(CH_2)_m-OR^{35}$ wherein m and $R^{35}$ are as defined above; $-(CH_2)_m-NR^{37}R^{38}$ wherein m, $R^{37}$ and $R^{38}$ are as defined above; a phenyl group; a pyridyl group; a pyrimidinyl group; a pyridazinyl group; a pyrazinyl group; a tetrazolyl group; a benzyl group; a pyridylmethyl group; a pyrimidinylmethyl group; a pyridazinylmethyl group; a pyrazinylmethyl group; a tetrazolylmethyl group; a hydroxyl group; an alkoxy group having 1 to 3 carbon atoms; or $-NR^{39}R^{40}$ wherein $R^{39}$ and $R^{40}$ are as defined above;

(d) when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group;

(2) when taken together, $R^{26}$ and $R^{27}$ form with the two nitrogen atoms and the one carbon atom a 5- to 7-membered saturated nitrogen-containing heterocyclic group wherein said 5- to 7-membered nitrogen-containing heterocyclic group may be substituted with one or two substituents independently selected from the group consisting of alkyl group, amino group, hydroxyl group, alkoxy group and oxo group; and $R^{25}$ and $R^{28}$ represent independently hydrogen atoms, alkyl groups having 1 to 3 carbon atoms, acetyl or $-(CH_2)_m-OR^{36}$ wherein m and $R^{36}$ are as defined above;

(3) the formula: $=C(NR^{25}R^{26})NR^{27}R^{28}$ is a group represented by the following formula:

$=C(NR^{41}R^{42})N=C(NH_2)NR^{43}R^{44}$ wherein $R^{41}$ and $R^{42}$ are as defined in the following (a') or (b'); and $R^{43}$ and $R^{44}$ are as defined in the following (c') or (d'):

(a') each represents independently a hydrogen atom, an alkyl group having 1 to 4 carbon atoms, $-(CH_2)_n-COCH_3$ wherein n is as defined above, $-(CH_2)_n-CO_2R^{32}$ wherein n and $R^{32}$ are as defined above, $-(CH_2)_n-CONR^{33}R^{34}$ wherein n, $R^{33}$ and $R^{34}$ are as defined above, $-(CH_2)_m-OR^{35}$ wherein m and $R^{35}$ are as defined above, $-(CH_2)_m-NR^{37}R^{38}$ wherein m, $R^{37}$ and $R^{38}$ are as defined above, a phenyl group, a pyridyl group, a pyrimidinyl group, a pyridazinyl group, a pyrazinyl group, a tetrazolyl group, a benzyl group, a pyridylmethyl group, a pyrimidinylmethyl group, a pyridazinylmethyl group, a pyrazinylmethyl group, a tetrazolylmethyl group, a hydroxyl group, an alkoxy group having 1 to 3 carbon atoms or $-NR^{39}R^{40}$ wherein $R^{39}$ and $R^{40}$ are as defined above;

(b') when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group;

(c') each represents independently a hydrogen atom, an alkyl group having 1 to 4 carbon atoms, $-(CH_2)_n-COCH_3$ wherein n is as defined above, $-(CH_2)_n-CO_2R^{32}$ wherein n and $R^{32}$ are as defined above, $-(CH_2)_n-CONR^{33}R^{34}$ wherein n, $R^{33}$ and $R^{34}$ are as defined above, $-(CH_2)_m-OR^{35}$ wherein m and $R^{35}$ are as defined above, $-(CH_2)_m-NR^{37}R^{38}$ wherein m, $R^{37}$ and $R^{38}$ are as defined above, a phenyl group, a pyridyl group, a pyrimidinyl group, a pyridazinyl group, a pyrazinyl group, a tetrazolyl group, a benzyl group, a pyridylmethyl group, a pyrimidinylmethyl group, a pyridazinylmethyl group, a pyrazinylmethyl group, a tetrazolylmethyl group, a hydroxyl group, an alkoxy group having 1 to 3 carbon atoms or $-NR^{39}R^{40}$ wherein $R^{39}$ and $R^{40}$ are as defined above;

(d') when taken together, they form with the nitrogen atom a 5- to 7-membered saturated nitrogen-containing heterocyclic group wherein said 5- to 7-membered saturated nitrogen-containing heterocyclic group may be substituted with one or two substituents arbitrarily selected from the group consisting of alkyl group, amino group, hydroxyl group, alkoxy group and oxo group; or represented by the formula:

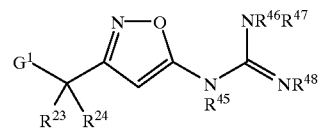

wherein $G^1$, $R^{23}$ and $R^{24}$ are as defined above; the formula: $-N(R^{45})C(NR^{46}R^{47})=NR^{48}$ is as defined in the following (1') or (2'):

(1') $R^{45}$ represents an alkyl group having 1 to 3 carbon atoms or an acetyl group; $R^{48}$ represents a hydrogen atom, an alkyl group having 1 to 3 carbon atoms or an acetyl group; and $R^{46}$ and $R^{47}$ are as defined in the following (a'') or (b''):

(a'') each represents independently a hydrogen atom, an alkyl group having 1 to 4 carbon atoms, $-(CH_2)_n-COCH_3$ wherein n is as defined above, $-(CH_2)_n-CO_2R^{32}$ wherein n and $R^{32}$ are as defined above, $-(CH_2)_n-CONR^{33}R^{34}$ wherein n, $R^{33}$ and $R^{34}$ are as defined above, $-(CH_2)_m-OR^{35}$ wherein m and $R^{35}$ are as defined above, $-(CH_2)_m-NR^{37}R^{38}$ wherein m, $R^{37}$ and $R^{38}$ are as defined above, a phenyl group, a pyridyl group, a pyrimidinyl group, a pyridazinyl group, a pyrazinyl group, a tetrazolyl group, a benzyl group, a pyridylmethyl group, a pyrimidinylmethyl group, a pyridazinylmethyl group, a pyrazinylmethyl group, a tetrazolylmethyl group, a hydroxyl group, an alkoxy group having 1 to 3 carbon atoms or $-NR^{39}R^{40}$ wherein $R^{39}$ and $R^{40}$ are as defined above;

(b″) when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group;

(2′) when taken together, $R^{45}$ and $R^{46}$ form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group; and $R^{47}$ and $R^{48}$ represent independently alkyl groups having 1 to 3 carbon atoms, acetyl groups or $-(CH_2)_m-OR^{36}$ wherein m and $R^{36}$ are as defined above;

[9] An isoxazole derivative or a pharmaceutically acceptable salt thereof according to [1], which is represented by the formula:

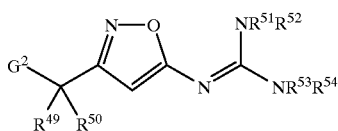

wherein $G^2$ represents 2-fluoro-biphenyl-4-yl, 2′-fluoro-biphenyl-4-yl or 3-benzoyl-phenyl; $R^{49}$ represents methyl; $R^{50}$ represents hydrogen, methyl, methoxy or ethoxy; and the formula: $=C(NR^{51}R^{52})NR^{53}R^{54}$ is as defined in the following (1″), (2″) or (3″):

(1″) $R^{51}$ and $R^{52}$ are as defined in the following (a‴), (b‴) or (c‴) and $R^{53}$ and $R5^4$ are as defined in the following (d‴), (e‴) or (f″):

(a‴) each represents independently a hydrogen atom or an alkyl group having 1 to 4 carbon atoms;

(b‴) one of them represents a hydrogen atom and the other represents $-(CH_2)_n-COCH_3$ wherein n is as defined above, $-(CH_2)_n-CO_2R^{32}$ wherein n and $R^{32}$ are as defined above, $-(CH_2)_n-CONR^{33}R^{34}$ wherein n, $R^{33}$ and $R^{34}$ are as defined above, $-(CH_2)_m-OR^{35}$ wherein m and $R^{35}$ are as defined above, or $-(CH_2)_m-NR^{37}R^{38}$ wherein m, $R^{37}$ and $R^{38}$ are as defined above;

(c‴) when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, and piperidine substituted in the 4-position with an amino group which may be substituted with one or two alkyl groups having 1 to 3 carbon atoms, may be substituted with one or two methyl groups;

(d‴) each represents independently a hydrogen atom or an alkyl group having 1 to 4 carbon atoms;

(e‴) one of them represents a hydrogen atom and the other represents $-(CH_2)_n-COCH_3$ wherein n is as defined above, $-(CH_2)_n-CO_2R^{32}$ wherein n and $R^{32}$ are as defined above, $-(CH_2)_n-CONR^{33}R^{34}$ wherein n, $R^{33}$ and $R^{34}$ are as defined above, $-(CH_2)_m-OR^{35}$ wherein m is as defined above and $R^{35}$ is as defined above, or $-(CH_2)_m-NR^{37}R^{38}$ wherein m, $R^{37}$ and $R^{38}$ are as defined above;

(f‴) when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, and piperidine substituted in the 4-position with an amino group which may be substituted with one or two alkyl groups having 1 to 3 carbon atoms, may be substituted with one or two methyl groups;

(2″) the formula: $=C(NR^{51}R^{52})NR^{53}R^{54}$ is a group represented by the following formula:

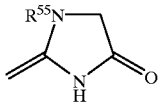

wherein $R^{55}$ represents an alkyl group having 1 to 3 carbon atom, acetyl or $-(CH_2)_m-OR^{56}$ wherein m is as defined above and $R^{56}$ represents a hydrogen atom or an alkyl group having 1 to 3 carbon atoms;

(3″) the formula: $=C(NR^{51}R^{52})NR^{53}R^{54}$ is a group represented by the following formula:

$$=C(NR^{57}R^{58})N=C(NH_2)NR^{59}R^{60}$$

wherein $R^{57}$ and $R^{58}$ are as defined in the following (a″″), (b″″) or (c″″); and $R^{59}$ and $R^{60}$ are as defined in the following (d″″), (e″″) or (f″″):

(a″″) each represents a hydrogen atom or an alkyl group having 1 to 4 carbon atoms;

(b″″) one of them represents a hydrogen atom and the other represents $-(CH_2)_n-COCH_3$ wherein n is as defined above, $-(CH_2)_n-CO_2R^{32}$ wherein n and $R^{32}$ are as defined above, $-(CH_2)_n-CONR^{33}R^{34}$ wherein n, $R^{33}$ and $R^{34}$ are as defined above, $-(CH_2)_m-OR^{35}$ wherein m and $R^{35}$ are as defined above, or $-(CH_2)_m-NR^{37}R^{38}$ wherein m, $R^{37}$ and $R^{38}$ are as defined above;

(c″″) when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine and piperidine substituted in the 4-position with an amino group which may be substituted with one or two alkyl groups having 1 to 3 carbon atoms, may be substituted with one or two methyl groups;

(d"") each represents independently a hydrogen atom or an alkyl group having 1 to 4 carbon atoms;

(e"") one of them represents a hydrogen atom and the other represents —$(CH_2)_n$—$COCH_3$ wherein n is as defined above, —$(CH_2)_n$—$CO_2R^{32}$ wherein n and $R^{32}$ are as defined above, —$(CH_2)_n$—$CONR^{33}R^{34}$ wherein n, $R^{33}$ and $R^{34}$ are as defined above, —$(CH_2)_m$—$OR^{35}$ wherein m and $R^{35}$ are as defined above, or —$(CH_2)_m$—$NR^{37}R^{38}$ wherein m, $R^{37}$ and $R^{38}$ are as defined above;

(f"") when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine and piperidine substituted in the 4-position with an amino group which may be substituted with one or two alkyl groups having 1 to 3 carbon atoms, may be substituted with one or two methyl groups.

[10] An isoxazole derivative or a pharmaceutically acceptable salt thereof according to [1], which is represented by the formula:

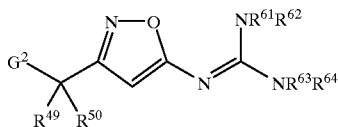

wherein $G^2$, $R^{49}$ and $R^{50}$ are as defined above; the formula: =$C(NR^{61}R^{62})NR^{63}R^{64}$ is as defined in the following (1'''), (2''') or (3'''):

(1''') $R^{63}$ and $R^{64}$ both represent hydrogen atoms; and $R^{61}$ and $R^{62}$ are as defined in the following (a'), (b') or (c'):

(a') each represents independently a hydrogen atom or an alkyl group having 1 to 3 carbon atoms;

(b') one of them represents a hydrogen atom and the other represents —$(CH_2)_n$—$CO_2R^{32}$ wherein n and $R^{32}$ are as defined above, —$(CH_2)_m$—$OR^{65}$ wherein m is 2 or 3 and $R^{65}$ represents a hydrogen atom or an alkyl group having 1 to 3 carbon atoms, 2-hydroxyethyl or 3-hydroxypropyl; or —$(CH_2)_m$—$NR^{66}R^{67}$ wherein m is as defined above and $R^{66}$ and $R^{67}$ represent independently hydrogen atoms or alkyl groups having 1 to 3 carbon atoms or, when taken together, form with the nitrogen atom pyrrolidine, piperidine, morpholine, or N-methylpiperazine wherein said pyrrolidine, piperidine, morpholine and N-methylpiperazine may be substituted with one or two methyl groups;

(c') when taken together, they form with the nitrogen atom pyrrolidine, piperidine, morpholine or N-methylpiperazine wherein said pyrrolidine, piperidine, morpholine and N-methylpiperazine may be substituted with one or two methyl groups;

(2''') the formula: =$C(NR^{61}R^{62})NR^{63}R^{64}$ is a group represented by the following formula:

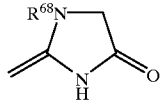

wherein $R^{68}$ represents an alkyl group having 1 to 3 carbon atoms, 2-hydroxyethyl or 3-hydroxypropyl.

(3''') when taken together, $R^{61}$ and $R^{62}$ form morpholine with the nitrogen atom; and when taken together, $R^{63}$ and $R^{64}$ form amino-morpholin-4-yl-methylene.

[11] An isoxazole derivative or a pharmaceutically acceptable salt thereof according to [1], which is selected from the group consisting of the following compounds:

({3-[1-(2-Fluoro-biphenyl-4-yl)-ethyl]-isoxazol-5-ylimino}-morpholin-4-yl-methyl)-amine;

[{3-[1-(2-Fluoro-biphenyl-4-yl)-ethyl]-isoxazol-5-ylimino}-(4-methyl-piperazin-1-yl)-methyl]-amine;

N-{3-[1-(2-Fluoro-biphenyl-4-yl)-ethyl]-isoxazol-5-yl}-N'-(2-morpholin-4-yl-ethyl)-guanidine;

({3-[1-(2-Fluoro-biphenyl-4-yl)-1-methyl-ethyl]-isoxazol-5-ylimino}-morpholin-4-yl-methyl)-amine;

[{3-[1-(2-Fluoro-biphenyl-4-yl)-1-methyl-ethyl]-isoxazol-5-ylimino}-(4-methyl-piperazin-1-yl)-methyl]-amine;

N-{3-[1-(2-Fluoro-biphenyl-4-yl)-1-methyl-ethyl]-isoxazol-5-yl}-N'-(2-morpholin-4-yl-ethyl)-guanidine;

({3-[1-(2'-Fluoro-biphenyl-4-yl)-ethyl]-isoxazol-5-ylimino}-morpholin-4-yl-methyl)-amine;

[{3-[1-(2'-Fluoro-biphenyl-4-yl)-ethyl]-isoxazol-5-ylimino}-(4-methyl-piperazin-1-yl)-methyl]-amine;

N-{3-[1-(2'-Fluoro-biphenyl-4-yl)-ethyl]-isoxazol-5-yl}-N'-(2-morpholin-4-yl-ethyl)-guanidine;

({3-[1-(2'-Fluoro-biphenyl-4-yl)-1-methyl-ethyl]-isoxazol-5-ylimino}-morpholin-4-yl-methyl)-amine;

[{3-[1-(2'-Fluoro-biphenyl-4-yl)-1-methyl-ethyl]-isoxazol-5-ylimino}-(4-methyl-piperazin-1-yl)-methyl]-amine;

N-{3-[1-(2'-Fluoro-biphenyl-4-yl)-1-methyl-ethyl]-isoxazol-5-yl}-N'-(2-morpholin-4-yl-ethyl)-guanidine;

(3-{1-[5-(Amino-morpholin-4-yl-methyleneamino)-isoxazol-3-yl]-ethyl}-phenyl)-phenyl-methanone;

[3-(1-{5-[Amino-(4-methyl-piperazin-1-yl)-methyleneamino]-isoxazol-3-yl}-ethyl)-phenyl]-phenyl-methanone;

N-{3-[1-(3-Benzoyl-phenyl)-ethyl]-isoxazol-5-yl}-N'-(2-morpholin-4-yl-ethyl)-guanidine;

(3-{1-[5-(Amino-morpholin-4-yl-methyleneamino)-isoxazol-3-yl]-1-methyl-ethyl}-phenyl)-phenyl-methanone;

[3-(1-{5-[Amino-(4-methyl-piperazin-1-yl)-methyleneamino]-isoxazol-3-yl}-1-methyl-ethyl)-phenyl]-phenyl-methane;

N-{3-[1-(3-Benzoyl-phenyl)-1-methyl-ethyl]-isoxazol-5-yl}-N'-(2-morpholin-4-yl-ethyl)-guanidine.

[12] A pharmaceutical composition comprising as an active ingredient an isoxazole derivative or a pharmaceutically acceptable salt thereof according to any one of [1] to [11], together with a pharmaceutically acceptable carrier.

[13] A pharmaceutcal composition according to [12], which is for the treatment or prophylaxis of autoimmune diseases.

[14] A pharmaceutical composition according to [12], which is for the treatment or prophylaxis of inflammatory diseases.

[15] A pharmaceutical composition according to [12], which is an antirheumatic drug.

[16] A pharmaceutical composition according to [12], which is an anti-inflammatory drug.

[17] A method for treating or preventing autoimmune diseases or inflammatory diseases, which comprises administering an isoxazole derivative or a pharmaceutically acceptable salt according to any one of [1] to [11] in an effectively amount to a human body.

[18] Use of an isoxazole derivative or a pharmaceutically acceptable salt according to any one of [1] to [11] in the manufacture of a medicament for the treatment or prophylaxis of autoimmune diseases or inflammatory diseases.

DETAILED DESCRIPTION OF THE INVENTION

Figure 1:
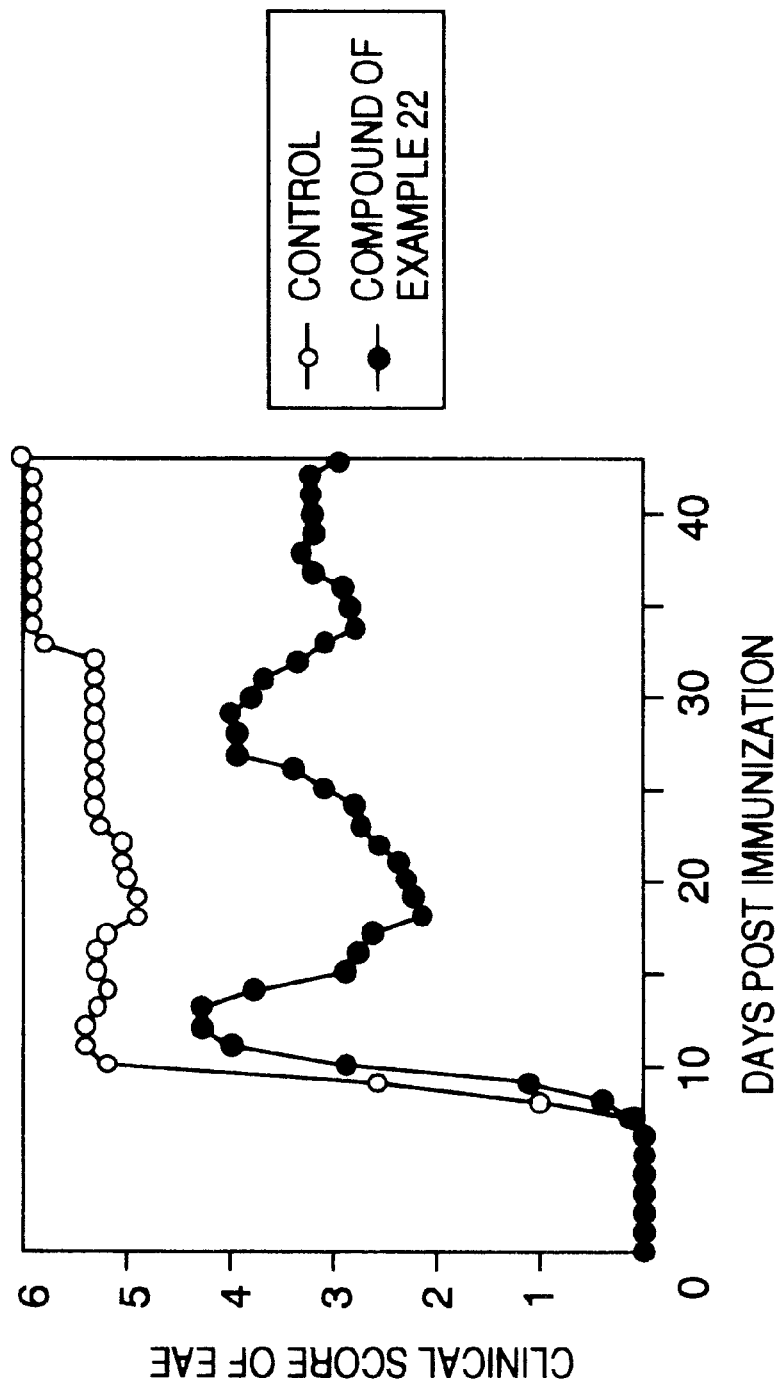
FIG. 1 is a graph showing the results of test of the compounds of this invention using experimental allergic encephalomyelitis mice which are animal models of multiple sclerosis.

The aryl group includes, for example, aryl groups of 6 to 14 carbon atoms. Specific examples thereof are phenyl, 1-naphthyl, 2-naphthyl, phenanthryl, anthryl, etc. Preferable examples thereof are phenyl, 1-naphtyl and 2-naphthyl.

The heterocyclic group includes, for example, 5- to 7-membered monocyclic to tricyclic saturated or unsaturated heterocyclic groups containing 1 to 6 nitrogen atoms, oxygen atoms and/or sulfur atoms.

Specific examples of the saturated heterocyclic groups are monocyclic to tricyclic 5-membered saturated heterocyclic groups such as tetrahydrofuryl, pyrrolidinyl, pyrazolidinyl, imidazolidinyl, etc.; monocyclic to tricyclic 6-membered saturated heterocyclic groups such as piperidinyl, morpholinyl, thiamorpholinyl, piperazinyl, hexahydropyrimidinyl, etc.; and monocyclic to tricyclic 7-membered saturated heterocyclic groups such as azepanyl, etc.

Specific examples of the unsaturated heterocyclic groups are monocyclic to tricyclic 5-membered unsaturated heterocyclic groups such as furyl, thienyl, indolyl, isothiazolyl, benzothienyl, isobenzofuranyl, pyrrolyl, benzofuryl, imidazolyl, 4,5-dihydro-1H-imidazolyl, pyrazolyl, isoxazolyl, isothiazolyl, thiazolyl, oxazolyl, benzimidazolyl, benzthiazolyl, benzoxazolyl, carbazolyl etc.; monocyclic to tricyclic 6-membered unsaturated heterocyclic groups such as pyridyl, pyrazinyl, pyrimidinynl, 1,4,5,6-tetrahydropyrimidinyl, 3,6-dihydro-2H-[1,3,5]oxadiazinyl, pyridazinyl, triazinyl, quinolyl, isoquinolyl, quinazolinyl, quinoxalinyl, chromenyl, 2,3-dihydrobenzo[1,4]dioxinyl, etc.; and monocyclic to tricyclic 7-membered unsaturated heterocyclic groups such as 4,5,6,7-tetrahydro-1H-[1,3] diazepinyl, etc.

As the substituent of each of the substituted aryl group and the substituted heterocyclic group, there may be exemplified any substituents in the following groups a) to g), and each of the substituted aryl group and the substituted heterocyclic group may optionally have one or more of these substituents.

a) Halogen atoms, nitro group, cyano group, azide group, mercapto group, substituted or unsubstituted amino groups, substituted or unsubstituted hydroxylamino groups, substituted or unsubstituted lower alkoxyamino groups, hydroxyl group, acyl groups, acyloxy groups, carboxyl group, substituted or unsubstituted carbamoyl groups, substituted or unsubstituted carbamoyloxy groups, sulfo group, and substituted or unsubstituted sulfamoyl groups.

b) $-R^{10}$, $-OR^{10}$, $-CO_2R^{10}$, $-SO_3R^{10}$, $-SR^{10}$, $-OCH_2R^{10}$ and $-SCH_2R^{10}$ wherein $R^{10}$ is a phenyl group or a monocyclic heterocyclic group, wherein said phenyl group and monocyclic heterocyclic group may be substituted by at least one member optionally selected from the group consisting of, for example, halogen atoms, lower alkyl groups, lower haloalkyl groups, cyano group, nitro group, azide group, hydroxyl group, lower alkoxy groups, lower haloalkoxy groups, substituted or unsubstituted amino groups, substituted or unsubstituted carbamoyl groups, carboxyl group, lower alkylcarbonyl groups, lower alkoxycarbonyl groups, lower alkylthio groups, lower alkylsulfinyl groups, lower alkylsulfonyl groups, etc.

c) Alkyl groups, alkoxy groups, alkoxycarbonyl groups, alkoxy(thiocarbonyl) groups, alkylthio groups, (alkylthio) thiocarbonyl groups, (alkylthio)carbonyl groups, alkylcarbonyl groups, alkylthioyl groups, alkylsulfinyl groups, alkylsulfonyl groups, alkylcarbonyloxy groups, alkylthioyloxy groups and alkylsulfonyloxy groups, each of which groups may be substituted by at least one member optionally selected from the group consisting of, for example, halogen atoms; nitro group; cyano group; mercapto group; oxo group; thioxo group; substituted or unsubstituted amino groups; hydroxyl group; acyl groups; acyloxy groups; carboxyl group; substituted or unsubstituted carbamoyl groups; substituted or unsubstituted carbamoyloxy groups; sulfo group; substituted or unsubstituted sulfamoyl groups; $-R^{10}$; $-OR^{10}$; $-SR^{10}$; $-OCH_2R^{10}$; $-SCH_2R^{10}$ wherein $R^{10}$ is as defined above;

lower cycloalkyl groups which may be substituted by at least one member optionally selected from the group consisting of, for example, halogen atoms, lower alkyl groups, lower haloalkyl groups, substituted or unsubstituted amino groups, hydroxyl group, lower alkoxy groups, lower haloalkoxy groups, etc.;

lower alkoxy groups; lower alkoxycarbonyl groups; and lower alkylthio groups, wherein said lower alkoxy groups, lower alkoxycarbonyl groups and lower alkylthio groups may be substituted by at least one member optionally selected from the group consisting of, for example, halogen atoms, lower cycloalkyl groups, monocyclic heterocyclic groups, phenyl group, cyano group, nitro group, hydroxyl group, lower alkoxy groups, lower haloalkoxy groups, substituted or unsubstituted amino groups, substituted or unsubstituted carbamoyl groups, carboxyl group, lower alkylcarbonyl groups, lower alkoxycarbonyl groups, lower alkylthio groups, lower alkylsulfinyl groups and lower alkylsulfonyl groups, etc.

d) Alkenyl groups, which may be substituted by at least one member optionally selected from the group consisting of, for example, halogen atoms, nitro group, cyano group, mercapto group, oxo group, thioxo group, substituted or unsubstituted amino groups, hydroxyl group, lower alkoxy groups, lower haloalkoxy groups, lower alkoxycarbonyl groups, lower alkylthio groups, acyl groups, acyloxy groups, carboxyl group, substituted or unsubstituted carbamoyl groups, $-R^{10}$, $-OR^{10}$, $-SR^{10}$, $-OCH_2R^{10}$ and $-SCH_2R^{10}$ wherein $R^{10}$ is as defined above, etc.

e) Alkynyl groups, which may be substituted by at least one member optionally selected from the group consisting of, for example, halogen atoms, nitro group, cyano group, mercapto group, oxo group, thioxo group, substituted or unsubstituted amino groups, hydroxyl group, lower alkoxy groups, lower haloalkoxy groups, lower alkoxycarbonyl groups, lower alkylthio groups, acyl groups, acyloxy groups, carboxyl group, substituted or unsubstituted carbamoyl groups, —$R^{10}$, —$OR^{10}$, —$SR^{10}$, —$OCH_2R^{10}$ and —$SCH_2R^{10}$ wherein $R^{10}$ is as defined above, etc.

f) Alkenyloxy groups, alkenyloxycarbonyl groups, alkenylcarbonyl groups, alkenylcarbonyloxy groups, alkynyloxy groups and alkynyloxycarbonyl groups, each of which groups may be substituted by at least one member optionally selected from the group consisting of, for example, halogen atoms, oxo group, substituted or unsubstituted amino groups, hydroxyl group, lower alkoxy groups, lower haloalkoxy groups, acyl groups, acyloxy groups, lower alkylthio groups, carboxyl group, substituted or unsubstituted carbamoyl groups, lower alkoxycarbonyl groups, phenyl group, etc.

g) Lower cycloalkyl groups, lower cycloalkyloxy groups, lower cycloalkylcarbonyl groups, lower cycloalkylcarbonyloxy groups, lower cycloalkyloxy carbonyl groups, lower cycloalkenyl groups, lower cycloalkenyloxy groups, lower cycloalkenylcarbonyl groups, lower cycloalkenylcarbonyloxy groups and lower cycloalkenyloxycarbonyl groups, each of which groups may be substituted by at least one member optionally selected from the group consisting of, for example, halogen atoms, nitro group, cyano group, mercapto group, oxo group, thioxo group, lower alkyl groups, lower haloalkyl groups, substituted or unsubstituted amino groups, hydroxyl group, lower alkoxy groups, lower haloalkoxy groups, acyl groups, acyloxy groups, lower alkylthio groups, carboxyl groups, substituted or unsubstituted carbamoyl groups, lower alkoxycarbonyl groups, etc.

Specific examples of the substituent of the substituted aryl group and substituted heterocyclic group are methyl, 2-methyl-1-propyl, hexyl, 2-methyl-2-propyl, 2-propyl, phenyl, trifluoromethyl, 2,2,2-trifluoroethyl, 1,1,2,2,2-pentafluoroethyl, 6,6,6-trifluorohexyl, hydroxymethyl, hydroxyethyl, methoxymethyl, hexyloxymethyl, cyclopropylmethoxymethyl, acetoxymethyl, N,N-dimethylcarbamoyloxymethyl, methanesulfonyloxymethyl, N,N-dimethylsulfamoyloxymethyl, 2-(1-pyrrolidinyl)ethoxymethyl, 2-methoxyethyl, carboxymethyl, methoxycarbonylmethyl, carbamoylmethyl, amidinomethyl, methylthiomethyl, cyanomethyl, aminomethyl, aminoethyl, N-acetylaminomethyl, ethenyl, 2-propenyl, ethynyl, 2-propynyl, 2-methoxycarbonylethenyl, fluoro, chloro, bromo, nitro, cyano, hydroxyl, amino, N,N-dimethylamino, mercapto, sulfo, carboxyl, amidino, methoxy, cyclopropylmethoxy, 2-(1-pyrrolidinyl)ethoxy, methoxycarbonylmethoxy, 2-acetoxyethoxy, 2-hydroxyethoxy, 2-methoxyethoxy, 4,4,5,5,5-pentafluoropentoxy, 2-methanesulfinylethoxy, phenoxy, benzyloxy, 4-methoxybenzyloxy, methoxycarbonyloxy, 1-pyrrolidinyl, 3-hydroxy-1-pyrrolidinyl, acetylamino, N-acetyl-N-methylamino, N-methanesulfonylamino, N-methanesulfonyl-N-methylamino, methoxycarbonyl, 2-methyl-2-propoxycarbonyl, 2,2,2-trifluoroethoxycarbonyl, carbamoyl, N,N-dimethylcarbamoyl, 2-thiazolidinyl, 2-oxazolidinyl, 5-tetrazolyl, methanesulfinyl, sulfamoyl, N,N-dimethylsulfamoyl, acetyl, benzoyl, pivaloyl, trifluoroacetyl, formyl, ethylenedioxymethyl, imino, methoxyimino, etc.

Of these substituents, specific examples of preferable substituent are methyl, 2-methyl-1-propyl, hexyl, 2-methyl-2-propyl, 2-propyl, phenyl, trifluoromethyl, 2,2,2-trifluoroethyl, hydroxymethyl, hydroxyethyl, methoxymethyl, cyclopropylmethoxymethyl, acetoxymethyl, N,N-dimethylcarbamoyloxymethyl, methanesulfonyloxymethyl, N,N-dimethylsulfamoyloxymethyl, 2-(1-pyrrolidinyl)ethoxymethyl, 2-methoxyethyl, carboxymethyl, methoxycarbonylmethyl, carbamoylmethyl, amidinomethyl, methylthiomethyl, cyanomethyl, aminomethyl, aminoethyl, N-acetylaminomethyl, fluoro, chloro, bromo, nitro, cyano, hydroxyl, amino, N,N-dimethylamino, methoxy, 2-(1-pyrrolidinyl)ethoxy, methoxycarbonylmethoxy, 2-acetoxyethoxy, 2-hydroxyethoxy, 2-methoxyethoxy, 2-methanesulfinylethoxy, 1-pyrrolidinyl, 3-hydroxy-1-pyrrolidinyl, acetylamino, N-acetyl-N-methylamino, N-methanesulfonylamino, N-methanesulfonyl-N-methylamino, methoxycarbonyl, 2-methyl-2-propoxycarbonyl, 2,2,2-trifluoroethoxycarbonyl, carbamoyl, N,N-dimethylcarbamoyl, methanesulfinyl, acetyl, benzoyl, pivaloyl, trifluoroacetyl, etc.

The number of substituents of each of the aryl group and the heterocyclic group is preferably 1, 2 or 3. As each of the aryl group and the heterocyclic group, an unsubstituted one is also preferable.

The alkyl group includes, for example, linear or branched alkyl groups of 1 to 10 carbon atoms. Specific examples thereof are methyl, ethyl, propyl, 1-methylethyl, butyl, 1-methylpropyl, 2-methyl-1-propyl, 1,1-dimethylethyl, pentyl, 1,1-dimethylpropyl, 2,2-dimethylpropyl, 1-methylbutyl, 3-methylbutyl, hexyl, 2-methylpentyl, 3,3-dimethylbutyl, heptyl, 1-ethylpentyl, 5-methylhexyl, octyl, 1,5-dimethylhexyl, 2-ethylhexyl, nonyl, decyl, etc. The lower alkyl group includes alkyl groups of 1 to 6 carbon atoms.

As the substituent of the substituted alkyl group, there may be exemplified any substituents in the following groups a) to d), and the substituted alkyl group may optionally have one or more of these substituents.

a) Halogen atoms, nitro group, cyano group, mercapto group, oxo group, thioxo group, substituted or unsubstituted amino groups, substituted or unsubstituted hydroxylamino groups, substituted or unsubstituted lower alkoxyamino groups, hydroxyl group, acyl groups, acyloxy groups, carboxyl group, substituted or unsubstituted carbamoyl groups, substituted or unsubstituted carbamoyloxy groups, sulfo group, and substituted or unsubstituted sulfamoyl groups.

b) Lower cycloalkyl groups, lower cycloalkyloxy groups, lower cycloalkylcarbonyl groups, lower cycloalkylcarbonyloxy groups, lower cycloalkyloxycarbonyl groups, lower cycloalkenyl groups, lower cycloalkenyloxy groups, lower cycloalkenylcarbonyl groups, lower cycloalkenylcarbonyloxy groups and lower cycloalkenyloxycarbonyl groups, each of which group may be substituted by at least one member optionally selected from the group consisting of, for example, halogen atoms, nitro group, cyano group, mercapto group, oxo group, thioxo group, lower alkyl groups, lower haloalkyl groups, substituted or unsubstituted amino groups, hydroxyl group, lower alkoxy groups, lower haloalkoxy groups, acyl groups, acyloxy groups, lower alkylthio groups, carboxyl groups, substituted or unsubstituted carbamoyl groups, lower alkoxycarbonyl groups, etc.

c) Alkoxy groups, alkoxycarbonyl groups, alkoxy (thiocarbonyl) groups, alkylthio groups, (alkylthio) thiocarbonyl groups, (alkylthio)carbonyl groups, alkylcarbonyl groups, alkylthioyl groups, alkylsulfinyl groups, alkylsulfonyl groups, alkylcarbonyloxy groups, alkylthioyloxy groups and alkylsulfonyloxy groups, each of which groups may be substituted by at least one member optionally selected from the group consisting of, for example, halogen atoms; nitro group; cyano group; mercapto group; oxo group; thioxo group; substituted or unsubstituted amino groups; hydroxyl group; acyl groups; acyloxy groups; carboxyl group; substituted or unsubstituted carbamoyl groups; substituted or unsubstituted carbamoyloxy groups; sulfo group; substituted or unsubstituted sulfamoyl groups; —$R^{10}$; —$OR^{10}$; —$SR^{10}$; —$OCH_2R^{10}$; —$SCH_2R^{10}$ wherein $R^{10}$ is as defined above;

lower cycloalkyl groups which may be substituted by at least one member optionally selected from the group consisting of, for example, halogen atoms, lower alkyl groups, lower haloalkyl groups, substituted or unsubstituted amino groups, hydroxyl group, lower alkoxy groups, lower haloalkoxy groups, etc.;

lower alkoxy groups; lower alkoxycarbonyl groups; and lower alkylthio groups, wherein said lower alkoxy groups, lower alkoxycarbonyl group and lower alkylthio groups may be substituted by at least one member optionally selected from the group consisting of, for example, halogen atoms, lower cycloalkyl groups, monocyclic heterocyclic groups, phenyl group, cyano group, nitro group, hydroxyl group, lower alkoxy groups, lower haloalkoxy groups, substituted or unsubstituted amino groups, substituted or unsubstituted carbamoyl groups, carboxyl group, lower alkylcarbonyl groups, lower alkoxycarbonyl groups, lower alkylthio groups, lower alkylsulfinyl groups and lower alkylsulfonyl groups, etc.

d) —$R^{10}$, —$OR^{10}$, —$SR^{10}$, —$OCH_2R^{10}$ and —$SCH_2R^{10}$ wherein $R^{10}$ is as defined above.

Specific examples of the substituted alkyl group are trifluoromethyl, 2-nitroethyl, 2-cyanopropyl, 4-mercaptobutyl, 3-oxobutyl, 2-piperidinoethyl, 2-hydroxyethyl, 3-methoxypropyl, ethoxycarbonylmethyl, cyclopropylmethyl, cyclohexylmethyl, 6-cyclohexylhexyl, 3-cyclohexenylbutyl, 2-phenylbutyl, benzyl, 2-naphthylmethyl, phenethyl, 2-pyridylmethyl, 3-pyridylmethyl, 4-pyridylmethyl, 2-quinolylmethyl, 3-quinolylmethyl, 3-thienylpropyl, hydroxymethyl, hydroxyethyl, aminomethyl, aminoethyl, carboxymethyl, ethoxycarbonylmethyl, carbamoylmethyl, etc.

The lower haloalkyl group represents a lower alkyl group substituted by 1 to 5 halogen atoms.

The alkoxy group represents to an oxy group having an alkyl group bonded thereto. Specific examples thereof are methoxy, ethoxy, propoxy, 2-propoxy, butoxy, 1,1-dimethylethoxy, pentoxy, hexoxy, etc. As the substituent of the substituted alkoxy group, there may be exemplified the same substituents as those exemplified above as the substituent of the substituted alkyl group. Specific examples of the substituted alkoxy group are cyclopropylmethoxy, trifluoromethoxy, 2-pyrrolidinoethoxy, benzyloxy, 2-pyridylmethoxy, etc.

The haloalkoxy group represents an alkoxy group substituted by 1 to 5 halogen atoms.

The alkoxycarbonyl group represents a carbonyl group having an alkoxy group bonded thereto. Specific examples thereof are methoxycarbonyl, ethoxycarbonyl, propoxycarbonyl, 2-propoxycarbonyl, etc. As the substituent of the substituted alkoxycarbonyl group, there may be exemplified the same substituents as those exemplified above as the substituent of the substituted alkyl group.

The alkenyl group includes linear or branched alkenyl groups of 2 to 10 carbon atoms having 1 to 3 double bonds. Specific examples thereof are ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl, 2-decenyl, etc. Preferable examples of the alkenyl group are, for example, ethenyl, 1-propenyl and 1-butenyl. The lower alkenyl group includes alkenyl groups of 2 to 6 carbon atoms.

The substituent of the substituted alkenyl group includes, for example, halogen atoms, nitro group, cyano group, mercapto group, oxo group, thioxo group, substituted or unsubstituted amino groups, hydroxyl group, lower alkoxy groups, lower haloalkoxy groups, lower alkoxycarbonyl groups, lower alkylthio groups, or unsubstituted carbamoyl groups, —$R^{10}$, —$OR^{10}$, —$SR^{10}$, —$OCH_2R^{10}$, —$SCH_2R^{10}$ wherein $R^{10}$ is as defined above etc.

The alkenyloxy group represents an oxy group having an alkenyl group bonded thereto.

The alkynyl group includes linear or branched alkynyl groups of 2 to 10 carbon atoms having 1 to 3 triple bonds. Specific examples thereof are ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, 2-decynyl, etc. Preferable examples of the alkynyl group are, for example, 1-propynyl, 1-butynyl, etc. The lower alkynyl group includes alkynyl groups of 2 to 6 carbon atoms.

The substituent of the substituted alkynyl group includes, for example, halogen atoms, nitro group, cyano group, mercapto group, oxo group, thioxo group, substituted or unsubstituted amino groups, hydroxyl group, lower alkoxy groups, lower haloalkoxy groups, acyl groups, acyloxy groups, lower alkylthio groups, carboxyl group, substituted or unsubstituted carbamoyl groups, lower alkoxycarbonyl groups, —$R^{10}$, —$OR^{10}$, —$SR^{10}$, —$OCH_2R^{10}$, —$SCH_2R^{10}$ wherein $R^{10}$ is as defined above, etc.

The alkynyloxy group represents an oxy group having an alkynyl group bonded thereto.

The cycloalkyl group includes, for example, cycloalkyl groups of 3 to 10 carbon atoms. Specific examples thereof are cyclopropyl, cyclobutyl, cyclopentyl, cyclohexyl, cycloheptyl, etc. The lower cycloalkyl group includes cycloalkyl groups of 3 to 6 carbon atoms. The cycloalkyloxy group represents an oxy group having a cycloalkyl group bonded thereto.

The cycloalkenyl group includes, for example, cycloalkenyl groups of 3 to 10 carbon atoms. Specific examples thereof are cyclohexenyl, etc. The lower cycloalkenyl group includes cycloalkenyl groups of 3 to 6 carbon atoms. The cycloalkenyloxy group refers to an oxy group having a cycloalkenyl group bonded thereto.

The substituent of each of the substituted cycloalkyl group and the substituted cycloalkenyl group includes, for example, halogen atoms, nitro group, cyano group, mercapto group, oxo group, thioxo group, lower alkyl groups, lower haloalkyl groups, substituted or unsubstituted amino groups, hydroxyl group, lower alkoxy groups, lower haloalkoxy groups, acyl groups, acyloxy groups, lower alkylthio groups, carboxyl group, substituted or unsubstituted carbamoyl groups, lower alkoxycarbonyl groups, etc.

The acyl group includes, for example, acyl groups of the formula: —Z—$R^{11}$ wherein Z is —CO—, —CS—, —SO— or —$SO_2$—, and $R^{11}$ is a substituted or unsubstituted alkyl group, a substituted or unsubstituted aryl group or a substituted or unsubstituted heterocyclic group. Specific examples of the acyl group are formyl, acetyl, propanoyl, 2-propanoyl, pivaloyl, valeryl, pivaloyl, trifluoroacetyl, benzoyl, naphthoyl, nicotinoyl, methanesulfonyl, trifluoromethanesulfonyl, p-toluenesulfonyl, etc. Preferable examples of the acyl group are acetyl group, etc. The acyloxy group represents an oxy group having an acyl group bonded thereto.

The substituent of the substituted carbamoyl group includes, for example, alkyl groups which may be substituted by an aryl group or a heterocyclic group, aryl groups, heterocyclic groups, etc. The substituted carbamoyl group may have a plurality of the same or different substituents independently introduced thereinto. Specific examples of the substituted carbamoyl group are ethylcarbamoyl, dimethylcarbamoyl, phenylcarbamoyl, 2-pyridylcarbamoyl, benzylcarbamoyl, (3-pyridylmethyl)carbamoyl, etc.

The substituent of the substituted sulfamoyl group includes, for example, alkyl groups, aryl groups, heterocyclic groups, etc. The substituted sulfamoyl group may have a plurality of the same or different substituents independently introduced thereinto. Specific examples of the substituted sulfamoyl group are ethylsulfamoyl, dimethylsulfamoyl, phenylsulfamoyl, 2-pyridylsulfamoyl, etc.

The substituent of the substituted amino group includes, for example, acyl groups, alkyl groups, etc. The substituted amino group may have a plurality of the same or different substituents independently introduced thereinto. Specific examples of the substituted amino group are acetamide, propionamide, butylamide, 2-butylamide, methylamino, 2-methyl-1-propylamino, diethylamino, etc.

The substituent of the substituted hydroxylamino group may be on either the nitrogen atom or the oxygen atom. As the substituent, there may be exemplified the same substituents as those exemplified above as the substituent of the substituted amino group.

The halogen atom includes, for example, fluorine atom, chlorine atom, bromine atom, iodine atom, etc.

The alkylene group includes, for example, linear or branched alkylene groups of 1 to 10 carbon atoms. Specific examples thereof are methylene, ethylene, trimethylene, tetramethylene, pentamethylene, hexamethylene, heptamethylene, octamethylene, nonamethylene, decamethylene, methylmethylene, ethylmethylene, dimethylmethylene, 1,1-dimethylethylene, 1,2-dimethylethylene, 1-methyltrimethylene, 2-methyltrimethylene, 1,1-dimethyltrimethylene, 1,2-dimethyltrimethylene, 1,3-dimethyltrimethylene, 2,2-dimethyltrimethylene, 1-ethyltrimethylene, 2-ethyltrimethylene, 1,1-diethyltrimethylene, 1,2-diethyltrimethylene, 1,3-diethyltrimethylene, 2,2-diethyltrimethylene, etc.

The lower alkylene group include, for example, linear or branched alkylene groups of 1 to 6 carbon atoms.

As the protecting group for NH group, various conventional protecting groups may be used, though preferable examples thereof are carbamate type protecting groups such as methoxycarbonyl, ethoxycarbonyl, tert-butoxycarbonyl, benzyloxycarbonyl and the like, amide type protecting groups such as acetyl, benzoyl and the like, benzyl, nitro, p-toluenesulfonyl, methanesulfonyl, etc.

In the substituted or unsubstituted heterocyclic ring which any two of $R^1$, $R^2$, $R^3$ and $R^4$ form when taken together with the nitrogen atom(s), the heterocyclic ring includes, for example, 5- to 7-membered monocyclic or bicyclic saturated or unsaturated heterocyclic rings containing 1 to 6 nitrogen atoms, oxygen atoms and/or sulfur atoms which contains at least one nitrogen atom. Specific examples thereof are pyrrolidine, imidazolidine, 4,5-dihydro-1H-imidazole, piperidine, piperidin-4-one, piperazine, morpholine, thiamorpholine, 1,4,5,6-tetrahydro-pyrimidine, hexahydropyrimidine, 3,6-dihydro-2H-[1,3,5]oxadiazine, etc. As the substituent of the substituted heterocyclic ring, there may be exemplified the same substituents as those exemplified above as the substituent of the substituted heterocyclic group.

The substituted or unsubstituted hydrocarbon ring which $R^8$ and $R^9$ form when taken together with the carbon atom, includes, for example, substituted or unsubstituted cycloalkane rings of 3 to 8 carbon atoms or substituted or unsubstituted cycloalkene rings of 3 to 8 carbon atoms. Specific examples of the cycloalkane rings or cycloalkene rings are cyclopropane, cyclobutane, cyclopentane, cyclohexane, cycloheptane, cyclopropene, cyclobutene, cyclopentene, cyclohexene, cycloheptene, etc. As the substituent of the substituted hydrocarbon ring, there may be exemplified the same substituents as those exemplified above as the substituent of the substituted cycloalkyl group.

When the isoxazole derivative of the formula 1 has a polar functional group introduced into the isoxazole ring, this compound possesses improved pharmacokinetics, has little side effect and may be administered f or a long period of time.

The present invention includes all stereoisomers, optical isomers, tautomers and the like of the isoxazole derivative of the formula 1. The present invention also includes solvates (e.g. hydrates and the like) and all crystal forms of the isoxazole derivative of the formula 1 or a pharmaceutically acceptable salt thereof.

The pharmaceutically acceptable salt of the isoxazole derivative of the formula 1 includes acid addition salts and base addition salts. The acid addition salts include, for example, salts with inorganic acids, such as hydrochloride, hydrobromide, sulfate, hydroiodate, nitrate, phosphate, etc.; and salts with organic acids, such as citrate, oxalate, acetate, formate, propionate, benzoate, trifluoroacetate, fumarate, maleate, tartrate, aspartate, glutamate, methanesulfonate, benzenesulfonate, camphorsulfonate, etc. The base addition salts include salts with inorganic bases, such as sodium salt, potassium salt, calcium salt, magnesium salt, ammonium salt, etc.; and salts with organic bases, such as triethylammonium salt, triethanol ammonium salt, pyridinium salt, diisopropylammonium salt, etc.

The isoxazole derivative of the formula 1 may be produced, for example, by any of the five processes described below. Although an explanation is given in the following reaction formulas by taking the case where A and B have one of the two combinations of meanings defined above, the derivative in which A and B have the other combination of meanings may be produced in the same manner.

Process 1

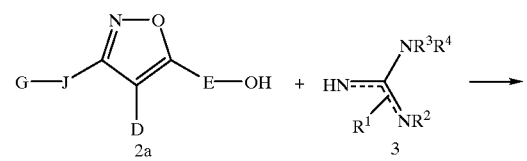

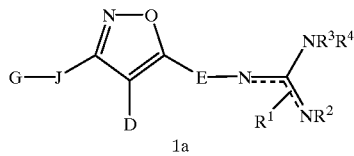

1a wherein D, E, J, G, $R^1$, $R^2$, $R^3$, $R^4$ and the broken lines are as defined above.

An isoxazole derivative (1a) of the present invention may be produced by reacting a compound of the formula 2a with a guanidine derivative of the formula 3 in an inert solvent at a reaction temperature of 0–25° C. under conditions of Mitsunobu reaction using a trialkylphosphine and an azodicarboxylic acid ester (Chem. Lett., 1994, 539; Tetrahedron Lett., 35, 977(1994)). The trialkylphosphine includes, for example, triphenylphosphine, tributylphosphine, etc. The azodicarboxylic acid ester includes, for example, diethyl azodicarboxylate, diisopropyl azodicarboxylate, 1,1'-(azodicarbonyl)dipiperidine, N,N,N',N'-tetramethylazodicarboxamide and N,N,N',N'-tetraisopropylazodicarboxamide, etc. Preferable examples of the solvent are tetrahydrofuran, benzene, toluene, etc.

When $R^1$, $R^2$, $R^3$ or $R^4$ is a protecting group for NH group in the compound of the formula 1a, deprotection may be carried out if desired. This deprotection may be carried out according to a conventional method, for example, the method described in "Protective Groups in Organic Synthesis" (2nd Edition, T. W. Greene and P. G. M. Wuts, John Willey and Sons, Inc., New York (1991), p 315–362). As the protecting group for NH group, various conventional protecting groups may be used. Preferable examples thereof are carbamate type protecting groups such as methoxycarbonyl, ethoxycarbonyl, tert-butoxycarbonyl, benzyloxycarbonyl and the like, amide type protecting groups such as N-acetyl, N-benzoyl and the like, benzyl, nitro, p-toluenesulfonyl, methanesulfonyl, etc.

1) Process for Producing a Compound of the Formula 2a Wherein E is an Alkylene (a Compound of the Formula $2a^1$)

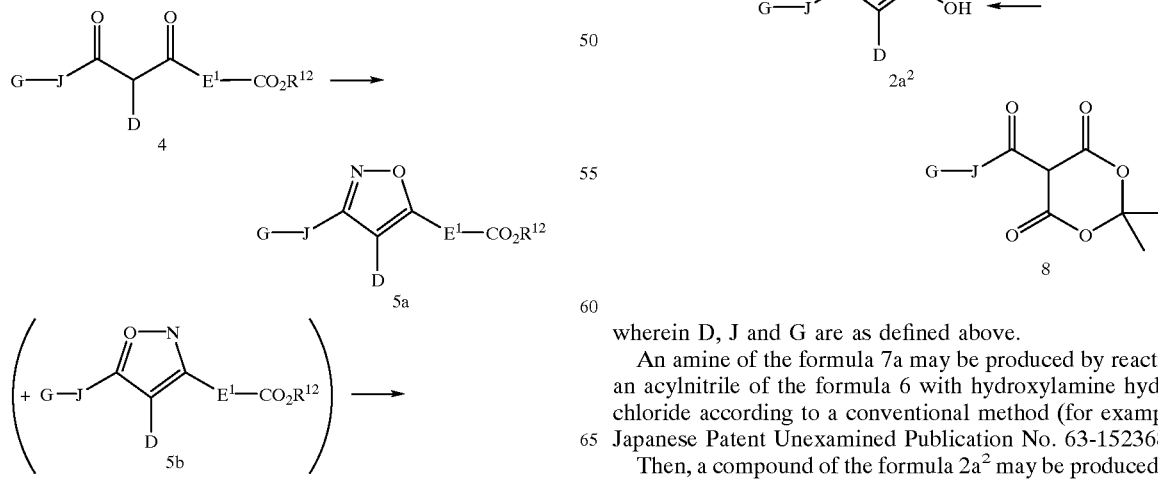

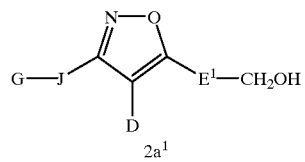

$2a^1$ wherein D, J and G are as defined above, $E^1$ is a single bond or an alkylene group, and $R^{12}$ is a lower alkyl group.

A compound of the formula 5a may be produced by reacting an ester derivative of β-diketone of the formula 4 with hydroxyamine or hydroxylamine hydrochloride in an inert solvent according to a conventional isoxazole synthesis process (for example, A. R. Katritzky et al., "Comprehensive Heterocyclic Chemistry", Vol. 6, Pergamon Press Ltd., New York (1984), p 61). In this case, a compound of the formula 5b is also produced in some cases, but it is also possible to produce only one of the compound of the formula 5a and the compound of the formula 5b by controlling the reaction conditions (for example, F. Lepage et al., Eur. J. Med. Chem., 27, 581(1992); and the above reference, A. R. Katritzky et al., Comprehensive Heterocyclic Chemistry, Vol. 6, Pergamon Press Ltd., New York (1984), p 62).

A compound of the formula $2a^1$ may be produced by treating the compound of the formula 5a with a reducing agent in an inert solvent. The reducing agent includes, for example, lithium aluminum hydride, etc. The solvent includes tetrahydrofuran, etc. The reaction temperature is preferably about 0° C.

2) Process for Producing a Compound of the Formula 2a Wherein E is a Single Bond (a Compound of the Formula $2a^2$)

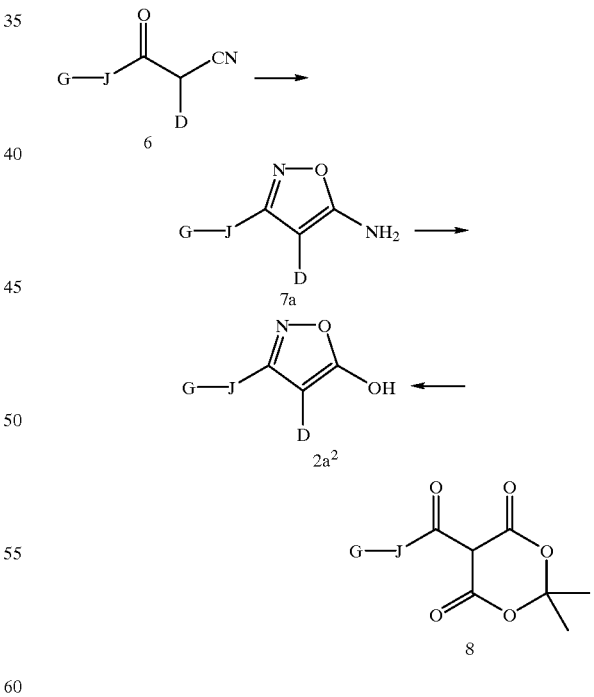

wherein D, J and G are as defined above.

An amine of the formula 7a may be produced by reacting an acylnitrile of the formula 6 with hydroxylamine hydrochloride according to a conventional method (for example, Japanese Patent Unexamined Publication No. 63-152368).

Then, a compound of the formula $2a^2$ may be produced by hydrolyzing the amine of the formula 7a with an acid according to a conventional method (for example, Japanese Patent Unexamined Publication No. 62-84064).

The compound of the formula 2a may be produced also by reacting a Meldrum's acid derivative of the formula 8 with hydroxylamine hydrochloride according to a conventional method (for example, Japanese Patent Unexamined Publication No. 52-106466).

3) Process for Producing a Compound of the Formula 2b Wherein E is a Single Bond (a Compound of the Formula $2b^2$)

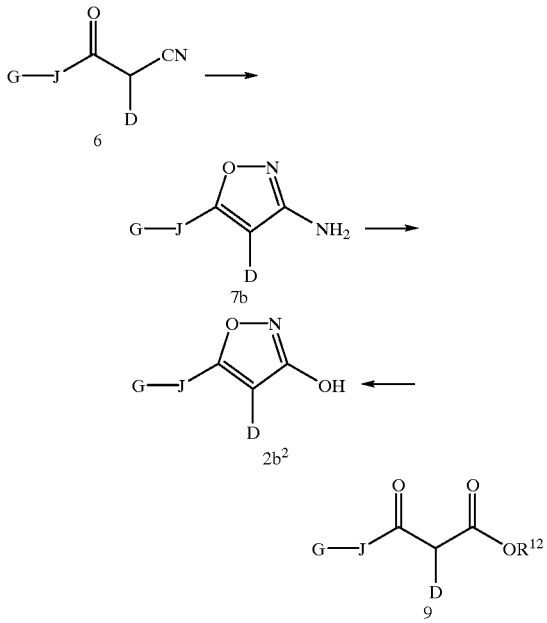

wherein D, J, G and $R^{12}$ are as defined above.

An amine of the formula 7b may be produced by treating an acylnitrile of the formula 6 with hydrogen chloride gas in methanol and reacting the treated acylnitrile with hydroxylamine hydrochloride, according to a conventional method (for example, Japanese Patent Unexamined Publication No. 54-3062).

Using the amine of the formula 7b, a compound of the formula $2b^2$ may be produced by the same process as for the production of the compound of the formula $2a^2$ from the amine of the formula 7a.

The compound of the formula $2b^2$ may be produced also by reacting a β-keto ester of the formula 9 with hydroxylamine hydrochloride according to a conventional method (for example, N. Jacobsen et al., Can. J. Chem., 62, 1940 (1984)).

Process 2

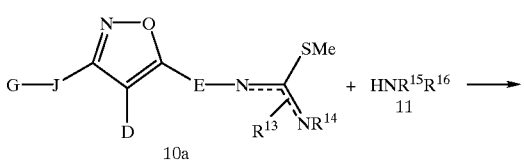

-continued

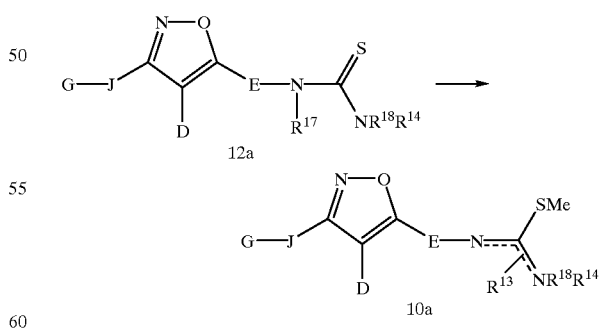

wherein D, E, J, G and the broken lines are as defined above, and $R^{13}$, $R^{14}$, $R^{15}$ and $R^{16}$ are independently a hydrogen atom, a halogen atom, a hydroxyl group, a mercapto group, a nitro group, a cyano group, a carboxyl group, a substituted or unsubstituted amino group, a substituted or unsubstituted hydroxylamino group, a substituted or unsubstituted carbamoyl group, a substituted or unsubstituted sulfamoyl group, a sulfo group, a protecting group for NH group, —$R^5$, —$OR^5$, —$CO_2R^6$, —$SR^7$, —$(CO)SR^7$, —$(CS)OR^7$ or —$CS_2R^7$ wherein $R^5$, $R^6$ and $R^7$ are as defined above.

A compound of the formula $1a^1$ may be produced by reacting a pseudothiourea derivative of the formula 10a with an amine of the formula 11 at a reaction temperature of 20–140° C. optionally in the presence of an additive optionally in an inert solvent. The additive includes, for example, ammonium acetate, sodium acetate, acetic acid, oxalic acid, sodium hydroxide, sodium carbonate, sodium hydrogencarbonate, 1,8-diazabicyclo[5.4.0]undec-7-ene, triethylamine and mixtures thereof, etc. Preferable examples of the solvent are water, methanol, ethanol, isopropanol, acetonitrile, N,N-dimethylformamide, tetrahydrofuran, 1,4-dioxane, pyridine, toluene, chloroform, methylene chloride and mixtures thereof, etc.

The compound of the formula $1a^1$ may be produced also by reacting the compound of the formula 10a with the amine of the formula 11 in the presence of silver nitrate and a base in an inert solvent at a reaction temperature of −10° C. to 50° C. according to the method of Web et al. using silver nitrate as an additive (J. Org. Chem., 56, 3009(1991)). The base includes, for example, triethylamine, etc. Preferable examples of the solvent are acetonitrile, etc.

When $R^{13}$, $R^{14}$, $R^{15}$ or $R^{16}$ is a protecting group for NH group in the compound of the formula $1a^1$, deprotection may be carried out in the same manner as above if desired.

The starting compounds in the production process described above are per se well-known compounds, or compounds producible by well-known synthetic processes. For example, the compound of the formula 10a may be produced by the following process:

wherein D, E, J, G, $R^{13}$, $R^{14}$ and the broken lines are as defined above, and one of $R^{17}$ and $R^{18}$ is a hydrogen atom, while the other is a hydrogen atom, a halogen atom, a hydroxyl group, a mercapto group, a nitro group, a cyano group, a carboxyl group, a substituted or unsubstituted amino group, a substituted or unsubstituted hydroxylamino group, a substituted or unsubstituted carbamoyl group, a substituted or unsubstituted sulfamoyl group, a sulfo group, a protecting group for NH group, —$R^5$, —$OR^5$, —$CO_2R^6$, —$SR^7$, —$(CO)SR^7$, —$(CS)OR^7$ or —$CS_2R^7$ wherein $R^5$, $R^6$ and $R^7$ are as defined above.

The compound of the formula 10a may be produced by reacting a methyl halide with a thiourea derivative of the formula 12a which is well-known or is producible by a well-known synthetic process (for example, Japanese Patent Unexamined Publication No. 63-152368), in an inert solvent in the presence of a base at a reaction temperature of 40–80° C. The methyl halide includes, for example, methyl iodide, etc. The base includes, for example, potassium carbonate, sodium carbonate, an aqueous potassium hydroxide solution, an aqueous sodium hydroxide solution, etc. The solvent includes, for example, methanol, ethanol, tetrahydrofuran, 1,4-dioxane, N,N-dimethylformamide, etc.

Process 3

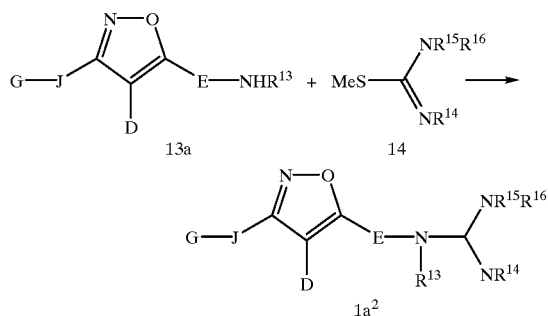

wherein D, E, J, G, $R^{13}$, $R^{14}$, $R^{15}$ and $R^{16}$ are as defined above.

A compound of the formula $1a^2$ may be produced by reacting a compound of the formula 13a with a pseudothiourea derivative of the formula 14 in the presence of a base in an inert solvent at a reaction temperature of 20–100° C. The base includes, for example, 1,8-diazabicyclo[5.4.0]undec-7-ene, triethylamine, etc. Preferable examples of the solvent are pyridine, acetonitrile, N,N-dimethylformamide, etc.

The compound of the formula $1a^2$ may be produced also by carrying out the reaction in the presence of silver nitrate and a base in an inert solvent at a reaction temperature of –10° C. to 50° C. according to the above-mentioned method of Web et al. using silver nitrate (J. Org. Chem., 56, 3009(1991)). The base includes, for example, triethylamine, etc. Preferable examples of the solvent are acetonitrile, etc.

When $R^{13}$, $R^{14}$, $R^{15}$ or $R^{16}$ is a protecting group for NH group in the compound of the formula $1a^2$, deprotection may be carried out in the same manner as above if desired.

The compound of the formula 13a may be produced, for example, by subjecting a compound of the formula 2a to halogenation, conversion to azide, etc. (for example, the process of Y. Pei et al. (Tetrahedron Lett., 34, 7509(1993)). If necessary, a substituent may be introduced into the amino group (for example, R. C. Larock, "Comprehensive Organic Transformations", VCH Publishers, Inc., New York (1989), p 397).

Process 4

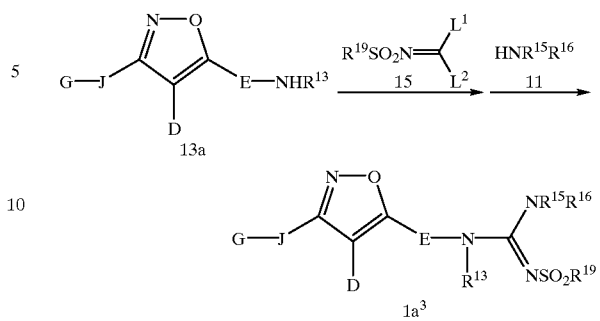

wherein D, E, J, G, $R^{13}$, $R^{15}$ and $R^{16}$ are as defined above, $R^{19}$ is a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, or a substituted or unsubstituted heterocyclic group, and $L^1$ and $L^2$ are independently a halogen atom or a methylthio group.

A compound of the formula $1a^3$ may be obtained by reacting a compound of the formula 13a with a methylenesulfonamide derivative of the formula 15 (for example Chem. Ber., 99, 2900(1966)) in an inert solvent at a reaction temperature of –20° C. to 80° C. and then with an amine of the formula 11. Preferable examples of the solvent are acetonitrile, diethyl ether, tetrahydrofuran, 1,4-dioxane, benzene, toluene, methylene chloride, carbon tetrachloride, etc.

When E is a single bond, the compound of the formula 15 is preferably a compound in which both $L^1$ and $L^2$ are chlorine atoms.

When $R^{13}$, $R^{15}$ or $R^{16}$ is a protecting group for NH group in the compound of the formula $1a^3$, deprotection may be carried out in the same manner as above if desired. It is also possible to remove the group represented by —$SO_2R^{19}$, in the same manner as above if desired.

Process 5

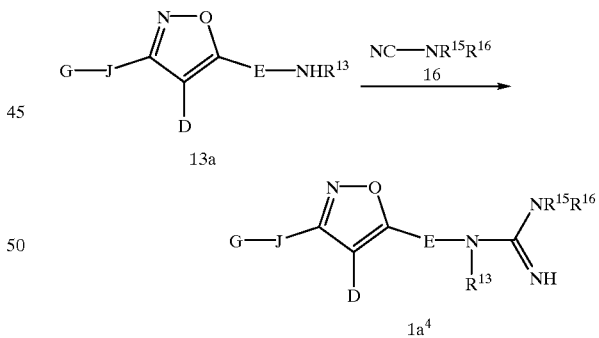

wherein D, E, J, G, $R^{13}$, $R^{15}$ and $R^{16}$ are as defined above.

A compound of the formula $1a^4$ may be obtained by reacting a compound of the formula 13a with a cyanoamido derivative of the formula 16 (for example, commercially available cyanomorphorine) in an inert solvent in the presence of a base at a temperature of 20° C. to 130° C. Examples of the base are sodium hydride, potassium carbonate, sodium amide, lithium amide, etc. Preferable examples of the solvent are N,N-dimethylformamide, tetrahydrofuran, toluene, acetonitrile, tert-buthanol, etc.

When $R^{13}$, $R^{15}$ or $R^{16}$ is a protecting group for NH group in the compound of the formula $1a^4$, deprotection may be carried out in the same manner as above if desired.

The compound represented by the formula 20a which becomes the starting compound in the abovementioned method can also be produced as follows:

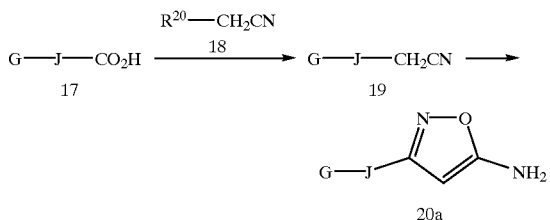

wherein G and J are as defined above; and $R^{20}$ represents —$CO_2R^{21}$ or —$SO_2R^{21}$ in which $R^{21}$ represents a lower alkyl group or an aryl group.

The compound of the formula 19 can be obtained by activating the carboxyl group of the compound of the formula 17, reacting it with the compound of the formula 18 which is, if necessary, treated with a base, in an inert solvent at a reaction temperature of −78 to 30° C. and subsequently removing the group represented by $R^{20}$.

Preferable examples of the inert solvent include tetrahydrofuran, methylene chloride, toluene and the like.

The method of activating the carboxyl group can be carried out by effecting the reaction in the inert solvent, if necessary, in the presence of an additive. As the activating agent, the additive and the reaction conditions, there can be used those which are usually used, and there are mentioned, for example, those stated in "Reactivity and Structure Concepts in Organic Chemistry, Vol. 21; The Practice of Peptide Synthesis" (M. Bodanszky and A. Bodanszky, Springer-Verlag, Berlin (1984), pp. 87–150). Preferable activating agents are, for example, 1,1'-carbonyldiimidazole, isobutyl chloroformate, n-butyl chloroformate and the like. Preferable additives are, for example, triethylamine, 4-(dimethylamino)pyridine, N-methylmorpholine and the like. Preferable solvents are, for example, N,N-dimethylformamide, tetrahydrofuran, methylene chloride, toluene and the like.

Preferable examples of the compound of the formula 18 are isopropyl cyanoacetate, tert-butyl cyanoacetate, methylsulfonylacetonitrile, phenylsulfonylacetonitrile and the like. Preferable examples of the base with which the compound of the formula 18 is, if necessary, treated are 4-(dimethyl-amino)pyridine, lithium diisopropylamide, magnesium ethoxide and the like, and more preferable examples are sodium hydride, lithium amide and the like.

As a method of removing the group represented by $R^{20}$, a conventional method can be used. When $R^{20}$ is —$CO_2R^{21}$, the method can be carried out, for example, by subjecting the compound to acid treatment at a reaction temperature of 0 to 100° C. in the inert solvent. Preferable examples of the acid are hydrochloric acid, sulfuric acid, trifluoroacetic acid and the like. Preferable examples of the inert solvent are tetrahydrofuran, methylene chloride, toluene and the like. When $R^{20}$ is —$SO_2R^{21}$, the method can be carried out according to the known method (for example, K. C. Santhosh et al., J. Chem. Soc., Chem. Commun., 1992, 224; R. Giovannini et al., Synlett, 1995, 973).

The amine of the formula 20a can be produced by reacting the compound of the formula 19 with hydroxylamine according to the known method (for example, Japanese Patent Unexamined Publication No. 63-152,368).

The compound of the formula 20a can be produced directly from the compound of the formula 17 without isolating the compound of the formula 19. That is to say, by allowing the compound of the formula 19 as produced to react with hydroxylamine in a water-soluble solvent having, if necessary, added thereto water or a buffer solution at a reaction temperature of 20 to 100° C., the amine of the formula 20a can be produced directly from the compound of the formula 17. Preferable examples of the water-soluble solvent are ethanol, isopropanol, tert-butanol, N,N-dimethylformamide and the like. Preferable examples of the buffer solution are phosphate buffer solution, acetate buffer solution and the like.

According to the above method, when there is an asymmetric carbon atom in the J position, it is possible to produce the amine of the formula 20a while keeping its optical purity.

As a process for producing an isoxazole derivative of the formula 1 wherein any two of $R^1$, $R^2$, $R^3$ and $R^4$ are taken together with the nitrogen atom(s) to form a heterocyclic ring, there are, for example, a process using a starting material having said ring structure, according to any of the above-mentioned process 1 to 5, and a process of carrying out ring closure of a substituent in the middle or the final step of any of the above-mentioned production processes [for example, condensation reaction of a carboxyl group with a NH group (for instance, J. Gen. Chem. U.S.S.R., 18, 2023 (1948), and ring-closing reaction using the following reagents for reaction]. The reagents for reaction used in the ring-closing reaction include 1,3-dibromopropane (J. Chem. Soc. Chem. Commun., 1992, 507), 1,4-diaminobutane (J. Am. Chem. Soc., 70, 430(1948)), bischloromethyl-methylamine (European Patent No. 428941), paraformaldehyde (European Patent No. 580553), butylamine and formaldehyde (J. Org. Chem., 25, 147(1960)), glyoxal (Tetrahedron Lett., 32, 5325(1991)), acrylic esters (Heterocycles, 20, 1769(1983)), benzylideneacetone (J. Heterocycl. Chem., 21, 65(1984)), epibromohydrin (Can. J. Chem., 53, 894(1975)), etc.

As a process for producing an isoxazole derivative of the formula 1 wherein J represents —$C(=CR^8R^9)$— wherein $R^8$ and $R^9$ are as defined above, there is, for example, a process which comprises treating an isoxazole derivative of the formula 1 wherein J represents —$C(R^{8a}R^{9a})$— wherein $R^{8a}$ represents a lower alkoxyl group and $R^{9a}$ represents a lower alkyl group, with an acid such as trifluoroacetic acid in an inert solvent such as methylene chloride.

As a process for producing an isoxazole derivative of the formula 1 wherein each of $R^8$ and $R^9$ represents a substituted or unsubstituted lower alkyl group, or $R^8$ and $R^9$ are bound to each other and taken together with a carbon atom to form a substituted or unsubstituted 1,3-dioxane or a substituted or unsubstituted 1,3-dioxolane, there is, for example, a process which comprises reacting an ester of 2-ketoalkanoic acid with an alchol, an trialkyl orthformate or its derivative, ethyleneglycol or its derivative, or 1,3-propanediol or its derivative in the presence of an acid (for example, "Protective Groups in Organic Synthesis", 2nd Edition, T. W. Greene and P. G. M. Wuts, John Wiley and Sons, Inc., New York (1991), p. 185–195); converting the reaction product into the compound of the formula 6 according to a known method (for example, Japanese Patent Unexamined Publication No. 63-152308); and further converting the resulted product into the objective compound according to the Process 1 or 2 as stated hereinbefore.

The isoxazole derivative of the formula 1 wherein D represents an alkoxylcarbonyl group may be subjected to hydrolysis followed by decarboxylation to form an isoxazole derivative of the formula 1 wherein D represents a hydrogen atom.

The isoxazole derivative of the formula 1 having at least one asymmetric center in the molecule may be produced by using the corresponding starting compound having the asymmetric center, or introducing the asymmetric center thereinto in the steps for producing the objective compound. For example, when producing the optical isomer of the isoxazole derivative, the isomer may be produced by using the corresponding optically active starting material, or making optical resolution in the steps for producing the objective compound.

When used as a medicine, the isoxazole derivative or pharmaceutically acceptable salt thereof of the present invention may be administered orally or parenterally (for example, intravenously, subcutaneously, intramuscularly, locally, rectally, percutaneously, or through nose). Pharmaceutical forms for the oral administration include, for example, tablets, capsules, pills, granules, powders, solutions, syrups, suspensions, etc. Pharmaceutical forms for the parenteral administration include, for example, aqueous or oily preparations for injection, ointments, creams, lotions, aerosols, suppositories, patches, etc. These preparations are prepared by conventional techniques and may contain conventional acceptable carriers, excipients, binders, stabilizers, etc. When said isoxazole derivative or salt thereof is used in the form of an injection, there may be added a buffer, a solubilizer, a tonicity agent and the like which are acceptable.

Although dose and frequency of administrations of the isoxazole derivative or pharmaceutically acceptable salt thereof of the present invention are varied depending on symptom, age, body weight and administration route, the isoxazole derivative or salt thereof may be administered to an adult usually in a dose of approximately 1–2,000 mg, preferably 10–500 mg, in terms of the compound of the present invention as active ingredient, per day in one portion or several portions.

Specific examples of compounds included in the present invention are the compounds described below. These compounds, however, are for exemplification, and the present invention is not limited to them.

N'-{3-[1-(2-Fluoro-biphenyl-4-yl)-ethyl]-isoxazol-5-ylmethyl}-N,N-dimethyl-guanidine;

N'-{5-[1-(2-Fluoro-biphenyl-4-yl)-ethyl]-isoxazol-3-yl}-N,N-dimethyl-guanidine;

N'-(2-{3-[1-(2-Fluoro-biphenyl-4-yl)-ethyl]-isoxazol-5-yl}-ethyl)-N,N-dimethyl-guanidine;

N'-(3-{3-[1-(2-Fluoro-biphenyl-4-yl)-ethyl]-isoxazol-5-yl}-propyl)-N,N-dimethyl-guanidine;

N'-(2-{5-[1-(2-Fluoro-biphenyl-4-yl)-ethyl]-isoxazol-3-yl}-ethyl)-N,N-dimethyl-guanidine;

N'-(3-{5-[1-(2-Fluoro-biphenyl-4-yl)-ethyl]-isoxazol-3-yl}-propyl)-N,N-dimethyl-guanidine;

N'-{3-[1-(2-Fluoro-biphenyl-4-yl)-ethyl]-4-methyl-isoxazol-5-yl}-N,N-dimethyl-guanidine;

N'-{3-[1-(2-Fluoro-biphenyl-4-yl)-ethyl]-4-methyl-isoxazol-5-ylmethyl}-N,N-dimethyl-guanidine;

N'-{5-[1-(2-Fluoro-biphenyl-4-yl)-ethyl]-4-methyl-isoxazol-3-yl}-N,N-dimethyl-guanidine;

N'-{-[1-(2-Fluoro-biphenyl-4-yl)-ethyl]-4-methyl-isoxazol-3-ylmethyl}-N,N-dimethyl-guanidine;

5-(N',N'-Dimethyl-guanidino)-3-[1-(2-fluoro-biphenyl-4-yl)-ethyl]-isoxazole-4-carboxylic acid;

5-(N',N'-Dimethyl-guanidinomethyl)-3-[1-(2-fluoro-biphenyl-4-yl)-ethyl]-isoxazole-4-carboxylic acid;

3-(N',N'-Dimethyl-guanidino)-5-[1-(2-fluoro-biphenyl-4-yl)-ethyl]-isoxazole-4-carboxylic acid;

3-(N',N'-Dimethyl-guanidinomethyl)-5-[1-(2-fluoro-biphenyl-4-yl)-ethyl]-isoxazole-4-carboxylic acid;

{5-(N',N'-Dimethyl-guanidino)-3-[1-(2-fluoro-biphenyl-4-yl)-ethyl]-isoxazol-4-yl}-acetic acid;

{5-(N',N'-Dimethyl-guanidinomethyl)-3-[1-(2-fluoro-biphenyl-4-yl)-ethyl]-isoxazol-4-yl}-acetic acid;

{3-(N',N'-Dimethyl-guanidino)-5-[1-(2-fluoro-biphenyl-4-yl)-ethyl]-isoxazol-4-yl}-acetic acid;

{3-(N',N'-Dimethyl-guanidinomethyl)-5-[1-(2-fluoro-biphenyl-4-yl)-ethyl]-isoxazol-4-yl}-acetic acid;

N'-{3-[1-(2-Fluoro-biphenyl-4-yl)-ethyl]-4-hydroxymethyl-isoxazol-5-yl}-N,N-dimethyl-guanidine;

N'-{3-[1-(2-Fluoro-biphenyl-4-yl)-ethyl]-4-hydroxymethyl-isoxazol-5-ylmethyl}-N,N-dimethyl-guanidine;

N'-{5-[1-(2-Fluoro-biphenyl-4-yl)-ethyl]-4-hydroxymethyl-isoxazol-3-yl}-N,N-dimethyl-guanidine;

N'-{5-[1-(2-Fluoro-biphenyl-4-yl)-ethyl]-4-hydroxymethyl-isoxazol-3-ylmethyl}-N,N-dimethyl-guanidine;

N'-{3-[1-(2-Fluoro-biphenyl-4-yl)-1-methyl-ethyl]-isoxazol-5-yl}-N,N-dimethyl-guanidine;

N'-{3-[1-(2-Fluoro-biphenyl-4-yl)-1-methyl-ethyl]-isoxazol-5-ylmethyl}-N,N-dimethyl-guanidine;

N'-{5-[1-(2-Fluoro-biphenyl-4-yl)-1-methyl-ethyl]-isoxazol-3-yl}-N,N-dimethyl-guanidine;

N'-{5-[1-(2-Fluoro-biphenyl-4-yl)-1-methyl-ethyl]-isoxazol-3-ylmethyl}-N,N-dimethyl-guanidine;

N'-[3-(2-Fluoro-biphenyl-4-ylmethyl)-isoxazol-5-yl]-N,N-dimethyl-guanidine;

N'-[3-(2-Fluoro-biphenyl-4-ylmethyl)-isoxazol-5-ylmethyl]-N,N-dimethyl-guanidine;

N'-[5-(2-Fluoro-biphenyl-4-ylmethyl)-isoxazol-3-yl]-N,N-dimethyl-guanidine;

N'-[5-(2-Fluoro-biphenyl-4-ylmethyl)-isoxazol-3-ylmethyl]-N,N-dimethyl-guanidine;

N'-{3-[1-(2-Fluoro-biphenyl-4-yl)-cyclopropyl]-isoxazol-5-yl}-N,N-dimethyl-guanidine;

N'-{3-[1-(2-Fluoro-biphenyl-4-yl)-cyclopropyl]-isoxazol-5-ylmethyl}-N,N-dimethyl-guanidine;

N'-{5-[1-(2-Fluoro-biphenyl-4-yl)-cyclopropyl]-isoxazol-3-yl}-N,N-dimethyl-guanidine;

N'-{5-[1-(2-Fluoro-biphenyl-4-yl)-cyclopropyl]-isoxazol-3-ylmethyl}-N,N-dimethyl-guanidine;

N'-{3-[1-(2-Fluoro-biphenyl-4-yl)-vinyl]-isoxazol-5-yl}-N,N-dimethyl-guanidine;

N'-{3-[1-(2-Fluoro-biphenyl-4-yl)-vinyl]-isoxazol-5-ylmethyl}-N,N-dimethyl-guanidine;

N'-{5-[1-(2-Fluoro-biphenyl-4-yl)-vinyl]-isoxazol-3-yl}-N,N-dimethyl-guanidine;

N'-{5-[1-(2-Fluoro-biphenyl-4-yl)-vinyl]-isoxazol-3-ylmethyl}-N,N-dimethyl-guanidine;

N'-{3-[1-(2-Fluoro-biphenyl-4-yl)-2-methyl-propenyl]-isoxazol-5-yl}-N,N-dimethyl-guanidine;

N'-{3-[1-(2-Fluoro-biphenyl-4-yl)-2-methyl-propenyl]-isoxazol-5-ylmethyl}-N,N-dimethyl-guanidine;

N'-{5-[1-(2-Fluoro-biphenyl-4-yl)-2-methyl-propenyl]-isoxazol-3-yl}-N,N-dimethyl-guanidine;

N'-{5-[1-(2-Fluoro-biphenyl-4-yl)-2-methyl-propenyl]-isoxazol-3-ylmethyl}-N,N-dimethyl-guanidine;

N'-{3-[1-(3-Benzoyl-phenyl)-ethyl]-isoxazol-5-yl}-N,N-dimethyl-guanidine;

N'-{3-[1-(3-Benzoyl-phenyl)-ethyl]-isoxazol-5-ylmethyl}-N,N-dimethyl-guanidine;

N'-{5-[1-(3-Benzoyl-phenyl)-ethyl]-isoxazol-3-yl}-N,N-dimethyl-guanidine;

N'-{5-[1-(3-Benzoyl-phenyl)-ethyl]-isoxazol-3-ylmethyl}-N,N-dimethyl-guanidine;

N'-{3-[1-(4-Isobutyl-phenyl)-ethyl]-isoxazol-5-yl}-N,N-dimethyl-guanidine;

N'-{3-[1-(4-Isobutyl-phenyl)-ethyl]-isoxazol-5-ylmethyl}-N,N-dimethyl-guanidine;
N'-{5-[1-(4-Isobutyl-phenyl)-ethyl]-isoxazol-3-yl}-N,N-dimethyl-guanidine;
N'-{5-[1-(4-Isobutyl-phenyl)-ethyl]-isoxazol-3-ylmethyl}-N,N-dimethyl-guanidine;
N'-{3-[1-(6-Methoxy-naphthalen-2-yl)-ethyl]-isoxazol-5-yl}-N,N-dimethyl-guaniline;
N'-{3-[1-(6-Methoxy-naphthalen-2-yl)-ethyl]-isoxazol-5-ylmethyl}-N,N-dimethyl-guanidine;
N'-{5-[1-(6-Methoxy-naphthalen-2-yl)-ethyl]-isoxazol-3-yl}-N,N-dimethyl-guanidine;
N'-{5-[1-(6-Methoxy-naphthalen-2-yl)-ethyl]-isoxazol-3-ylmethyl}-N,N-dimethyl-guanidine;
({3-[1-(2-Fluoro-biphenyl-4-yl)-ethyl]-isoxazol-5-ylmethylimino}-piperidin-1-yl-methyl)-amine;
({5-[1-(2-Fluoro-biphenyl-4-yl)-ethyl]-isoxazol-3-ylimino}-piperidin-1-yl-methyl)-amine;
[(2-{3-[1-(2-Fluoro-biphenyl-4-yl)-ethyl]-isoxazol-5-yl}-ethylimino)-piperidin-1-yl-methyl]-amine;
[(3-{3-[1-(2-Fluoro-biphenyl-4-yl)-ethyl]-isoxazol-5-yl}-propylimino)-piperidin-1-yl-methyl]-amine;
[(2-{5-[1-(2-Fluoro-biphenyl-4-yl)-ethyl]-isoxazol-3-yl}-ethylimino)-piperidin-1-yl-methyl]-amine;
[(3-{5-[1-(2-Fluoro-biphenyl-4-yl)-ethyl]-isoxazol-3-yl}-propylimino)-piperidin-1-yl-methyl]-amine;
({3-[1-(2-Fluoro-biphenyl-4-yl)-ethyl]-4-methyl-isoxazol-5-ylimino}-piperidin-1-yl-methyl)-amine;
({3-[1-(2-Fluoro-biphenyl-4-yl)-ethyl]-4-methyl-isoxazol-5-ylmethylimino}-piperidin-1-yl-methyl)-amine;
({5-[1-(2-Fluoro-biphenyl-4-yl)-ethyl]-4-methyl-isoxazol-3-ylimino}-piperidin-1-yl-methyl)-amine;
({5-[1-(2-Fluoro-biphenyl-4-yl)-ethyl]-4-methyl-isoxazol-3-ylmethylimino}-piperidin-1-yl-methyl)-amine;
5-(Amino-piperidin-1-yl-methyleneamino)-3-[1-(2-fluoro-biphenyl-4-yl)-ethyl]-isoxazole-4-carboxylic acid;
5-(Amino-piperidin-1-yl-methyleneamino-methyl)-3-[1-(2-fluoro-biphenyl-4-yl)-ethyl]-isoxazole-4-carboxylic acid;
3-(Amino-piperidin-1-yl-methyleneamino)-5-[1-(2-fluoro-biphenyl-4-yl)-ethyl]-isoxazole-4-carboxylic acid;
3-(Amino-piperidin-1-yl-methyleneamino-methyl)-5-[1-(2-fluoro-biphenyl-4-yl)-ethyl]-isoxazole-4-carboxylic acid;
{5-(Amino-piperidin-1-yl-methyleneamino)-3-[1-(2-fluoro-biphenyl-4-yl)-ethyl]-isoxazol-4-yl}-acetic acid;
{5-(Amino-piperidin-1-yl-methyleneamino-methyl)-3-[1-(2-fluoro-biphenyl-4-yl)-ethyl]-isoxazol-4-yl}-acetic acid;
{3-(Amino-piperidin-1-yl-methyleneamino)-5-[1-(2-fluoro-biphenyl-4-yl)-ethyl]-isoxazol-4-yl}-acetic acid;
{3-(Amino-piperidin-1-yl-methyleneamino-methyl)-5-[1-(2-fluoro-biphenyl-4-yl)-ethyl]-isoxazol-4-yl}-acetic acid;
{5-(Amino-piperidin-1-yl-methyleneamino)-3-[1-(2-fluoro-biphenyl-4-yl)-ethyl]-isoxazol-4-yl}-methanol;
{5-(Amino-piperidin-1-yl-methyleneamino-methyl)-3-[1-(2-fluoro-biphenyl-4-yl)-ethyl]-isoxazol-4-yl}-methanol;
{3-(Amino-piperidin-1-yl-methyleneamino)-5-[1-(2-fluoro-biphenyl-4-yl)-ethyl]-isoxazol-4-yl}-methanol;
{3-(Amino-piperidin-1-yl-methyleneamino-methyl)-5-[1-(2-fluoro-biphenyl-4-yl)-ethyl]-isoxazol-4yl}-methanol;
({3-[1-(2-Fluoro-biphenyl-4-yl)-1-methyl-ethyl]-isoxazol-5-ylimino}-piperidin-1-yl-methyl)-amine;
({3-[1-(2-Fluoro-biphenyl-4-yl)-1-methyl-ethyl]-isoxazol-5-ylmethylimino}-piperidin-1-yl-methyl)-amine;
({5-[1-(2-Fluoro-biphenyl-4-yl)-1-methyl-ethyl]-isoxazol-3-ylimino}-piperidin-1-yl-methyl)-amine;
({5-[1-(2-Fluoro-biphenyl-4-yl)-1-methyl-ethyl]-isoxazol-3-ylmethylimino}-piperidin-1-yl-methyl)-amine;
{[3-(2-Fluoro-biphenyl-4-ylmethyl)-isoxazol-5-ylimino]-piperidin-1-yl-methyl}-amine;
{[3-(2-Fluoro-biphenyl-4-ylmethyl)-isoxazol-5-ylmethylimino]-piperidin-1-yl-methyl}-amine;
{[5-(2-Fluoro-biphenyl-4-ylmethyl)-isoxazol-3-ylimino]-piperidin-1-yl-methyl}-amine;
{[5-(2-Fluoro-biphenyl-4-ylmethyl)-isoxazol-3-ylmethylimino]-piperidin-1-yl-methyl}-amine;
({3-[1-(2-Fluoro-biphenyl-4-yl)-cyclopropyl]-isoxazol-5-ylimino}-piperidin-1-yl-methyl)-amine;
({3-[1-(2-Fluoro-biphenyl-4-yl)-cyclopropyl]-isoxazol-5-ylmethylimino}-piperidin-1-yl-methyl)-amine;
({5-[1-(2-Fluoro-biphenyl-4-yl)-cyclopropyl]-isoxazol-3-ylimino}-piperidin-1-yl-methyl)-amine;
({5-[1-(2-Fluoro-biphenyl-4-yl)-cyclopropyl]-isoxazol-3-ylmethylimino}-piperidin-1-yl-methyl)-amine;
({3-[1-(2-Fluoro-biphenyl-4-yl)-vinyl]-isoxazol-5-ylimino}-piperidin-1-yl-methyl)-amine;
({3-[1-(2-Fluoro-biphenyl-4-yl)-vinyl]-isoxazol-5-ylmethylimino}-piperidin-1-yl-methyl)-amine;
({5-[1-(2-Fluoro-biphenyl-4-yl)-vinyl]-isoxazol-3-ylimino}-piperidin-1-yl-methyl)-amine;
({5-[1-(2-Fluoro-biphenyl-4-yl)-vinyl]-isoxazol-3-ylmethylimino}-piperidin-1-yl-methyl)-amine;
({3-[1-(2-Fluoro-biphenyl-4-yl)-2-methyl-propenyl]-isoxazol-5-ylimino}-piperidin-1-yl-methyl)-amine;
({3-[1-(2-Fluoro-biphenyl-4-yl)-2-methyl-propenyl]-isoxazol-5-ylmethylimino}-piperidin-1-yl-methyl)-amine;
({5-[1-(2-Fluoro-biphenyl-4-yl)-2-methyl-propenyl]-isoxazol-3-ylimino}-piperidin-1-yl-methyl)-amine;
({5-[1-(2-Fluoro-biphenyl-4-yl)-2-methyl-propenyl]-isoxazol-3-ylmethylimino}-piperidin-1-yl-methyl)-amine;
(3-{1-[5-(Amino-piperidin-1-yl-methyleneamino)-isoxazol-3-yl]-ethyl}-phenyl)-phenyl-methanone;
(3-{1-[5-(Amino-piperidin-1-yl-methyleneamino-methyl)-isoxazol-3-yl]-ethyl}-phenyl)-phenyl-methanone;
(3-{1-[3-(Amino-piperidin-1-yl-methyleneamino)-isoxazol-5-yl]-ethyl}-phenyl)-phenyl-methanone;
(3-{1-[3-(Amino-piperidin-1-yl-methyleneamino-methyl)-isoxazol-5-yl]-ethyl}-phenyl)-phenyl-methanone;
({3-[1-(4-Isobutyl-phenyl)-ethyl]-isoxazol-5-ylimino}-piperidin-1-yl-methyl)-amine;
({3-[1-(4-Isobutyl-phenyl)-ethyl]-isoxazol-5-ylmethylimino}-piperidin-1-yl-methyl)-amine;
({5-[1-(4-Isobutyl-phenyl)-ethyl]-isoxazol-3-ylimino}-piperidin-1-yl-methyl)-amine;
({5-[1-(4-Isobutyl-phenyl)-ethyl]-isoxazol-3-ylmethylimino}-piperidin-1-yl-methyl)-amine;
({3-[1-(6-Methoxy-naphthalen-2-yl)-ethyl]-isoxazol-5-ylimino}-piperidin-1-yl-methyl)-amine;
({3-[1-(6-Methoxy-naphthalen-2-yl)-ethyl]-isoxazol-5-ylmethylimino}-piperidin-1-yl-methyl)-amine;
({5-[1-(6-Methoxy-naphthalen-2-yl)-ethyl]-isoxazol-3-ylimino}-piperidin-1-yl-methyl)-amine;
({5-[1-(6-Methoxy-naphthalen-2-yl)-ethyl]-isoxazol-3-ylmethylimino}-piperidin-1-yl-methyl)-amine;
({3-[1-(2-Fluoro-biphenyl-4-yl)-ethyl]-isoxazol-5-ylmethylimino}-morpholin-4-yl-methyl)-amine;
({5-[1-(2-Fluoro-biphenyl-4-yl)-ethyl]-isoxazol-3-ylimino}-morpholin-4-yl-methyl)-amine;
[(2-{3-[1-(2-Fluoro-biphenyl-4-yl)-ethyl]-isoxazol-5-yl}-ethylimino)-morpholin-4-yl-methyl]-amine;
[(3-{3-[1-(2-Fluoro-biphenyl-4-yl)-ethyl]-isoxazol-5-yl}-propylimino)-morpholin-4-yl-methyl]-amine;
[(2-{5-[1-(2-Fluoro-biphenyl-4-yl)-ethyl]-isoxazol-3-yl}-ethylimino)-morpholin-4-yl-methyl]-amine;

[(3-{5-[1-(2-Fluoro-biphenyl-4-yl)-ethyl]-isoxazol-3-yl}-propylimino)-morpholin-4-yl-methyl]-amine;

({3-[1-(2-Fluoro-biphenyl-4-yl)-ethyl]-4-methyl-isoxazol-5-ylimino}-morpholin-4-yl-methyl)-amine;

({3-[1-(2-Fluoro-biphenyl-4-yl)-ethyl]-4-methyl-isoxazol-5-ylmethylimino}-morpholin-4-yl-methyl)-amine;

({5-[1-(2-Fluoro-biphenyl-4-yl)-ethyl]-4-methyl-isoxazol-3-ylimino}-morpholin-4-yl-methyl)-amine;

({5-[1-(2-Fluoro-biphenyl-4-yl)-ethyl]-4-methyl-isoxazol-3-ylmethylimino}-morpholin-4-yl-methyl)-amine;

5-(Amino-morpholin-4-yl-methyleneamino)-3-[1-(2-fluoro-biphenyl-4-yl)-ethyl]-isoxazole-4-carboxylic acid;

5-(Amino-morpholin-4-yl-methyleneamino-methyl)-3-[1-(2-fluoro-biphenyl-4-yl)-ethyl]-isoxazole-4-carboxylic acid;

3-(Amino-morpholin-4-yl-methyleneamino)-5-[1-(2-fluoro-biphenyl-4-yl)-ethyl]-isoxazole-4-carboxylic acid;

3-(Amino-morpholin-4-yl-methyleneamino-methyl)-5-[1-(2-fluoro-biphenyl-4-yl)-ethyl]-isoxazole-4-carboxylic acid;

{5-(Amino-morpholin-4-yl-methyleneamino)-3-[1-(2-fluoro-biphenyl-4-yl)-ethyl]-isoxazol-4-yl}-acetic acid;

{5-(Amino-morpholin-4-yl-methyleneamino-methyl)-3-[1-(2-fluoro-biphenyl- 4-yl)-ethyl]-isoxazol-4-yl}-acetic acid;

{3-(Amino-morpholin-4-yl-methyleneamino)-5-[1-(2-fluoro-biphenyl-4-yl)-ethyl]-isoxazol-4-yl}-acetic acid;

{3-(Amino-morpholin-4-yl-methyleneamino-methyl)-5-[1-(2-fluoro-biphenyl-4-yl)-ethyl]-isoxazol-4-yl}-acetic acid;

{5-(Amino-morpholin-4-yl-methyleneamino)-3-[1-(2-fluoro-biphenyl-4-yl)-ethyl]-isoxazol-4-yl}-methanol;

{5-(Amino-morpholin-4-yl-methyleneamino-methyl)-3-[1-(2-fluoro-biphenyl-4-yl)-ethyl]-isoxazol-4-yl}-methanol;

{3-(Amino-morpholin-4-yl-methyleneamino)-5-[1-(2-fluoro-biphenyl-4-yl)-ethyl]-isoxazol-4-yl}-methanol;

{3-(Amino-morpholin-4-yl-methyleneamino-methyl)-5-[1-(2-fluoro-biphenyl-4-yl)-ethyl]-isoxazol-4-yl}-methanol;

({3-[1-(2-Fluoro-biphenyl-4-yl)-1-methyl-ethyl]-isoxazol-5-ylmethylimino}-morpholin-4-yl-methyl)-amine;

({5-[1-(2-Fluoro-biphenyl-4-yl)-1-methyl-ethyl]-isoxazol-3-ylimino}-morpholin-4-yl-methyl)-amine;

({5-[1-(2-Fluoro-biphenyl-4-yl)-1-methyl-ethyl]-isoxazol-3-ylmethylimino}-morpholin-4-yl-methyl)-amine;

{[3-(2-Fluoro-biphenyl-4-ylmethyl)-isoxazol-5-ylmethylimino]-morpholin-4-yl-methyl}-amine;

{[5-(2-Fluoro-biphenyl-4-ylmethyl)-isoxazol-3-ylimino]-morpholin-4-yl-methyl}-amine;

{[5-(2-Fluoro-biphenyl-4-ylmethyl)-isoxazol-3-ylmethylimino]-morpholin-4-yl-methyl}-amine;

({3-[1-(2-Fluoro-biphenyl-4-yl)-cyclopropyl]-isoxazol-5-ylmethylimino}-morpholin-4-yl-methyl)-amine;

({5-[1-(2-Fluoro-biphenyl-4-yl)-cyclopropyl]-isoxazol-3-ylimino}-morpholin-4-yl-methyl)-amine;

({5-[1-(2-Fluoro-biphenyl-4-yl)-cyclopropyl]-isoxazol-3-ylmethylimino}-morpholin-4-yl-methyl)-amine;

({3-[1-(2-Fluoro-biphenyl-4-yl)-vinyl]-isoxazol-5-ylimino}-morpholin-4-yl-methyl)-amine;

({3-[1-(2-Fluoro-biphenyl-4-yl)-vinyl]-isoxazol-5-ylmethylimino}-morpholin-4-yl-methyl)-amine;

({5-[1-(2-Fluoro-biphenyl-4-yl)-vinyl]-isoxazol-3-ylimino}-morpholin-4-yl-methyl)-amine;

({5-[1-(2-Fluoro-biphenyl-4-yl)-vinyl]-isoxazol-3-ylmethylimino}-morpholin-4-yl-methyl)-amine;

({3-[1-(2-Fluoro-biphenyl-4-yl)-2-methyl-propenyl]-isoxazol-5-ylimino}-morpholin-4-yl-methyl)-amine;

({3-[1-(2-Fluoro-biphenyl-4-yl)-2-methyl-propenyl]-isoxazol-5-ylmethylimino}-morpholin-4-yl-methyl)-amine;

({5-[1-(2-Fluoro-biphenyl-4-yl)-2-methyl-propenyl]-isoxazol-3-ylimino}-morpholin-4-yl-methyl)-amine;

({5-[1-(2-Fluoro-biphenyl-4-yl)-2-methyl-propenyl]-isoxazol- 3-ylmethylimino}-morpholin-4-yl-methyl)-amine;

(3-{1-[5-(Amino-morpholin-4-yl-methyleneamino-methyl)-isoxazol-3-yl]-ethyl}-phenyl)-phenyl-methanone;

(3-{1-[3-(Amino-morpholin-4-yl-methyleneamino)-isoxazol-5-yl]-ethyl}-phenyl)-phenyl-methanone;

(3-{1-[3-(Amino-morpholin-4-yl-methyleneamino-methyl)-isoxazol-5-yl]-ethyl}-phenyl)-phenyl-methanone;

({3-[1-(4-Isobutyl-phenyl)-ethyl]-isoxazol-5-ylmethylimino}-morpholin-4-yl-methyl)-amine;

({5-[1-(4-Isobutyl-phenyl)-ethyl]-isoxazol-3-ylimino}-morpholin-4-yl-methyl)-amine;

({5-[1-(4-Isobutyl-phenyl)-ethyl]-isoxazol-3-ylmethylimino}-morpholin-4-yl-methyl)-amine;

({3-[1-(6-Methoxy-naphthalen-2-yl)-ethyl]-isoxazol-5-ylmethylimino}-morpholin-4-yl-methyl)-amine;

({5-[1-(6-Methoxy-naphthalen-2-yl)-ethyl]-isoxazol-3-ylimino}-morpholin-4-yl-methyl)-amine;

({5-[1-(6-Methoxy-naphthalen-2-yl)-ethyl]-isoxazol-3-ylmethylimino}-morpholin-4-yl-methyl)-amine;

N-{3-[1-(2-Fluoro-biphenyl-4-yl)-ethyl]-isoxazol-5-ylmethyl}-guanidine;

N-{5-[1-(2-Fluoro-biphenyl-4-yl)-ethyl]-isoxazol-3-yl}-guanidine;

N-{3-[1-(2-Fluoro-biphenyl-4-yl)-ethyl]-isoxazol-5-ylmethyl}-N'-methyl-guanidine;

N-{5-[1-(2-Fluoro-biphenyl-4-yl)-ethyl]-isoxazol-3-yl}-N'-methyl-guanidine;

N-Ethyl-N'-{3-[1-(2-fluoro-biphenyl-4-yl)-ethyl]-isoxazol-5-ylmethyl}-guanidine;

N-Ethyl-N'-{5-[1-(2-fluoro-biphenyl-4-yl)-ethyl]-isoxazol-3-yl}-guanidine;

N-Ethyl-N'-{5-[1-(2-fluoro-biphenyl-4-yl)-ethyl]-isoxazol-3-ylmethyl}-guanidine;

N-{3-[1-(2-Fluoro-biphenyl-4-yl)-ethyl]-isoxazol-5-ylmethyl}-N'-phenyl-guanidine;

N-{5-[1-(2-Fluoro-biphenyl-4-yl)-ethyl]-isoxazol-3-yl}-N'-phenyl-guanidine;

N-{5-[1-(2-Fluoro-biphenyl-4-yl)-ethyl]-isoxazol-3-ylmethyl}-N'-phenyl-guanidine;

N-{3-[1-(2-Fluoro-biphenyl-4-yl)-ethyl]-isoxazol-5-yl}-N'-p-toluyl-guanidine;

N-{3-[1-(2-Fluoro-biphenyl-4-yl)-ethyl]-isoxazol-5-ylmethyl}-N'-p-toluyl-guanidine;

N-{5-[1-(2-Fluoro-biphenyl-4-yl)-ethyl]-isoxazol-3-yl}-N'-p-toluyl-guanidine;

N-{5-[1-(2-Fluoro-biphenyl-4-yl)-ethyl]-isoxazol-3-ylmethyl}-N'-p-toluyl-guanidine;

N-{3-[1-(2-Fluoro-biphenyl-4-yl)-ethyl]-isoxazol-5-yl}-N'-(4-methoxy-phenyl)-guanidine;

N-{3-[1-(2-Fluoro-biphenyl-4-yl)-ethyl]-isoxazol-5-ylmethyl}-N'-(4-methoxy-phenyl)-guanidine;

N-{5-[1-(2-Fluoro-biphenyl-4-yl)-ethyl]-isoxazol-3-yl}-N'-(4-methoxy-phenyl)-guanidine;

N-{5-[1-(2-Fluoro-biphenyl-4-yl)-ethyl]-isoxazol-3-ylmethyl}-N'-(4-methoxy-phenyl)-guanidine;

N-Benzyl-N'-{3-[1-(2-fluoro-biphenyl-4-yl)-ethyl]-isoxazol-5-yl}-guanidine;

N-Benzyl-N'-{3-[1-(2-fluoro-biphenyl-4-yl)-ethyl]-isoxazol-5-ylmethyl}-guanidine;

N-Benzyl-N'-{5-[1-(2-fluoro-biphenyl-4-yl)-ethyl]-isoxazol-3-yl}-guanidine;

N-Benzyl-N'-{5-[1-(2-fluoro-biphenyl-4-yl)-ethyl]-isoxazol-3-ylmethyl}-guanidine;

N-{3-[1-(2-Fluoro-biphenyl-4-yl)-ethyl]-isoxazol-5-yl}-N'-phenethyl-guanidine;
N-{3-[1-(2-Fluoro-biphenyl-4-yl)-ethyl]-isoxazol-5-ylmethyl}-N'-phenethyl-guanidine;
N-{5-[1-(2-Fluoro-biphenyl-4-yl)-ethyl]-isoxazol-3-yl}-N'-phenethyl-guanidine;
N-{5-[1-(2-Fluoro-biphenyl-4-yl)-ethyl]-isoxazol-3-ylmethyl}-N'-phenethyl-guanidine;
N-(2-Amino-ethyl)-N'-{3-[1-(2-fluoro-biphenyl-4-yl)-ethyl]-isoxazol-5-yl}-guanidine;
N-(2-Amino-ethyl)-N'-{3-[1-(2-fluoro-biphenyl-4-yl)-ethyl]-isoxazol-5-ylmethyl}-guanidine;
N-(2-Amino-ethyl)-N'-{5-[1-(2-fluoro-biphenyl-4-yl)-ethyl]-isoxazol-3-yl}-guanidine;
N-(2-Amino-ethyl)-N'-{5-[1-(2-fluoro-biphenyl-4-yl)-ethyl]-isoxazol-3-ylmethyl}-guanidine;
[{3-[1-(2-Fluoro-biphenyl-4-yl)-ethyl]-isoxazol-5-ylimino}-(4-methyl-piperidin-1-yl)-methyl]-amine;
[{3-[1-(2-Fluoro-biphenyl-4-yl)-ethyl]-isoxazol-5-ylmethylimino}-(4-methyl-piperidin-1-yl)-methyl]-amine;
[{5-[1-(2-Fluoro-biphenyl-4-yl)-ethyl]-isoxazol-3-ylimino}-(4-methyl-piperidin-1-yl)-methyl]-amine;
[{5-[1-(2-Fluoro-biphenyl-4-yl)-ethyl]-isoxazol-3-ylmethylimino}-(4-methyl-piperidin-1-yl)-methyl]-amine;
((2,6-Dimethyl-piperidin-1-yl)-{3-[1-(2-fluoro-biphenyl-4-yl)-ethyl]-isoxazol-5-ylimino}-methyl)-amine;
((2,6-Dimethyl-piperidin-1-yl)-{3-[1-(2-fluoro-biphenyl-4-yl)-ethyl]-isoxazol-5-ylmethylimino}-methyl)-amine;
((2,6-Dimethyl-piperidin-1-yl)-{5-[1-(2-fluoro-biphenyl-4-yl)-ethyl]-isoxazol-3-ylimino}-methyl)-amine;
((2,6-Dimethyl-piperidin-1-yl)-{5-[1-(2-fluoro-biphenyl-4-yl)-ethyl]-isoxazol-3-ylmethylimino}-methyl)-amine;
1-(Amino-{3-[1-(2-fluoro-biphenyl-4-yl)-ethyl]-isoxazol-5-ylmethylimino}-methyl)-piperidin-4-ol;
1-(Amino-{5-[1-(2-fluoro-biphenyl-4-yl)-ethyl]-isoxazol-3-ylimino}-methyl)-piperidin-4-ol;
1-(Amino-{5-[1-(2-fluoro-biphenyl-4-yl)-ethyl]-isoxazol-3-ylmethylimino}-methyl)-piperidin-4-ol;
[{3-[1-(2-Fluoro-biphenyl-4-yl)-ethyl]-isoxazol-5-ylimino}-(4-methoxy-piperidin-1-yl)-methyl]-amine;
[{3-[1-(2-Fluoro-biphenyl-4-yl)-ethyl]-isoxazol-5-ylmethylimino}-(4-methoxy-piperidin-1-yl)-methyl]-amine;
[{5-[1-(2-Fluoro-biphenyl-4-yl)-ethyl]-isoxazol-3-ylimino}-(4-methoxy-piperidin-1-yl)-methyl]-amine;
[{5-[1-(2-Fluoro-biphenyl-4-yl)-ethyl]-isoxazol-3-ylmethylimino}-(4-methoxy-piperidin-1-yl)-methyl]-amine;
((4-Amino-piperidin-1-yl)-{3-[1-(2-fluoro-biphenyl-4-yl)-ethyl]-isoxazol-5-ylimino}-methyl)-amine;
((4-Amino-piperidin-1-yl)-{3-[1-(2-fluoro-biphenyl-4-yl)-ethyl]-isoxazol-5-ylmethylimino}-methyl)-amine;
((4-Amino-piperidin-1-yl)-{5-[1-(2-fluoro-biphenyl-4-yl)-ethyl]-isoxazol-3-ylimino}-methyl)-amine;
((4-Amino-piperidin-1-yl)-{5-[1-(2-fluoro-biphenyl-4-yl)-ethyl]-isoxazol-3-ylmethylimino}-methyl)-amine;
((4-Dimethylamino-piperidin-1-yl)-{3-[1-(2-fluoro-biphenyl-4-yl)-ethyl]-isoxazol-5-ylimino}-methyl)-amine;
((4-Dimethylamino-piperidin-1-yl)-{3-[1-(2-fluoro-biphenyl-4-yl)-ethyl]-isoxazol-5-ylmethylimino}-methyl)-amine;
((4-Dimethylamino-piperidin-1-yl)-{5-[1-(2-fluoro-biphenyl-4-yl)-ethyl]-isoxazol-3-ylimino}-methyl)-amine;
ethyl)-amine;
((4-Dimethylamino-piperidin-1-yl)-{5-[1-(2-fluoro-biphenyl-4-yl)-ethyl]-isoxazol-3-ylmethylimino}-methyl)-amine;
1-(Amino-{3-[1-(2-fluoro-biphenyl-4-yl)-ethyl]-isoxazol-5-ylimino}-methyl)-piperidine-4-carboxylic acid;
1-(Amino-{3-[1-(2-fluoro-biphenyl-4-yl)-ethyl]-isoxazol-5-ylmethylimino}-methyl)-piperidine-4-carboxylic acid;
1-(Amino-{5-[1-(2-fluoro-biphenyl-4-yl)-ethyl]-isoxazol-3-ylimino}-methyl)-piperidine-4-carboxylic acid;
1-(Amino-{5-[1-(2-fluoro-biphenyl-4-yl)-ethyl]-isoxazol-3-ylmethylimino}-methyl)-piperidine-4-carboxylic acid;
1-(Amino-{3-[1-(2-fluoro-biphenyl-4-yl)-ethyl]-isoxazol-5-ylimino}-methyl)-piperidine-4-carboxamide;
1-(Amino-{3-[1-(2-fluoro-biphenyl-4-yl)-ethyl]-isoxazol-5-ylmethylimino}-methyl)-piperidine-4-carboxamide;
1-(Amino-{5-[1-(2-fluoro-biphenyl-4-yl)-ethyl]-isoxazol-3-ylimino}-methyl)-piperidine-4-carboxamide;
1-(Amino-{5-[1-(2-fluoro-biphenyl-4-yl)-ethyl]-isoxazol-3-ylmethylimino}-methyl)-piperidine-4-carboxamide;
1-(Amino-{3-[1-(2-fluoro-biphenyl-4-yl)-ethyl]-isoxazol-5-ylimino}-methyl)-piperidine-3-carboxylic acid;
1-(Amino-{3-[1-(2-fluoro-biphenyl-4-yl)-ethyl]-isoxazol-5-ylmethylimino}-methyl)-piperidine-3-carboxylic acid;
1-(Amino-{5-[1-(2-fluoro-biphenyl-4-yl)-ethyl]-isoxazol-3-ylimino}-methyl)-piperidine-3-carboxylic acid;
1-(Amino-{5-[1-(2-fluoro-biphenyl-4-yl)-ethyl]-isoxazol-3-ylmethylimino}-methyl)-piperidine-3-carboxylic acid;
1-(Amino-{3-[1-(2-fluoro-biphenyl-4-yl)-ethyl]-isoxazol-5-ylimino}-methyl)-piperidine-3-carboxamide;
1-(Amino-{3-[1-(2-fluoro-biphenyl-4-yl)-ethyl]-isoxazol-5-ylmethylimino}-methyl)-piperidine-3-carboxamide;
1-(Amino-{5-[1-(2-fluoro-biphenyl-4-yl)-ethyl]-isoxazol-3-ylimino}-methyl)-piperidine-3-carboxamide;
1-(Amino-{5-[1-(2-fluoro-biphenyl-4-yl)-ethyl]-isoxazol-3-ylmethylimino}-methyl)-piperidine-3-carboxamide;
1-(Amino-{3-[1-(2-fluoro-biphenyl-4-yl)-ethyl]-isoxazol-5-ylmethylimino}-methyl)-piperidin-4-one;
1-(Amino-{5-[1-(2-fluoro-biphenyl-4-yl)-ethyl]-isoxazol-3-ylimino}-methyl)-piperidin-4-one;
1-(Amino-{5-[1-(2-fluoro-biphenyl-4-yl)-ethyl]-isoxazol-3-ylmethylimino}-methyl)-piperidin-4-one;
((3,5-Dimethyl-morpholin-4-yl)-{3-[1-(2-fluoro-biphenyl-4-yl)-ethyl]-isoxazol-5-ylimino}-methyl)-amine;
((3,5-Dimethyl-morpholin-4-yl)-{3-[1-(2-fluoro-biphenyl-4-yl)-ethyl]-isoxazol-5-ylmethylimino}-methyl)-amine;
((3,5-Dimethyl-morpholin-4-yl)-{5-[1-(2-fluoro-biphenyl-4-yl)-ethyl]-isoxazol-3-ylimino}-methyl)-amine;
((3,5-Dimethyl-morpholin-4-yl)-{5-[1-(2-fluoro-biphenyl-4-yl)-ethyl]-isoxazol-3-ylmethylimino}-methyl)-amine;
((2,6-Dimethyl-morpholin-4-yl)-{3-[1-(2-fluoro-biphenyl-4-yl)-ethyl]-isoxazol-5-ylimino}-methyl)-amine;
((2,6-Dimethyl-morpholin-4-yl)-{3-[1-(2-fluoro-biphenyl-4-yl)-ethyl]-isoxazol-5-ylmethylimino}-methyl)-amine;
((2,6-Dimethyl-morpholin-4-yl)-{5-[1-(2-fluoro-biphenyl-4-yl)-ethyl]-isoxazol-3-ylimino}-methyl)-amine;
((2,6-Dimethyl-morpholin-4-yl)-{5-[1-(2-fluoro-biphenyl-4-yl)-ethyl]-isoxazol-3-ylmethylimino}-methyl)-amine;
({3-[1-(2-Fluoro-biphenyl-4-yl)-ethyl]-isoxazol-5-ylmethylimino}-thiamorpholin-4-yl-methyl)-amine;

({5-[1-(2-Fluoro-biphenyl-4-yl)-ethyl]-isoxazol-3-ylimino}-thiamorpholin-4-yl-methyl)-amine;
({5-[1-(2-Fluoro-biphenyl-4-yl)-ethyl]-isoxazol-3-ylmethylimino}-thiamorpholin-4-yl-methyl)-amine;
({3-[1-(2-Fluoro-biphenyl-4-yl)-ethyl]-isoxazol-5-ylmethylimino}-piperazin-1-yl-methyl)-amine;
({5-[1-(2-Fluoro-biphenyl-4-yl)-ethyl]-isoxazol-3-ylimino}-piperazin-1-yl-methyl)-amine;
({5-[1-(2-Fluoro-biphenyl-4-yl)-ethyl]-isoxazol-3-ylmethylimino}-piperazin-1-yl-methyl)-amine;
[{3-[1-(2-Fluoro-biphenyl-4-yl)-ethyl]-isoxazol-5-ylmethylimino}-(4-methyl-piperazin-1-yl)-methyl]-amine;
[{5-[1-(2-Fluoro-biphenyl-4-yl)-ethyl]-isoxazol-3-ylimino}-(4-methyl-piperazin-1-yl)-methyl]-amine;
[{5-[1-(2-Fluoro-biphenyl-4-yl)-ethyl]-isoxazol-3-ylmethylimino}-(4-methyl-piperazin-1-yl)-methyl]-amine;
2-[4-(Amino-{3-[1-(2-fluoro-biphenyl-4-yl)-ethyl]-isoxazol-5-ylimino}-methyl)-piperazin-1-yl]-ethanol;
2-[4-(Amino-{3-[1-(2-fluoro-biphenyl-4-yl)-ethyl]-isoxazol-5-ylmethylimino}-methyl)-piperazin-1-yl]-ethanol;
2-[4-(Amino-{5-[1-(2-fluoro-biphenyl-4-yl)-ethyl]-isoxazol-3-ylimino}-methyl)-piperazin-1-yl]-ethanol;
2-[4-(Amino-{5-[1-(2-fluoro-biphenyl-4-yl)-ethyl]-isoxazol-3-ylmethylimino}-methyl)-piperazin-1-yl]-ethanol;
([4-(2-Amino-ethyl)-piperazin-1-yl]-{3-[1-(2-fluoro-biphenyl-4-yl)-ethyl]-isoxazol-5-ylimino}-methyl)-amine;
([4-(2-Amino-ethyl)-piperazin-1-yl]-{3-[1-(2-fluoro-biphenyl-4-yl)-ethyl]-isoxazol-5-ylmethylimino}-methyl)-amine;
([4-(2-Amino-ethyl)-piperazin-1-yl]-{5-[1-(2-fluoro-biphenyl-4-yl)-ethyl]-isoxazol-3-ylimino}-methyl)-amine;
([4-(2-Amino-ethyl)-piperazin-1-yl]-{5-[1-(2-fluoro-biphenyl-4-yl)-ethyl]-isoxazol-3-ylmethylimino}-methyl)-amine;
1-[4-(Amino-{3-[1-(2-fluoro-biphenyl-4-yl)-ethyl]-isoxazol-5-ylimino}-methyl)-piperazin-1-yl]-ethanone;
1-[4-(Amino-{3-[1-(2-fluoro-biphenyl-4-yl)-ethyl]-isoxazol-5-ylmethylimino}-methyl)-piperazin-1-yl]-ethanone;
1-[4-(Amino-{5-[1-(2-fluoro-biphenyl-4-yl)-ethyl]-isoxazol-3-ylimino}-methyl)-piperazin-1-yl]-ethanone;
1-[4-(Amino-{5-[1-(2-fluoro-biphenyl-4-yl)-ethyl]-isoxazol-3-ylmethylimino}-methyl)-piperazin-1-yl]-ethanone;
(N'-{3-[1-(2-Fluoro-biphenyl-4-yl)-ethyl]-isoxazol-5-ylmethyl}-guanidino)-acetic acid;
(N'-{5-[1-(2-Fluoro-biphenyl-4-yl)-ethyl]-isoxazol-3-yl}-guanidino)-acetic acid;
(N'-{5-[1-(2-Fluoro-biphenyl-4-yl)-ethyl]-isoxazol-3-ylmethyl}-guanidino)-acetic acid;
(N'-{3-[1-(2-Fluoro-biphenyl-4-yl)-ethyl]-isoxazol-5-yl}-N-methyl-guanidino)-acetic acid;
(N'-{3-[1-(2-Fluoro-biphenyl-4-yl)-ethyl]-isoxazol-5-ylmethyl}-N-methyl-guanidino)-acetic acid;
(N'-{5-[1-(2-Fluoro-biphenyl-4-yl)-ethyl]-isoxazol-3-yl}-N-methyl-guanidino)-acetic acid;
(N'-{5-[1-(2-Fluoro-biphenyl-4-yl)-ethyl]-isoxazol-3-ylmethyl}-N-methyl-guanidino)-acetic acid;
Ethyl (N'-{3-[1-(2-fluoro-biphenyl-4-yl)-ethyl]-isoxazol-5-ylmethyl}-guanidino)-acetate;
Ethyl (N'-{5-[1-(2-fluoro-biphenyl-4-yl)-ethyl]-isoxazol-3-yl}-guanidino)-acetate;
Ethyl (N'-{5-[1-(2-fluoro-biphenyl-4-yl)-ethyl]-isoxazol-3-ylmethyl}-guanidino)-acetate;
2-(N'-{3-[1-(2-Fluoro-biphenyl-4-yl)-ethyl]-isoxazol-5-yl}-guanidino)-acetamide;
2-(N'-{3-[1-(2-Fluoro-biphenyl-4-yl)-ethyl]-isoxazol-5-ylmethyl}-guanidino)-acetamide;
2-(N'-{5-[1-(2-Fluoro-biphenyl-4-yl)-ethyl]-isoxazol-3-yl}-guanidino)-acetamide;
2-(N'-{5-[1-(2-Fluoro-biphenyl-4-yl)-ethyl]-isoxazol-3-ylmethyl}-guanidino)-acetamide;
2-(N'-{3-[1-(2-Fluoro-biphenyl-4-yl)-ethyl]-isoxazol-5-yl}-guanidino)-propionic acid;
2-(N'-{3-[1-(2-Fluoro-biphenyl-4-yl)-ethyl]-isoxazol-5-ylmethyl}-guanidino)-propionic acid;
2-(N'-{5-[1-(2-Fluoro-biphenyl-4-yl)-ethyl]-isoxazol-3-yl}-guanidino)-propionic acid;
2-(N'-{5-[1-(2-Fluoro-biphenyl-4-yl)-ethyl]-isoxazol-3-ylmethyl}-guanidino)-propionic acid;
2-(N'-{3-[1-(2-Fluoro-biphenyl-4-yl)-ethyl]-isoxazol-5-yl}-guanidino)-succinic acid;
2-(N'-{3-[1-(2-Fluoro-biphenyl-4-yl)-ethyl]-isoxazol-5-ylmethyl}-guanidino)-succinic acid;
2-(N'-{5-[1-(2-Fluoro-biphenyl-4-yl)-ethyl]-isoxazol-3-yl}-guanidino)-succinic acid;
2-(N'-{5-[1-(2-Fluoro-biphenyl-4-yl)-ethyl]-isoxazol-3-ylmethyl}-guanidino)-succinic acid;
1-(Amino-{3-[1-(2-fluoro-biphenyl-4-yl)-ethyl]-isoxazol-5-ylimino}-methyl)-pyrrolidine-2-carboxylic acid;
1-(Amino-{3-[1-(2-fluoro-biphenyl-4-yl)-ethyl]-isoxazol-5-ylmethylimino}-methyl)-pyrrolidine-2-carboxylic acid;
1-(Amino-{5-[1-(2-fluoro-biphenyl-4-yl)-ethyl]-isoxazol-3-ylimino}-methyl)-pyrrolidine-2-carboxylic acid;
1-(Amino-{5-[1-(2-fluoro-biphenyl-4-yl)-ethyl]-isoxazol-3-ylmethylimino}-methyl)-pyrrolidine-2-carboxylic acid;
N-{3-[1-(2-Fluoro-biphenyl-4-yl)-ethyl]-isoxazol-5-yl}-N',N"-dimethyl-guanidine;
N-{3-[1-(2-Fluoro-biphenyl-4-yl)-ethyl]-isoxazol-5-ylmethyl}-N',N"-dimethyl-guanidine;
N-{5-[1-(2-Fluoro-biphenyl-4-yl)-ethyl]-isoxazol-3-yl}-N',N"-dimethyl-guanidine;
N-{5-[1-(2-Fluoro-biphenyl-4-yl)-ethyl]-isoxazol-3-ylmethyl}-N',N"-dimethyl-guanidine;
N-{3-[1-(2-Fluoro-biphenyl-4-yl)-ethyl]-isoxazol-5-yl}-N'-methyl-N"-phenyl-guanidine;
N-{3-[1-(2-Fluoro-biphenyl-4-yl)-ethyl]-isoxazol-5-ylmethyl}-N'-methyl-N"-phenyl-guanidine;
N-{5-[1-(2-Fluoro-biphenyl-4-yl)-ethyl]-isoxazol-3-yl}-N'-methyl-N"-phenyl-guanidine;
N-{5-[1-(2-Fluoro-biphenyl-4-yl)-ethyl]-isoxazol-3-ylmethyl}-N'-methyl-N"-phenyl-guanidine;
N"-{3-[1-(2-Fluoro-biphenyl-4-yl)-ethyl]-isoxazol-5-yl}-N,N,N',N'-tetramethyl-guanidine;
N"-{3-[1-(2-Fluoro-biphenyl-4-yl)-ethyl]-isoxazol-5-ylmethyl}-N,N,N',N'-tetramethyl-guanidine;
N"-{5-[1-(2-Fluoro-biphenyl-4-yl)-ethyl]-isoxazol-3-yl}-N,N,N',N'-tetramethyl-guanidine;
N"-{5-[1-(2-Fluoro-biphenyl-4-yl)-ethyl]-isoxazol-3-ylmethyl}-N,N,N',N'-tetramethyl-guanidine;
(Di-piperidin-1-yl-methylene)-{3-[1-(2-fluoro-biphenyl-4-yl)-ethyl]-isoxazol-5-yl}-amine;
(Di-piperidin-1-yl-methylene)-{3-[1-(2-fluoro-biphenyl-4-yl)-ethyl]-isoxazol-5-ylmethyl}-amine;
(Di-piperidin-1-yl-methylene)-{5-[1-(2-fluoro-biphenyl-4-yl)-ethyl]-isoxazol-3-yl}-amine;
(Di-piperidin-1-yl-methylene)-{5-[1-(2-fluoro-biphenyl-4-yl)-ethyl]-isoxazol-3-ylmethyl}-amine;
(Di-morpholin-4-yl-methylene)-{3-[1-(2-fluoro-biphenyl-4-yl)-ethyl]-isoxazol-5-yl}-amine;
(Di-morphilin-4-yl-methylene)-{3-[1-(2-fluoro-biphenyl-4-yl)-ethyl]-isoxazol-5-ylmethyl}-amine:

(Di-morphilin-4-yl-methylene)-{5-[1-(2-fluoro-biphenyl-4-yl)-ethyl]-isoxazol-3-yl}-amine;
(Di-morphilin-4-yl-methylene)-{5-[1-(2-fluoro-biphenyl-4-yl)-ethyl]-isoxazol-3-ylmethyl}-amine;
(Di-piperazin-4-yl-methylene)-{3-[1-(2-fluoro-biphenyl-4-yl)-ethyl]-isoxazol-5-yl}-amine;
(Di-piperazin-4-yl-methylene)-{3-[1-(2-fluoro-biphenyl-4-yl)-ethyl]-isoxazol-5-ylmethyl}-amine;
(Di-piperazin-4-yl-methylene)-{5-[1-(2-fluoro-biphenyl-4-yl)-ethyl]-isoxazol-3-yl}-amine;
(Di-piperazin-4-yl-methylene)-{5-[1-(2-fluoro-biphenyl-4-yl)-ethyl]-isoxazol-3-ylmethyl}-amine;
(4,5-Dihydro-1H-imidazol-2-yl)-{3-[1-(2-fluoro-biphenyl-4-yl)-ethyl]-isoxazol-5-yl}-amine;
(4,5-Dihydro-1H-imidazol-2-yl)-{3-[1-(2-fluoro-biphenyl-4-yl)-ethyl]-isoxazol-5-ylmethyl}-amine;
(4,5-Dihydro-1H-imidazol-2-yl)-{5-[1-(2-fluoro-biphenyl- 4-yl)-ethyl]-isoxazol-3-yl}-amine;
(4,5-Dihydro-1H-imidazol-2-yl)-{5-[1-(2-fluoro-biphenyl-4-yl)-ethyl]-isoxazol-3-ylmethyl}-amine;
1-{3-[1-(2-Fluoro-biphenyl-4-yl)-ethyl]-isoxazol-5-yl}-4,5-dihydro-1H-imidazol-2-ylamine;
1-{3-[1-(2-Fluoro-biphenyl-4-yl)-ethyl]-isoxazol-5-ylmethyl}-4,5-dihydro-1H-imidazol-2-ylamine;
1-{5-[1-(2-Fluoro-biphenyl-4-yl)-ethyl]-isoxazol-3-yl}-4,5-dihydro-1H-imidazol-2-ylamine;
1-{5-[1-(2-Fluoro-biphenyl-4-yl)-ethyl]-isoxazol-3-ylmethyl}-4,5-dihydro-1H-imidazol-2-ylamine;
{3-[1-(2-Fluoro-biphenyl-4-yl)-ethyl]-isoxazol-5-yl}-(1,4,5,6-tetrahydro-pyrimidin-2-yl)-amine;
{3-[1-(2-Fluoro-biphenyl-4-yl)-ethyl]-isoxazol-5-ylmethyl}-(1,4,5,6-tetrahydro-pyrimidin-2-yl)-amine;
{5-[1-(2-Fluoro-biphenyl-4-yl)-ethyl]-isoxazol-3-yl}-(1,4,5,6-tetrahydro-pyrimidin-2-yl)-amine;
{5-[1-(2-Fluoro-biphenyl-4-yl)-ethyl]-isoxazol-3-ylmethyl}-(1,4,5,6-tetrahydro-pyrimidin-2-yl)-amine;
1-{3-[1-(2-Fluoro-biphenyl-4-yl)-ethyl-]-isoxazol-5-yl}-1,4,5,6-tetrahydro-pyrimidin-2-ylamine;
1-{3-[1-(2-Fluoro-biphenyl-4-yl)-ethyl-]-isoxazol-5-ylmethyl}-1,4,5,6-tetrahydro-pyrimidin-2-ylamine;
1-{5-[1-(2-Fluoro-biphenyl-4-yl)-ethyl-]-isoxazol-3-yl}-1,4,5,6-tetrahydro-pyrimidin-2-ylamine;
1-{5-[1-(2-Fluoro-biphenyl-4-yl)-ethyl-]-isoxazol-3-ylmethyl}-1,4,5,6-tetrahydro-pyrimidin-2-ylamine;
(3,6-Dihydro-2H-[1,3,5]oxadiazin-4-yl)-{3-[1-(2-fluoro-biphenyl-4-yl)-ethyl]-isoxazol-5-yl}-amine;
(3,6-Dihydro-2H-[1,3,5]oxadiazin-4-yl)-{3-[1-(2-fluoro-biphenyl-4-yl)-ethyl]-isoxazol-5-ylmethyl}-amine;
(3,6-Dihydro-2H-[1,3,5]oxadiazin-4-yl)-{5-[1-(2-fluoro-biphenyl-4-yl)-ethyl]-isoxazol-3-yl}-amine;
(3,6-Dihydro-2H-[1,3,5]oxadiazin-4-yl)-{5-[1-(2-fluoro-biphenyl-4-yl)-ethyl]-isoxazol-3-ylmethyl}-amine;
3-{3-[1-(2-Fluoro-biphenyl-4-yl)-ethyl]-isoxazol-5-yl}-3,6-dihydro-2H-[1,3,5]oxadiazin-4-ylamine;
3-{3-[1-(2-Fluoro-biphenyl-4-yl)-ethyl]-isoxazol-5-ylmethyl}-3,6-dihydro-2H-[1,3,5]oxadiazin-4-ylamine;
3-{5-[1-(2-Fluoro-biphenyl-4-yl)-ethyl]-isoxazol-3-yl}-3,6-dihydro-2H-[1,3,5]oxadiazin-4-ylamine;
3-{5-[1-(2-Fluoro-biphenyl-4-yl)-ethyl]-isoxazol-3-ylmethyl}-3,6-dihydro-2H-[1,3,5]oxadiazin-4-ylamine;
{3-[1-(2-Fluoro-biphenyl-4-yl)-ethyl]-isoxazol-5-yl}-(1,4,5,6-tetrahydro-[1,3,5]triazin-2-yl)-amine;
{3-[1-(2-Fluoro-biphenyl-4-yl)-ethyl]-isoxazol-5-ylmethyl}-(1,4,5,6-tetrahydro-[1,3,5]triazin- 2-yl)-amine;
{5-[1-(2-Fluoro-biphenyl-4-yl)-ethyl]-isoxazol-3-yl}-(1,4,5,6-tetrahydro-[1,3,5]triazin-2-yl)-amine;
{5-[1-(2-Fluoro-biphenyl-4-yl)-ethyl]-isoxazol-3-ylmethyl}-(1,4,5,6-tetrahydro-[1,3,5]triazin-2-yl)-amine;
{3-[1-(2-Fluoro-biphenyl-4-yl)-ethyl]-isoxazol-5-yl}-(5-methyl-1,4,5,6-tetrahydro-[1,3,5]triazin-2-yl)-amine;
{3-[1-(2-Fluoro-biphenyl-4-yl)-ethyl]-isoxazol-5-ylmethyl}-(5-methyl-1,4,5,6-tetrahydro-[1,3,5]triazin-2-yl)-amine;
{5-[1-(2-Fluoro-biphenyl-4-yl)-ethyl]-isoxazol-3-yl}-(5-methyl-1,4,5,6-tetrahydro-[1,3,5]triazin-2-yl)-amine;
{5-[1-(2-Fluoro-biphenyl-4-yl)-ethyl]-isoxazol-3-ylmethyl}-(5-methyl-1,4,5,6-tetrahydro-[1,3,5]triazin-2-yl)-amine;
1-{3-[1-(2-Fluoro-biphenyl-4-yl)-ethyl]-isoxazol-5-yl}-1,4,5,6-tetrahydro-[1,3,5]triazin-2-ylamine;
1-{3-[1-(2-Fluoro-biphenyl-4-yl)-ethyl]-isoxazol-5-ylmethyl}-1,4,5,6-tetrahydro-[1,3,5]triazin-2-ylamine;
1-{5-[1-(2-Fluoro-biphenyl-4-yl)-ethyl]-isoxazol-3-yl}-1,4,5,6-tetrahydro-[1,3,5]triazin-2-ylamine;
1-{5-[1-(2-Fluoro-biphenyl-4-yl)-ethyl]-isoxazol-3-ylmethyl}-1,4,5,6-tetrahydro-[1,3,5]triazin-2-ylamine;
1-{3-[1-(2-Fluoro-biphenyl-4-yl)-ethyl]-isoxazol-5-yl}-5-methyl-1,4,5,6-tetrahydro-[1,3,5]triazin-2-ylamine;
1-{3-[1-(2-Fluoro-biphenyl-4-yl)-ethyl]-isoxazol-5-yl}-5-methyl-1,4,5,6-tetrahydro-[1,3,5]triazin-2-ylamine;
1-{5-[1-(2-Fluoro-biphenyl-4-yl)-ethyl]-isoxazol-3-yl}-5-methyl-1,4,5,6-tetrahydro-[1,3,5]triazin-2-ylamine;
1-{5-[1-(2-Fluoro-biphenyl-4-yl)-ethyl]-isoxazol-3-yl}-5-methyl-1,4,5,6-tetrahydro-[1,3,5]triazin-2-ylamine;
2-{3-[1-(2-Fluoro-biphenyl-4-yl)-ethyl]-isoxazol-5-ylamino}-1,4,5,6-tetrahydro-pyrimidin-5-ol;
2-({3-[1-(2-Fluoro-biphenyl-4-yl)-ethyl]-isoxazol-5-ylmethyl}-amino)-1,4,5,6-tetrahydro-pyrimidin-5-ol;
2-{5-[1-(2-Fluoro-biphenyl-4-yl)-ethyl]-isoxazol-3-ylamino}-1,4,5,6-tetrahydro-pyrimidin-5-ol;
2-({5-[1-(2-Fluoro-biphenyl-4-yl)-ethyl]-isoxazol-3-ylmethyl}-amino)-1,4,5,6-tetrahydro-pyrimidin-5-ol;
{3-[1-(2-Fluoro-biphenyl-4-yl)-ethyl]-isoxazol-5-yl}-(5-methoxy-1,4,5,6-tetrahydro-pyrimidin-2-yl)-amine;
{3-[1-(2-Fluoro-biphenyl-4-yl)-ethyl]-isoxazol-5-ylmethyl}-(5-methoxy-1,4,5,6-tetrahydro-pyrimidin-2-yl)-amine;
{5-[1-(2-Fluoro-biphenyl-4-yl)-ethyl]-isoxazol-3-yl}-(5-methoxy-1,4,5,6-tetrahydro-pyrimidin-2-yl)-amine;
{5-[1-(2-Fluoro-biphenyl-4-yl)-ethyl]-isoxazol-3-ylmethyl}-(5-methoxy-1,4,5,6-tetrahydro-pyrimidin-2-yl)-amine;
2-Amino-1-{3-[1-(2-fluoro-biphenyl-4-yl)-ethyl]-isoxazol-5-yl}-1,4,5,6-tetrahydro-pyrimidin-5-ol;
2-Amino-1-{3-[1-(2-fluoro-biphenyl-4-yl)-ethyl]-isoxazol-5-ylmethyl}-1,4,5,6-tetrahydro-pyrimidin-5-ol;
2-Amino-1-{5-[1-(2-fluoro-biphenyl-4-yl)-ethyl]-isoxazol-3-yl}-1,4,5,6-tetrahydro-pyrimidin-5-ol;
2-Amino-1-{5-[1-(2-fluoro-biphenyl-4-yl)-ethyl]-isoxazol-3-ylmethyl}-1,4,5,6-tetrahydro-pyrimidin-5-ol;
1-{3-[1-(2-Fluoro-biphenyl-4-yl)-ethyl]-isoxazol-5-yl}-5-methoxy-1,4,5,6-tetrahydro-pyrimidin-2-ylamine;
1-{3-[1-(2-Fluoro-biphenyl-4-yl)-ethyl]-isoxazol-5-ylmethyl}-5-methoxy-1,4,5,6-tetrahydro-pyrimidin-2-ylamine;
1-{5-[1-(2-Fluoro-biphenyl-4-yl)-ethyl]-isoxazol-3-yl}-5-methoxy-1,4,5,6-tetrahydro-pyrimidin-2-ylamine;
1-{5-[1-(2-Fluoro-biphenyl-4-yl)-ethyl]-isoxazol-3-ylmethyl}-5-methoxy-1,4,5,6-tetrahydro-pyrimidin-2-ylamine;
{3-[1-(2-Fluoro-biphenyl-4-yl)-ethyl]-isoxazol-5-yl}-(4,5,6,7-tetrahydro-1H-[1,3]diazepin-2-yl)-amine;
{3-[1-(2-Fluoro-biphenyl-4-yl)-ethyl]-isoxazol-5-ylmethyl}-(4,5,6,7-tetrahydro-1H-[1,3]diazepin-2-yl)-amine;

{5-[1-(2-Fluoro-biphenyl-4-yl)-ethyl]-isoxazol-3-yl}-(4,5,6,7-tetrahydro-1H-[1,3]diazepin-2-yl)-amine;

{5-[1-(2-Fluoro-biphenyl-4-yl)-ethyl]-isoxazol-3-ylmethyl}-(4,5,6,7-tetrahydro-1H-[1,3]diazepin-2-yl)-amine;

1-{3-[1-(2-Fluoro-biphenyl-4-yl)-ethyl]-isoxazol-5-yl}-4,5,6,7-tetrahydro-1H-[1,3]diazepin-2-ylamine;

1-{3-[1-(2-Fluoro-biphenyl-4-yl)-ethyl]-isoxazol-5-ylmethyl}-4,5,6,7-tetrahydro-1H-[1,3]diazepin-2-ylamine;

1-{5-[1-(2-Fluoro-biphenyl-4-yl)-ethyl]-isoxazol-3-yl}-4,5,6,7-tetrahydro-1H-[1,3]diazepin-2-ylamine;

1-{5-[1-(2-Fluoro-biphenyl-4-yl)-ethyl]-isoxazol-3-ylmethyl}-4,5,6,7-tetrahydro-1H-[1,3]diazepin-2-ylamine;

({3-[1-(2-Fluoro-biphenyl-4-yl)-ethyl]-isoxazol-5-ylmethylimino}-pyrrolidin-1-yl-methyl)-amine;

({5-[1-(2-Fluoro-biphenyl-4-yl)-ethyl]-isoxazol-3-ylimino}-pyrrolidin-1-yl-methyl)-amine;

({5-[1-(2-Fluoro-biphenyl-4-yl)-ethyl]-isoxazol-3-ylmethylimino}-pyrrolidin-1-yl-methyl)-amine;

(Azepan-1-yl-{3-[1-(2-fluoro-biphenyl-4-yl)-ethyl]-isoxazol-5-ylimino}-methyl)-amine;

({3-[1-(2-Fluoro-biphenyl-4-yl)-ethyl]-isoxazol-5-ylimino}-thiazolidin-3-yl-methyl)-amine;

1-(Amino-{3-[1-(2-fluoro-biphenyl-4-yl)-ethyl]-isoxazol-5-ylimino}-methyl)-piperidin-2-one;

N-{3-[1-(2-Fluoro-biphenyl-4-yl)-ethyl]-isoxazol-5-yl}-N'-(2-oxo-propyl)-guanidine;

Ethyl 3-(N'-{3-[1-(2-fluoro-biphenyl-4-yl)-ethyl]-isoxazol-5-yl}-guanidino)-propionate;

2-(N'-{3-[1-(2-Fluoro-biphenyl-4-yl)-ethyl]-isoxazol-5-yl}-guanidino)-N,N-dimethyl-acetamide;

3-(N'-{3-[1-(2-Fluoro-biphenyl-4-yl)-ethyl]-isoxazol-5-y}-guanidino)-N,N-dimethyl-propionamide;

N-{3-[1-(2-Fluoro-biphenyl-4-yl)-ethyl]-isoxazol-5-yl}-N'-(3-hydroxy-propyl)-guanidine;

N-{3-[1-(2-Fluoro-biphenyl-4-yl)-ethyl]-isoxazol-5-yl}-N'-(2-pyrrolidin-1-yl-ethyl)-guanidine;

N-{3-[1-(2-Fluoro-biphenyl-4-yl)-ethyl]-isoxazol-5-yl}-N'-(2-piperidin-1-yl-ethyl)-guanidine;

N-{3-[1-(2-Fluoro-biphenyl-4-yl)-ethyl]-isoxazol-5-yl}-N'-[2-(4-methyl-piperazin-1-yl)-ethyl]-guanidine;

N-{3-[1-(2-Fluoro-biphenyl-4-yl)-ethyl]-isoxazol-5-yl}-N'-(3-morpholin-4-yl-propyl)-guanidine;

N-{3-[1-(2-Fluoro-biphenyl-4-yl)-ethyl]-isoxazol-5-yl}-N'-[2-(2-methoxy-ethoxy)-ethyl]-guanidine;

N-{3-[1-(2-Fluoro-biphenyl-4-yl)-ethyl]-isoxazol-5-yl}-N'-[2-(3-hydroxy-propoxy)-ethyl]-guanidine;

2-{3-[1-(2-Fluoro-biphenyl-4-yl)-ethyl]-isoxazol-5-ylimino}-1-(2-methoxy-ethyl)-imidazolidin-4-one;

N-({3-[1-(2-Fluoro-biphenyl-4-yl)-ethyl]-isoxazol-5-ylimino}-methylamino-methyl)-N'-methyl-guanidine;

N'-(Dimethylamino-{3-[1-(2-fluoro-biphenyl-4-yl)-ethyl]-isoxazol-5-ylimino}-methyl)-N,N-dimethyl-guanidine;

[[{3-[1-(2-Fluoro-biphenyl-4-yl)-ethyl]-isoxazol-5-ylimino}-(4-methyl-piperazin-1-yl)-methylimino]-(4-methyl-piperazin-1-yl)-methyl]-amine;

N-[{3-[1-(2-Fluoro-biphenyl-4-yl)-ethyl]-isoxazol-5-ylimino)-(2-morpholin-4-yl-ethylamino)-methyl]-N'-(2-morpholin-4-yl-ethyl)-guanidine;

N-[{3-[1-(2-Fluoro-biphenyl-4-yl)-ethyl]-isoxazol-5-ylimino}-(2-hydroxy-ethylamino)-methyl]-N'-(2-hydroxy-ethyl)-guanidine;

N-{{3-[1-(2-Fluoro-biphenyl-4-yl)-ethyl]-isoxazol-5-ylimino}-[2-(2-hydroxy-ethoxy)-ethylamino]-methyl}-N'-[2-(2-hydroxy-ethoxy)-ethyl]-guanidine;

[Bis-(4-methyl-piperazin-1-yl)-methylene]-{3-[1-(2-fluoro-biphenyl-4-yl)-ethyl]-isoxazol-5-yl}-amine;

N-{3-[1-(2-fluoro-biphenyl-4-yl)-ethyl]-isoxazol-5-yl}-N',N''-bis-(2-morpholin-4-yl-ethyl)-guanidine;

N-{3-[1-(2-Fluoro-biphenyl-4-yl)-ethyl]-isoxazol-5-yl}-N',N''-bis-(2-hydroxy-ethyl)-guanidine;

N-{3-[1-(2-Fluoro-biphenyl-4-yl)-ethyl]-isoxazol-5-yl}-N',N''-bis-[2-(2-hydroxy-ethoxy)-ethyl]-guanidine;

N-{3-[1-(2-Fluoro-biphenyl-4-yl)-ethyl]-isoxazol-5-yl}-N'-(methylamino)-guanidine;

N-{3-[1-(2-Fluoro-biphenyl-4-yl)-ethyl]-isoxazol-5-yl}-N'-(dimethylamino)-guanidine;

N-{3-[1-(2-Fluoro-biphenyl-4-yl)-ethyl]-isoxazol-5-yl}-N'-(pyridin-2-yl-amino)-guanidine;

N-{3-[1-(2-Fluoro-biphenyl-4-yl)-ethyl]-isoxazol-5-yl}-N'-pyridin-2-yl-guanidine;

N-{3-[1-(2-Fluoro-biphenyl-4-yl)-ethyl]-isoxazol-5-yl}-N'-pyridin-4-yl-guanidine;

N-{3-[1-(2-Fluoro-biphenyl-4-yl)-ethyl]-isoxazol-5-yl}-N'-pyrimidin-2-yl-guanidine;

N-{3-[1-(2-Fluoro-biphenyl-4-yl)-ethyl]-isoxazol-5-yl}-N'-(1H-tetrazol-5-yl)-guanidine;

[{3-[1-(2-Fluoro-biphenyl-4-yl)-ethyl]-isoxazol-5-ylimino}-(1-oxo-[1,4]thiazinan-4-yl)-methyl]-amine;

((1,1-Dioxo-[1,4]thiazinan-4-yl)-{3-[1-(2-fluoro-biphenyl-4-yl)-ethyl]-isoxazol-5-ylimino}-methyl)-amine;

{3-[1-(2-Fluoro-biphenyl-4-yl)-ethyl]-isoxazol-5-yl}-(imino-morpholin-4-yl-methyl)-methyl-amine;

N-{3-[1-(2-Fluoro-biphenyl-4-yl)-1-methyl-ethyl]-isoxazol-5-yl}-N'-methyl-guanidine;

N-Ethyl-N'-{3-[1-(2-fluoro-biphenyl-4-yl)-1-methyl-ethyl]-isoxazol-5-yl}-guanidine;

N,N-Diethyl-N'-{3-[1-(2-fluoro-biphenyl-4-yl)-1-methyl-ethyl]-isoxazol-5-yl}-guanidine;

({3-[1-(2-Fluoro-biphenyl-4-yl)-1-methyl-ethyl]-isoxazol-5-ylimino}-pyrrolidin-1-yl-methyl)-amine;

(Azepan-1-yl-{3-[1-(2-fluoro-biphenyl-4-yl)-1-methyl-ethyl]-isoxazol-5-ylimino}-methyl)-amine;

[{3-[1-(2-Fluoro-biphenyl-4-yl)-1-methyl-ethyl]-isoxazol-5-ylimino}-(4-methyl-piperazin-1-yl)-methyl]-amine;

({3-[1-(2-Fluoro-biphenyl-4-yl)-1-methyl-ethyl]-isoxazol-5-ylimino}-thiazolidin-3-yl-methyl)-amine;

[{3-[1-(2-Fluoro-biphenyl-4-yl)-1-methyl-ethyl]-isoxazol-5-ylimino}-(4-methyl-piperidin-1-yl)-methyl]-amine;

((2,6-Dimethyl-morpholin-4-yl)-{3-[1-(2-fluoro-biphenyl-4-yl)-1-methyl-ethyl]-isoxazol-5-ylimino}-methyl)-amine;

((4-Dimethylamino-piperidin-1-yl)-{3-[1-(2-fluoro-biphenyl-4-yl)-1-methyl-ethyl]-isoxazol-5-ylimino}-methyl)-amine;

1-(Amino-{3-[1-(2-fluoro-biphenyl-4-yl)-1-methyl-ethyl]-isoxazol-5-ylimino}-methyl)-piperidin-4-one;

1-(Amino-{3-[1-(2-fluoro-biphenyl-4-yl)-1-methyl-ethyl]-isoxazol-5-ylimino}-methyl)-piperidin-2-one;

1-(Amino-{3-[1-(2-fluoro-biphenyl-4-yl)-1-methyl-ethyl]-isoxazol-5-ylimino}-methyl)-piperidin-4-ol;

[{3-[1-(2-Fluoro-biphenyl-4-yl)-1-methyl-ethyl]-isoxazol-5-ylimino}-(4-methoxy-piperidin-1-yl)-methyl]-amine;

({3-[1-(2-Fluoro-biphenyl-4-yl)-1-methyl-ethyl]-isoxazol-5-ylimino}-[1,4]thiazinan-4-yl-methyl)-amine;

1-[4-(Amino-{3-[1-(2-fluoro-biphenyl-4-yl)-1-methyl-ethyl]-isoxazol-5-ylimino}-methyl)-piperazin-1-yl]-ethanone;

N-{3-[1-(2-Fluoro-biphenyl-4-yl)-1-methyl-ethyl]-isoxazol-5-yl}-N'-(2-oxo-propyl)-guanidine;

Ethyl (N'-{3-[1-(2-fluoro-biphenyl-4-yl)-1-methyl-ethyl]-isoxazol-5-yl}-guanidino)-acetate;

Ethyl 3-(N'-{3-[1-(2-fluoro-biphenyl-4-yl)-1-methyl-ethyl]-isoxazol-5-yl}-guanidino)-propionate;

2-(N'-{3-[1-(2-Fluoro-biphenyl-4-yl)-1-methyl-ethyl]-isoxazol-5-yl}-guanidino)-N,N-dimethyl-acetamide;

3-(N'-{3-[1-(2-Fluoro-biphenyl-4-yl)-1-methyl-ethyl]-isoxazol-5-yl}-guanidino)-N,N-dimethyl-propionamide;

N-{3-[1-(2-Fluoro-biphenyl-4-yl)-1-methyl-ethyl]-isoxazol-5-yl}-N'-(2-hydroxy-ethyl)-guanidine;

N-{3-[1-(2-Fluoro-biphenyl-4-yl)-1-methyl-ethyl]-isoxazol-5-yl}-N'-(3-hydroxy-propyl)-guanidine;

N-{3-[1-(2-Fluoro-biphenyl-4-yl)-1-methyl-ethyl]-isoxazol-5-yl}-N'-(2-methoxy-ethyl)-guanidine;

N-(2-Dimethylamino-ethyl)-N'-{3-[1-(2-fluoro-biphenyl-4-yl)-1-methyl-ethyl]-isoxazol-5-yl}-guanidine;

N-{3-[1-(2-Fluoro-biphenyl-4-yl)-1-methyl-ethyl]-isoxazol-5-yl}-N'-(2-pyrrolidin-1-yl-ethyl)-guanidine;

N-{3-[1-(2-Fluoro-biphenyl-4-yl)-1-methyl-ethyl]-isoxazol-5-yl}-N'-(2-piperidin-1-yl-ethyl)-guanidine;

N-{3-[1-(2-Fluoro-biphenyl-4-yl)-1-methyl-ethyl]-isoxazol-5-yl}-N'-(2-morpholin-4-yl-ethyl)-guanidine;

N-{3-[1-(2-Fluoro-biphenyl-4-yl)-1-methyl-ethyl]-isoxazol-5-yl}-N'-[2-(4-methyl-piperazin-1-yl)-ethyl]-guanidine;

N-{3-[1-(2-Fluoro-biphenyl-4-yl)-1-methyl-ethyl]-isoxazol-5-yl}-N'-(3-morpholin-4-yl-propyl)-guanidine;

N-{3-[1-(2-Fluoro-biphenyl-4-yl)-1-methyl-ethyl]-isoxazol-5-yl}-N'-[2-(2-hydroxy-ethoxy)-ethyl]-guanidine;

N-{3-[1-(2-Fluoro-biphenyl-4-yl)-1-methyl-ethyl]-isoxazol-5-yl}-N'-[2-(2-methoxy-ethoxy)-ethyl]-guanidine;

N-{3-[1-(2-Fluoro-biphenyl-4-yl)-1-methyl-ethyl]-isoxazol-5-yl}-N'-[2-(3-hydroxy-propoxy)-ethyl]-guanidine;

2-{3-[1-(2-Fluoro-biphenyl-4-yl)-1-methyl-ethyl]-isoxazol-5-ylimino}-1-methyl-imidazolidin-4-one;

2-{3-[1-(2-Fluoro-biphenyl-4-yl)-1-methyl-ethyl]-isoxazol-5-ylimino}-1-(2-hydroxy-ethyl)-imidazolidin-4-one;

2-{3-[1-(2-Fluoro-biphenyl-4-yl)-1-methyl-ethyl]-isoxazol-5-ylimino}-1-(2-methoxy-ethyl)-imidazolidin-4-one;

N-({3-[1-(2-Fluoro-biphenyl-4-yl)-1-methyl-ethyl]-isoxazol-5-ylimino}-methylamino-methyl)-N'-methyl-guanidine;

N'-(Dimethylamino-{3-[1-(2-fluoro-biphenyl-4-yl)-1-methyl-ethyl]-isoxazol-5-ylimino}-methyl)-N,N-dimethyl-guanidine;

[({3-[1-(2-Fluoro-biphenyl-4-yl)-1-methyl-ethyl]-isoxazol-5-ylimino}-morpholin-4-yl-methylimino)-morpholin-4-yl-methyl]-amine;

[[{3-[1-(2-Fluoro-biphenyl-4-yl)-1-methyl-ethyl]-isoxazol-5-ylimino}-(4-methyl-piperazin-1-yl)-methylimino]-(4-methyl-piperazin-1-yl)-methyl]-amine;

N-[{3-[1-(2-Fluoro-biphenyl-4-yl)-1-methyl-ethyl]-isoxazol-5-ylimino}-(2-morpholin-4-yl-ethylamino)-methyl]-N'-(2-morpholin-4-yl-ethyl)-guanidine;

N-[{3-[1-(2-Fluoro-biphenyl-4-yl)-1-methyl-ethyl]-isoxazol-5-ylimino}-(2-hydroxy-ethylamino)-methyl]-N'-(2-hydroxy-ethyl)-guanidine;

N-{{3-[1-(2-Fluoro-biphenyl-4-yl)-1-methyl-ethyl]-isoxazol-5-ylimino}-[2-(2-hydroxy-ethoxy)-ethylamino]-methyl}-N'-[2-(2-hydroxy-ethoxy)-ethyl]-guanidine;

N-{3-[1-(2-Fluoro-biphenyl-4-yl)-1-methyl-ethyl]-isoxazol-5-yl}-N',N"-dimethyl-guanidine;

N"-{3-[1-(2-Fluoro-biphenyl-4-yl)-1-methyl-ethyl]-isoxazol-5-yl}-N,N,N',N'-tetramethyl-guanidine;

(Di-morpholin-4-yl-methylene)-{3-[1-(2-fluoro-biphenyl-4-yl)-1-methyl-ethyl]-isoxazol-5-yl}-amine;

[Bis-(4-methyl-piperazin-1-yl)-methylene]-{3-[1-(2-fluoro-biphenyl-4-yl)-1-methyl-ethyl]-isoxazol-5-yl}-amine;

N-{3-[1-(2-Fluoro-biphenyl-4-yl)-1-methyl-ethyl]-isoxazol-5-yl}-N',N"-bis-(2-morpholin-4-yl-ethyl)-guanidine;

N-{3-[1-(2-Fluoro-biphenyl-4-yl)-1-methyl-ethyl]-isoxazol-5-yl}-N',N"-bis-(2-hydroxy-ethyl)-guanidine;

N-{3-[1-(2-Fluoro-biphenyl-4-yl)-1-methyl-ethyl]-isoxazol-5-yl}-N',N"-bis-[2-(2-hydroxy-ethoxy)-ethyl]-guanidine;

N-{3-[1-(2'-Fluoro-biphenyl-4-yl)-ethyl]-isoxazol-5-yl}-N'-methyl-guanidine;

N'-{3-[1-(2'-Fluoro-biphenyl-4-yl)-ethyl]-isoxazol-5-yl}-N,N-dimethyl-guanidine;

N-Ethyl-N'-{3-[1-(2'-fluoro-biphenyl-4-yl)-ethyl]-isoxazol-5-yl}-guanidine;

N,N-Diethyl-N'-{3-[1-(2'-fluoro-biphenyl-4-yl)-ethyl]-isoxazol-5-yl}-guanidine;

({3-[1-(2'-Fluoro-biphenyl-4-yl)-ethyl]-isoxazol-5-ylimino}-pyrrolidin-1-yl-methyl)-amine ({3-[1-(2'-Fluoro-biphenyl-4-yl)-ethyl]-isoxazol-5-ylimino}-piperidin-1-yl-methyl)-amine;

(Azepan-1-yl-{3-[1-(2'-fluoro-biphenyl-4-yl)-ethyl]-isoxazol-5-ylimino}-methyl)-amine;

[{3-[1-(2'-Fluoro-biphenyl-4-yl)-ethyl]-isoxazol-5-ylimino}-(4-methyl-piperazin-1-yl)-methyl]-amine;

({3-[1-(2'-Fluoro-biphenyl-4-yl)-ethyl]-isoxazol-5-ylimino}-thiazolidin-3-yl-methyl)-amine;

[{3-[1-(2'-Fluoro-biphenyl-4-yl)-ethyl]-isoxazol-5-ylimino}-(4-methyl-piperidin-1-yl)-methyl]-amine;

((2,6-Dimethyl-morpholin-4-yl)-{3-[1-(2'-fluoro-biphenyl-4-yl)-ethyl]-isoxazol-5-ylimino}-methyl)-amine;

((4-Dimethylamino-piperidin-1-yl)-{3-[1-(2'-fluoro-biphenyl-4-yl)-ethyl]-isoxazol-5-ylimino}-methyl)-amine;

1-(Amino-{3-[1-(2'-fluoro-biphenyl-4-yl)-ethyl]-isoxazol-5-ylimino}-methyl)-piperidin-4-one;

1-(Amino-{3-[1-(2'-fluoro-biphenyl-4-yl)-ethyl]-isoxazol-5-ylimino}-methyl)-piperidin-2-one;

1-(Amino-{3-[1-(2'-fluoro-biphenyl-4-yl)-ethyl]-isoxazol-5-ylimino}-methyl)-piperidin-4-ol;

[{3-[1-(2'-Fluoro-biphenyl-4-yl)-ethyl]-isoxazol-5-ylimino}-(4-methoxy-piperidin-1-yl)-methyl]-amine;

({3-[1-(2'-Fluoro-biphenyl-4-yl)-ethyl]-isoxazol-5-ylimino}-[1,4]thiazinan-4-yl-methyl)-amine;

1-[4-(Amino-{3-[1-(2'-fluoro-biphenyl-4-yl)-ethyl]-isoxazol-5-ylimino}-methyl)-piperazin-1-yl]-ethanone;

N-{3-[1-(2'-Fluoro-biphenyl-4-yl)-ethyl]-isoxazol-5-yl}-N'-(2-oxo-propyl)-guanidine;

Ethyl (N'-{3-[1-(2'-fluoro-biphenyl-4-yl)-ethyl]-isoxazol-5-yl)-guanidino)-acetate;

Ethyl 3-(N'-{3-[1-(2'-fluoro-biphenyl-4-yl)-ethyl]-isoxazol-5-yl}-guanidino)-propionate;

2-(N'-{3-[1-(2'-Fluoro-biphenyl-4-yl)-ethyl]-isoxazol-5-yl}-guanidino)-N,N-dimethyl-acetamide;

3-(N'-{3-[1-(2'-Fluoro-biphenyl-4-yl)-ethyl]-isoxazol-5-yl}-guanidino)-N,N-dimethyl-propionamide;

N-{3-[1-(2'-Fluoro-biphenyl-4-yl)-ethyl]-isoxazol-5-yl}-N'-(2-hydroxy-ethyl)-guanidine:

N-{3-[1-(2'-Fluoro-biphenyl-4-yl)-ethyl]-isoxazol-5-yl}-N'-(3-hydroxy-propyl)-guanidine N-{3-[1-(2'-Fluoro-biphenyl-4-yl)-ethyl]-isoxazol-5-yl}-N'-(2-methoxy-ethyl)-guanidine;

N-(2-Dimethylamino-ethyl)-N'-{3-[1-(2'-fluoro-biphenyl-4-yl)-ethyl]-isoxazol-5-yl}-guanidine;

N-{3-[1-(2'-Fluoro-biphenyl-4-yl)-ethyl]-isoxazol-5-yl}-N'-(2-pyrrolidin-1-yl-ethyl)-guanidine;

N-{3-[1-(2'-Fluoro-biphenyl-4-yl)-ethyl]-isoxazol-5-yl}-N'-(2-piperidin-1-yl-ethyl)-guanidine;
N-{3-[1-(2'-Fluoro-biphenyl-4-yl)-ethyl]-isoxazol-5-yl}-N'-(2-morpholin-4-yl-ethyl)-guanidine
N-{3-[1-(2'-Fluoro-biphenyl-4-yl)-ethyl]-isoxazol-5-yl}-N'-[2-(4-methyl-piperazin-1-yl)-ethyl]-guanidine;
N-{3-[1-(2'-Fluoro-biphenyl-4-yl)-ethyl]-isoxazol-5-yl}-N'-(3-morpholin-4-yl-propyl)-guanidine;
N-{3-[1-(2'-Fluoro-biphenyl-4-yl)-ethyl]-isoxazol-5-yl}-N'-[2-(2-hydroxy-ethoxy)-ethyl]-guanidine;
N-{3-[1-(2'-Fluoro-biphenyl-4-yl)-ethyl]-isoxazol-5-yl}-N'-[2-(2-methoxy-ethoxy)-ethyl]-guanidine;
N-{3-[1-(2'-Fluoro-biphenyl-4-yl)-ethyl]-isoxazol-5-yl}-N'-[2-(3-hydroxy-propoxy)-ethyl]-guanidine;
2-{3-[1-(2'-Fluoro-biphenyl-4-yl)-ethyl]-isoxazol-5-ylimino}-1-methyl-imidazolidin-4-one;
2-(3-[1-(2'-Fluoro-biphenyl-4-yl)-ethyl]-isoxazol-5-ylimino}-1-(2-hydroxy-ethyl)-imidazolidin-4-one;
2-{3-[1-(2'-Fluoro-biphenyl-4-yl)-ethyl]-isoxazol-5-ylimino}-1-(2-methoxy-ethyl)-imidazolidin-4-one;
N-({3-[1-(2'-Fluoro-biphenyl-4-yl)-ethyl]-isoxazol-5-ylimino}-methylamino-methyl)-N'-methyl-guanidine;
N'-(Dimethylamino-{3-[1-(2'-fluoro-biphenyl-4-yl)-ethyl]-isoxazol-5-ylimino}-methyl)-N,N-dimethyl-guanidine;
[({3-[1-(2'-Fluoro-biphenyl-4-yl)-ethyl]-isoxazol-5-ylimino}-morpholin-4-yl-methylimino)-morpholin-4-yl-methyl]-amine;
[[{3-[1-(2'-Fluoro-biphenyl-4-yl)-ethyl]-isoxazol-5-ylimino}-(4-methyl-piperazin-1-yl)-methylimino]-(4-methyl-piperazin-1-yl)-methyl]-amine;
N-[{3-[1-(2'-Fluoro-biphenyl-4-yl)-ethyl]-isoxazol-5-ylimino}-(2-morpholin-4-yl-ethylamino)-methyl]-N'-(2-morpholin-4-yl-ethyl)-guanidine;
N-[{3-[1-(2'-Fluoro-biphenyl-4-yl)-ethyl]-isoxazol-5-ylimino}-(2-hydroxy-ethylamino)-methyl]-N'-(2-hydroxy-ethyl)-guanidine;
N-{{3-[1-(2'-Fluoro-biphenyl-4-yl)-ethyl]-isoxazol-5-ylimino}-[2-(2-hydroxy-ethoxy)-ethylamino]-methyl}-N'-[2-(2-hydroxy-ethoxy)-ethyl]-guanidine;
N-{3-[1-(2'-Fluoro-biphenyl-4-yl)-ethyl]-isoxazol-5-yl}-N',N''-dimethyl-guanidine
N''-{3-[1-(2'-Fluoro-biphenyl-4-yl)-ethyl]-isoxazol-5-yl}-N,N,N',N'-tetramethyl-guanidine;
(Di-morpholin-4-yl-methylene)-{3-[1-(2'-fluoro-biphenyl-4-yl)-ethyl]-isoxazol-5-yl}-amine;
[Bis-(4-methyl-piperazin-1-yl)-methylene]-{3-[1-(2'-fluoro-biphenyl-4-yl)-ethyl]-isoxazol-5-yl}-amine;
N-{3-[1-(2'-Fluoro-biphenyl-4-yl)-ethyl]-isoxazol-5-yl}-N',N''-bis-(2-morpholin-4-yl-ethyl)-guanidine;
N-{3-[1-(2'-Fluoro-biphenyl-4-yl)-ethyl]-isoxazol-5-yl}-N',N''-bis-(2-hydroxy-ethyl)-guanidine;
N-{3-[1-(2'-Fluoro-biphenyl-4-yl)-ethyl]-isoxazol-5-yl}-N',N''-bis-[2-(2-hydroxy-ethoxy)-ethyl]-guanidine;
N-{3-[1-(2'-Fluoro-biphenyl-4-yl)-1-methyl-ethyl]-isoxazol-5-yl}-N'-methyl-guanidine;
N'-{3-[1-(2'-Fluoro-biphenyl-4-yl)-1-methyl-ethyl]-isoxazol-5-yl}-N,N-dimethyl-guanidine;
N-Ethyl-N'-{3-[1-(2'-fluoro-biphenyl-4-yl)-1-methyl-ethyl]-isoxazol-5-yl}-guanidine;
N,N-Diethyl-N'-{3-[1-(2'-fluoro-biphenyl-4-yl)-1-methyl-ethyl]-isoxazol-5-yl}-guanidine;
({3-[1-(2'-Fluoro-biphenyl-4-yl)-1-methyl-ethyl]-isoxazol-5-ylimino}-pyrrolidin-1-yl-methyl)-amine;
({3-[1-(2'-Fluoro-biphenyl-4-yl)-1-methyl-ethyl]-isoxazol-5-ylimino}-piperidin-1-yl-methyl)-amine;
(Azepan-1-yl-{3-[1-(2'-fluoro-biphenyl-4-yl)-1-methyl-ethyl]-isoxazol-5-ylimino}-methyl)-amine;
({3-[1-(2'-Fluoro-biphenyl-4-yl)-1-methyl-ethyl]-isoxazol-5-ylimino}-morpholin-4-yl-methyl)-amine;
[{3-[1-(2'-Fluoro-biphenyl-4-yl)-1-methyl-ethyl]-isoxazol-5-ylimino}-(4-methyl-piperazin-1-yl)-methyl]-amine;
({3-[1-(2'-Fluoro-biphenyl-4-yl)-1-methyl-ethyl]-isoxazol- 5-ylimino}-thiazolidin-3-yl-methyl)-amine;
[{3-[1-(2'-Fluoro-biphenyl-4-yl)-1-methyl-ethyl]-isoxazol-5-ylimino}-(4-methyl-piperidin-1-yl)-methyl]-amine;
((2,6-Dimethyl-morpholin-4-yl)-{3-[1-(2'-fluoro-biphenyl-4-yl)-1-methyl-ethyl]-isoxazol-5-ylimino}-methyl)-amine;
((4-Dimethylamino-piperidin-1-yl)-{3-[1-(2'-fluoro-biphenyl-4-yl)-1-methyl-ethyl]-isoxazol-5-ylimino}-methyl)-amine;
1-(Amino-{3-[1-(2'-fluoro-biphenyl-4-yl)-1-methyl-ethyl]-isoxazol-5-ylimino}-methyl)-piperidin-4-one;
1-(Amino-{3-[1-(2'-fluoro-biphenyl-4-yl)-1-methyl-ethyl]-isoxazol-5-ylimino}-methyl)-piperidin-2-one;
1-(Amino-{3-[1-(2'-fluoro-biphenyl-4-yl)-1-methyl-ethyl]-isoxazol-5-ylimino}-methyl)-piperidin-4-ol;
[{3-[1-(2'-Fluoro-biphenyl-4-yl)-1-methyl-ethyl]-isoxazol-5-ylimino}-(4-methoxy-piperidin-1-yl)-methyl]-amine;
({3-[1-(2'-Fluoro-biphenyl-4-yl)-1-methyl-ethyl]-isoxazol-5-ylimino}-[1,4]thiazinan-4-yl-methyl)-amine;
1-[4-(Amino-{3-[1-(2'-fluoro-biphenyl-4-yl)-1-methyl-ethyl]-isoxazol-5-ylimino}-methyl)-piperazin-1-yl]-ethanone;
N-{3-[1-(2'-Fluoro-biphenyl-4-yl)-1-methyl-ethyl]-isoxazol-5-yl}-N'-(2-oxo-propyl)-guanidine;
Ethyl (N'-{3-[1-(2'-fluoro-biphenyl-4-yl)-1-methyl-ethyl]-isoxazol-5-yl}-guanidino)-acetate;
Ethyl 3-(N'-{3-[1-(2'-fluoro-biphenyl-4-yl)-1-methyl-ethyl]-isoxazol-5-yl}-guanidino)-propionate;
2-(N'-{3-[1-(2'-Fluoro-biphenyl-4-yl)-1-methyl-ethyl]-isoxazol-5-yl}-guanidino)-N,N-dimethyl-acetamide;
3-(N'-{3-[1-(2'-Fluoro-biphenyl-4-yl)-1-methyl-ethyl]-isoxazol-5-yl}-guanidino)-N,N-dimethyl-propionamide;
N-{3-[1-(2'-Fluoro-biphenyl-4-yl)-1-methyl-ethyl]-isoxazol-5-yl}-N'-(2-hydroxy-ethyl)-guanidine;
N-{3-[1-(2'-Fluoro-biphenyl-4-yl)-1-methyl-ethyl]-isoxazol-5-yl}-N'-(3-hydroxy-propyl)-guanidine;
N-{3-[1-(2'-Fluoro-biphenyl-4-yl)-1-methyl-ethyl]-isoxazol-5-yl}-N'-(2-methoxy-ethyl)-guanidine;
N-(2-Dimethylamino-ethyl)-N'-{3-[1-(2'-fluoro-biphenyl-4-yl)-1-methyl-ethyl]-isoxazol-5-yl}-guanidine;
N-{3-[1-(2'-Fluoro-biphenyl-4-yl)-1-methyl-ethyl]-isoxazol-5-yl}-N'-(2-pyrrolidin-1-yl-ethyl)-guanidine;
N-{3-[1-(2'-Fluoro-biphenyl-4-yl)-1-methyl-ethyl]-isoxazol-5-yl}-N'-(2-piperidin-1-yl-ethyl)-guanidine;
N-{3-[1-(2'-Fluoro-biphenyl-4-yl)-1-methyl-ethyl]-isoxazol-5-yl}-N'-(2-morpholin-4-yl-ethyl)-guanidine;
N-{3-[1-(2'-Fluoro-biphenyl-4-yl)-1-methyl-ethyl]-isoxazol-5-yl}-N'-[2-(4-methyl-piperazin-1-yl)-ethyl]-guanidine;
N-{3-[1-(2'-Fluoro-biphenyl-4-yl)-1-methyl-ethyl]-isoxazol-5-yl}-N'-(3-morpholin-4-yl-propyl)-guanidine;
N-{3-[1-(2'-Fluoro-biphenyl-4-yl)-1-methyl-ethyl]-isoxazol-5-yl}-N'-[2-(2-hydroxy-ethoxy)-ethyl]-guanidine;
N-{3-[1-(2'-Fluoro-biphenyl-4-yl)-1-methyl-ethyl]-isoxazol-5-yl}-N'-[2-(2-methoxy-ethoxy)-ethyl]-guanidine;
N-{3-[1-(2'-Fluoro-biphenyl-4-yl)-1-methyl-ethyl]-isoxazol-5-yl}-N'-[2-(3-hydroxy-propoxy)-ethyl]-guanidine;
2-{3-[1-(2'-Fluoro-biphenyl-4-yl)-1-methyl-ethyl]-isoxazol-5-ylimino}-1-methyl-imidazolidin-4-one;

2-{3-[1-(2'-Fluoro-biphenyl-4-yl)-1-methyl-ethyl]-isoxazol-5-ylimino}-1-(2-hydroxy-ethyl)-imidazolidin-4-one;

2-{3-[1-(2'-Fluoro-biphenyl-4-yl)-1-methyl-ethyl]-isoxazol-5-ylimino}-1-(2-methoxy-ethyl)-imidazolidin-4-one;

N-({3-[1-(2'-Fluoro-biphenyl-4-yl)-1-methyl-ethyl]-isoxazol-5-ylimino}-methylamino-methyl)-N'-methyl-guanidine;

N'-(Dimethylamino-{3-[1-(2'-fluoro-biphenyl-4-yl)-1-methyl-ethyl]-isoxazol-5-ylimino}-methyl)-N,N-dimethyl-guanidine;

[({3-[1-(2'-Fluoro-biphenyl-4-yl)-1-methyl-ethyl]-isoxazol-5-ylimino}-morpholin-4-yl-methylimino)-morpholin-4-yl-methyl]-amine;

[[{3-[1-(2'-Fluoro-biphenyl-4-yl)-1-methyl-ethyl]-isoxazol-5-ylimino}-(4-methyl-piperazin-1-yl)-methylimino]-(4-methyl-piperazin-1-yl)-methyl]-amine;

N-[{3-[1-(2'-Fluoro-biphenyl-4-yl)-1-methyl-ethyl]-isoxazol-5-ylimino}-(2-morpholin-4-yl-ethylamino)-methyl]-N'-(2-morpholin-4-yl-ethyl)-guanidine;

N-[{3-[1-(2'-Fluoro-biphenyl-4-yl)-1-methyl-ethyl]-isoxazol-5-ylimino}-(2-hydroxy-ethylamino)-methyl]-N'-(2-hydroxy-ethyl)-guanidine;

N-{{3-[1-(2'-Fluoro-biphenyl-4-yl)-1-methyl-ethyl]-isoxazol-5-ylimino}-[2-(2-hydroxy-ethoxy)-ethylamino]-methyl}-N'-[2-(2-hydroxy-ethoxy)-ethyl]-guanidine;

N-{3-[1-(2'-Fluoro-biphenyl-4-yl)-1-methyl-ethyl]-isoxazol-5-yl}-N',N''-dimethyl-guanidine;

N''-{3-[1-(2'-Fluoro-biphenyl-4-yl)-1-methyl-ethyl]-isoxazol-5-yl}-N,N,N',N'-tetramethyl-guanidine;

(Di-morpholin-4-yl-methylene)-{3-[1-(2'-fluoro-biphenyl-4-yl)-1-methyl-ethyl]-isoxazol-5-yl}-amine;

[Bis-(4-methyl-piperazin-1-yl)-methylene]-{3-[1-(2'-fluoro-biphenyl-4-yl)-1-methyl-ethyl]-isoxazol-5-yl}-amine;

N-{3-[1-(2'-Fluoro-biphenyl-4-yl)-1-methyl-ethyl]-isoxazol-5-yl}-N',N''-bis-(2-morpholin-4-yl-ethyl)-guanidine;

N-{3-[1-(2'-Fluoro-biphenyl-4-yl)-1-methyl-ethyl]-isoxazol-5-yl}-N',N''-bis-(2-hydroxy-ethyl)-guanidine;

N-{3-[1-(2'-Fluoro-biphenyl-4-yl)-1-methyl-ethyl]-isoxazol-5-yl}-N',N''-bis-[2-(2-hydroxy-ethoxy)-ethyl]-guanidine;

N-{3-[1-(3-Benzoyl-phenyl)-ethyl]-isoxazol-5-yl}-N'-methyl-guanidine;

N-{3-[1-(3-Benzoyl-phenyl)-ethyl]-isoxazol-5-yl}-N'-ethyl-guanidine;

N'-{3-[1-(3-Benzoyl-phenyl)-ethyl]-isoxazol-5-yl}-N,N-diethyl-guanidine;

(3-{1-[5-(Amino-pyrrolidin-1-yl-methyleneamino)-isoxazol-3-yl]-ethyl}-phenyl)-phenyl-methanone;

(3-{1-[5-(Amino-azepan-1-yl-methyleneamino)-isoxazol-3-yl]-ethyl}-phenyl)-phenyl-methanone;

[3-(1-{5-[Amino-(4-methyl-piperazin-1-yl)-methylenemaino]-isoxazol-3-yl}-ethyl)-phenyl]-phenyl-methanone;

(3-{1-[5-(Amino-thiazolidin-3-yl-methyleneamino)-isoxazol-3-yl]-ethyl}-phenyl)-phenyl-methanone;

[3-(1-{5-[Amino-(4-methyl-piperidin-1-yl)-methyleneamino]-isoxazol-3-yl}-ethyl)-phenyl]-phenyl-methanone;

[3-(1-{5-[Amino-(2,6-dimethyl-morpholin-4-yl)-methyleneamino]-isoxazol- 3-yl}-ethyl)-phenyl]-phenyl-methanone;

[3-(1-{5-[Amino-(4-dimethylamino-piperidin-1-yl)-methyleneamino]-isoxazol-3-yl}-ethyl)-phenyl]-phenyl-methanone;

1-(Amino-{3-[1-(3-benzoyl-phenyl)-ethyl]-isoxazol-5-ylimino}-methyl)-piperidin-4-one;

1-(Amino-{3-[1-(3-benzoyl-phenyl)-ethyl]-isoxazol-5-ylimino}-methyl)-piperidin-2-one;

[3-(1-{5-[Amino-(4-hydroxy-piperidin-1-yl)-methyleneamino]-isoxazol-3-yl}-ethyl)-phenyl]-phenyl-methanone;

[3-(1-{5-[Amino-(4-methoxy-piperidin-1-yl)-methyleneamino]-isoxazol-3-yl}-ethyl)-phenyl]-phenyl-methanone;

(3-{1-[5-(Amino-[1,4]thiazinan-4-yl-methyleneamino)-isoxazol-3-yl]-ethyl}-phenyl)-phenyl-methanone;

1-[4-(Amino-{3-[1-(3-benzoyl-phenyl)-ethyl]-isoxazol-5-ylimino}-methyl)-piperazin-1-yl]-ethanone;

N-{3-[1-(3-Benzoyl-phenyl)-ethyl]-isoxazol-5-yl}-N'-(2-oxo-propyl)-guanidine;

Ethyl (N'-{3-[1-(3-benzoyl-phenyl)-ethyl]-isoxazol-5-yl}-guanidino)-acetate;

Ethyl 3-(N'-{3-[1-(3-benzoyl-phenyl)-ethyl]-isoxazol-5-yl}-guanidino)-propionate;

2-(N'-{3-[1-(3-Benzoyl-phenyl)-ethyl]-isoxazol-5-yl}-guanidino)-N,N-dimethyl-acetamide;

3-(N'-{3-[1-(3-Benzoyl-phenyl)-ethyl]-isoxazol-5-yl}-guanidino)-N,N-dimethyl-propionamide;

N-{3-[1-(3-Benzoyl-phenyl)-ethyl]-isoxazol-5-yl}-N'-(2-hydroxy-ethyl)-guanidine;

N-{3-[1-(3-Benzoyl-phenyl)-ethyl]-isoxazol-5-yl}-N'-(3-hydroxy-propyl)-guanidine;

N-{3-[1-(3-Benzoyl-phenyl)-ethyl]-isoxazol-5-yl}-N'-(2-methoxy-ethyl)-guanidine;

N-{3-[1-(3-Benzoyl-phenyl)-ethyl]-isoxazol-5-yl}-N'-(2-dimethylamino-ethyl)-guanidine;

N-{3-[1-(3-Benzoyl-phenyl)-ethyl]-isoxazol-5-yl}-N'-(2-pyrrolidin-1-yl-ethyl)-guanidine;

N-{3-[1-(3-Benzoyl-phenyl)-ethyl]-isoxazol-5-yl}-N'-(2-piperidin-1-yl-ethyl)-guanidine;

N-{3-[1-(3-Benzoyl-phenyl)-ethyl]-isoxazol-5-yl}-N'-(2-morpholin-4-yl-ethyl)-guanidine;

N-{3-[1-(3-Benzoyl-phenyl)-ethyl]-isoxazol-5-yl}-N'-[2-(4-methyl-piperazin-1-yl)-ethyl]-guanidine;

N-{3-[1-(3-Benzoyl-phenyl)-ethyl]-isoxazol-5-yl}-N'-(3-morpholin-4-yl-propyl)-guanidine;

N-{3-[1-(3-Benzoyl-phenyl)-ethyl]-isoxazol-5-yl}-N'-[2-(2-hydroxyl-ethoxy)-ethyl]-guanidine;

N-{3-[1-(3-Benzoyl-phenyl)-ethyl]-isoxazol-5-yl}-N'-[2-(2-methoxy-ethoxy)-ethyl]-guanidine;

N-{3-[1-(3-Benzoyl-phenyl)-ethyl]-isoxazol-5-yl}-N'-[2-(3-hydroxy-propoxy)-ethyl]-guanidine;

2-{3-[1-(3-Benzoyl-phenyl)-ethyl]-isoxazol-5-ylimino}-1-methyl-imidazolidin-4-one;

2-{3-[1-(3-Benzoyl-phenyl)-ethyl]-isoxazol-5-ylimino}-1-(2-hydroxy-ethyl)-imidazolidin-4-one;

2-{3-[1-(3-Benzoyl-phenyl)-ethyl]-isoxazol-5-ylimino}-1-(2-methoxy-ethyl)-imidazolidin-4-one;

N-({3-[1-(3-Benzoyl-phenyl)-ethyl]-isoxazol-5-ylimino}-methylamino-methyl)-N'-methyl-guanidine;

N'-({3-[1-(3-Benzoyl-phenyl)-ethyl]-isoxazol-5-ylimino}-dimethylamino-methyl)-N,N-dimethyl-guanidine;

[3-(1-{5-[(Amino-morpholin-4-yl-methyleneamino)-morpholin-4-yl-methyleneamino]-isoxazol-3-yl}-ethyl)-phenyl]-phenyl-methanone;

[3-(1-{5-[[Amino-(4-methyl-piperazin-1-yl)-methyleneamino]-(4-methyl-piperazin-1-yl)-methyleneamino]-isoxazol-3-yl}-ethyl)-phenyl]-phenyl-methanone;

N-[{3-[1-(3-Benzoyl-phenyl)-ethyl]-isoxazol-5-ylimino}-(2-morpholin-4-yl-ethylamino)-methyl]-N'-(2-morpholin-4-yl-ethyl)-guanidine;

N-[{3-[1-(3-Benzoyl-phenyl)-ethyl]-isoxazol-5-ylimino}-(2-(hydroxy-ethylamino)-methyl]-N'-(2-hydroxy-ethyl)-guanidine;

N-{{3-[1-(3-Benzoyl-phenyl)-ethyl]-isoxazol-5-ylimino}-[2-(2-hydroxy-ethoxy)-ethylamino]-methyl}-N'-[2-(2-hydroxy-ethoxy)-ethyl]-guanidine;

N-{3-[1-(3-Benzoyl-phenyl)-ethyl]-isoxazol-5-yl}-N',N"-dimethyl-guanidine;

N"-{3-[1-(3-Benzoyl-phenyl)-ethyl]-isoxazol-5-yl}-N,N,N',N'-tetramethyl-guanidine;

(3-{1-[5-(Di-morpholin-4-yl-methyleneamino)-isoxazol-3-yl]-ethyl}-phenyl)-phenyl-methanone;

[3-(1-{5-[Bis-(4-methyl-piperazin-1-yl)-methyleneamino]-isoxazol-3-yl}-ethyl)-phenyl]-phenyl-methanone;

N-{3-[1-(3-Benzoyl-phenyl)-ethyl)-isoxazol-5-yl}-N',N"-bis-(2-morpholin-4-yl-ethyl)-guanidine;

N-{3-[1-(3-Benzoyl-phenyl)-ethyl]-isoxazol-5-yl}-N',N"-bis-(2-hydroxy-ethyl)-guanidine;

N-{3-[1-(3-Benzoyl-phenyl)-ethyl]-isoxazol-5-yl}-N',N"-bis-[2-(2-hydroxy-ethoxy)-ethyl]-guanidine;

N-{3-[1-(3-Benzoyl-phenyl)-1-methyl-ethyl]-isoxazol-5-yl}-N'-methyl-guanidine;

N'-{3-[1-(3-Benzoyl-phenyl)-1-methyl-ethyl]-isoxazol-5-yl}-N,N-dimethyl-guanidine;

N-{3-[1-(3-Benzoyl-phenyl)-1-methyl-ethyl]-isoxazol-5-yl}-N'-ethyl-guanidine;

N'-{3-[1-(3-Benzoyl-phenyl)-1-methyl-ethyl]-isoxazol-5-yl}-N,N-diethyl-guanidine;

(3-{1-[5-(Amino-pyrrolidin-1-yl-methyleneamino)-isoxazol-3-yl]-1-methyl-ethyl}-phenyl)-phenyl-methanone;

(3-{1-[5-(Amino-piperidin-1-yl-methyleneamino)-isoxazol-3-yl]-1-methyl-ethyl}-phenyl)-phenyl-methanone;

(3-{1-[5-(Amino-azepan-1-yl-methyleneamino)-isoxazol-3-yl]-1-methyl-ethyl}-phenyl)-phenyl-methanone;

(3-{1-[5-(Amino-morpholin-4-yl-methyleneamino)-isoxazol-3-yl]-1-methyl-ethyl}-phenyl)-phenyl-methanone;

[3-(1-{5-[Amino-(4-methyl-piperazin-1-yl)-methyleneamino]-isoxazol-3-yl}-1-methyl-ethyl)-phenyl]-phenyl-methanone;

(3-{1-[5-(Amino-thiazolidin-3-yl-methyleneamino)-isoxazol-3-yl]-1-methyl-ethyl}-phenyl)-phenyl-methanone;

[3-(1-{5-[Amino-(4-methyl-piperidin-1-yl)-methyleneamino]-isoxazol-3-yl}-1-methyl-ethyl)-phenyl]-phenyl-methanone;

[3-(1-{5-[Amino-(2,6-dimethyl-morpholin-4-yl)-methyleneamino]-isoxazol-3-yl}-1-methyl-ethyl)-phenyl]-phenyl-methanone;

[3-(1-{5-[Amino-(4-dimethylamino-piperidin-1-yl)-methyleneamino]-isoxazol-3-yl}-1-methyl-ethyl)-phenyl]-phenyl-methanone;

1-(Amino-{3-[1-(3-benzoyl-phenyl)-1-methyl-ethyl]-isoxazol-5-ylimino}-methyl)-piperidin-4-one;

1-(Amino-{3-[1-(3-benzoyl-phenyl)-1-methyl-ethyl]-isoxazol-5-ylimino}-methyl)-piperidin-2-one;

[3-(1-{5-[Amino-(4-hydroxy-piperidin-1-yl)-methyleneamino]-isoxazol-3-yl}-1-methyl-ethyl)-phenyl]-phenyl-methanone;

[3-(1-{5-[Amino-(4-methoxy-piperidin-1-yl)-methyleneamino]-isoxazol-3-yl}-1-methyl-ethyl)-phenyl]-phenyl-methanone;

(3-{1-[5-(Amino-[1,4]thiazinan-4-yl-methyleneamino)-isoxazol-3-yl]-1-methyl-ethyl}-phenyl)-phenyl-methanone;

1-[4-(Amino-{3-[1-(3-benzoyl-phenyl)-1-methyl-ethyl]-isoxazol-5-ylimino}-methyl)-piperazin-1-yl]-ethanone;

N-{3-[1-(3-Benzoyl-phenyl)-1-methyl-ethyl]-isoxazol-5-yl}-N'-(2-oxo-propyl)-guanidine;

Ethyl (N'-{3-[1-(3-benzoyl-phenyl)-1-methyl-ethyl]-isoxazol-5-yl}-guanidino)-acetate;

Ethyl 3-(N'-{3-[1-(3-benzoyl-phenyl)-1-methyl-ethyl]-isoxazol-5-yl}-guanidino)-propionate;

2-(N'-{3-[1-(3-Benzoyl-phenyl)-1-methyl-ethyl]-isoxazol-5-yl}-guanidino)-N,N-dimethyl-acetamide;

3-(N'-{3-[1-(3-Benzoyl-phenyl)-1-methyl-ethyl]-isoxazol-5-yl}-guanidino)-N,N-dimethyl-propionamide;

N-{3-[1-(3-Benzoyl-phenyl)-1-methyl-ethyl]-isoxazol-5-yl}-N'-(2-hydroxy-ethyl)-guanidine;

N-{3-[1-(3-Benzoyl-phenyl)-1-methyl-ethyl]-isoxazol-5-yl}-N'-(3-hydroxy-propyl)-guanidine;

N-{3-[1-(3-Benzoyl-phenyl)-1-methyl-ethyl]-isoxazol-5-yl}-N'-(2-methoxy-ethyl)-guanidine;

N-{3-[1-(3-Benzoyl-phenyl)-1-methyl-ethyl]-isoxazol-5-yl}-N'-(2-dimethylamino-ethyl)-guanidine;

N-{3-[1-(3-Benzoyl-phenyl)-1-methyl-ethyl]-isoxazol-5-yl}-N'-(2-pyrrolidin-1-yl-ethyl)-guanidine;

N-{3-[1-(3-Benzoyl-phenyl)-1-methyl-ethyl]-isoxazol-5-yl}-N'-(2-piperidin-1-yl-ethyl)-guanidine;

N-{3-[1-(3-Benzoyl-phenyl)-1-methyl-ethyl]-isoxazol-5-yl}-N'-(2-morpholin-4-yl-ethyl)-guanidine;

N-{3-[1-(3-Benzoyl-phenyl)-1-methyl-ethyl]-isoxazol-5-yl}-N'-[2-(4-methyl-piperazin-1-yl)-ethyl]-guanidine;

N-{3-[1-(3-Benzoyl-phenyl)-1-methyl-ethyl]-isoxazol-5-yl}-N'-(3-morpholin-4-yl-propyl)-guanidine;

N-{3-[1-(3-Benzoyl-phenyl)-1-methyl-ethyl]-isoxazol-5-yl}-N'-[2-(2-hydroxy-ethoxy)-ethyl]-guanidine;

N-{3-[1-(3-Benzoyl-phenyl)-1-methyl-ethyl]-isoxazol-5-yl}-N'-[2-(2-methoxy-ethoxy)-ethyl]-guanidine;

N-{3-[1-(3-Benzoyl-phenyl)-1-methyl-ethyl]-isoxazol-5-yl}-N'-[2-(3-hydroxy-propoxy)-ethyl]-guanidine;

2-{3-[1-(3-Benzoyl-phenyl)-1-methyl-ethyl]-isoxazol-5-ylimino}-1-methyl-imidazolidin-4-one;

2-{3-[1-(3-Benzoyl-phenyl)-1-methyl-ethyl]-isoxazol-5-ylimino}-1-(2-hydroxy-ethyl)-imidazolidin-4-one;

2-{3-[1-(3-Benzoyl-phenyl)-1-methyl-ethyl]-isoxazol-5-ylimino}-1-(2-methoxy-ethyl)-imidazolin-4-one;

N-({3-[1-(3-Benzoyl-phenyl)-1-methyl-ethyl]-isoxazol-5-ylimino}-methylamino-methyl)-N'-methyl-guanidine;

N'-({3-[1-(3-Benzoyl-phenyl)-1-methyl-ethyl]-isoxazol-5-ylimino}-dimethylamino-methyl)-N,N-dimethyl-guanidine;

[3-(1-{5-[(Amino-morpholin-4-yl-methyleneamino)-morpholin-4-yl-methyleneamino]-isoxazol-3-yl}-1-methyl-ethyl)-phenyl]-phenyl-methanone;

[3-(1-{5-[[Amino-(4-methyl-piperazin-1-yl)-methyleneamino]-(4-methyl-piperazin-1-yl)-methyleneamino]-isoxazol-3-yl}-1-methyl-ethyl)-phenyl]-phenyl-methane;

N-[{3-[1-(3-Benzoyl-phenyl)-1-methyl-ethyl]-isoxazol-5-ylimino}-(2-morpholin-4-yl-ethylamino)-methyl]-N'-(2-morpholin-4-yl-ethyl)-guanidine;

N-[{3-[1-(3-Benzoyl-phenyl)-1-methyl-ethyl]-isoxazol-5-ylimino}-(2-hydroxy-ethylamino)-methyll-N'-(2-hydroxy-ethyl)-guanidine;

N-{{3-[1-(3-Benzoyl-phenyl)-1-methyl-ethyl]-isoxazol-5-ylimino}-[2-(2-hydroxy-ethoxy)-ethylamino]-methyl}-N'-[2-(2-hydroxy-ethoxy)-ethyl]-guanidine;

N-{3-[1-(3-Benzoyl-phenyl)-1-methyl-ethyl]-isoxazol-5-yl}-N',N"-dimethyl-guanidine;

N"-{3-[1-(3-Benzoyl-phenyl)-1-methyl-ethyl]-isoxazol-5-yl}-N,N,N',N'-tetramethyl-guanidine;

(3-{1-[5-(Di-morpholin-4-yl-methyleneamino)-isoxazol-3-yl]-1-methyl-ethyl}-phenyl)-phenyl-methanone;

[3-(1-{5-[Bis-(4-methyl-piperazin-1-yl)-methyleneamino]-isoxazol-3-yl)-1-methyl-ethyl)-phenyl]-phenyl-methanone;

N-{3-[1-(3-Benzoyl-phenyl)-1-methyl-ethyl]-isoxazol-5-yl}-N',N''-bis-(2-morpholin-4-yl-ethyl)-guanidine;

N-{3-[1-(3-Benzoyl-phenyl)-1-methyl-ethyl]-isoxazol-5-yl}-N',N''-bis-(2-hydroxy-ethyl)-guanidine;

N-{3-[1-(3-Benzoyl-phenyl)-1-methyl-ethyl]-isoxazol-5-yl}-N',N''-bis-[2-(2-hydroxy-ethoxy)-ethyl]-guanidine;

({3-[1-Ethoxy-1-(2'-fluoro-biphenyl-4-yl)-ethyl]-isoxazol-5-ylimino}-morpholin-4-yl-methyl)-amine;

(3-{1-[5-(Amino-morpholin-4-yl-methyleneamino)-isoxazol-3-yl]-1-ethoxy-ethyl}-phenyl)-phenyl-methanone;

({3-[(2-Fluoro-biphenyl-4-yl)-dimethoxy-methyl]-isoxazol-5-ylimino}-morpholin-4-yl-methyl)-amine;

([3-(1-Biphenyl-4-yl-vinyl)-isoxazol-5-ylimino]-morpholin-4-yl-methyl)-amine;

({3-[1-(1-Methyl-1H-indol-2-yl)-vinyl]-isoxazol-5-ylimino}-morpholin-4-yl-methyl)-amine;

(Morpholin-4-yl-{3-[1-(6-phenyl-pyridazin-3-yl)-ethyl]-isoxazol-5-ylimino}-methyl)-amine;

(Morpholin-4-yl-{3-[1-(5-phenyl-pyrimidin-2-yl)-ethyl]-isoxazol-5-ylimino}-methyl)-amine;

(Morpholin-4-yl-{3-[1-(4-phenyl-pyrimidin-2-yl)-ethyl]-isoxazol-5-ylimino}-methyl)-amine;

(Morpholin-4-yl-[3-(1-quinolin-6-yl-ethyl)-isoxazol-5-ylimino]-methyl}-amine;

N-{3-[1-(2-Fluoro-biphenyl-4-yl)-ethyl]-isoxazol-5-yl}-N'-pyridin-3-ylmethyl-guanidine

EXAMPLES

The present invention is explained below with examples and reference examples but is, of course, not limited by them.

In the examples and the like, the meanings of the abbreviations used are as follows:

Boc: tert-butoxycarbonyl
Tos: p-toluenesulfonyl
Me: methyl
Et: ethyl
Pr$^n$: n-propyl
Bu$^t$: tert-butyl
Ph: phenyl
Ac: Acetyl
TFA: Trifluoroacetic acid
TMS: Trimethylsilyl Example 1

N'-(tert-Butoxycarbonyl)-N''-{3-[1-(2-fluoro-biphenyl-4-yl)-ethyl]-isoxazol-5-yl}-N,N-dimethyl-guanidine

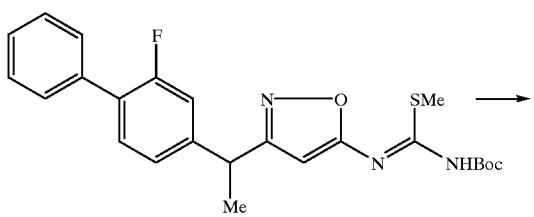

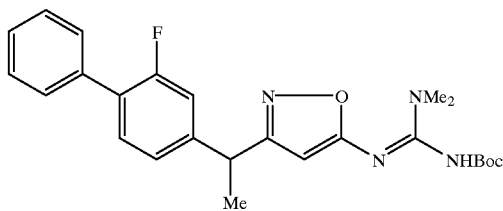

The compound (2.10 g) obtained in Reference Example 2 was dissolved in acetonitrile (100 ml), followed by adding thereto triethylamine (1.77 g), and a 40% aqueous dimethylamine solution (1.04 g) was added dropwise under ice-cooling. Then, a solution of silver nitrate (1.33 g) in acetonitrile (20 ml) was added dropwise over a period of 30 minutes, and the resulting mixture was stirred at room temperature for 18 hours. The insoluble materials were filtered off and washed with acetonitrile, after which the mother liquor was concentrated under reduced pressure and the residue was purified by a silica gel column chromatography to obtain the desired compound (1.76 g).

Melting point 108–111° C. (decomp.).

$^1$H-NMR (270 MHz, CDCl$_3$) δ ppm: 1.43(s, 9H), 1.66(d, 3H, J=7.1 Hz), 3.07(s, 6H), 4.16(q, 1H, J=7.1 Hz), 5.24(s, 1H), 6.74(s, 1H), 7.07–7.17(m, 2H), 7.32–7.54(m, 6H).

IR (KBr) [cm$^{-1}$]: 3383, 2975, 1733, 1614, 1482, 1403.

MS (FD) [m/e]: 452 (M$^+$).

Elementary analysis; Calculated: C 66.35, H 6.46, N 12.38 Found: C 66.22, H 6.45, N 12.46

Example 2

N-(tert-Butoxycarbonyl)-N'-{3-[1-(2-fluoro-biphenyl-4-yl)-ethyl]-isoxazol-5-yl}-N''-ethyl-guanidine

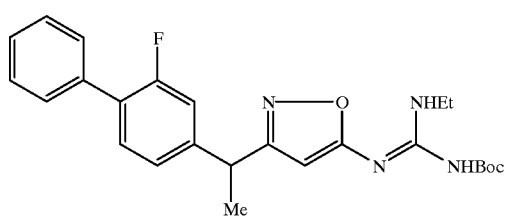

The desired compound was obtained by the same procedure as in Example 1.

Melting point 87–92° C.

$^1$H-NMR (270 MHz, CDCl$_3$) δ ppm: 1.21(t, 3H, J=7.3 Hz), 1.49(s, 9H), 1.67(d, 3H, J=7.3 Hz), 3.40(m, 2H), 4.14(q, 1H, J=7.3 Hz), 5.32(s, 1H), 7.07–7.17(m, 2H), 7.31–7.54(m, 6H), 7.94(br, 1H), 8.48(br, 1H).

IR (KBr) [cm$^{-1}$]: 3410, 3340, 2980, 1730, 1628, 1603, 1556, 1445, 1240, 1152.

Example 3

(tert-Butoxycarbonyl)-({3-[1-(2-fluoro-biphenyl-4-yl)-ethyl]-isoxazol-5-ylimino}-piperidin-1-yl-methyl)-amine

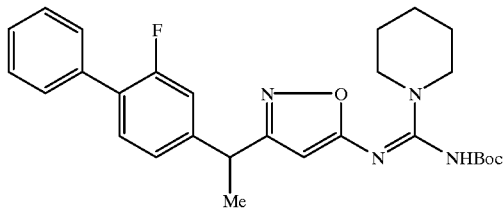

The desired compound was obtained by the same procedure as in Example 1.

$^1$H-NMR (270 MHz, CDCl$_3$) δ ppm: 1.42(s, 9H), 1.65 (br-s, 6H), 1.66(d, 3H, J=6.3 Hz), 3.40–3.60(br, 4H), 4.15(q, 1H, J=6.3 Hz), 5.24(s, 1H), 6.60–6.80(br, 1H), 7.06–7.17(m, 2H), 7.32–7.54(m, 6H).

IR (KBr) [cm$^{-1}$]: 3390, 2940, 1726, 1600, 1483, 1435, 1365, 1152.

Example 4

(tert-Butoxycarbonyl)-({3-[1-(2-fluoro-biphenyl-4-yl)-ethyl]-isoxazol-5-ylimino}-morpholin-4-yl-methyl)-amine

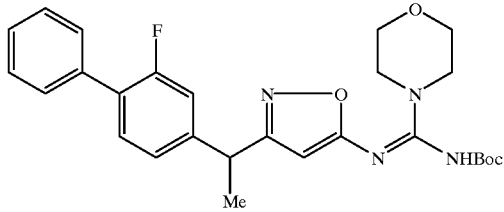

The desired compound was obtained by the same procedure as in Example 1.

Melting point 152–153° C.

$^1$H-NMR (270 MHz, CDCl$_3$) δ ppm: 1.44(s, 9H), 1.67(d, 3H, J=7.2 Hz), 3.57(m, 4H), 3.75(m, 4H), 4.16(q, 1H, J=7.2 Hz), 5.28(s, 1H), 6.86(s, 1H), 7.06–7.16(m, 2H), 7.32–7.53 (m, 6H).

IR (KBr) [cm$^{-1}$]: 3374, 2976, 1726, 1609, 1482, 1431, 1115.

MS (FD) [m/e]: 495 (M+1).

Elementary analysis; Calculated: C 65.57, H 6.32, N 11.33 Found: C 65.45, H 6.39, N 11.36

Example 5 tert-Butyl (N'-(tert-butoxycarbonyl)-N''-{3-[1-(2-fluoro-biphenyl-4-yl)-ethyl]-isoxazol-5-yl}-guanidino)-acetate

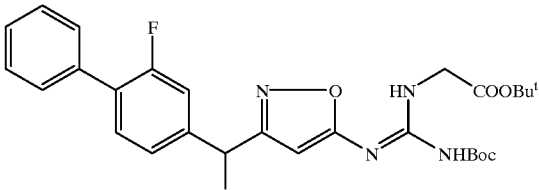

The desired compound was obtained by the same procedure as in Example 1.

Melting point 101.5–103.5° C.

$^1$H-NMR (270 MHz, CDCl$_3$) δ ppm: 1.48(s, 9H), 1.50(s, 9H), 1.66(d, 3H, J=7.3 Hz), 4.03(d, 2H, J=4.6 Hz), 4.14(q, 1H, J=7.3 Hz), 5.31(s, 1H), 7.06–7.16(m, 2H), 7.32–7.54(m, 6H), 8.50–8.52(br-m, 2H).

IR (KBr) [cm$^{-1}$]: 3407, 3351, 2980, 1743, 1643, 1560, 1485, 1452.

MS (FD) [m/e]: 538 (M$^+$).

Elementary analysis; Calculated: C 64.67, H 6.55, N 10.40 Found: C 64.36, H 6.57, N 10.35

Example 6 tert-Butyl (N'-(tert-butoxycarbonyl)-N''-{3-[1-(2-fluoro-biphenyl-4-yl)-ethyl]-isoxazol-5-yl}-N-methyl-guanidino)-acetate

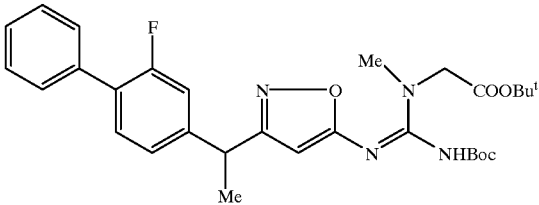

The desired compound was obtained by the same procedure as in Example 1.

Melting point 190–198° C. (decomp.).

$^1$H-NMR (270 MHz, CDCl$_3$) δ ppm: 1.42(s, 9H), 1.47(s, 9H), 1.65(d, 3H, J=7.2 Hz), 3.12(s, 3H), 4.00(s, 2H), 4.12(q, 1H, J=7.2 Hz), 5.29(s, 1H), 6.87(br-s, 1H), 7.06–7.16(m, 2H), 7.32–7.54(m, 6H).

IR (KBr) [cm$^{-1}$]: 3388, 2984, 1744, 1733, 1608, 1483, 1413.

MS (FD) [m/e]: 552 (M$^+$).

Elementary analysis; Calculated: C 65.20, H 6.75, N 10.14 Found: C 64.90, H 6.74, N 9.93

Example 7

Ethyl (N'-(tert-butoxycarbonyl)-N"-{3-[1-(2-fluoro-biphenyl-4-yl)-ethyl]-isoxazol-5-yl}-guanidino)-acetate

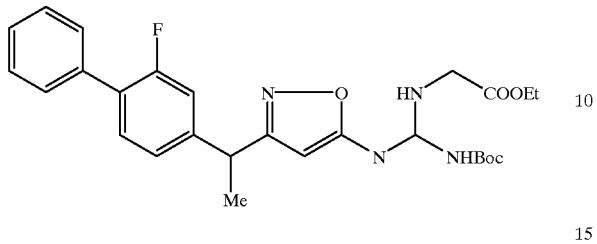

The desired compound was obtained by the same procedure as in Example 1.

$^1$H-NMR (270 MHz, CDCl$_3$) δ ppm: 1.28(t, 3H, J=7.1 Hz), 1.50(s, 9H), 1.66(d, 3H, J=7.3 Hz), 4.12(d, 2H, J=5.0 Hz), 4.16(q, 1H, J=7.3 Hz), 4.23(q, 2H, J=7.1 Hz), 5.33(s, 1H), 7.07–7.16(m, 2H), 7.35–7.54(m, 6H), 8.54(br-m, 2H).

IR (neat) [cm$^{-1}$]: 3398, 2981, 1732, 1634, 1608, 1557, 1486, 1455.

Example 8

N'-Benzoyl-N-{3-[1-(2-fluoro-biphenyl-4-yl)-ethyl]-isoxazol-5-yl}-N-methyl-N"-propyl-guanidine

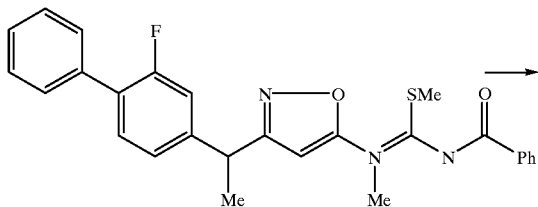

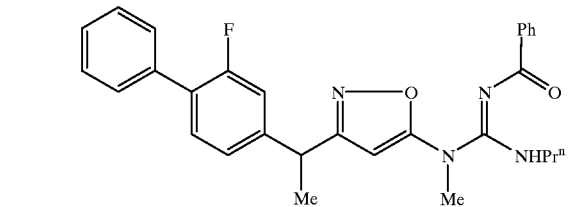

The desired compound was obtained by the same procedure as in Example 1.

$^1$H-NMR (270 MHz, CDCl$_3$) δ ppm: 0.90(t, 3H, J=7.3 Hz), 1.56(sext., 2H, J=7.3 Hz), 1.70(d, 3H, J=7.3 Hz), 2.85–2.97(m, 2H), 3.51(s, 3H), 4.21(q, 1H, J=7.3 Hz), 5.50(s, 1H), 7.02–7.27(m, 3H), 7.32–7.52(m, 8H), 8.17–8.22(m, 2H), 10.30–10.60(m, 1H).

Example 9

N'-Benzoyl-N-{3-[1-(2-fluoro-biphenyl-4-yl)-ethyl]-isoxazol-5-yl}-N,N"-dimethyl-guanidine

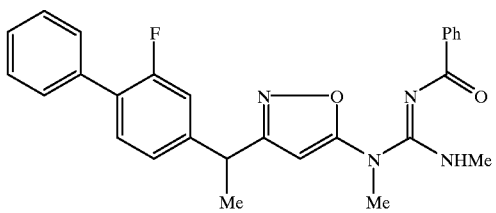

The desired compound was obtained by the same procedure as in Example 1.

$^1$H-NMR (270 MHz, CDCl$_3$) δ ppm: 1.70(d, 3H, J=7.3 Hz), 2.74–2.76(m, 3H), 3.51(s, 3H), 4.21(q, 1H, J=7.3 Hz), 5.49(s, 1H), 7.04–7.16(m, 2H), 7.33–7.55(m, 9H), 8.16–8.22(m, 2H), 10.20–10.55(br, 1H).

IR (neat) [cm$^{-1}$]: 3260, 3070, 2980, 1622, 1495, 1453, 1418, 1396, 1362.

Example 10

N,N'-Di-(tert-butoxycarbonyl)-N"-{5-[1-(2-fluoro-biphenyl-4-yl)-ethyl]-isoxazol-3-ylmethyl}-guanidine

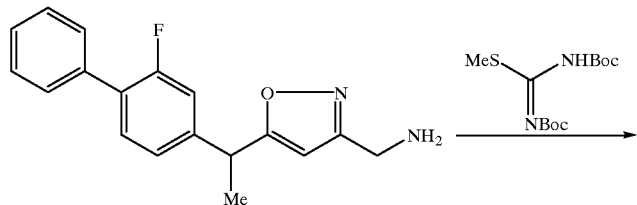

-continued

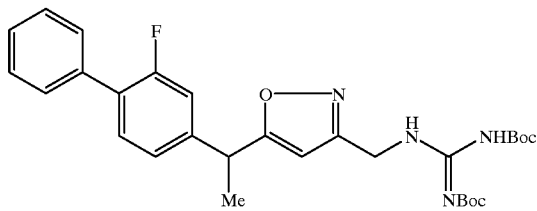

The compound (1.12 g) obtained in Reference Example 10 and 1,3-di-(tert-butoxycarbonyl)-2-methylisothiourea (Japanese Patent Unexamined Publication No. 2-3661) (2.20 g) were dissolved in pyridine (5 ml), followed by adding thereto 1,8-diazabicyclo[5.4.0]undec-7-ene (636 mg), and the resulting mixture was stirred at room temperature for 24 hours. Water was added to the reaction mixture, followed by extraction with ethyl acetate, and the extract solution was washed with water and dried. The solvent was distilled off under reduced pressure and the residue was purified by a silica gel column chromatography to obtain the desired compound (1.24 g).

$^1$H-NMR (270 MHz, CDCl$_3$) δ ppm: 1.49(s, 9H), 1.50(s, 9H), 1.69(d, 3H, J=7.1 Hz), 4.26(q, 1H, J=7.1 Hz), 4.67(d, 2H, J=5.3 Hz), 6.05(s, 1H), 7.03–7.12(m, 2H), 7.33–7.55(m, 6H), 8.84(br-s, 1H), 11.47(br-s, 1H).

Example 11

N,N''-Di-(tert-butoxycarbonyl)-N-{5-[1-(2-fluoro-biphenyl-4-yl)-ethyl]-isoxazol-3-ylmethyl}-N',N'-dimethyl-guanidine

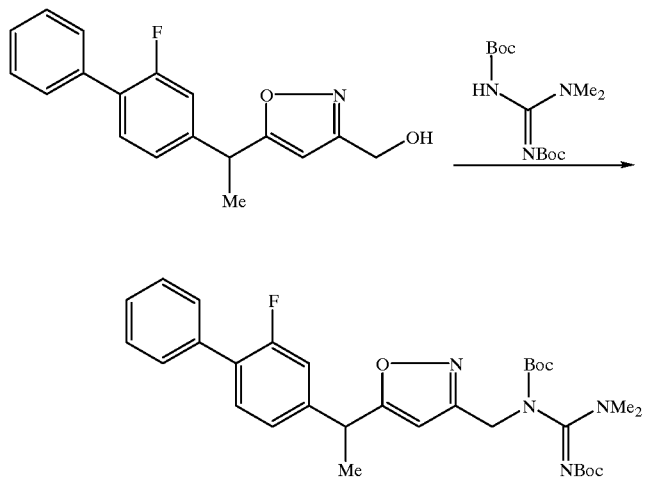

The compound (2.38 g) obtained in Reference Example 7, the compound (2.18 g) obtained in Reference Example 11 and tributylphosphine (3.49 g) were dissolved in tetrahydrofuran, followed by adding thereto 1,1'-(azodicarbonyl)dipiperidine (4.36 g) at 0° C., and the resulting mixture was brought back to room temperature and stirred for 24 hours. Water was added to the reaction mixture, followed by extraction with ethyl acetate, and the extract solution was washed with water and dried. The insoluble materials were filtered off, after which the mother liquor was concentrated under reduced pressure and the residue was purified by a silica gel column chromatography to obtain the desired compound (3.02 g).

$^1$H-NMR (270 MHz, CDCl$_3$) δ ppm: 1.46(s, 9H), 1.49(s, 9H), 1.68(d, 3H, J=7.1 Hz), 2.98(br-s, 6H), 4.25(q, 1H, J=7.1 Hz), 4.26(br-s, 1H), 4.85(br-s, 1H), 6.09(s, 1H), 6.98–7.23(m, 2H), 7.28–7.54(m, 6H).

IR (neat) [cm$^{-1}$]: 2978, 1722, 1680, 1602, 1485, 1417.

MS (FD) [m/e]: 566 (M$^+$).

Example 12

(tert-Butoxycarbonyl)-{5-[1-(2-fluoro-biphenyl-4-yl)-ethyl]-isoxazol-3-ylmethyl}-{morpholin-1-yl-[(tert-butoxycarbonyl)-imino]-methyl}-amine

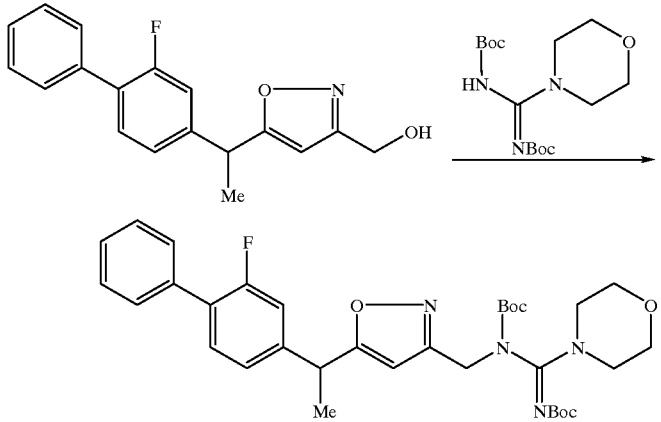

By the same procedure as in Example 11, the desired compound was obtained from the compound obtained in Reference Example 7 and the compound obtained in Reference Example 13.

$^1$H-NMR (270 MHz, CDCl$_3$) δ ppm: 1.46(s, 9H), 1.48(s, 9H), 1.68(d, 3H, J=7.2 Hz), 3.41–3.80(br-m, 8H), 4.23(br-s, 1H), 4.24(q, 1H, J=7.2 Hz), 4.87(br-s, 1H), 6.06(s, 1H), 6.98–7.10(m, 2H), 7.30–7.63(m, 6H).

IR (neat) [cm$^{-1}$]: 2978, 1723, 1683, 1595, 1484, 1111.
MS (FD) [m/e]: 608 (M$^+$).

Example 13

(tert-Butoxycarbonyl)-{5-[1-(2-fluoro-biphenyl-4-yl)-ethyl]-isoxazol-3-ylmethyl}-{piperidin-1-yl-[(tert-butoxycarbonyl)-imino]-methyl}-amine

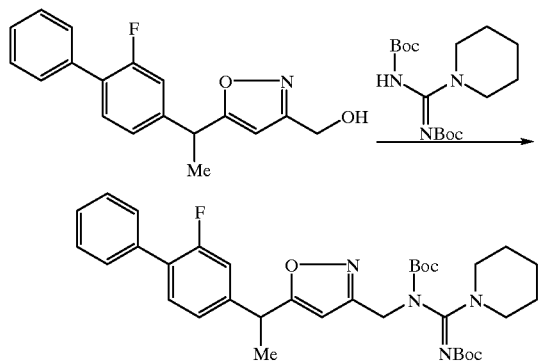

From the compound obtained in Reference Example 7 and the compound obtained in Reference Example 12, the desired compound was obtained by the same process as in Example 11 except for using triphenylphosphine and diethyl azodicarboxylate in place of tributylphosphine and 1,1'-(azodicarbonyl)dipiperidine.

$^1$H-NMR (270 MHz, CDCl$_3$) δ ppm: 1.41–1.54(m, 6H), 1.46(s, 9H), 1.49(s, 9H), 1.68(d, 3H, J=7.3 Hz), 3.19(br-s, 1H), 3.35(br-s, 2H), 3.77(br-s, 1H), 4.22(br-s, 1H), 4.26 (q, 1H, J=7.3 Hz), 4.90(br-s, 1H), 6.12(s, 1H), 6.99–7.11(m, 2H), 7.33–7.54(m, 6H).

Example 14

N,N'-Di-(tert-butoxycarbonyl)-N''-{5-[1-(2-fluoro-biphenyl-4-yl)-ethyl]-isoxazol-3-ylmethyl}-N-methyl-guanidine

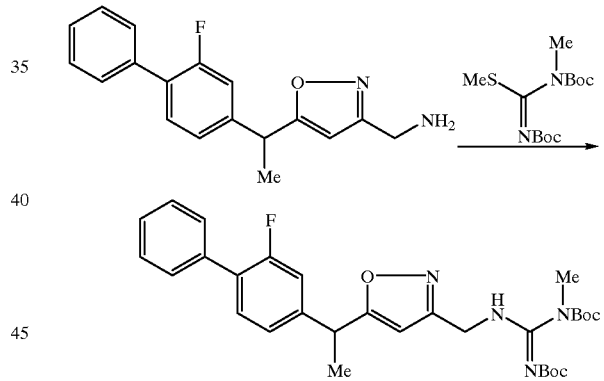

The compound (1.50 g) obtained in Reference Example 10 and the compound (2.00 g) obtained in Reference Example 14 were dissolved in acetonitrile (50 ml), and triethylamine (1.54 g) was added, after which a solution of silver nitrate (2.58 g) in acetonitrile (20 ml) was added dropwise under ice-cooling over a period of 30 minutes, and the resulting mixture was stirred at room temperature for 2 days. The insoluble materials were filtered off and washed with acetonitrile, after which the mother liquor was concentrated under reduced pressure and the residue was purified by a silica gel column chromatography to obtain the desired compound (2.54 g).

$^1$H-NMR (270 MHz, CDCl$_3$) δ ppm: 1.46(s, 9H), 1.48(s, 9H), 1.69(d, 3H, J=7.1 Hz), 3.10(s, 3H), 4.26(q, 1H, J=7.1 Hz), 4.49(s, 2H), 6.04(s, 1H), 7.01–7.11(m, 2H), 7.32–7.53 (m, 6H).

Example 15

1-(tert-Butoxycarbonyl)-2-[(tert-butoxycarbonyl)-imino]-3-{5-[1-(2-fluoro-biphenyl-4-yl)-ethyl]-isoxazol-3-ylmethyl}-imidazolidin-4-one

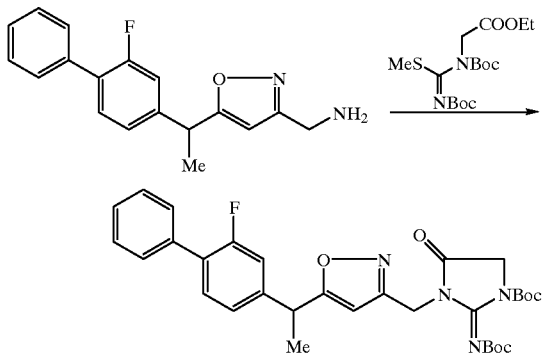

By the same procedure as in Example 14, the desired compound was obtained from the compound obtained in Reference Example 10 and the compound obtained in Reference Example 15.

$^1$H-NMR (270 MHz, CDCl$_3$) δ ppm: 1.51(s, 9H), 1.52(s, 9H), 1.67(d, 3H, J=7.3 Hz), 4.24(q, 1H, J=7.3 Hz), 4.25(s, 2H), 4.81(s, 2H), 6.08(d, 1H, J=1.0 Hz), 7.02–7.11(m, 2H), 7.33–7.55(m, 6H).

IR (KBr) [cm$^{-1}$]: 2980, 1740, 1708, 1659, 1368.

Elementary analysis; Calculated: C 64.35, H 6.10, N 9.68 Found: C 64.02, H 6.24, N 9.60

Example 16

N-({5-[1-(2-Fluoro-biphenyl-4-yl)-ethyl]-isoxazol-3-ylamino}-methylamino-methylene)-4-methyl-benzenesulfonamide

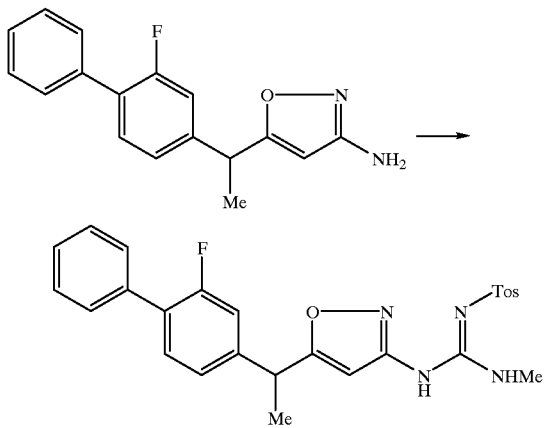

5-[1-(2-Fluoro-biphenyl-4-yl)-ethyl)]-isoxazol-3-ylamine (1.41 g), a well-known compound was added to a solution of N-dichloromethylene-4-methyl-benzenesulfonamide (Chem. Ber., 99, 2900(1966)) (1.33 g) in acetonitrile (40 ml) under ice-cooling. After 30 minutes, triethylamine (0.73 ml) was slowly dropped thereinto and the resulting mixture was stirred under ice-cooling for another 1 hour. Methylamine (2 ml of a 40% ethanolic solution) was added dropwise thereto and stirred for 1 hour, followed by extraction. The extract was purified by a silica gel column chromatography to obtain the desired compound (735 mg).

Melting point 125–127° C.

$^1$H-NMR (270 MHz, CDCl$_3$) δ ppm: 1.70(d, 3H, J=7.3 Hz), 2.39(s, 3H), 2.95(d, 3H, J=4.6 Hz), 4.22(q, 1H, J=7.3 Hz), 5.87(d, 1H, J=0.7 Hz), 7.01–7.11(m, 2H), 7.25(d, 2H, J=8.4 Hz), 7.34–7.55(m, 6H), 7.80(d, 2H, J=8.4 Hz), 7.97 (m, 1H), 10.12(s, 1H).

Example 17

N-{3-[1-(2-Fluoro-biphenyl-4-yl)-ethyl]-isoxazol-5-yl}-guanidine

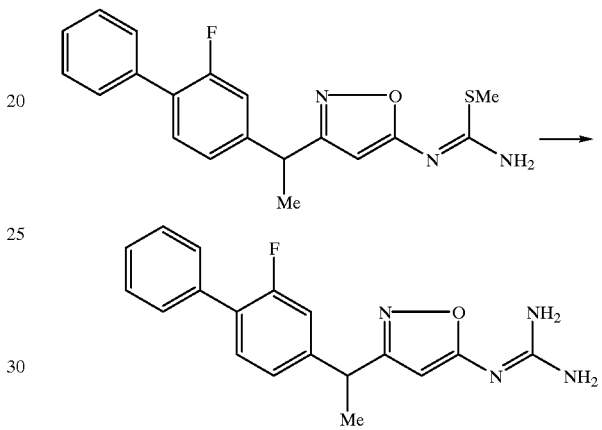

The compound (500 mg) obtained in Reference Example 1 was dissolved in N,N-dimethylformamide (2 ml), and ammonium acetate (5.00 g) was added, after which the resulting mixture was stirred at 120° C., and ammonia gas was introduced thereinto for 1.5 hours. A saturated aqueous sodium chloride solution was added to the reaction mixture, followed by extraction with ethyl acetate, and the extract solution was washed with water and dried. The solvent was distilled off under reduced pressure and the residue was purified by a silica gel column chromatography to obtain the desired compound (316 mg).

$^1$H-NMR (270 MHz, d$_6$-DMSO) δ ppm: 1.54(d, 3H, J=7.1 Hz), 4.08(q, 1H, J=7.1 Hz), 5.32(s, 1H), 6.02(br-s, 4H), 7.21–7.25(m, 2H), 7.38–7.54(m, 6H).

IR (KBr) [cm$^{-1}$]: 3449, 3345, 3106, 1657, 1614, 1562, 1472, 1414.

Example 18

N-{3-[1-(2-Fluoro-biphenyl-4-yl)-ethyl]-isoxazol-5-yl}-N'-methyl-guanidine hydrochloride

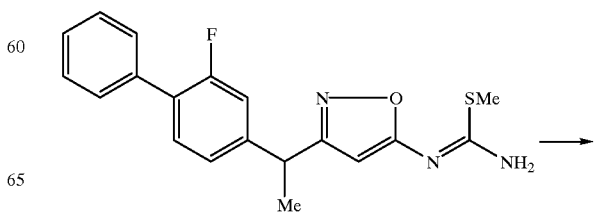

-continued

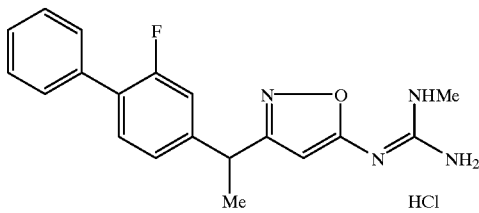

The compound (600 mg) obtained in Reference Example 1 was dissolved in N,N-dimethylformamide (5 ml), followed by adding thereto a methylamine-water-acetic acid solution prepared from a 40% aqueous methylamine solution (1.31 g) and acetic acid (10 ml), and the resulting mixture was stirred at 120° C. for 30 minutes. Chloroform (50 ml) and a 5 M aqueous sodium hydroxide solution (300 ml) were added to the reaction mixture, followed by extraction with chloroform, and the extract solution was washed with water and dried. The solvent was distilled off under reduced pressure and the residue was purified by a silica gel column chromatography and treated with a hydrogen chloride-isopropanol solution to obtain the desired compound (367 mg).

$^1$H-NMR (270 MHz, CDCl$_3$) δ ppm: 1.64(d, 3H, J=7.2 Hz), 2.85(s, 3H), 4.12(q, 1H, J=7.2 Hz), 5.19(s, 1H), 5.30 (br-s, 2H), 5.59(br-s, 1H), 7.06–7.15(m, 2H), 7.33–7.53(m, 6H).

IR (KBr) [cm$^{-1}$]: 3144, 1680, 1637, 1484, 1417.

Example 19

N'-{3-[1-(2-Fluoro-biphenyl-4-yl)-ethyl]-isoxazol-5-yl}-N,N-dimethyl-guanidine hydrochloride

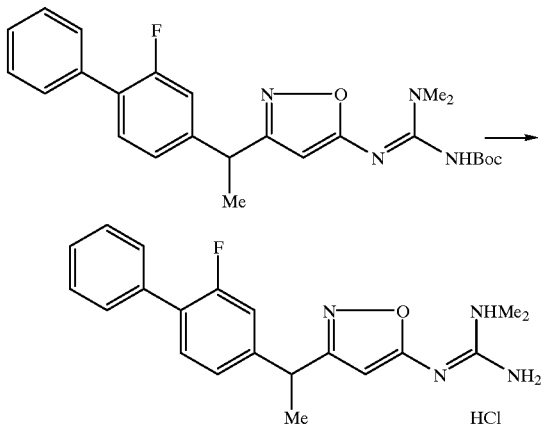

The compound (1.68 g) obtained in Example 1 was dissolved in methylene chloride (20 ml), followed by adding thereto trifluoroacetic acid (12 ml), and the resulting mixture was stirred at room temperature for 2 hours and the solvent was distilled off under reduced pressure. The residue was dissolved in methylene chloride and treated with a hydrogen chloride-diethyl ether solution to obtain the desired compound (1.39 g).

Melting point 73–81° C. (decomp.).

$^1$H-NMR (270 MHz, d$_6$-DMSO) δ ppm: 1.61(d, 3H, J=7.0 Hz), 3.08(s, 6H), 4.29(q, 1H, J=7.0 Hz), 6.04(s, 1H), 7.26–7.34(m, 2H), 7.37–7.55(m, 6H), 8.27(br-s, 2H).

IR (KBr) [cm$^{-1}$]: 3132, 1673, 1634, 1484, 1417.

Example 20

N-Ethyl-N'-{3-[1-(2-fluoro-biphenyl-4-yl)-ethyl]-isoxazol-5-yl}-guanidine hydrochloride

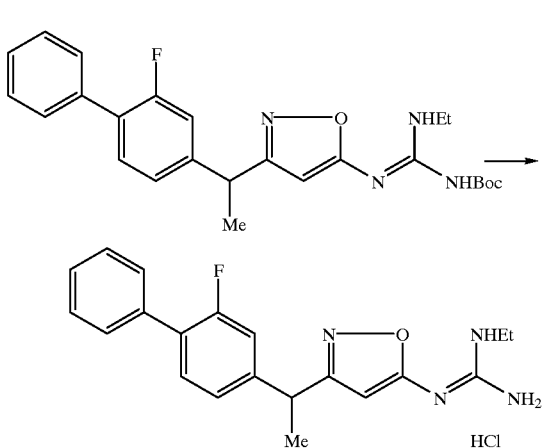

The desired compound was obtained by the same procedure as in Example 19 except for using the compound obtained in Example 2.

$^1$H-NMR (270 MHz, d$_6$-DMSO) δ ppm: 1.13(t, 3H, J=7.1 Hz), 1.60(d, 3H, J=7.3 Hz), 3.31(q, 2H, J=7.1 Hz), 4.29(q, 1H, J=7.3 Hz), 6.17(s, 1H), 7.24–7.52(m, 8H), 8.10–8.70(br, 2H), 8.45–8.65(br, 1H), 11.30–11.65(br, 1H).

IR (KBr) [cm$^{-1}$]: 3600–2400, 2980, 1675, 1623, 1580, 1482, 1415, 1131.

Example 21

({3-[1-(2-Fluoro-biphenyl-4-yl)-ethyl]-isoxazol-5-ylimino}-piperidin-1-yl-methyl)-amine hydrochloride

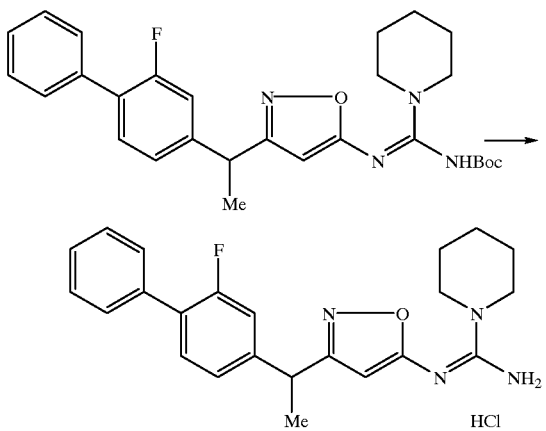

The desired compound was obtained by the same procedure as in Example 19 except for using the compound obtained in Example 3.

$^1$H-NMR (270 MHz, CDCl$_3$) δ ppm: 1.55–1.75(m, 9H), 3.52(br, 4H), 4.15(q, 1H, J=7.3 Hz), 5.71(s, 1H), 7.02–7.12 (m, 2H), 7.31–7.50(m, 6H), 8.30(br, 2H), 11.20(br, 1H).

IR (KBr) [cm$^{-1}$]: 3600–2500, 2945, 1660, 1633, 1538, 1484, 1447, 1418.

Example 22

({3-[1-(2-Fluoro-biphenyl-4-yl)-ethyl]-isoxazol-5-ylimino}-morpholin-4-yl-methyl)-amine hydrochloride

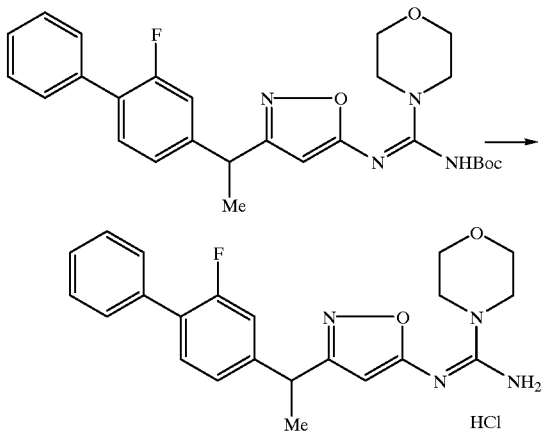

The desired compound was obtained by the same procedure as in Example 19 except for using the compound obtained in Example 4.

Melting point 174–176° C. (decomp.).

$^1$H-NMR (270 MHz, $d_6$-DMSO) δ ppm: 1.60(d, 3H, J=7.1 Hz), 3.56(m, 4H), 3.67(m, 4H), 4.28(q, 1H, J=7.1 Hz), 6.02(s, 1H), 7.26–7.37(m, 2H), 7.38–7.54(m, 6H), 8.51(br-s, 2H).

Example 23

(N'-{3-[1-(2-Fluoro-biphenyl-4-yl)-ethyl]-isoxazol-5-yl}-guanidino)-acetic acid hydrochloride

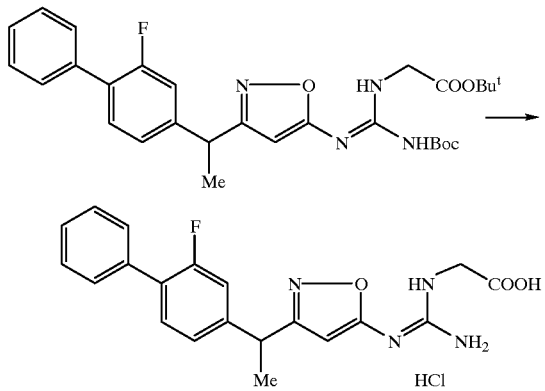

The desired compound was obtained by the same procedure as in Example 19 except for using the compound obtained in Example 5.

Melting point 62° C. (decomp.).

$^1$H-NMR (270 MHz, CDCl$_3$) δ ppm: 1.54(d, 3H, J=7.1 Hz), 3.85(d, 2H, J=5.6 Hz), 4.10(q, 1H, J=7.1 Hz), 5.40(s, 1H), 6.19(br-s, 2H), 6.41(t, 1H, J=5.6 Hz), 7.21–7.24(m, 2H), 7.36–7.54(m, 6H).

IR (KBr) [cm$^{-1}$]: 3142, 2978, 1684, 1624, 1484, 1411.

Example 24

2-{3-[1-(2-Fluoro-biphenyl-4-yl)-ethyl]-isoxazol-5-ylimino}-1-methyl-imidazolidin-4-one hydrochloride

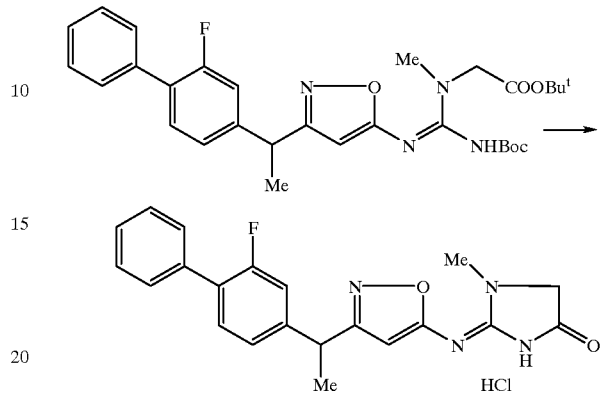

The desired compound was obtained by the same procedure as in Example 19 except for using the compound obtained in Example 6.

Melting point 158–160° C. (decomp.).

$^1$H-NMR (270 MHz, CDCl$_3$) δ ppm: 1.66(d, 3H, J=7.1 Hz), 3.07(s, 3H), 3.97(s, 2H), 4.16(q, 1H, J=7.1 Hz), 5.41(s, 1H), 7.05–7.15(m, 2H), 7.32–7.54(m, 6H), 8.91(br-s, 1H).

IR (KBr) [cm$^{-1}$]: 3153, 2972, 1761, 1668, 1603, 1578, 1484, 1452, 1418.

Example 25

Ethyl (N'-{3-[1-(2-fluoro-biphenyl-4-yl)-ethyl]-isoxazol-5-yl}-guanidino)-acetate hydrochloride

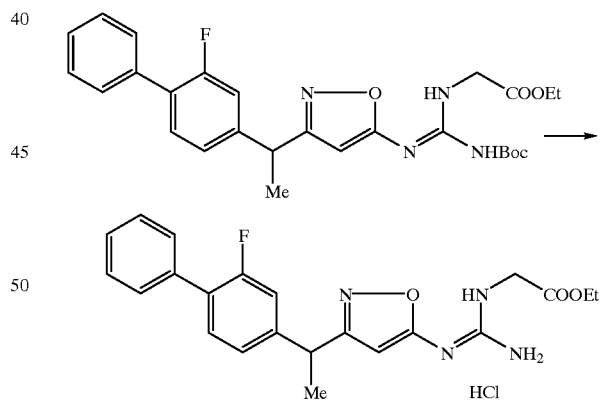

The desired compound was obtained by the same procedure as in Example 19 except for using the compound obtained in Example 7.

Melting point 144–146° C. (decomp.).

$^1$H-NMR (270 MHz, CDCl$_3$) δ ppm: 1.26(t, 3H, J=7.1 Hz), 1.65(d, 3H, J=7.3 Hz), 4.16–4.28(m, 3H), 4.38(s, 2H), 5.78(s, 1H), 7.02–7.10(m, 2H), 7.32–7.56(m, 6H), 8.00–8.30(m, 2H).

IR (KBr) [cm$^{-1}$]: 3088, 2981, 1736, 1684, 1650, 1589, 1485, 1413.

Example 26

N-{5-[1-(2-Fluoro-biphenyl-4-yl)-ethyl]-isoxazol-3-ylmethyl}-guanidine

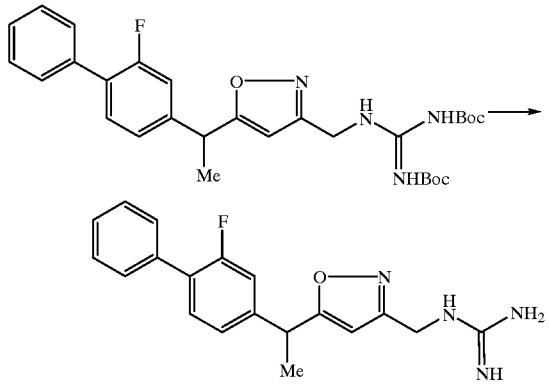

The compound (1.24 g) obtained in Example 10 was dissolved in trifluoroacetic acid (10 ml), and the solution was stirred at room temperature for 2 hours and then the solvent was distilled off under reduced pressure. The residue was dissolved in ethyl acetate and the resulting solution was neutralized with a 1N aqueous sodium hydroxide solution, after which the organic layer was separated, washed with water, dried and then concentrated under reduced pressure. The residue was purified by a silica gel column chromatography to obtain the desired compound (562 mg).

$^1$H-NMR (270 MHz, CDCl$_3$) δ ppm: 1.50(d, 3H, J=6.9 Hz), 4.12(q, 1H, J=6.9 Hz), 4.42(br-s, 2H), 6.08(s, 1H), 6.90–6.97(m, 2H), 7.19–7.57(m, 9H), 8.21(br-s, 1H).

Example 27

N'-{5-[1-(2-Fluoro-biphenyl-4-yl)-ethyl]-isoxazol-3-ylmethyl}-N,N-dimethyl-guanidine hydrochloride

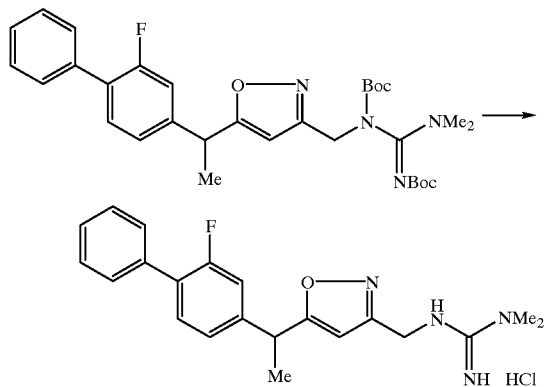

The compound (2.69 g) obtained in Example 11 was dissolved in a solution of trifluoroacetic acid (10 ml) in water (10 ml), and the resulting solution was stirred at room temperature for 2 hours. The solvent was distilled off under reduced pressure. The residue was dissolved in methylene chloride and treated with a hydrogen chloride-diethyl ether solution to obtain the desired compound (897 mg).

$^1$H-NMR (270 MHz, d$_6$-DMSO) δ ppm: 1.62(d, 3H, J=7.0 Hz), 3.00(s, 6H), 4.47(q, 1H, J=7.0 Hz), 4.53(d, 2H, J=5.9 Hz), 6.40(s, 1H), 7.22–7.28(m, 2H), 7.37–7.54(m, 6H), 7.69(br-s, 2H), 8.06(t, 1H, J=5.9 Hz).

IR (KBr) [cm$^{-1}$]: 3422, 3228, 1658, 1630, 1562, 1485, 1418.

Example 28

({5-[1-(2-Fluoro-biphenyl-4-yl)-ethyl]-isoxazol-3-ylmethylimino}-morpholin-4-yl-methyl)-amine hydrochloride

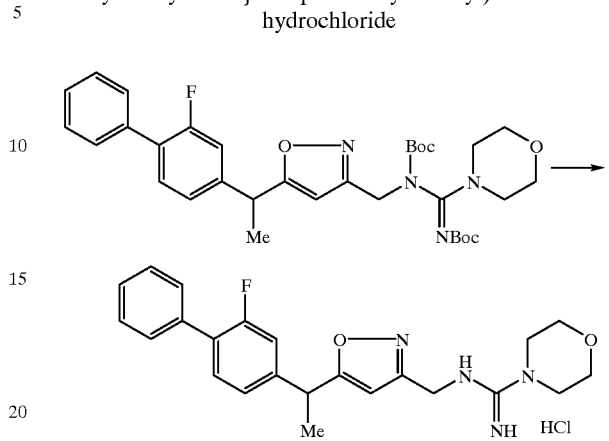

The desired compound was obtained by the same procedure as in Example 27 except for using the compound obtained in Example 12.

Melting point 161–163° C.

$^1$H-NMR (270 MHz, d$_6$-DMSO) δ ppm: 1.63(d, 3H, J=7.3 Hz), 3.46(m, 4H), 3.64(m, 4H), 4.48(q, 1H, J=7.3 Hz), 4.55(d, 2H, J=5.8 Hz), 6.42(s, 1H), 7.22–7.29(m, 2H), 7.37–7.54(m, 6H), 8.00(br-s, 2H), 8.43(t, 1H, J=5.8 Hz).

IR (KBr) [cm$^{-1}$]: 3393, 3356, 1655, 1612, 1561, 1485, 1418, 1116.

Example 29

({5-[1-(2-Fluoro-biphenyl-4-yl)-ethyl]-isoxazol-3-ylmethylimino}-piperidin-1-yl-methyl)-amine hydrochloride

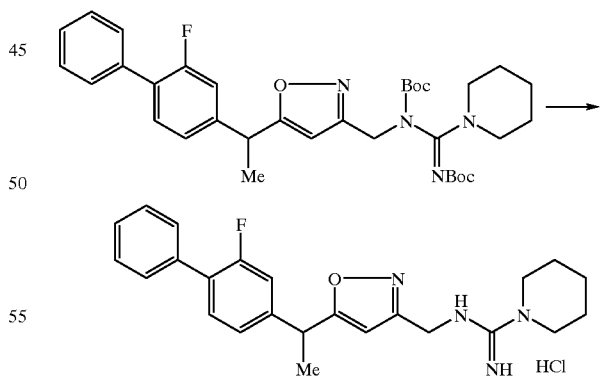

The desired compound was obtained by the same procedure as in Example 27 except for using the compound obtained in Example 13.

$^1$H-NMR (270 MHz, d$_6$-DMSO) δ ppm: 1.52(br-s, 6H), 1.62(d, 3H, J=7.3 Hz), 3.50(br-s, 4H), 4.47(q, 1H, J=7.3 Hz), 4.53(d, 2H, J=5.6 Hz), 6.37(s, 1H), 7.21–7.27(m, 2H), 7.39–7.53(m, 6H), 7.81(br-s, 2H), 8.25(br-s, 1H).

Example 30

N-{5-[1-(2-Fluoro-biphenyl-4-yl)-ethyl]-isoxazol-3-ylmethyl}-N'-methyl-guanidine hydrochloride

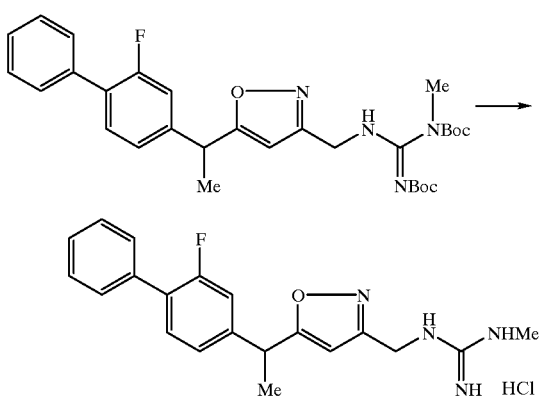

The desired compound was obtained by the same procedure as in Example 27 except for using the compound obtained in Example 14.

Melting point 71–74° C. (decomp.).

$^1$H-NMR (270 MHz, CDCl$_3$) δ ppm: 1.68(d, 3H, J=7.3 Hz), 2.89(d, 3H, J=4.6 Hz), 4.25(q, 1H, J=7.3 Hz), 4.42(br-s, 2H), 6.17(s, 1H), 7.00–7.10(m, 2H), 7.36–7.54(m, 6H).

IR (KBr) [cm$^{-1}$]: 3338, 1646, 1602, 1484, 1418.

Example 31

2-Amino-3-{5-[1-(2-fluoro-biphenyl-4-yl)-ethyl]-isoxazol-3-ylmethyl}-3,5-dihydro-imidazol-4-one hydrochloride

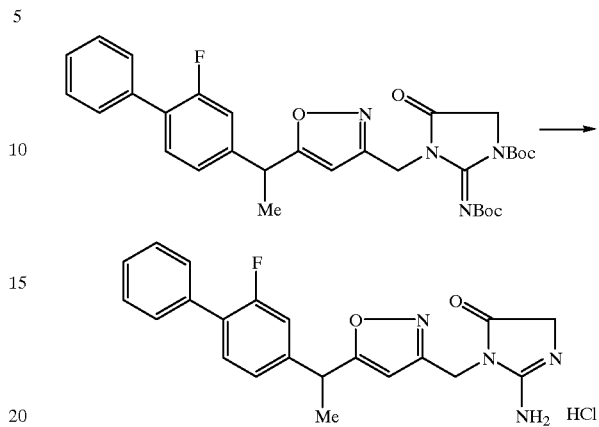

The desired compound was obtained by the same procedure as in Example 27 except for using the compound obtained in Example 15.

Melting point 210–232° C. (decomp.).

$^1$H-NMR (270 MHz, d$_6$-DMSO) δ ppm: 1.62(d, 3H, J=7.1 Hz), 4.31(s, 2H), 4.47(q, 1H, J=7.1 Hz), 4.94(s, 2H), 6.45(s, 1H), 7.21–7.29(m, 2H), 7.37–7.55(m, 6H), 9.53(br-s, 3H).

IR (KBr) [cm$^{-1}$]: 3061, 2983, 1778, 1706, 1689, 1604, 1544, 1485, 1419.

Example 32

Methyl [2-(N'-(tert-butoxycarbonyl)-N''-{3-[1-(2-fluoro-biphenyl-4-yl)-ethyl]-isoxazol-5-yl}-guanidino)-ethoxy]-acetate

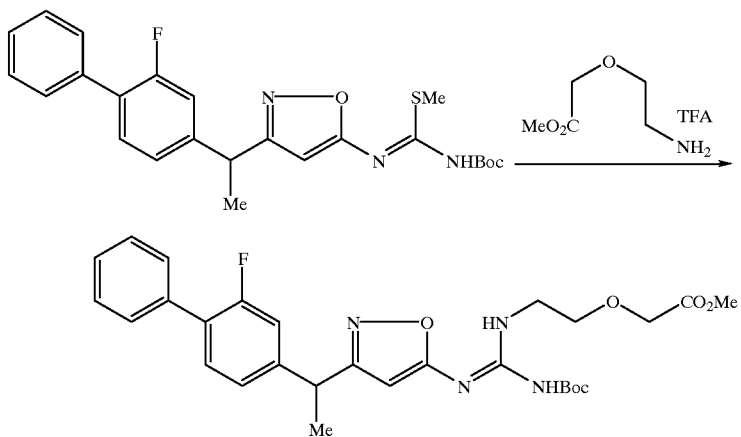

The desired compound was obtained by the same procedure as in Example 1 except for using the trifluoroacetic acid salt of methyl (2-amino-ethoxy)-acetate.

$^1$H-NMR (300 MHz, CDCl$_3$) δ ppm: 1.49(s, 9H), 1.67(d, 3H, J=7.3 Hz), 3.59–3.64 (m, 2H), 3.70–3.76(m, 2H), 3.79 (s, 3H), 4.11–4.18(m, 1H), 4.14(s, 2H), 5.30(s, 1H), 7.07–7.17(m, 2H), 7.32–7.46(m, 4H), 7.51–7.54(m, 2H), 8.28(br-s, 1H), 8.49(br-s, 1H)

IR (neat) [cm$^{-1}$]: 3399, 3349, 2978, 1750, 1732, 1634, 1606, 1556, 1486, 1455, 1416, 1370, 1241, 1151, 770, 670

Example 33

N-(tert-Butoxycarbonyl)-N'-{3-[1-(2-fluoro-biphenyl-4-yl)-ethyl]-isoxazol-5-yl)-N"-[2-(2-hydroxy-ethoxy-ethyl)]-guanidine

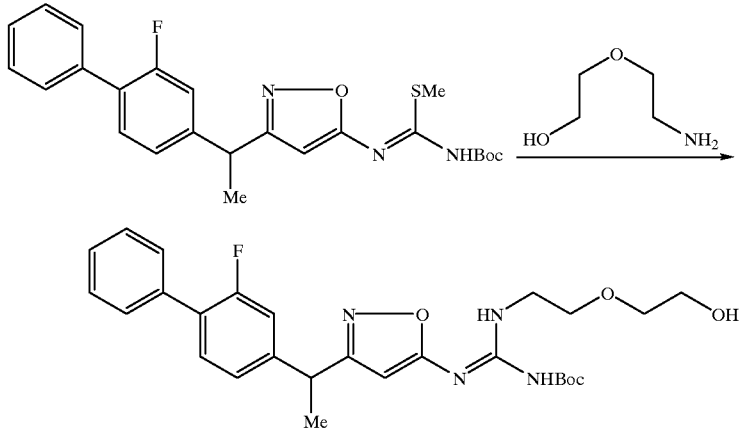

The desired compound was obtained by the same procedure as in Example 1 except for using 2-(2-amino-ethoxy)-ethanol.

$^1$H-NMR (300 MHz, CDCl$_3$) δ ppm: 1.49(s, 9H), 1.67(d, 3H, J=7.1 Hz), 2.40(br-s, 1H), 3.55–3.70(m, 6H), 3.70–3.80 (m, 2H), 4.15 (q, 1H, J=7.1 Hz), 5.32(s, 1H), 7.07–7.16(m, 2H), 7.32–7.54(m, 6H), 8.36(br-s, 1H), 8.51(s, 1H)

$^1$H-NMR (300 MHz, CDCl$_3$) δ ppm: 1.50(s, 9H), 1.67(d, 3H, J=7.1 Hz), 3.56–3.60 (m, 3H), 3.77–3.82(m, 2H), 4.14 (q, 1H, J=7.1 Hz), 5.34(s, 1H), 7.06–7.16(m, 2H), 7.32–7.46 (m, 4H), 7.51–7.54(m, 2H), 8.41(br-s, 1H), 8.59(br-s, 1H)

Example 34

N-(tert-Butoxycarbonyl)-N'-{3-[1-(2-fluoro-biphenyl-4-yl)-ethyl]-isoxazol-5-yl}-N"-(2-hydroxy-ethyl)-guanidine

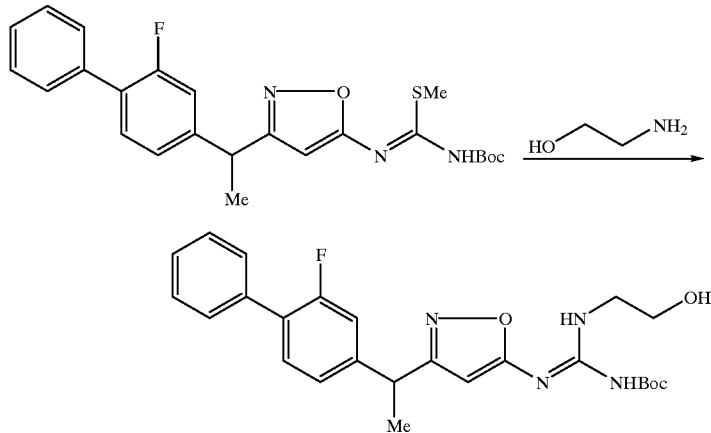

The desired compound was obtained by the same procedure as in Example 1 except for using 2-amino-ethanol.

Example 35 tert-Butyl [N'-(tert-butoxycarbonyl)-N''-{3-[1-(2-fluoro-biphenyl-4-yl)-ethyl]-isoxazol-5-yl}-N-(2-hydroxy-ethyl)-guanidino]-acetate

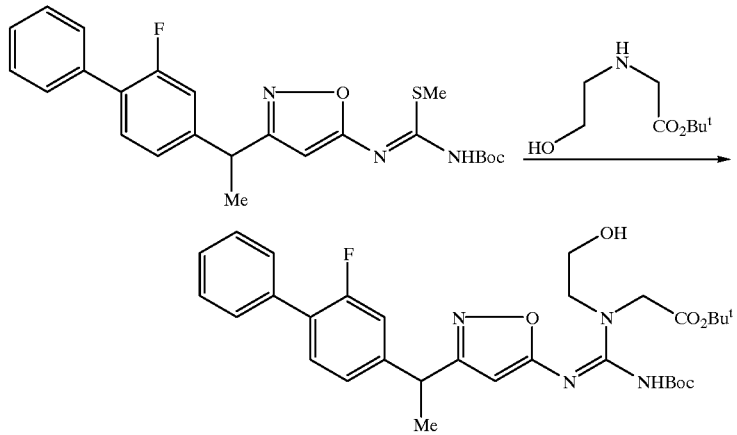

The desired compound was obtained by the same procedure as in Example 1 except for using tert-butyl 3-(2-hydroxy-ethylamino)-propionate.

$^1$H-NMR (300 MHz, CDCl$_3$) δ ppm: 1.33(s, 9H), 1.44(s, 9H), 1.64(d, 3H, J=7.1 Hz), 3.55–3.65(m, 2H), 3.74–3.82(m, 2H), 3.86–3.94(m, 1H), 4.02–4.17(m, 3H), 5.30(s, 1H), 7.04–7.15(m, 2H), 7.32–7.46(m, 4H), 7.50–7.53 (m, 2H)

IR (KBr) [cm$^{-1}$]: 3254, 2979, 2936, 1738, 1614, 1484, 1459, 1418, 1369, 1249, 1152, 1060, 769, 699

Example 36

4-[(tert-Butoxycarbamoyl)-{3-[1-(2-fluoro-biphenyl-4-yl)-ethyl]-isoxazol-5-ylimino}-methyl]-morpholin-3-ol

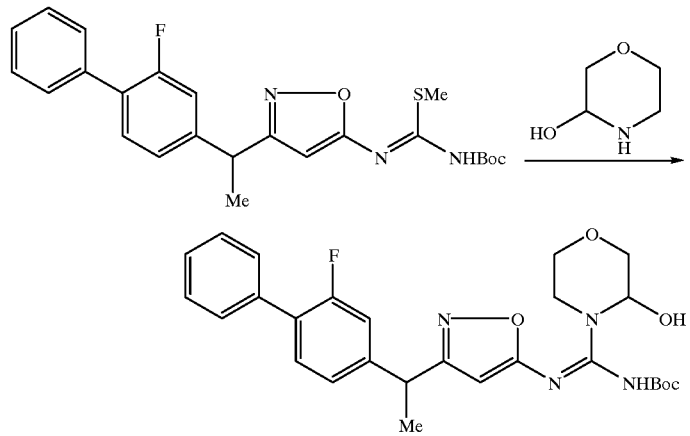

Example 37

(tert-Butoxycarbonyl)-({3-[1-(4-isobutyl-phenyl)-ethyl]-isoxazol-5-ylimino}-morpholin-4-yl-methyl)-amine

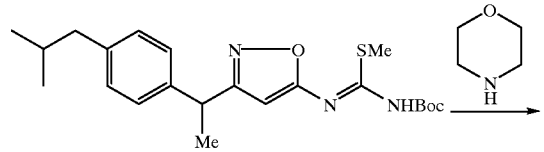

The desired compound was obtained by the same procedure as in Example 1 except for using piperidin-2-ol.

$^1$H-NMR (300 MHz, CDCl$_3$) δ ppm: 1.48(s, 9H), 1.66(d, 3H, J=7.0 Hz), 3.44–4.00 (m, 6H), 4.10–4.25(m, 1H), 5.32 (s, 1H), 6.47 (br-s, 0.5H), 6.66(br-s, 0.5H), 6.91–6.96(m, 1H), 7.07–7.16(m, 2H), 7.32–7.53(m, 6H)

73
-continued

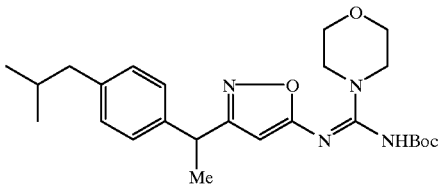

The desired compound was obtained by the same procedure as in Example 1 except for using the compound obtained in Reference Example 18.

¹H-NMR (300 MHz, CDCl₃) δ ppm: 0.89(d, 6H, J=6.6 Hz), 1.44(s, 9H), 1.62(d, 3H, J=7.3 Hz), 1.83(m, 1H, J=6.6 Hz), 2.42(d, 2H, J=7.3 Hz), 3.54–3.58(m, 4H), 3.72–3.77(m, 4H), 4.09(q, 1H, J=7.2 Hz), 5.23(s, 1H), 7.05–7.09 (m, 2H), 7.17–7.20(m, 2H)

Example 38

(tert-Butoxycarbonyl)-({3-[1-(6-methoxy-naphthalen-2-yl)-ethyl]-isoxazol-5-ylimino)-morpholin-4-yl-methyl)-amine

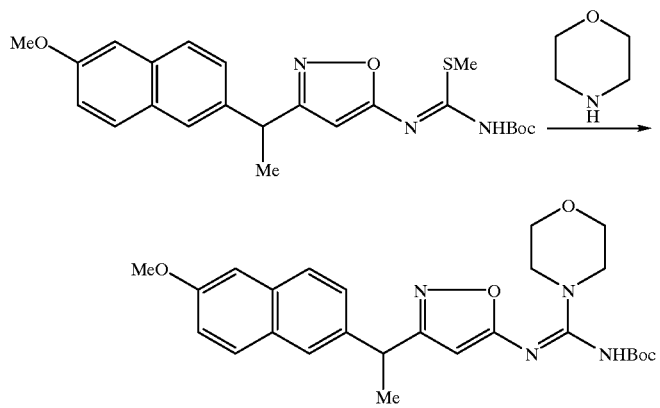

The desired compound was obtained by the same procedure as in Example 1 except for using the compound obtained in Reference Example 19.

¹H-NMR (300 MHz, CDCl₃) δ ppm: 1.35(s, 9H), 1.72(d, 3H, J=7.2 Hz), 3.54–3.56 (m, 4H), 3.71–3.75(m, 4H), 3.91 (s, 3H), 4.25 (q, 1H, J=7.1 Hz), 5.21(s, 1H), 7.10–7.14(m, 2H), 7.37(dd, 1H, J=8.2, 1.5 Hz), 7.66–7.70 (m, 3H)

Example 39

N'-{3-[1-(2-Fluoro-biphenyl-4-yl)-ethyl]-isoxazol-5-yl}-N,N-diethyl-guanidine methanesulfonate

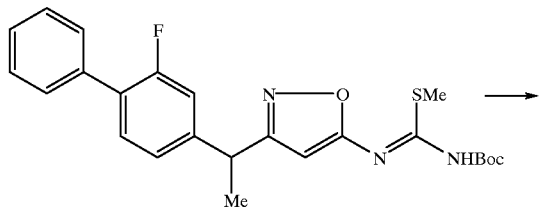

74
-continued

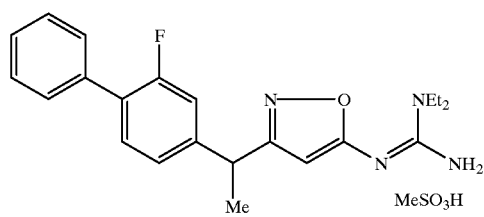

The compound (5.0 g) obtained in Reference Example 2 was dissolved in acetonitrile (100 ml) and triethylamine (3.8 ml) was added thereto, after which a 40% aqueous dimethylamine solution (2.84 ml) was added dropwise thereto under ice-cooling. Thereafter, a solution of silver nitrate (2.05 g) in acetonitrile (10 ml) was added dropwise thereto and the resulting mixture was stirred at room temperature for 18 hours. The insoluble materials were filtered off and, after washing with chloroform, the mother liquor was concentrated under reduced pressure. The residue was dissolved in a 83% (V/V) aqueous trifluoroacetic acid solution (100 ml) and the solution was stirred at room temperature for 8 hours, after which the solvent was removed by azeotropic distillation using toluene. A saturated aqueous sodium bicarbonate solution was added to the residue and the resulting mixture was subjected to extraction with ethyl acetate. The organic layer was dried over sodium sulfate and then concentrated under reduced pressure. The residue was purified by a silica gel column chromatography (hexane/ethyl acetate=4/1). This purified product was dissolved in 1,4-dioxane and treated with methanesulfonic acid (0.56 ml) to obtain the desired compound (3.42 g).

Melting point 154–155° C.

¹H-NMR (300 MHz, CDCl₃) δ ppm: 1.21(t, 6H, J=7.1 Hz), 1.66(d, 3H, J=7.1 Hz), 2.70(s, 3H), 3.42(q, 4H, J=7.1 Hz), 4.17(q, 1H, J=7.1 Hz), 5.69(s, 1H), 7.02–7.13(m, 2H), 7.26–7.54(m, 6H), 8.24(br-s, 2H), 10.83(br-s, 1H)

Example 40

N'-{3-[1-(2-Fluoro-biphenyl-4-yl)-ethyl]-isoxazol-5-yl}-N,N-bis-(2-methoxy-ethyl)-guanidine methanesulfonate

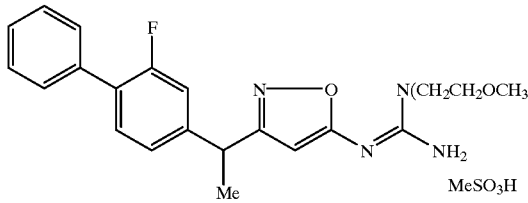

The desired compound was obtained by the same procedure as in Example 39 except for using bis-(2-methoxyethyl)-amine.

$^1$H-NMR (300 MHz, CDCl$_3$) δ ppm: 1.68(d, 3H, J=7.1 Hz), 2.80(s, 3H), 3.43(s, 6H), 3.65–3.75(m, 8H), 4.23(q, 1H, J=7.1 Hz), 6.04(s, 1H), 7.07–7.25(m, 2H), 7.32–7.54(m, 6H), 7.76(br-s, 1H), 8.00(br-s, 2H)

Example 41

({3-[1-(2-Fluoro-biphenyl-4-yl)-ethyl]-isoxazol-5-ylimino}-pyrrolidin-1-yl-methyl)-amine methanesulfonate

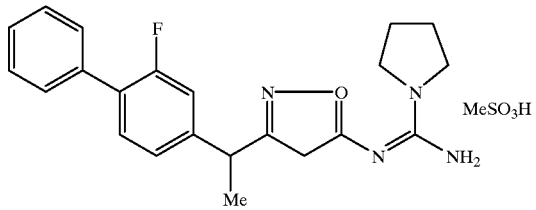

The desired compound was obtained by the same procedure as in Example 39 except for using pyrrolidine.

Melting point 182–183° C. (decomp.)

$^1$H-NMR (300 MHz, CD$_3$OD) δ ppm: 1.68(d, 3H, J=7.1 Hz), 2.04–2.15(m, 4H), 2.67 (s, 3H), 3.50–3.65(m, 4H), 4.28(q, 1H, J=7.1 Hz), 6.03(s, 1H), 7.14–7.26(m, 2H), 7.35–7.57 (m, 6H)

Example 42

({3-[1-(2-Fluor-biphenyl-4-yl)-ethyl]-isoxazol-5-ylimino}-piperazin-1-yl-methyl)-amine methanesulfonate

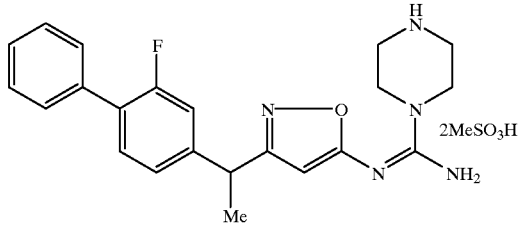

The desired compound was obtained by the same procedure as in Example 39 except for using piperazine.

Melting point 185° C. (decomp.)

$^1$H-NMR (300 MHz, CD$_3$OD) δ ppm: 1.68(d, 3H, J=7.1 Hz), 2.69(s, 6H), 3.40(t, 4H, J=5.3 Hz), 3.86(t, 4H, J=5.3 Hz), 4.28(q, 1H, J=7.1 Hz), 5.99(s, 1H), 7.13–7.25(m, 2H), 7.35–7.51(m, 6H)

Example 43

[{3-[1-(2-Fluoro-biphenyl-4-yl)-ethyl]-isoxazol-5-ylimino}-(4-methyl-piperazin-1-yl)-methyl]-amine methanesulfonate

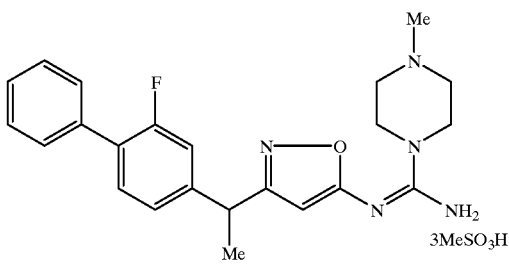

The desired compound was obtained by the same procedure as in Example 39 except for using 1-methyl-piperazine.

Melting point 186–187° C. (decomp.)

$^1$H-NMR (300 MHz, CD$_3$OD) δ ppm: 1.68(d, 3H, J=7.1 Hz), 2.69(s, 9H), 2.98(s, 3H), 3.31(br-s, 2H), 3.64(br-s, 4H), 4.15(br-s, 2H), 4.28(q, 1H, J=7.1 Hz), 6.00(s, 1H), 7.13–7.25(m, 2H), 7.32–7.52(m, 6H)

Example 44

N-{3-[1-(2-Fluoro-biphenyl-4-yl)-ethyl]-isoxazol-5-yl]-N'-(2-morpholin-4-yl-ethyl)-guanidine

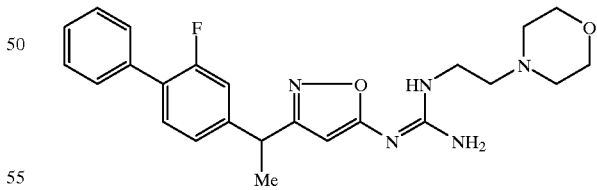

The desired compound was obtained by the same procedure as in Example 39 except for using 2-morpholin-4-yl-ethylamine.

$^1$H-NMR (300 MHz, CDCl$_3$) δ ppm: 1.64(d, 3H, J=7.3 Hz), 2.49–2.57(m, 6H), 3.30–3.31(m, 2H), 3.69(t, 4H, J=4.3 Hz), 4.41(q, 1H, J=7.3 Hz), 5.18(s, 1H), 5.70(s, 1H), 6.13(s, 2H), 7.07–7.17(m, 2H), 7.32–7.54(m, 6H)

Example 45

N-{3-[1-(2-Fluoro-biphenyl-4-yl)-ethyl]-isoxazol-5-yl}-N'-(2-methoxy-ethyl)-guanidine

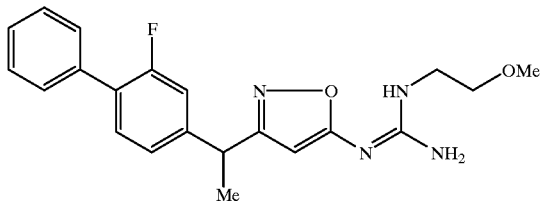

The desired compound was obtained by the same procedure as in Example 39 except for using 2-methoxy-ethylamine.

$^1$H-NMR (300 MHz, CDCl$_3$) δ ppm: 1.65(d, 3H, J=7.3 Hz), 3.38(s, 3H), 3.41(m, 2H), 3.52(t, 2H, J=4.3 Hz), 4.14(q, 1H, J=7.3 Hz), 5.19(s, 1H), 5.50–5.70(m, 3H), 7.08–7.16 (m, 2H), 7.33–7.54(m, 6H)

Example 46

({3-[1-(4-Isobutyl-phenyl)-ethyl]-isoxazol-5-ylimino}-morpholin-4-yl-methyl)-amine hydrochloride

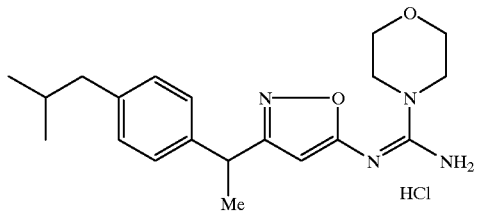

The desired compound was obtained by the same procedure as in Example 19 except for using the compound obtained in Example 37.

Melting point 94–99° C.

$^1$H-NMR (300 MHz, CDCl$_3$) δ ppm: 0.89(d, 6H, J=6.6 Hz), 1.60(d, 3H, J=7.1 Hz), 1.78–1.88(m, 1H), 2.43(d, 2H, J=7.1 Hz), 3.55–3.62(m, 4H), 3.72–3.80(m, 4H), 4.09(q, 1H, J=7.1 Hz), 5.65(s, 1H), 7.08(d, 2H, J=8.3 Hz), 7.14(d, 2H, J=8.1 Hz), 8.38(br-s, 1H)

Example 47

({3-[1-(6-Methoxy-naphthalen-2-yl)-ethyl]-isoxazol-5-ylimino}-morpholin-4-yl-methyl)-amine hydrochlo-ride

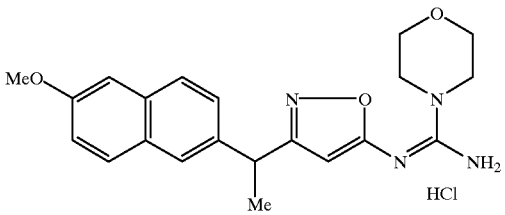

The desired compound was obtained by the same procedure as in Example 19 except for using the compound obtained in Example 38.

$^1$H-NMR (300 MHz, CDCl$_3$) δ ppm: 1.70(d, 3H, J=7.1 Hz), 3.44–3.48(m, 4H), 3.69–3.73(m, 4H), 3.91(s, 3H), 4.24(q, 1H, J=7.2 Hz), 5.21(s, 1H), 5.31(br-s, 1H), 7.10–7.13 (m, 2H), 7.39(d, 1H, J=8.6 Hz), 7.66–7.70(m, 3H)

Example 48

Methyl [2-(N'-{3-[1-(2-fluoro-biphenyl-4-yl)-ethyl]-isoxazol-5-yl}-guanidino)-ethoxyl]-acetate

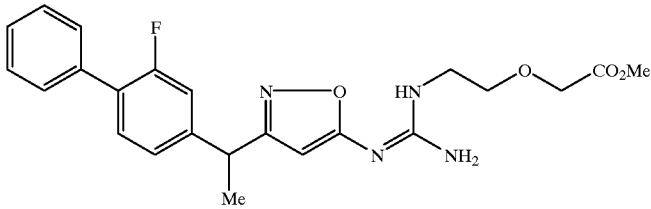

Trifluoroacetic acid (15.0 ml) was added to the compound (5.74 g) obtained in Example 32 and the resulting mixture was stirred at room temperature for one hour. A saturated aqueous sodium bicarbonate solution was added to the reaction mixture, and the solution was thereafter subjected to extraction with ethyl acetate, after which the organic layer was dried over magnesium sulfate and then concentrated under reduced pressure. The residue was purified by a silica gel column chromatography (chloroform alone→chloroform/methanol=99/1→39/1) to obtain the desired compound (4.32 g).

$^1$H-NMR (300 MHz, CDCl$_3$) δ ppm: 1.65(d, 3H, J=7.1 Hz), 3.44–3.51(m, 2H), 3.64–3.67(m, 2H), 3.74(s, 3H), 4.10(s, 2H), 4.10–4.16(m, 1H), 5.20(s, 1H), 5,60(br-s, 2H), 6.07(br-s, 1H), 7.07–7.17(m, 2H), 7.32–7.46(m, 4H), 7.50–7.54(m, 2H)

IR (Neat) [cm$^{-1}$]: 3374, 2952, 1749, 1624, 1572, 1483, 1457, 1222, 1132, 969, 915, 769, 729, 699

Example 49

N-{3-[1-(2-Fluoro-biphenyl-4-yl)-ethyl]-isoxazol-5-yl}-N'-[2-(2-hydroxy-ethoxy-ethyl)]-guanidine

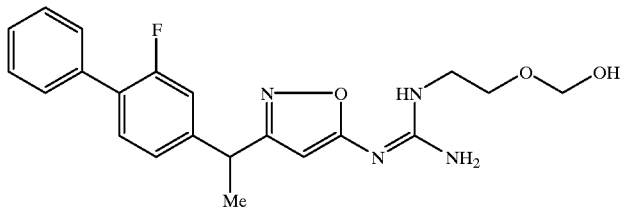

Trifluoroacetic acid (10 ml) was added the compound (5.09 g) obtained in Example 33 and the resulting mixture was stirred at room temperature for one hour. The reaction mixture was subjected to azeotropic distillation using toluene to remove the solvent, and the residue was thereafter dissolved in 1,4-dioxane, after which the solution was treated with 4 N hydrogen chloride/diethyl ether solution and then concentrated under reduced pressure. The concentrated solution was diluted with chloroform, then neutralized with an aqueous sodium hydroxide solution, and thereafter subjected to extraction with chloroform. The organic layer was dried over sodium sulfate and then concentrated under reduced pressure. The residue was purified by a silica gel column chromatography (chloroform alone→chloroform/methane=30/1) to obtain the desired compound (3.34 g).

$^1$H-NMR (300 MHz, CDCl$_3$) δ ppm: 1.65(d, 3H, J=7.0 Hz), 3.42–3.48(m, 2H), 3.57–3.66(m, 4H), 3.73–3.78(m, 2H), 4.13(q, 1H, J=7.1 Hz), 5.55(s, 1H), 5.69(br-s, 2H), 7.07–7.16(m, 2H), 7.31–7.55(m, 6H)

Example 50

N-{3-[1-(2-Fluoro-biphenyl-4-yl)-ethyl]-isoxazol-5-yl}-N'-(2-hydroxy-ethyl)-guanidine

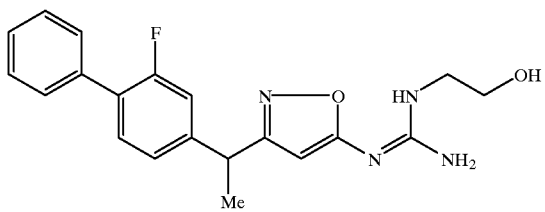

The desired compound was obtained by the same procedure as in Example 49 except for using the compound obtained in Example 34.

$^1$H-NMR (300 MHz, CD$_3$OD) δ ppm: 1.62(d, 3H, J=7.1 Hz), 3.28–3.36(m, 2H), 3.62–3.66(m, 2H), 4.13(q, 1H, J=7.3 Hz), 5.33(s, 1H), 7.10–7.21(m, 2H), 7.30–7.44(m, 6H), 7.49–7.52(m, 2H)

IR (KBr) [cm$^{-1}$]: 3433, 1639, 1572, 1478, 1456, 1417, 1068, 786, 695

MS (FD) [m/e]: 368 (M$^+$)

Example 51

({3-[1-(2-Fluoro-biphenyl-4-yl)-1-methyl-ethyl]-isoxazol-5-ylimino}-morpholin-4-yl-methyl)-amine

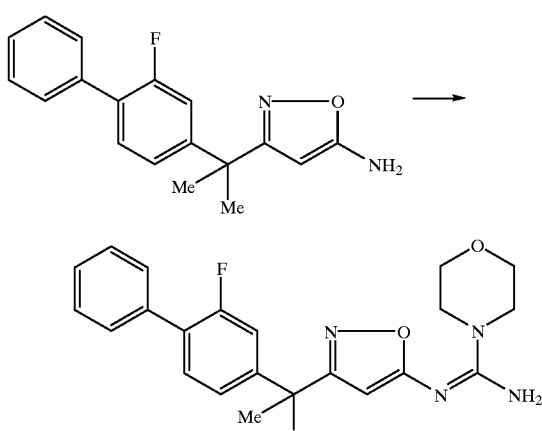

The compound (4.57 g) obtained in Reference Example 20 was dissolved in cyanomorpholine (8.64 g), and potassium carbonate (4.26 g) was added thereto, after which the resulting mixture was heated under reflux at 130° C. for 8 hours. After cooling to room temperature, a saturated aqueous sodium chloride solution was added, after which the resulting mixture was subjected to extraction with ethyl acetate. The organic layer was dried over sodium sulfate and then concentrated under reduced pressure. The residue was purified by a silica gel column chromatography (hexane/ethyl acetate=2/1→1/2) to obtain the desired compound (1.53 g).

$^1$H-NMR (300 MHz, CDCl$_3$) δ ppm: 1.71(s, 6H), 3.47–3.50(m, 4H), 3.71–3.74(m, 4H), 5.19(s, 1H), 5.39(s, 2H), 7.11–7.20(m, 2H), 7.32–7.46(m, 4H), 7.50–7.54(m, 2H)

Example 52

(Morpholin-4-yl-{3-[1-(3-phenoxy-phenyl)-ethyl]-isoxazol-5-ylimino}-methyl)-amine

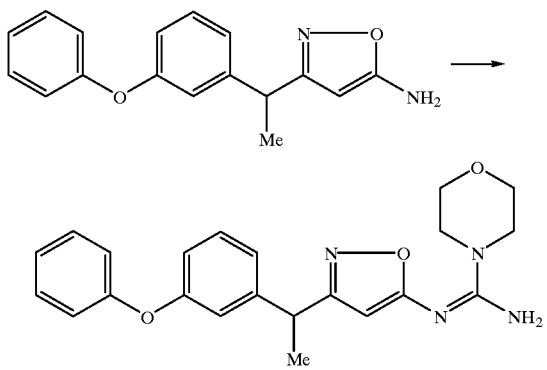

The desired compound was obtained by the same procedure as in Example 51 except for using the compound obtained in Reference Example 25.

$^1$H-NMR (300 MHz, CDCl$_3$) δ ppm: 1.61(d, 3H, J=7.3 Hz), 3.48(t, 4H, J=4.9 Hz), 3.72(t, 4H, J=4.9 Hz), 4.08(q, 1H, J=7.3 Hz), 5.21(s, 1H), 5.37(br-s, 2H), 6.80–6.84(m, 1H), 6.97–7.12(m, 5H), 7.21–7.35(m, 3H)

Example 53

({3-[1-Ethoxy-1-(2-fluoro-biphenyl-4-yl)-ethyl]-isoxazol- 5-ylimino}-morpholin-4-yl-methyl)-amine methanesulfonate

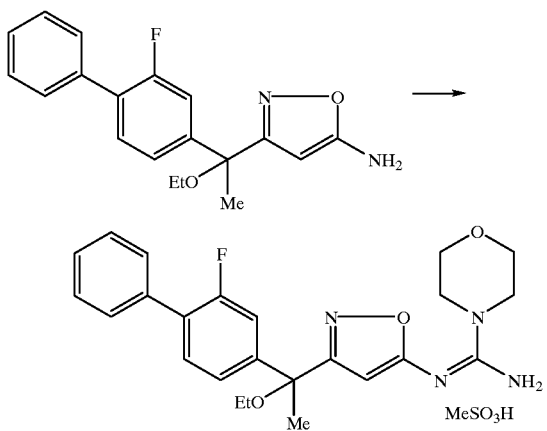

The compound (5.0 g) obtained in Reference Example 21 was dissolved in cyanomorpholine (7.75 g) and potassium carbonate (4.24 g) was added thereto, after which the mixture was heated under reflux at 130° C. for 8 hours. After cooling to room temperature, a saturated aqueous sodium chloride solution was added, and thereafter, the resulting mixture was subjected to extraction with ethyl acetate. The organic layer was dried over magnesium sulfate and then concentrated under reduced pressure. The residue was purified by a silica gel column chromatography (hexane/ethyl acetate=2/1→1/2). This purified product was dissolved in 1,4-dioxane and methanesulfonic acid (0.34 ml) was added thereto under ice-cooling, and the resulting mixture was concentrated under reduced pressure. The crude product was purified by a recrystallization method from isopropanol to obtain the desired compound (850 mg).

Melting point 158–160° C.

$^1$H-NMR (300 MHz, CDCl$_3$) δ ppm: 1.71(t, 3H, J=6.7 Hz), 1.90(s, 3H), 2.71(s, 3H), 3.32–3.57(m, 6H), 3.73–3.75 (m, 4H), 5.68(s, 1H), 7.22–7.54(m, 8H), 8.69(br-s, 2H), 11.16(br-s, 1H)

Example 54

(R)-({3-[1-(2-Fluoro-biphenyl-4-yl)-ethyl]-isoxazol-5-ylimino}-morpholin-4-yl-methyl)-amine

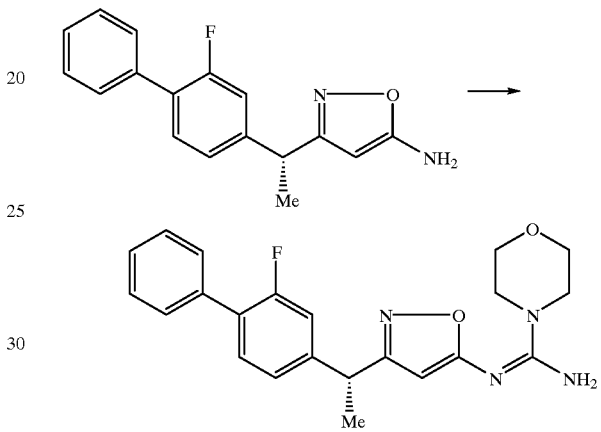

1) Sodium hydride (25 mg, 60% oily) was added to a tetrahydrofuran solution (4 ml) of the compound (118 mg, 93% e.e.) obtained in Reference Example 26 under a nitrogen atmosphere, and thereafter, the resulting mixture was stirred at 40° C. for 10 minutes. It was again cooled under ice-cooling and thereafter cyanomorpholine (0.084 ml) was added thereto, after which the temperature was brought back to room temperature and stirred for 6 hours. The reaction mixture was diluted with ethyl acetate and then neutralized with a saturated aqueous ammonium chloride solution. After extraction with ethyl acetate, the organic layer was dried over sodium sulfate and then concentrated under reduced pressure. The residue was purified by a silica gel column chromatography (hexane/ethyl acetate=1/1→1/4) to obtain the desired compound (137 mg, 93% e.e.).

2) ({3-[1-(2-Fluoro-biphenyl-4-yl)-ethyl]-isoxazol-5-ylimino}-morpholin-4-yl-methyl)-amine (3 g) was separated using a preparative optical active column (CHIRALCEL OD, a registered trade mark of DAICEL CHEMICAL INDUSTRIES, LTD., 2 cmØ×25 cm) to obtain the desired compound (1.5 g).

Separation conditions: Eluent: Hexane/ethanol=100/15 Observation wavelength: 254 nm Flow rate: 20 ml/min $^1$H-NMR (300 MHz, CDCl$_3$) δ ppm: 1.66(d, 3H, J=7.1 Hz), 3.45–3.60(m, 4H), 3.70–3.80(m, 4H), 4.15(q, 1H, J=7.1 Hz), 5.25(s, 1H), 5.37(br-s, 2H), 7.05–7.17(m, 2H), 7.33–7.54(m, 6H)

$[α]_D^{22}$=−20.0° (c: 1.00, CHCl$_3$)

Example 55

(S)-({3-[1-(2-Fluoro-biphenyl-4-yl)-ethyl]-isoxazol-5-ylimino}-morpholin-4-yl-methyl)-amine

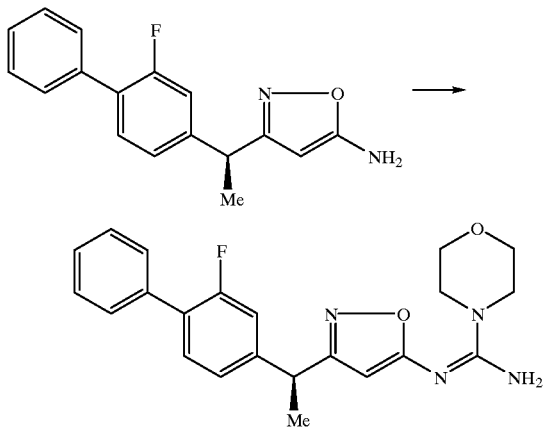

1) The desired compound was obtained by the same procedure as in Example 54 except for using the compound obtained in Reference Example 27.
2) The separation was conducted by the same procedure as in Example 54 to obtain the desired compound.

¹H-NMR (300 MHz, CDCl₃) δ ppm: 1.66(d, 3H, J=7.1 Hz), 3.45–3.55(m, 4H), 3.65–3.75(m, 4H), 4.15(q, 1H, J=7.1 Hz), 5.25(s, 1H), 5.38(br-s, 2H), 7.05–7.17(m, 2H), 7.33–7.54(m, 6H)

$[\alpha]_D^{22}$=+19.8° (c: 1.00, CHCl₃)

Example 56

({3-[1-(2-Fluoro-2',3',4',5',6'-pentadeutero-biphenyl-4-yl)-ethyl]-isoxazol-5-ylimino}-morpholin-4-yl-methyl)-amine

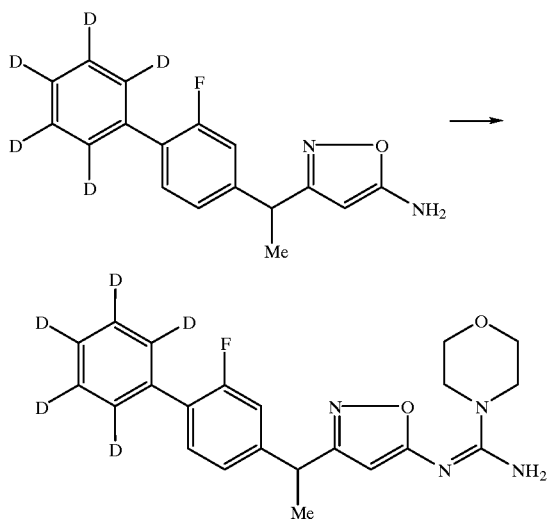

The desired compound was obtained by the same procedure as in Example 54 except for using the compound obtained in Reference Example 29.

¹H-NMR (300 MHz, CDCl₃) δ ppm: 1.66(d, 3H, J=7.1 Hz), 3.47–3.51(m, 4H), 3.71–3.75(m, 4H), 4.15(q, 1H, J=7.1 Hz), 5.25(s, 1H), 5.37(br-s, 2H), 7.07–7.17(m, 2H), 7.37 (t, 1H, J=8.1 Hz)

IR (KBr) [cm⁻¹]: 3454, 3360, 2971, 1629, 1578, 1548, 1444, 1277, 1124, 1110, 975, 872

Example 57

({3-[1-(2-Fluoro-2'-methoxy-biphenyl-4-yl)-ethyl]-isoxazol-5-ylimino}-morpholin-4-yl-methyl)-amine

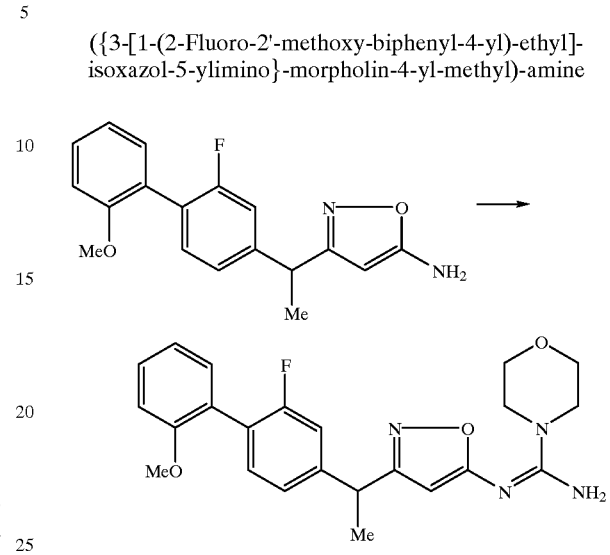

The desired compound was obtained by the same procedure as in Example 54 except for using the compound obtained in Reference Example 30.

¹H-NMR (300 MHz, CDCl₃) δ ppm: 1.66(d, 3H, J=7.2 Hz), 3.47–3.50(m, 4H), 3.71–3.75(m, 4H), 3.80(s, 3H), 4.15(q, 1H, J=7.2 Hz), 5.27(s, 1H), 5.34(br-s, 2H), 6.97–7.13(m, 4H), 7.23–7.38(m, 3H)

Example 58

({3-[1-(2'-Fluoro-biphenyl-4-yl)-ethyl]-isoxazol-5-ylimino}-morpholin-4-yl-methyl)-amine

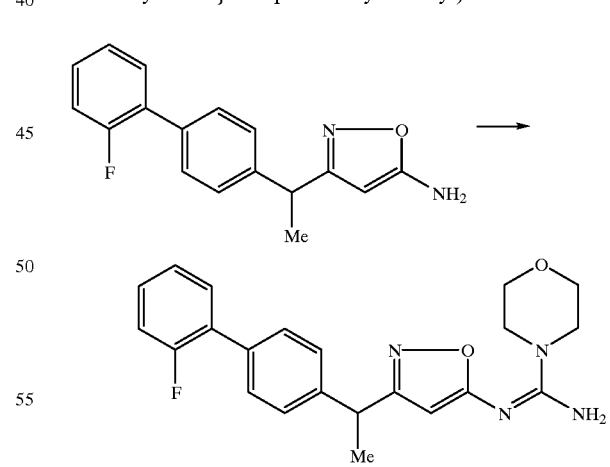

The desired compound was obtained by the same procedure as in Example 54 except for using the compound obtained in Reference Example 31.

¹H-NMR (300 MHz, CDCl₃) δ ppm: 1.67(d, 3H, J=7.1 Hz), 3.48(t, 4H, J=4.8 Hz), 3.72(t, 4H, J=4.8 Hz), 4.16(q, 1H, J=7.1 Hz), 5.25(s, 1H), 5.34(br-s, 2H), 7.10–7.51(m, 8H)

Example 59

({3-[1-(2-Fluoro-biphenyl-4-yl)-cyclopropyl]-isoxazol-5-ylimino}-morpholin-4-yl-methyl)-amine

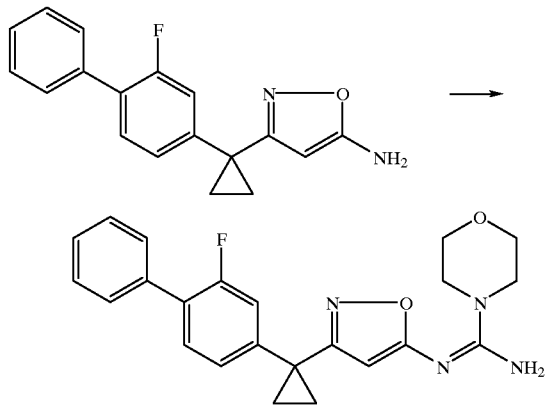

The desired compound was obtained by the same procedure as in Example 54 except for using the compound obtained in Reference Example 22.

$^1$H-NMR (300 MHz, CDCl$_3$) δ ppm: 1.31–1.34(m, 2H), 1.46–1.51(m, 2H), 3.47(t, 4H, J=4.8 Hz), 3.73(t, 4H, J=4.8 Hz), 5.17(s, 1H), 5.35(br-s, 2H), 7.14–7.25(m, 2H), 7.33–7.55(m, 6H)

Example 60

[3-Biphenyl-4-ylmethyl-isoxazol-5-ylimino)-morpholin-4-yl-methyl]-amine

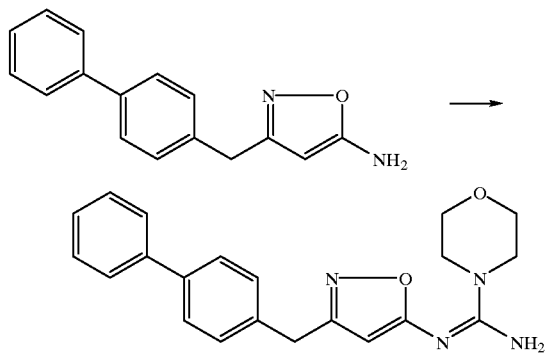

The desired compound was obtained by the same procedure as in Example 54 except for using the compound obtained in Reference Example 28.

$^1$H-NMR (300 MHz, CDCl$_3$) δ ppm: 3.48(t, 4H, J=5.3 Hz), 3.72(t, 4H, J=5.3 Hz), 3.94(s, 2H), 5.24(s, 1H), 5.34(s, 2H), 7.34–7.58(m, 9H)

Example 61

{[3-(1-Biphenyl-4-yl-ethyl)-isoxazol-5-ylimino]-morpholin-4-yl-methyl]-amine

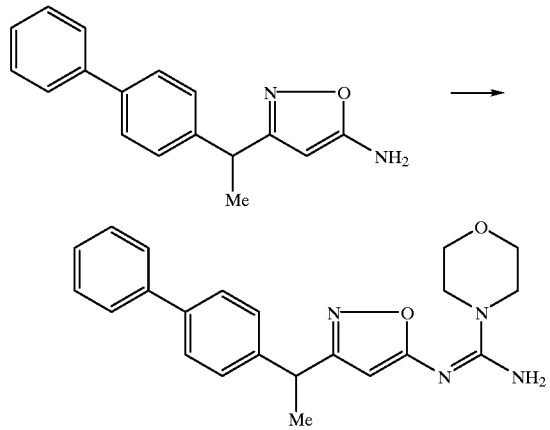

The desired compound was obtained by the same procedure as in Example 54 except for using the compound obtained in Reference Example 23.

$^1$H-NMR (300 MHz, CDCl$_3$) δ ppm: 1.67(d, 3H, J=7.3 Hz), 3.48(t, 4H, J=4.3 Hz), 3.72 (t, 4H, J=4.3 Hz), 4.16(q, 1H, J=7.3 Hz), 5.24(s, 1H), 5.35(s, 2H), 7.30–7.58(m, 9H)

Example 62

{[3-(1-Biphenyl-4-yl-1-methyl-ethyl)-isoxazol-5-ylimino]-morpholin-4-yl-methyl}-amine

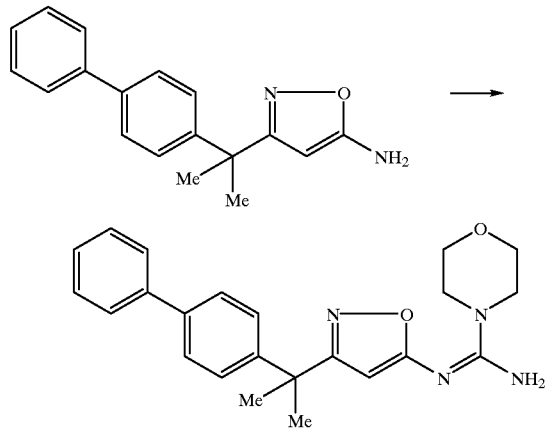

The desired compound was obtained by the same procedure as in Example 54 except for using the compound obtained in Reference Example 24.

$^1$H-NMR (300 MHz, CDCl$_3$) δ ppm: 1.72(s, 6H), 3.47(t, 4H, J=5.3 Hz), 3.72(t, 4H, J=5.3 Hz), 5.18(s, 1H), 5.38(s, 2H), 7.32–7.58 (m, 9H)

Example 63

({3-[1-(2-Fluoro-4'-methoxy-biphenyl-4-yl)-ethyl]-isoxazol-5-ylimino}-morpholin-4-yl-methyl)-amine

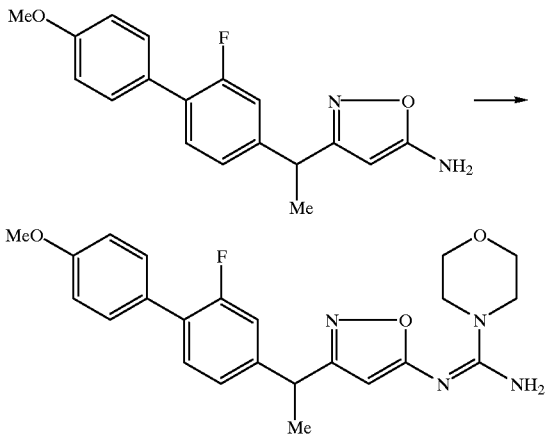

The desired compound was obtained by the same procedure as in Example 54 except for using the compound obtained in Reference Example 32.

$^1$H-NMR (300 MHz, CDCl$_3$) δ ppm: 1.65(d, 3H, J=7.2 Hz), 3.46–3.50(m, 4H), 3.70–3.74(m, 4H), 3.85(s, 3H), 4.13(q, 1H, J=7.2 Hz), 5.25(s, 1H), 5.36(br-s, 2H), 6.94–7.00 (m, 2H), 7.05–7.14(m, 2H), 7.33(t, 1H, J=8.0 Hz), 7.43–7.49(m, 2H)

Example 64

4'-{1-[5-(Amino-morpholin-4-yl-methyleneamino)-isoxazol-3-yl]-ethyl}-2'-fluoro-biphenyl-4-ol

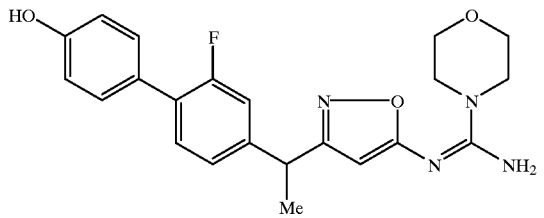

The compound (5.16 g) obtained in Example 63 was dissolved in tetrahydrofuran (100 ml) under a nitrogen atmosphere and then a methylene chloride solution (40 ml) of boron tribromide (1.6 ml) was added at −78° C., after which the temperature was elevated to room temperature over one hour and the stirring was further conducted at room temperature for 3 hours. The reaction mixture was neutralized with a 15% aqueous sodium hydroxide solution and then subjected to extraction with ethyl acetate and methanol. The organic layer was dried over sodium sulfate and then concentrated under reduced pressure. The residue was purified by a silica gel column chromatography (chloroform alone→chloroform/methanol=50/1→33/1) to obtain the desired compound (2.67 g).

$^1$H-NMR (300 MHz, d$_6$-DMSO) δ ppm: 1.52(d, 3H, J=7.2 Hz), 3.38–3.44(m, 4H), 3.54–3.59(m, 4H), 4.06(q, 1H, J=7.2 Hz), 5.39(s, 1H), 6.43(br-s, 2H), 6.83(d, 2H, J=8.3 Hz), 7.13–7.20(m, 2H), 7.30–7.40(m, 3H), 9.61(br-s, 1H)

IR (KBr) [cm$^{-1}$]: 3335, 3190, 1660, 1568, 1497, 1448, 1274, 1114, 983, 827

Example 65

4'-{1-[5-(Amino-morpholin-4-yl-methyleneamino)-isoxazol-3-yl]-ethyl}-2'-fluoro-biphenyl-2-ol

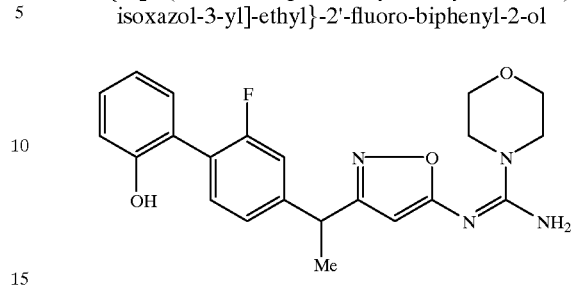

The desired compound was obtained by the same procedure as in Example 64 except for using the compound obtained in Example 57.

$^1$H-NMR (300 MHz, d$_6$-DMSO) δ ppm: 1.57(d, 3H, J=7.1 Hz), 3.21–3.22(m, 2H), 3.46–3.51(m, 4H), 3.79–3.84(m, 2H), 4.21(q, 1H, J=7.1 Hz), 6.15(s, 1H), 6.84(t, 1H, J=7.5 Hz), 6.91(d, 1H, J=7.9 Hz), 7.12–7.21(m, 4H), 7.26–7.31(m, 1H), 9.53(br-s, 1H)

IR (KBr) [cm$^{-1}$]: 3275, 2964, 1659, 1605, 1493, 1451, 1419, 1358

Example 66

N-{3-[1-(2-Fluoro-biphenyl-4-yl)-ethyl]-isoxazol-5-yl}-N'-[2-hydroxy-ethoxy-ethyl)]-guanidine hydrochloride

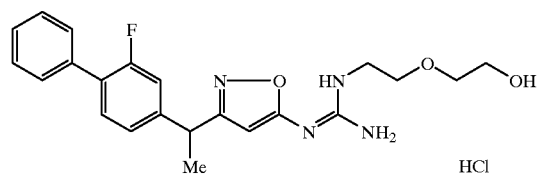

The compound (3.34 g) obtained in Example 49 was dissolved in 1,4-dioxane and treated with 4 N hydrochloric acid to obtain the desired compound (521 mg).

Melting point 127–128° C.

$^1$H-NMR (300 MHz, CD$_3$OD) δ ppm: 1.68(d, 3H, J=7.3 Hz), 3.48–3.54(m, 2H), 3.54–3.62(m, 2H), 3.63–3.70(m, 4H), 4.27(q, 1H, J=7.1 Hz), 5.98(s, 1H), 7.12–7.24(m, 2H), 7.31–7.52(m, 6H)

IR (KBr) [cm$^{-1}$]: 3223, 3121, 2934, 1684, 1644, 1616, 1582, 1532, 1484, 1418, 1353, 1267, 1137, 1108, 1064, 698

MS (FD) [m/e]: 413 (M-HCl)

Example 67

N-{3-[1-(2-Fluoro-biphenyl-4-yl)-ethyl]-isoxazol-5-yl}-N'-(2-hydroxy-ethyl)-guanidine hydrochloride

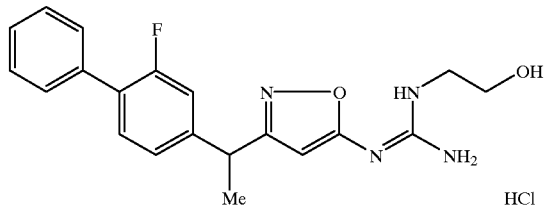

The desired compound was obtained by the same procedure as in Example 66 except for using the compound obtained in Example 50.

$^1$H-NMR (300 MHz, CDCl$_3$) δ ppm: 1.59(d, 3H, J=7.1 Hz), 3.47–3.58(m, 2H), 3.70–3.83(m, 2H), 4.13(q, 1H, J=7.0 Hz), 5.78(s, 1H), 7.00–7.07(m, 2H), 7.31–7.49(m, 6H), 7.98 (br-s, 1H)

Example 68

4'-{1-[5-(Amino-morpholin-4-yl-methyleneamino)-isoxazol-3-yl]-ethyl}-2'-fluoro-biphenyl-4-ol hydrochloride

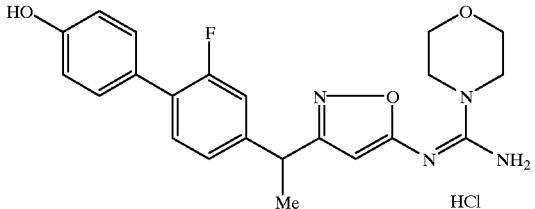

The desired compound was obtained by the same procedure as in Example 66 except for using the compound obtained in Example 64.

Melting point 195–210° C. (decomp.)

$^1$H-NMR (300 MHz, d$_6$-DMSO) δ ppm: 1.58(d, 3H, J=7.2 Hz), 3.40–3.67(m, 8H), 4.24 (q, 1H, J=7.3 Hz), 5.99(s, 1H), 6.84(d, 2H, J=8.4 Hz), 7.19–7.45(m, 5H), 8.49(br-s, 2H), 9.67(br-s, 1H)

IR (KBr) [cm$^{-1}$]: 3215, 3114, 1647, 1614, 1532, 1495, 1418, 1272, 1116, 820

Elementary analysis: Calculated: C 59.13, H 5.41, N 12.54 Found: C 59.05, H 5.26, N 12.47

Example 69

N-{3-[1-(2-Fluoro-biphenyl-4-yl)-ethyl]-isoxazol-5-yl}-N'-(2-morpholin-4-yl-ethyl)-guanidine hydrochloride

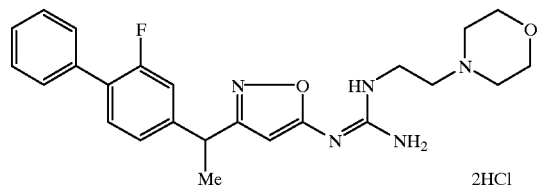

The desired compound was obtained by the same procedure as in Example 66 except for using the compound obtained in Example 44.

$^1$H-NMR (300 MHz, CD$_3$OD) δ ppm: 1.69(d, 3H, J=7.3 Hz), 3.43–3.48(m, 6H), 3.86 (t, 2H, J=7.3 Hz), 3.90–4.10 (br-s, 6H), 4.30(q, 1H, J=7.3 Hz), 6.08(s, 1H), 7.15–7.25(m, 2H), 7.36–7.53(m, 6H)

Example 70

N-{3-[1-(2-Fluoro-biphenyl-4-yl)-ethyl]-isoxazol-5-yl}-N'-(2-methoxy-ethyl)-guanidine hydrochloride

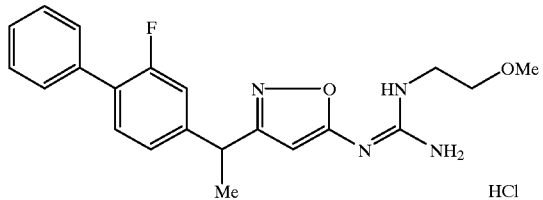

The desired compound was obtained by the same procedure as in Example 66 except for using the compound obtained in Example 45.

$^1$H-NMR (300 MHz, CD$_3$OD) δ ppm: 1.65(d, 3H, J=7.3 Hz), 3.39(s, 3H), 3.52(t, 2H, J=4.6 Hz), 3.62(t, 2H, J=4.6 Hz), 4.28(q, 1H, J=7.3 Hz), 5.98(s, 1H), 7.15–7.35(m, 2H), 7.38–7.52(m, 6H)

Example 71

2-{3-[1-(2-Fluoro-biphenyl-4-yl)-ethyl]-isoxazol-5-ylimino}-1-(2-hydroxy-ethyl)-imidazolidin-4-one hydrochloride

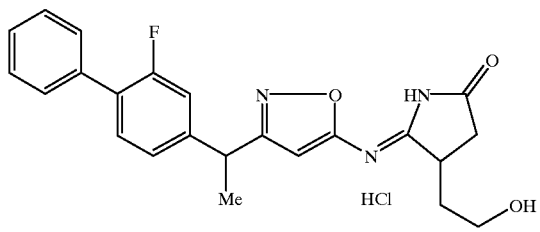

The compound (3.3 g) obtained in Example 35 was dissolved in tetrahydrofuran (30 ml) and conc. hydrochloric acid was added, after which the solution was stirred at room temperature for 30 minutes. The reaction mixture was concentrated under reduced pressure and purified by a recrystallization method from toluene to obtain the desired compound (1.4 g).

Melting point 159–167° C. (decomp.)

¹H-NMR (300 MHz, CD₃OD) δ ppm: 1.73(d, 3H, J=7.3 Hz), 3.71–3.76(m, 2H), 3.82–3.86(m, 2H), 4.39(q, 1H, J=7.1 Hz), 4.53(s, 2H), 6.65(s, 1H), 7.18–7.27(m, 2H), 7.35–7.52 (m, 6H)

IR (KBr) [cm⁻¹]: 3452, 3192, 2939, 1807, 1707, 1616, 1526, 1485, 1450, 1417, 1147, 1051, 697

MS (FD) [m/e]: 444 (M⁺), 409 (M-HCl)

Example 72

({3-[1-(2-Fluoro-biphenyl-4-yl)-1-methyl-ethyl]-isoxazol-5-ylimino}-morpholin-4-yl-methyl)-amine methanesulfonate

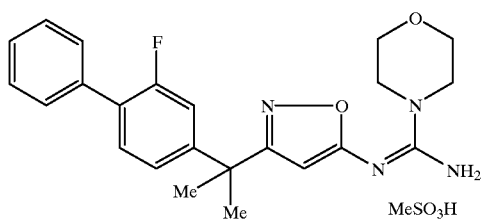

The compound (1.53 g) obtained in Example 51 was dissolved in 1,4-dioxane and methanesulfonic acid (0.27 ml) was added under ice-cooling, after which the solution was stirred for 30 minutes. Subsequently, it was purified by a recrystallization method from 1,4-dioxane to obtain the desired compound (1.89 g).

¹H-NMR (300 MHz, CDCl₃) δ ppm: 1.71(s, 6H), 2.71(s, 3H), 3.45–3.52(m, 4H), 3.71–3.78(m, 4H), 5.51(s, 1H), 7.07(dd, 1H, J=12.3, 1.8 Hz), 7.13(dd, 1H, J=8.3, 1.8 Hz), 7.34–7.46(m, 4H), 7.50–7.54(m, 2H), 8.64(br-s, 2H), 11.10 (br-s, 1H)

Example 73

(Morpholin-4-yl-{3-[1-(3-phenoxy-phenyl)-ethyl]-isoxazol-5-ylimino}-methyl)-amine methanesulfonate

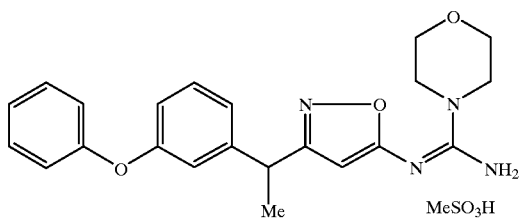

The desired compound was obtained by the same procedure as in Example 72 except for using the compound obtained in Example 52.

¹H-NMR (300 MHz, CDCl₃) δ ppm: 1.62(d, 3H, J=7.2 Hz), 2.72(s, 3H), 3.43–3.47 (m, 4H), 3.72–3.76(m, 4H), 4.11(q, 1H, J=7.2 Hz), 5.53(s, 1H), 6.83–7.01(m, 5H), 7.09–7.15 (m, 1H), 7.23–7.37(m, 3H), 8.63(br-s, 2H), 11.10 (br-s, 1H)

Example 74

({3-[1-(2'-Fluoro-biphenyl-4-yl)-ethyl]-isoxazol-5-ylimino}-morpholin-4-yl-methyl)-amine methanesulfonate

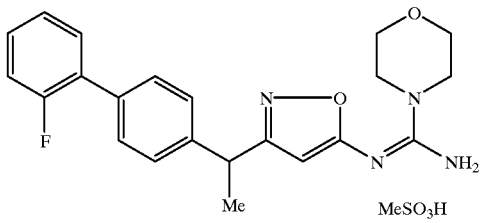

The desired compound was obtained by the same procedure as in Example 72 except for using the compound obtained in Example 58.

¹H-NMR (300 MHz, d₆-DMSO) δ ppm: 1.67(d, 3H, J=7.1 Hz), 2.73(s, 3H), 3.46–3.50 (m, 4H), 3.72–3.76(m, 4H), 4.18(q, 1H, J=7.1 Hz), 5.58(s, 1H), 7.11–7.61(m, 8H), 8.56(br-s, 2H)

Example 75

({3-[1-(2-Fluoro-biphenyl-4-yl)-cyclopropyl]-isoxazol-5-ylimino}-morpholin-4-yl-methyl)-amine methanesulfonate

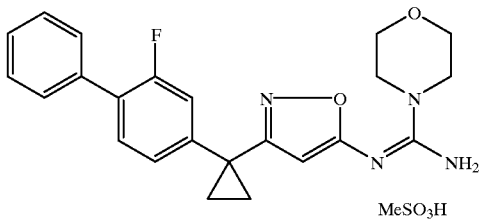

The desired compound was obtained by the same procedure as in Example 72 except for using the compound obtained in Example 59.

¹H-NMR (300 MHz, CDCl₃) δ ppm: 1.36–1.41(m, 2H), 1.47–1.52(m, 2H), 2.74(s, 3H), 3.46–3.50(m, 4H), 3.73–3.78(m, 4H), 5.50 (s, 1H), 7.12–7.23(m, 2H), 7.33–7.48(m, 4H), 7.51–7.56(m, 2H), 8.61(br-s, 2H), 11.10 (br-s, 1H)

Example 76

[(3-Biphenyl-4-ylmethyl-isoxazol-5-ylimino)-morpholin-4-yl-methyl]-amine methanesulfonate

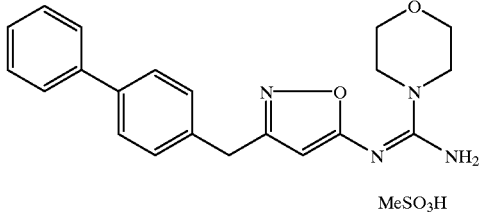

The desired compound was obtained by the same procedure as in Example 72 except for using the compound obtained in Example 60.

¹H-NMR (300 MHz, CD₃OD) δ ppm: 2.69(s, 3H), 3.60(t, 4H, J=5.3 Hz), 3.77(t, 4H, J=5.3 Hz), 4.02(s, 2H), 5.92(s, 1H), 7.32–7.45 (m, 5H), 7.56–7.60(m, 4H)

Example 77

{[3-(1-Biphenyl-4-yl-ethyl)-isoxazol-5-ylimino]-morpholin-4-yl-methyl}-amine methanesulfonate

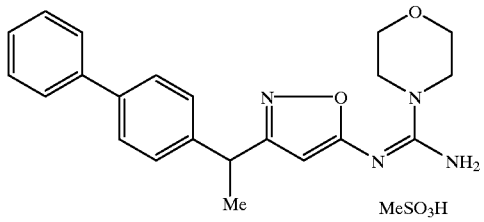

The desired compound was obtained by the same procedure as in Example 72 except for using the compound obtained in Example 61.

¹H-NMR (300 MHz, CD₃OD) δ ppm: 1.68(d, 3H, J=7.3 Hz), 2.69(s, 3H), 3.57(t, 4H, J=4.3 Hz), 3.76(t, 4H, J=4.3 Hz), 4.23(q, 1H, J=7.3 Hz), 5.91(s, 1H), 7.29–7.44(m, 5H), 7.57–7.60(m, 4H)

Example 78

{[3-(1-Biphenyl-4-yl-1-methyl-ethyl)-isoxazol-5-ylimino]-morpholin-4-yl-methyl}-amine methanesulfonate

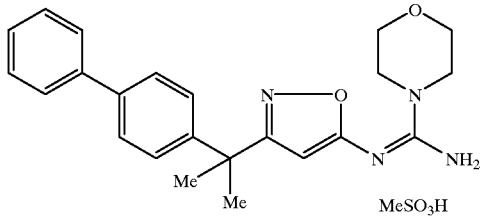

The desired compound was obtained by the same procedure as in Example 72 except for using the compound obtained in Example 62.

¹H-NMR (300 MHz, CD₃OD) δ ppm: 1.75(s, 6H), 2.68(s, 3H), 3.58(t, 4H, J=5.3 Hz), 3.76(t, 4H, J=5.3 Hz), 5.83(s, 1H), 7.32–7.45(m, 5H), 7.56–7.60(m, 4H)

Example 79

({3-[1-(2-Fluoro-4'-methoxy-biphenyl-4-yl)-ethyl]-isoxazol-5-ylimino}-morpholin-4-yl-methyl)-amine methanesulfonate

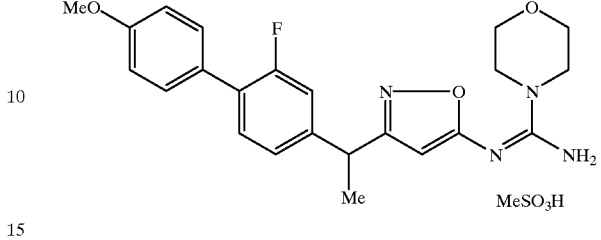

The desired compound was obtained by the same procedure as in Example 72 except for using the compound obtained in Example 63.

Melting point 187–189° C. (decomp.)

¹H-NMR (300 MHz, d₆-DMSO) δ ppm: 1.59(d, 3H, J=7.0 Hz), 2.29(s, 3H), 3.40–3.53 (m, 4H), 3.63–3.67(m, 4H), 3.78(s, 3H), 4.26 (q, 1H, J=7.2 Hz), 6.00(s, 1H), 7.02(d, 2H, J=8.4 Hz), 7.19–7.30(m, 2H), 7.41–7.48(m, 3H), 8.40(br-s, 2H)

IR (KBr) [cm⁻¹]: 3098, 1674, 1634, 1614, 1496, 1456, 1251, 1182, 1116, 1048, 825

Elementary Analysis Calculated: C 55.37, H 5.62, N 10.76 Found: C 55.32, H 5.60, N 10.77

Example 80

[2-(N'-(tert-Butoxycarbonyl)-N''-{3-[1-(2-fluoro-biphenyl-4-yl)-ethyl]-isoxazol-5-yl)-guanidino)-ethoxy]-acetic acid

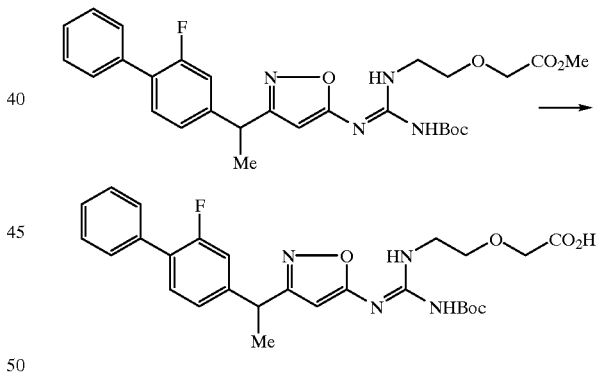

The compound (52 mg) obtained in Example 32 was dissolved in tetrahydrofuran (1 ml) and a 5% aqueous sodium hydroxide solution (1 ml) was added, after which the solution was stirred at room temperature for 3 hours. To the reaction mixture was added a saturated aqueous ammonium chloride solution and thereafter the resulting mixture was subjected to extraction with ethyl acetate. The organic layer was dried over magnesium sulfate and then concentrated under reduced pressure. The residue was purified by a silica gel column chromatography (chloroform/methanol=9/1) to obtain the desired compound (25 mg).

¹H-NMR (300 MHz, CDCl₃) δ ppm: 1.42(s, 9H), 1.62(d, 3H, J=7.1 Hz), 3.50–3.64 (m, 2H), 3.65–3.75(m, 2H), 4.06 (s, 2H), 4.06–4.14(m, 1H), 5.31(s, 1H), 7.05–7.13(m, 2H), 7.30–7.42(m, 4H), 7.48–7.51(m, 2H), 8.18(br-s, 1H), 8.44 (br-s, 1H)

IR (neat) [cm$^{-1}$]: 3397, 3348, 2980, 2934, 1731, 1634, 1606, 1562, 1486, 1455, 1418, 1370, 1242, 1150, 912, 770, 733, 699

Example 81

Sodium [2-(N'-{3-[1-(2-fluoro-biphenyl-4-yl)-ethyl]-isoxazol-5-yl}-guanidino)-ethoxy]-acetate

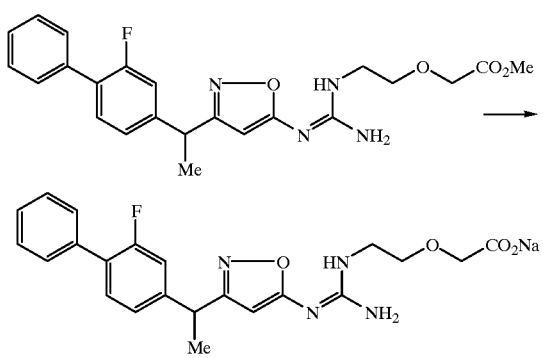

The compound (4.32 g) obtained in Example 48 was dissolved in tetrahydrofuran (80 ml) and a 5% aqueous sodium hydroxide solution (80 ml) was added, after which the solution was stirred at room temperature for one hour. The reaction mixture was concentrated under reduced pressure and then filtered, after which the solid materials were washed with ethyl acetate and water. The filtrate was concentrated and thereafter the solid materials were again separated by filtration and then washed with ethyl acetate and water. The combined crude crystals were purified by a recrystallization method from water to obtain the desired compound (3.08 g).

$^1$H-NMR (300 MHz, CD$_3$OD), δ ppm: 1.63(d, 3H, J=7.1 Hz), 3.38–3.42(m, 2H), 3.56–3.60(m, 2H), 3.87(s, 2H), 4.13(q, 1H, J=7.2 Hz), 5.35(s, 1H), 7.11–7.21(m, 2H), 7.30–7.43 (m, 4H), 7.49–7.52(m, 2H)

R (neat) [cm$^{-1}$]; 3429, 1573, 1453, 1430, 1330, 694

Elementary analysis Calculated: C 57.77, H 5.07, N 12.25 Found: C 57.86, H 5.15, N 12.19

Example 82

(R)-({3-[1-(2-Fluoro-biphenyl-4-yl)-ethyl]-isoxazol-5-ylimino}-morpholin-4-yl-methyl)-amine hydrochloride

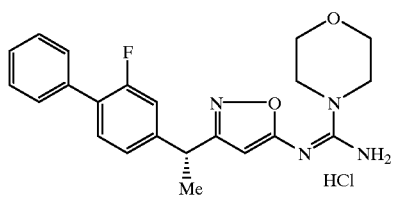

The desired compound was obtained by the same procedure as in Example 66 except for using the compound obtained in Example 54.

Melting point 134–136° C.

$^1$H-NMR (300 MHz, CDCl$_3$) δ ppm: 1.64(d, 3H, J=7.1 Hz), 3.45–3.65(m, 4H), 3.70–3.80(m, 4H), 4.15(q, 1H, J=7.1 Hz), 5.69(s, 1H), 7.03–7.11(m, 2H), 7.33–7.52(m, 6H), 8.45 (br-s, 2H), 11.31(br-s, 1H)

$[α]_D^{22}$=−16.0° (c: 1.00, CHCl$_3$)

Example 83

(S)-({3-[1-(2-Fluoro-biphenyl-4-yl)-ethyl]-isoxazol-5-ylimino}-morpholin-4-yl-methyl)-amine hydrochloride

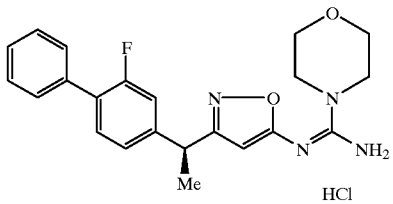

The desired compound was obtained by the same procedure as in Example 66 except for using the compound obtained in Example 55.

Melting point 134–136° C.

$^1$H-NMR (300 MHz, CDCl$_3$) δ ppm: 1.64(d, 3H, J=7.3 Hz), 3.45–3.60(m, 4H), 3.60–3.80(m, 4H), 4.15(q, 1H, J=7.3 Hz), 5.69(s, 1H), 7.02–7.12(m, 2H), 7.32–7.52(m, 6H), 8.44 (br-s, 2H)

$[α]_D^{22}$=+14.4° (c: 1.00, CHCl$_3$)

Example 84

(R)-({3-[1-(2-Fluoro-biphenyl-4-yl)-ethyl]-isoxazol-5-ylimino}-morpholin-4-yl-methyl)-amine phosphate

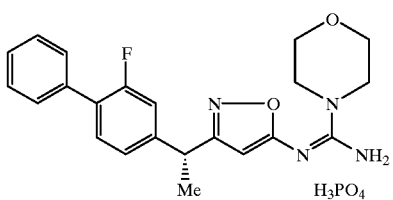

The desired compound was obtained by treating the compound obtained in Example 54 with phosphoric acid.

$^1$H-NMR (300 MHz, CDCl$_3$) δ ppm: 1.54(d, 3H, J=7.3 Hz), 3.40–3.43(m, 4H), 3.55–3.58(m, 4H), 4.11(q, 1H, J=7.3 Hz), 5.42(s, 1H), 6.46(br-s, 2H), 7.21–7.26(m, 2H), 7.38–7.53(m, 6H)

IR (neat) [cm$^{-1}$]: 3381, 2973, 2361, 1682, 1618, 1552, 1484, 1456, 1411, 1274, 1113

$[α]_D^{20}$=−27.2° (c: 0.60, MeOH)

Example 85

(S)-({3-[1-(2-Fluoro-biphenyl-4-yl)-ethyl]-isoxazol-5-ylimino}-morpholin-4-yl-methyl)-amine phosphate

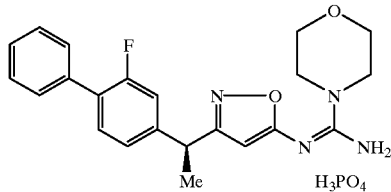

The desired compound was obtained by the same procedure as in Example 84 except for using the compound obtained in Example 55.

$^1$H-NMR (300 MHz, CDCl$_3$) δ ppm: Same as in Example 84.

IR (neat) [cm$^{-1}$]: Same as in Example 84.

$[α]_D^{20}$=+27.7° (c: 0.52, MeOH)

Example 86

(R)-({3-[1-(2-Fluoro-biphenyl-4-yl)-ethyl]-isoxazol-5-ylimino}-morpholin-4-yl-methyl)-amine methanesulfonate

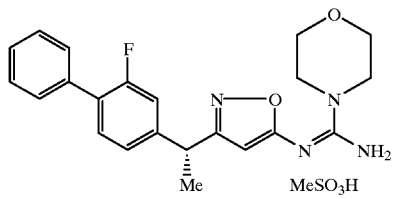

The desired compound was obtained by the same procedure as in Example 72 except for using the compound obtained in Example 54.

Melting point: 166–167° C.

$^1$H-NMR (300 MHz, CDCl$_3$) δ ppm: 1.66(d, 3H, J=7.1 Hz), 2.72(s, 3H), 3.46–3.51 (m, 4H), 3.71–3.77(m, 4H), 4.17(q, 1H, J=7.2 Hz), 5.59(s, 1H), 7.02–7.12(m, 2H), 7.33–7.46 (m, 4H), 7.50–7.53(m, 2H), 8.62(br-s, 2H), 11.14 (br-s, 1H)

IR (neat) [cm$^{-1}$]: 2974, 1668, 1634, 1548, 1484, 1446, 1270, 1194, 1117, 1043, 776, 699

$[α]_D^{22}$=−14.0° (c: 1.00, CHCl$_3$)

Example 87

(S)-({3-[1-(2-Fluoro-biphenyl-4-yl)-ethyl]-isoxazol-5-ylimino}-morpholin-4-yl-methyl)-amine methanesulfonate

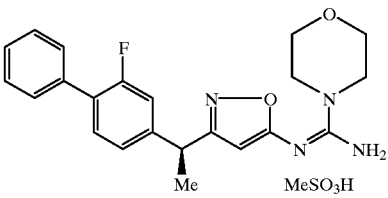

The desired compound was obtained by the same procedure as in Example 72 except for using the compound obtained in Example 55.

Melting point 162–165° C.

$^1$H-NMR (300 MHz, CDCl$_3$) δ ppm: 1.66(d, 3H, J=7.3 Hz), 2.72(s, 3H), 3.46–3.51 (m, 4H), 3.71–3.78(m, 4H), 4.17(q, 1H, J=7.1 Hz), 5.59(s, 1H), 7.02–7.12(m, 2H), 7.33–7.46 (m, 4H), 7.50–7.53(m, 2H), 8.62(br-s, 2H), 11.13 (br-s, 1H)

IR (neat) [cm$^{-1}$]: 2972, 1668, 1634, 1548, 1484, 1446, 1418, 1198, 1116, 1062, 1010, 768, 699

$[α]_D^{22}$=+12.0° (c: 0.80, CHCl$_3$)

Example 88

(R)-({3-[1-(2-Fluoro-biphenyl-4-yl)-ethyl]-isoxazol-5-ylimino}-morpholin-4-yl-methyl)-amine benzenesulfonate

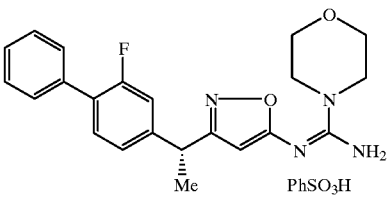

The desired compound was obtained by treating the compound obtained in Example 54 with benzenesulfonic acid.

$^1$H-NMR (300 MHz, CDCl$_3$) δ ppm: 1.59(d, 3H, J=7.1 Hz), 3.50(m, 4H), 3.66(m, 4H), 4.26(q, 1H, J=7.1 Hz), 5.98(s, 1H), 7.25–7.59(m, 13H)

IR (neat) [cm$^{-1}$]: 3135, 1679, 1630, 1552, 1484, 1445, 1418 $[α]_D^{20}$=−16.9° (c: 0.53, MeOH)

Example 89

(S)-({3-[1-(2-Fluoro-biphenyl-4-yl)-ethyl]-isoxazol-5-ylimino}-morpholin-4-yl-methyl)-amine benzenesulfonate

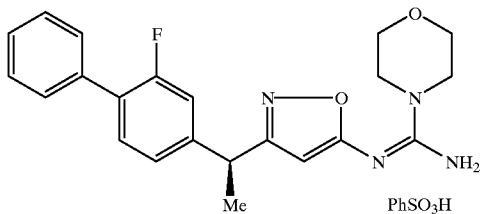

The desired compound was obtained by the same procedure as in Example 88 except for using the compound obtained in Example 55.

¹H-NMR (300 MHz, CDCl₃) δ ppm: Same as in Example 88.

IR (neat) [cm⁻¹]: Same as in Example 88.

[α]$_D^{20}$=+16.8° (c: 0.51, MeOH)

Example 90

(R)-({3-[1-(2-Fluoro-biphenyl-4-yl)-ethyl]-isoxazol-5-ylimino}-morpholin-4-yl-methyl)-amine sulfate

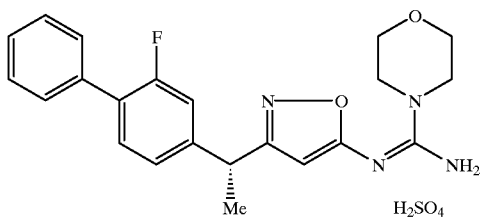

The desired compound was obtained by treating the compound obtained in Example 54 with sulfuric acid.

¹H-NMR (300 MHz, CDCl₃) δ ppm: 1.53(d, 3H, J=7.3 Hz), 3.30–3.80(m, 8H), 4.07 (q, 1H, J=6.8 Hz), 5.72(s, 1H), 6.97–7.05(m, 2H), 7.28–7.44(m, 6H), 7.95(br-s, 2H)

[α]$_D^{22}$=−20.2° (c: 1.00, THF)

Example 91

(S)-({3-[1-(2-Fluoro-biphenyl-4-yl)-ethyl]-isoxazol-5-ylimino}-morpholin-4-yl-methyl)-amine sulfate

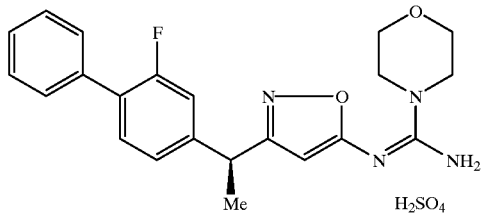

The desired compound was obtained by the same procedure as in Example 90 except for using the compound obtained in Example 55.

¹H-NMR (300 MHz, CDCl₃) δ ppm: 1.53(d, 3H, J=6.8 Hz), 3.30–3.80(m, 8H), 4.05–4.10(m, 1H), 5.72(s, 1H), 6.97–7.05(m, 2H), 7.28–7.44(m, 6H), 7.95(br-s, 1H)

[α]$_D^{22}$=+20.2° (c: 1.00, THF)

Example 92

(R)-({3-[1-(2-Fluoro-biphenyl-4-yl)-ethyl]-isoxazol-5-ylimino}-morpholin-4-yl-methyl)-amine D-camphorsulfonate

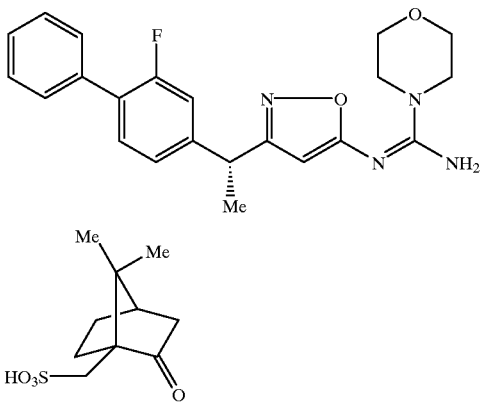

The desired compound was obtained by treating the compound obtained in Example 54 with D-camphorsulfonic acid.

Melting point 167–169° C.

¹H-NMR (300 MHz, CDCl₃) δ ppm: 0.76(s, 3H), 0.95(s, 3H), 1.23–1.32(m, 1H), 1.53–1.62(m, 1H), 1.66(d, 3H, J=7.3 Hz), 1.79 (d, 1H, J=18.1 Hz), 1.82–1.88(m, 1H), 1.96–2.00 (m, 1H), 2.21–2.28(m, 1H), 2.35–2.47(m, 1H), 2.76(d, 1H, J=14.6 Hz), 3.26(d, 1H, J=14.6 Hz), 3.48–3.52 (m, 4H), 3.73–3.76(m, 4H), 4.17(q, 1H, J=7.1 Hz), 5.63(s, 1H), 7.03–7.53(m, 8H), 8.35(br-s, 2H), 11.12(br-s, 2H)

Example 93

(S)-({3-[1-(2-Fluoro-biphenyl-4-yl)-ethyl]-isoxazol-5-ylimino}-morpholin-4-yl-methyl)-amine D-camphorsulfonate

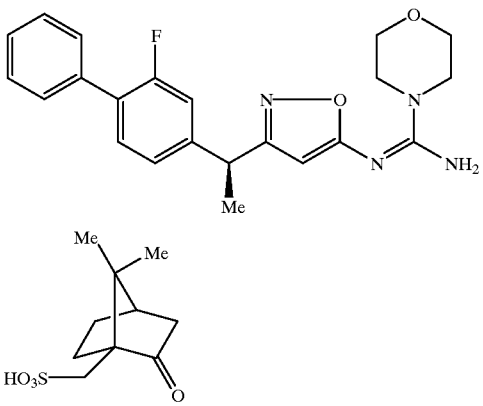

The desired compound was obtained by the same procedure as in Example 92 except for using the compound obtained in Example 55.

Melting point 167–168° C.

¹H-NMR (300 MHz, CDCl₃) δ ppm: 0.76(s, 3H), 0.95(s, 3H), 1.24–1.32(m, 1H), 1.54–1.65(m, 1H), 1.66(d, 3H, J=7.1 Hz), 1.79 (d, 1H, J=18.1 Hz), 1.82–1.91(m, 1H), 1.96–2.00(m, 1H), 2.21–2.30(m, 1H), 2.35–2.47(m, 1H), 2.75(d, 1H, J=14.6 Hz), 3.26(d, 1H, J=14.7 Hz), 3.48–3.52 (m, 4H), 3.73–3.76(m, 4H), 4.17(q, 1H, J=7.1 Hz), 5.66(s, 1H), 7.04–7.14 (m, 2H), 7.33–7.52(m, 6H), 8.53(br-s, 2H), 11.11(br-s, 1H)

Example 94

(R)-({3-[1-(2-Fluoro-biphenyl-4-yl)-ethyl]-isoxazol-5-ylimino}-morpholin-4-yl-methyl)-amine 3-bromo-(+)-camphor-10-sulfonate

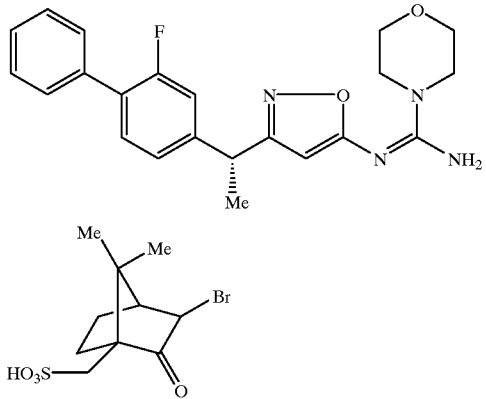

The desired compound was obtained by treating the compound obtained in Example 54 with 3-bromo-(+)-camphor-10-sulfonic acid.

$^1$H-NMR (300 MHz, CDCl$_3$) δ ppm: 0.97(s, 3H), 1.25(s, 3H), 1.47–1.54(m, 1H), 1.68(d, 3H, J=7.1 Hz), 1.85–2.00(m, 1H), 2.00–2.10(m, 1H), 2.23–2.26(m, 1H), 2.65–2.69(m, 1H), 2.83(d, 1H, J=14.8 Hz), 3.23–3.28(m, 1H), 3.55–3.59 (m, 4H), 3.74–3.78(m, 4H), 4.27(q, 1H, J=7.1 Hz), 4.76–4.79(m, 1H), 5.91(s, 1H), 7.13–7.23(m, 2H), 7.34–7.51(m, 6H)

Example 95

(S)-({3-[1-(2-Fluoro-biphenyl-4-yl)-ethyl]-isoxazol-5-ylimino}-morpholin-4-yl-methyl)-amine 3-bromo-(+)-camphor-10-sulfonate

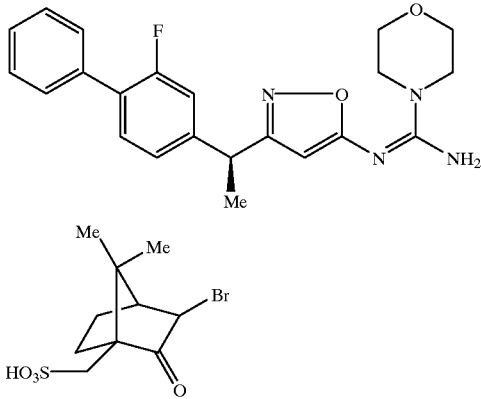

The desired compound was obtained by the same procedure as in Example 94 except for using the compound obtained in Example 55.

$^1$H-NMR (300 MHz, CDCl$_3$) δ ppm: 0.95(s, 3H), 1.23(s, 3H), 1.49–1.59(m, 1H), 1.67(d, 3H, J=7.4 Hz), 1.80–2.15(m, 2H), 2.21–2.24(m, 1H), 2.62–2.66(m, 1H), 2.83(d, 1H, J=15.0 Hz), 3.23–3.28(m, 1H), 3.53–3.60(m, 4H), 3.73–3.77 (m, 4H), 4.21(q, 1H), J=7.3 Hz), 4.62–4.65(m, 1H), 5.79(s, 1H), 7.06–7.17(m, 2H), 7.30–7.49(m, 6H)

Example 96

(R)-({3-[1-(2-Fluoro-biphenyl-4-yl)-ethyl]-isoxazol-5-ylimino}-morpholin-4-yl-methyl)-amine 3-bromo-(+)-camphor-8-sulfonate

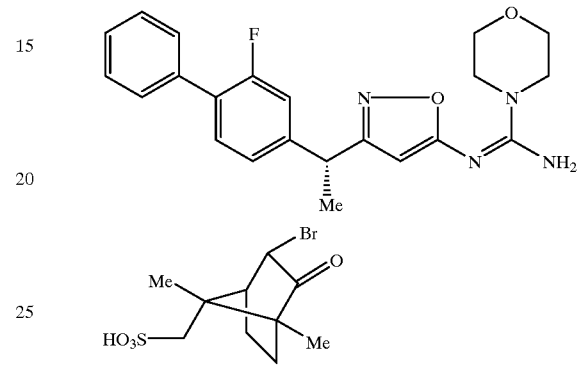

The desired compound was obtained by treating the compound obtained in Example 54 with 3-bromo-(+)-camphor-8-sulfonic acid.

$^1$H-NMR (300 MHz, CDCl$_3$) δ ppm: 0.90(s, 3H), 1.22(s, 3H), 1.37–1.43(m, 1H), 1.50–1.63(m, 1H), 1.67(d, 3H, J=7.1 Hz), 1.90–2.15(m, 2H), 2.76(d, 1H, J=14.3 Hz), 2.94(s, 1H), 3.15(d, 1H, J=14.6 Hz), 3.40–3.52(m, 4H), 3.72–3.77(m, 4H), 4.17(q, 1H, J=7.1 Hz), 4.50 (d, 1H, J=4.7 Hz), 5.50(s, 1H), 7.01–7.12(m, 2H), 7.34–7.53(m, 6H)

Example 97

(S)-({3-[1-(2-Fluoro-biphenyl-4-yl)-ethyl]-isoxazol-5-ylimino}-morpholin-4-yl-methyl)-amine 3-bromo-(+)-camphor-8-sulfonate

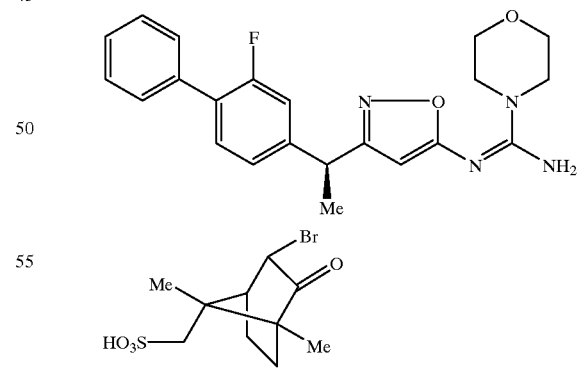

The desired compound was obtained by the same procedure as in Example 96 except for using the compound obtained in Example 54.

$^1$H-NMR (300 MHz, CDCl$_3$) δ ppm: 0.90(s, 3H), 1.11(s, 3H), 1.37–1.48(m, 1H), 1.50–1.63(m, 1H), 1.67(d, 3H, J=7.1 Hz), 1.95–2.15(m, 2H), 2.76(d, 1H, J=14.3 Hz), 2.94(s, 1H), 3.15(d, 1H, J=14.5 Hz), 3.40–3.52(m, 4H), 3.72–3.77(m, 4H), 4.18(q, 1H, J=7.1 Hz), 4.49 (d, 1H, J=4.8 Hz), 5.52(s, 1H), 7.02–7.12(m, 2H), 7.36–7.53(m, 6H)

Example 98

({3-[1-(9H-Carbazol-2-yl)-ethyl]-isoxazol-5-ylimino}-morpholin-4-yl-methyl)-amine

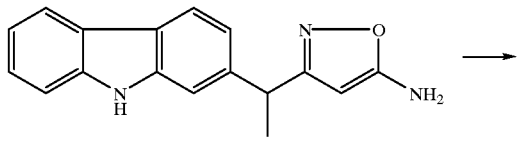

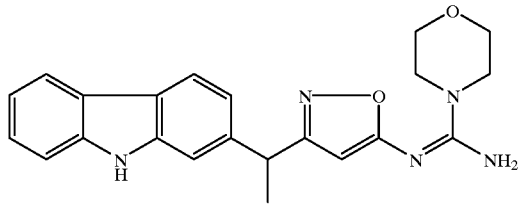

The desired compound was obtained by the same procedure as in Example 54 except for using the compound obtained in Reference Example 34.

Melting point 113° C. (decomp.)

¹H-NMR (300 MHz, CDCl₃) δ ppm: 1.71(d, 3H, J=7.1 Hz), 3.42–3.46(m, 4H), 3.66–3.71(m, 4H), 4.27(q, 1H, J=7.1 Hz), 5.26(s, 1H), 5.35(br-s, 2H), 7.16–7.23(m, 2H), 7.33–7.42(m, 3H), 7.96–8.04(m, 2H), 8.15(s, 1H)

Example 99

{[3-(2-Fluoro-biphenyl-4-ylmethyl)-isoxazol-5-ylimino]-morpholin-4-yl-methyl}-amine

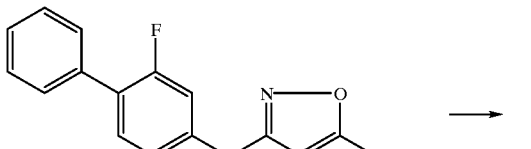

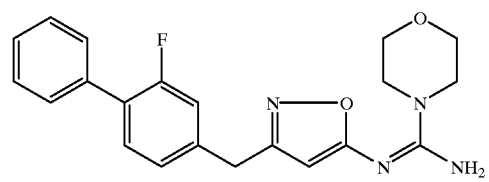

The desired compound was obtained by the same procedure as in Example 54 except for using the compound obtained in Reference Example 35.

¹H-NMR (300 MHz, CDCl₃) δ ppm: 3.47–3.51(m, 4H), 3.71–3.75(m, 4H), 3.92(s, 2H), 5.26(s, 1H), 5.38(br-s, 2H), 7.04–7.14(m, 2H), 7.33–7.47(m, 4H), 7.50–7.55(m, 2H)

Example 100

{[3-(2-Fluoro-biphenyl-4-ylmethyl)-isoxazol-5-ylimino]-morpholin-4-yl-methyl}-amine methanesulfonate

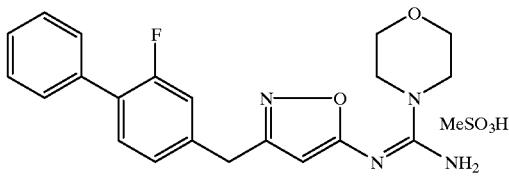

The desired compound was obtained by the same procedure as in Example 72 except for using the compound obtained in Example 99.

Melting point 71–74° C. (decomp.)

¹H-NMR (300 MHz, CDCl₃) δ ppm: 2.73(s, 3H), 3.47–3.51(m, 4H), 3.69–3.73(m, 4H), 3.96(s, 2H), 5.63(s, 1H), 7.01–7.11(m, 2H), 7.34–7.47(m, 4H), 7.50–7.54(m, 2H), 8.63(br-s, 2H), 11.2(br-s, 1H)

Example 101

({3-[1-(2,3-Dihydro-benzo[1,4]dioxin-6-yl)-ethyl]-isoxazol-5-ylimino}-morpholin-4-yl-methyl)-amine

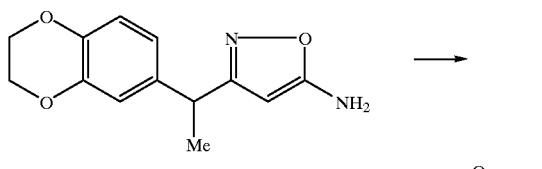

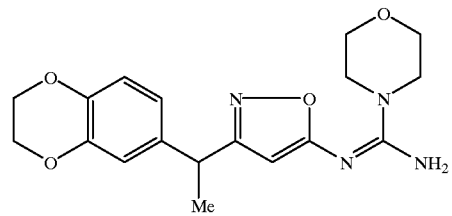

The desired compound was obtained by the same procedure as in Example 54 except for using the compound 15 obtained in Reference Example 37.

¹H-NMR (270 MHz, CDCl₃) δ ppm: 1.58(d, 3H, J=7.3 Hz), 3.47(t, 4H, J=4.6 Hz), 3.72(t, 4H, J=4.6 Hz), 4.00(q, 1H, J=7.3 Hz), 4.22(s, 4H), 5.20(s, 1H), 5.35(br-s, 2H), 6.77–6.80(m, 3H)

Example 102

({3-[1-(1-Methyl-1H-indol-3-yl)-ethyl]-isoxazol-5-ylimino}-morpholin-4-yl-methyl)-amine

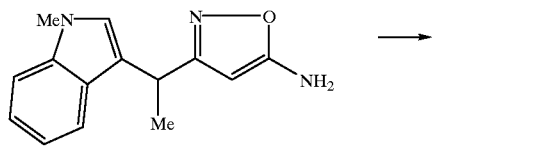

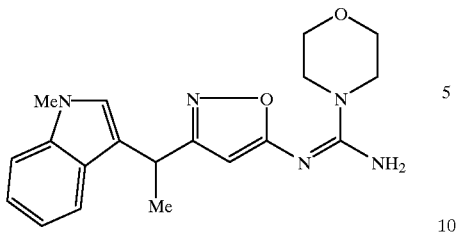

The desired compound was obtained by the same procedure as in Example 54 except for using the compound obtained in Reference Example 38.

$^1$H-NMR (270 MHz, CDCl$_3$) δ ppm: 1.72(d, 3H, J=7.3 Hz), 3.43(t, 4H, J=4.6 Hz), 3.68(t, 4H, J=4.6 Hz), 3.73(s, 3H), 4.40(q, 1H, J=7.3 Hz), 5.24(s, 1H), 5.31(br-s, 2H), 6.92(s, 1H), 7.03–7.28(m, 3H), 7.61(d, 1H, J=7.9 Hz)

Example 103

({3-[1-(1H-Indol-3-yl)-ethyl]-isoxazol-5-ylimino}-morpholin-4-yl-methyl)-amine

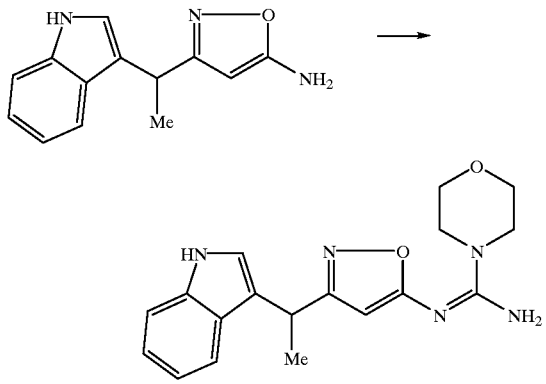

The desired compound was obtained by the same procedure as in Example 54 except for using the compound obtained in Reference Example 39.

$^1$H-NMR (270 MHz, CDCl$_3$) δ ppm: 1.72(d, 3H, J=7.3 Hz), 3.44(t, 4H, J=5.0 Hz), 3.69(t, 4H, J=5.0 Hz), 4.41(q, 1H, J=7.3 Hz), 5.23(s, 1H), 5.28(br-s, 2H), 7.04–7.19(m, 3H), 7.33(d, 1H, J=7.9 Hz), 7.63(d, 1H, J=7.9 Hz), 8.03(br-s, 1H)

Example 104

({3-[1-(1-Methyl-1H-indol-2-yl)-ethyl]-isoxazol-5-ylimino}-morpholin-4-yl-methyl)-amine

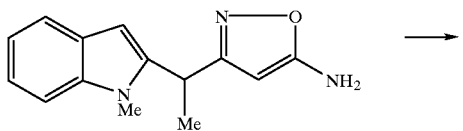

The desired compound was obtained by the same procedure as in Example 54 except for using the compound obtained in Reference Example 41.

$^1$H-NMR (270 MHz, CDCl$_3$) δ ppm: 1.73(d, 3H, J=7.3 Hz), 3.44(t, 4H, J=4.6 Hz), 3.64(s, 3H), 3.70(t, 4H, J=4.6 Hz), 4.34(q, 1H, J=7.3 Hz), 5.12(s, 1H), 5.26(br-s, 2H), 6.45(s, 1H), 7.04–7.26(m, 3H), 7.56(d, 1H, J=7.3 Hz)

Example 105

{[3-(1-Benzofuran-5-yl-ethyl)-isoxazol-5-ylimino]-morpholin-4-yl-methyl}-amine

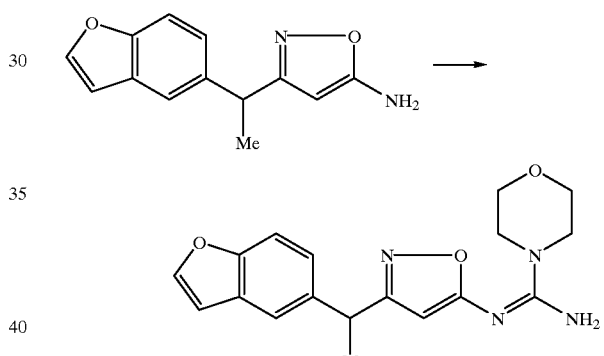

The desired compound was obtained by the same procedure as in Example 54 except for using the compound obtained in Reference Example 43.

$^1$H-NMR (270 MHz, CDCl$_3$) δ ppm: 1.67(d, 3H, J=7.3 Hz), 3.46(t, 4H, J=4.6 Hz), 3.71(t, 4H, J=4.6 Hz), 4.19(q, 1H, J=7.3 Hz), 5.20(s, 1H), 5.34(br-s, 2H), 6.71(d, 1H, J=2.3 Hz), 7.21–7.26(m, 1H), 7.42(d, 1H, J=8.6 Hz), 7.51(d, 1H, J=1.7 Hz), 7.59(d, 1H, J=2.3 Hz)

Example 106

{[3-(1-Benzofuran-6-yl-ethyl)-isoxazol-5-ylimino]-morpholin-4-yl-methyl}-amine

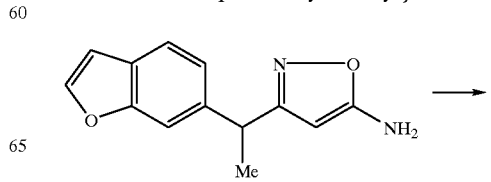

-continued

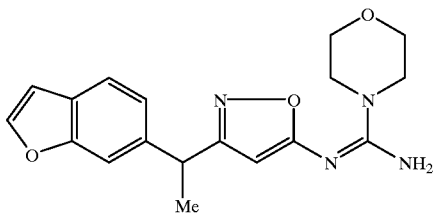

The desired compound was obtained by the same procedure as in Example 54 except for using the compound obtained in Reference Example 45.

¹H-NMR (270 MHz, CDCl₃) δ ppm: 1.68(d, 3H, J=7.3 Hz), 3.46(t, 4H, J=4.6 Hz), 3.71(t, 4H, J=4.6 Hz), 4.23(q, 1H, J=7.3 Hz), 5.21(s, 1H), 5.33(br-s, 2H), 6.72(d, 1H, J=2.3 Hz), 7.19(dd, 1H, J=8.3, 1.7 Hz), 7.45–7.52 (m, 2H), 7.58(d, 1H, J=2.3 Hz)

Example 107

(3-{1-[5-(Amino-morpholin-4-yl-methyleneamino)-isoxazol-3-yl]-ethyl}-phenyl)-phenyl-methanone methanesulfonate

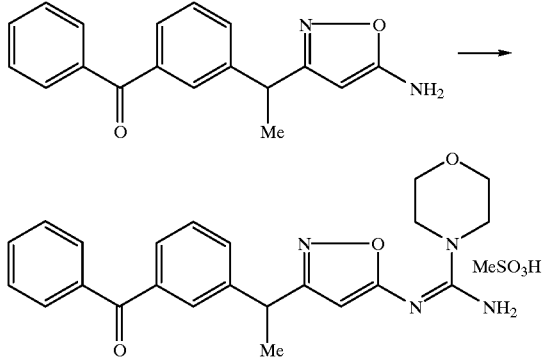

The desired compound was obtained by the same procedure as in Example 54 and Example 72 except for using {3-[1-(5-amino-isoxazol-3-yl)-ethyl]-phenyl)-phenyl-methanone (Japanese Patent Unexamined Publication No. 63-152,368).

¹H-NMR (300 MHz, CDCl₃) δ ppm: 1.67(d, 3H, J=7.1 Hz), 2.72(s, 3H), 3.45–3.51 (m, 4H), 3.72–3.76(m, 4H), 4.22(q, 1H, J=7.1 Hz), 5.57(s, 1H), 7.40–7.51(m, 4H), 7.57–7.65 (m, 2H), 7.71(s, 1H), 7.77–7.79(m, 2H), 8.61 (br-s, 2H), 11.13(br-s, 1H)

Example 108

[({3-[1-(2-Fluoro-biphenyl-4-yl)-ethyl]-isoxazol-5-ylimino}-morpholin-4-yl-methylimino)-morpholine-4-yl-methyl]-amine

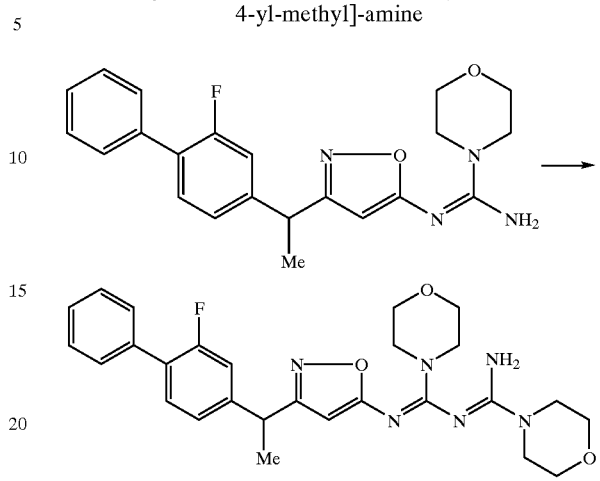

A mixture of the free form of the compound (2.20 g) obtained in Example 22, 4-morphlinecarbonitrile (2.8 ml) and sodium amide (0.44 g) was stirred at room temperature for 5 hours. The reaction mixture was poured into a saturated aqueous ammonium chloride solution and then subjected to extraction with chloroform. The organic layer was dried over magnesium sulfate and then concentrated under reduced pressure, after which the residue was purified by a silica gel column chromatography to obtain the desired compound (1.62 g).

¹H-NMR (300 MHz, CDCl₃) δ ppm: 1.62(d, 3H, J=7.3 Hz), 3.26–3.29(m, 4H), 3.54–3.57(m, 4H), 3.63–3.66(m, 8H), 4.11(q, 1H, J=7.2 Hz), 4.63(br-s, 2H), 5.01(s, 1H), 7.05–7.17(m, 2H), 7.33–7.54(m, 6H)

Example 109

[({3-[1-(2-Fluoro-biphenyl-4-yl)-ethyl]-isoxazol-5-ylimino}-morpholin-4-yl-methylimino)-morpholin-4-yl-methyl]-amine hydrochloride

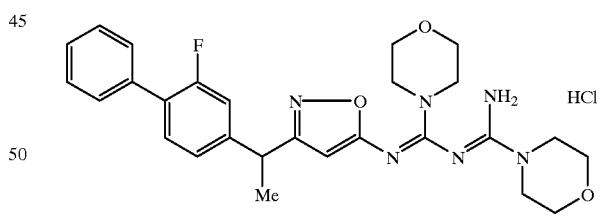

The compound (1.66 g) obtained in Example 108 was dissolved in 1,4-dioxane (20 ml) and thereto was added a 4 N hydrogen chloride/1,4-dioxane solution (1.00 ml), after which the resulting mixture was stirred at room temperature for 2 hours, upon which a white precipitate separated. The reaction mixture was heated to 100° C. to dissolve the precipitate and thereafter allowed to slowly cool with stirring. The resulting white precipitate was separated by filtration to obtain the desired compound (1.19 g).

¹H-NMR (300 MHz, CDCl₃) δ ppm: 1.66(d, 3H, J=7.1 Hz), 3.44–3.56(m, 4H), 3.60–3.68(m, 4H), 3.68–3.83(m, 8H), 4.16(q, 1H, J=7.0 Hz), 5.52(s, 1H), 7.03–7.15(m, 4H), 7.35–7.55(m, 6H)

Example 110

({3-[1-(2-Fluoro-biphenyl-4-yl)-vinyl]-isoxazol-5-ylimino}-morpholin-4-yl-methyl)-amine

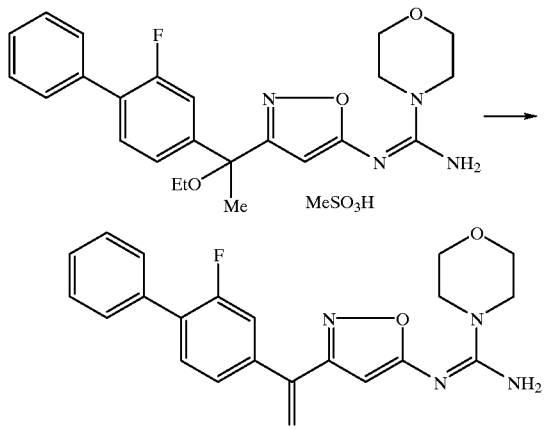

Trifluoroacetic acid (4 ml) was added to a solution of the compound (30.0 mg) obtained in Example 53 in methylene chloride (1 ml), and the resulting mixture was stirred at room temperature for 8 hours. After the addition of a saturated aqueous sodium chloride solution, the mixture was subjected to extraction with ethyl acetate, and the organic layer was washed successively with a saturated aqueous sodium bicarbonate solution and a saturated aqueous sodium chloride solution, thereafter dried over sodium sulfate and then concentrated under reduced pressure. The residue was purified by a silica gel column chromatography to obtain the desired compound (20 mg).

Melting point 167.5° C. (decomp.)

$^1$H-NMR (300 MHz, CDCl$_3$) δ ppm: 3.51–3.55(m, 4H), 3.74–3.78(m, 4H), 5.42(br-s, 2H), 5.54(s, 1H), 5.69(s, 1H), 5.84(s, 1H), 7.26–7.59(m, 8H)

Example 111

{Morpholin-4-yl-[3-(1-quinolin-3-yl-ethyl)-isoxazol-5-ylimino]-methyl}-amine

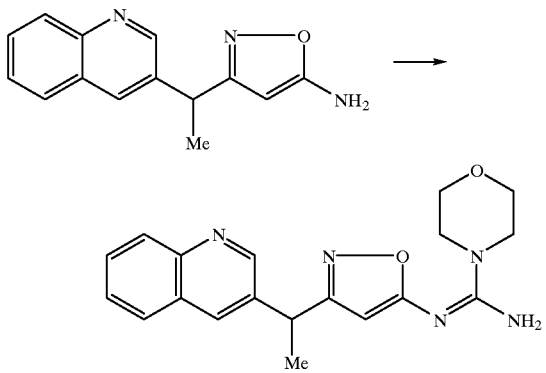

The desired compound was obtained by the same procedure as in Example 54 except for using the compound obtained in Reference Example 47.

$^1$H-NMR (270 MHz, CDCl$_3$) δ ppm: 1.76(d, 3H, J=7.3 Hz), 3.48(t, 4H, J=4.6 Hz), 3.72(t, 4H, J=4.6 Hz), 4.34(q, 1H, J=7.3 Hz), 5.24(s, 1H), 5.33(br-s, 2H), 7.50–7.79(m, 3H), 8.02–8.09(m, 2H), 8.89(d, 1H, J=2.3 Hz).

Example 112

{[3-(1-Isoquinolin-4-yl-ethyl)-isoxazol-5-ylimino]-morpholin-4-yl-methyl}-amine

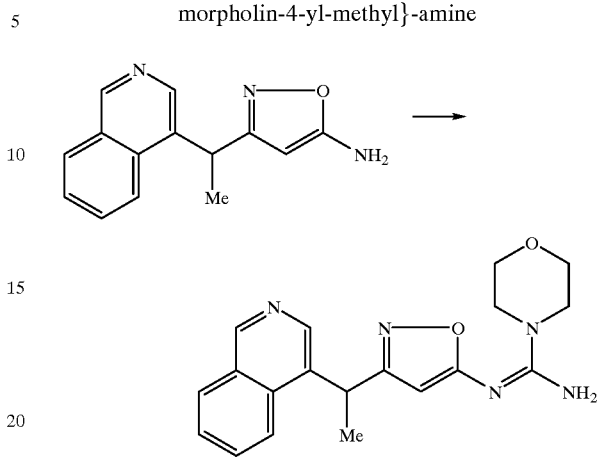

The desired compound was obtained by the same procedure as in Example 54 except for using the compound obtained in Reference Example 48.

$^1$H-NMR (270 MHz, CDCl$_3$) δ ppm: 1.83(d, 3H, J=7.3 Hz), 3.45(t, 4H, J=4.6 Hz), 3.68(t, 4H, J=4.6 Hz), 4.79(q, 1H, J=7.3 Hz), 5.13(s, 1H), 5.40(br-s, 2H), 7.56–7.72(m, 2H), 7.97(d, 1H, J=7.6 Hz), 8.14(d, 1H, J=8.6 Hz), 8.52(s, 1H), 9.15(s, 1H).

Example 113

{[3-(1-Biphenyl-4-yl-dimethoxy-methyl)-isoxazol-5-ylimino]-morpholin-4-yl-methyl}-amine

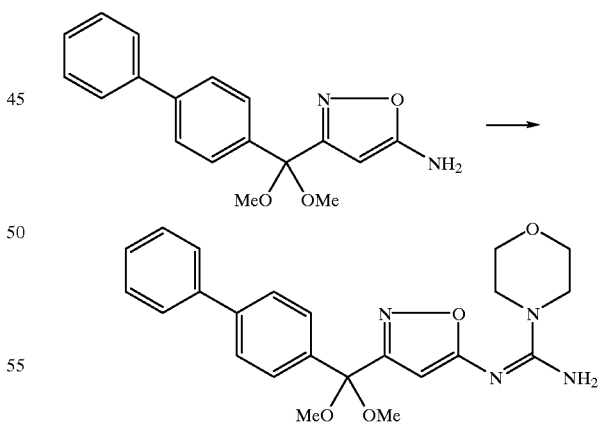

The desired compound was obtained by the same procedure as in Example 54 except for using the compound obtained in Reference Example 50.

$^1$H-NMR (270 MHz, CDCl$_3$) δ ppm: 3.28(s, 6H), 3.47(t, 4H, J=4.6 Hz), 3.71(t, 4H, J=4.6 Hz), 5.32(s, 1H), 5.36(br-s, 2H), 7.33–7.45(m, 3H), 7.54–7.67(m, 6H).

Example 114

({3-[Dimethoxy-(1-methyl-1H-indol-2-yl)-methyl]-isoxazol-5-ylimino}-morpholin-4-yl-methyl)-amine

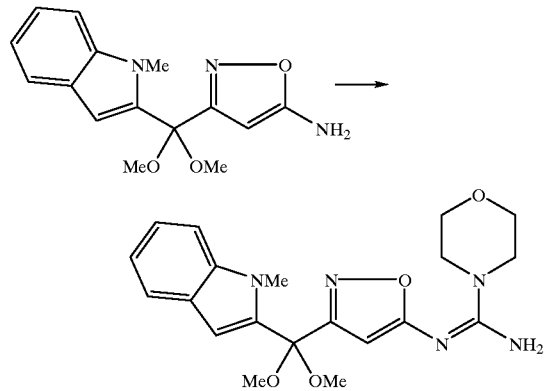

The desired compound was obtained by the same procedure as in Example 54 except for using the compound obtained in Reference Example 52.

¹H-NMR (270 MHz, CDCl₃) δ ppm: 3.27(s, 6H), 3.44(t, 4H, J=4.6 Hz), 3.66(s, 3H), 3.69(t, 4H, J=4.6 Hz), 5.26(s, 1H), 5.30(br-s, 2H), 6.87(s, 1H), 7.06–7.28(m, 3H), 7.62(d, 1H, J=7.6 Hz).

Example 115

N-(tert-Butoxycarbonyl)-N'-{3-[1-(2-fuoro-biphenyl-4-yl)-ethyl]-isoxazol-5-yl}-N''-phenyl-guanidine

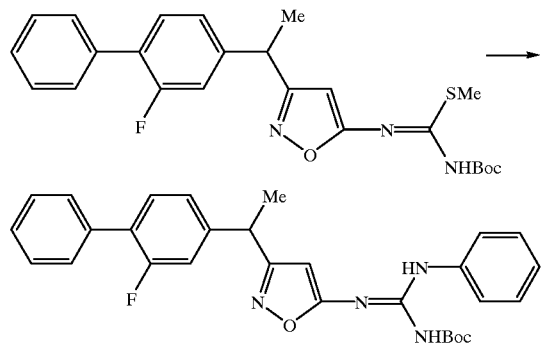

The desired compound was obtained by the same procedure as in Example 1.

¹H-NMR (300 MHz, CDCl₃) δ ppm: 1.54(s, 9H), 1.68(d, 3H, J=7.1 Hz), 4.16(q, 1H, J=7.1 Hz), 5.45(s, 1H), 7.07–7.17 (m, 3H), 7.27–7.46(m, 6H), 7.51–7.61(m, 4H), 8.63(br-s, 1H), 10.10(br-s, 1H).

Example 116

N-(tert-Butoxycarbonyl)-N'-{3-[1-(2-fuoro-biphenyl-4-yl)-ethyl]-isoxazol-5-yl}-N''-pyridin-3-yl-guanidine

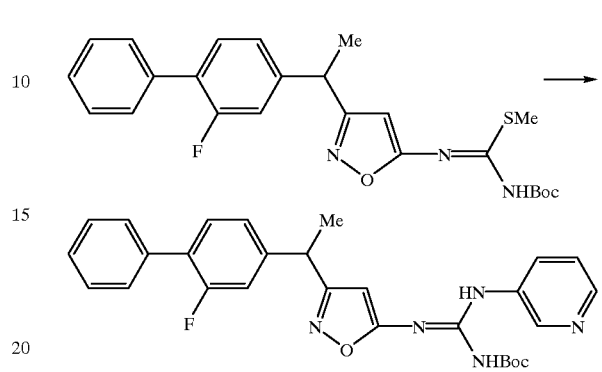

The desired compound was obtained by the same procedure as in Example 1.

¹H-NMR (300 MHz, CDCl₃) δ ppm: 1.55(s, 9H), 1.69(d, 3H, J=7.1 Hz), 4.18(q, 1H, J=7.1 Hz), 5.45(s, 1H), 7.07–7.25 (m, 2H), 7.27–7.46(m, 4H), 7.51–7.55(m, 2H), 8.14–8.18 (m, 1H), 8.32–8.35(m, 1H), 8.69–8.71(m, 2H), 10.22(br-s, 1H).

Example 117

(tert-Butoxycarbonyl)-({3-[1-(2-fluoro-biphenyl-4-yl)-ethyl]-isoxazol-5-ylimino}-thiamorpholin-4-yl-methyl)-amine

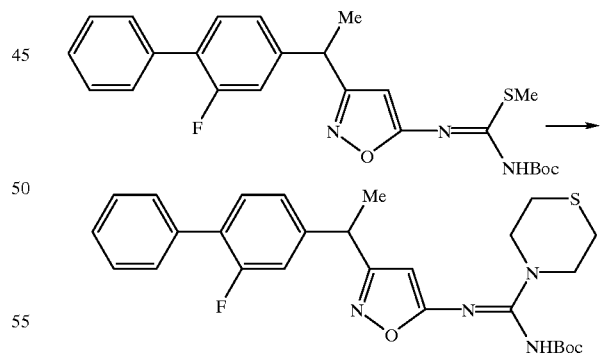

The desired compound was obtained by the same procedure as in Example 1.

¹H-NMR (300 MHz, CDCl₃) δ ppm: 1.43(s, 9H), 1.66(d, 3H, J=7.3 Hz), 2.68–2.74(m, 4H), 3.84(br-s, 4H), 4.16(q, 1H, J=7.1 Hz), 5.28(s, 1H), 6.81(br-s, 1H), 7.07–7.16(m, 2H), 7.34–7.46(m, 4H), 7.50–7.54(m, 2H).

Example 118

1-([(tert-Butoxycarbonyl)-amino]-{3-[1-(2-fluoro-biphenyl-4-yl)-ethyl]-isoxazol-5-ylimino}-methyl)-piperidin-4-one

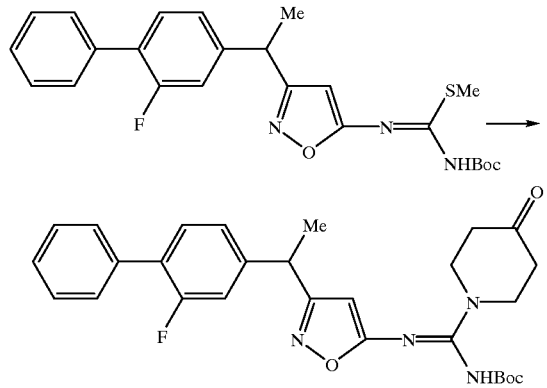

The desired compound was obtained by the same procedure as in Example 1.

¹H-NMR (300 MHz, CDCl₃) δ ppm: 1.46(s, 9H), 1.68(d, 3H, J=7.3 Hz), 2.60(t, 4H, J=6.2 Hz), 3.84(t, 4H, J=6.2 Hz), 4.18(q, 1H, J=7.0 Hz), 5.34(s, 1H), 7.06(br-s, 1H), 7.07–7.17(m, 2H), 7.33–7.46(m, 4H), 7.50–7.55(m, 2H).

Example 119

1-([(tert-Butoxycarbonyl)-amino]-{3-[1-(2-fluoro-biphenyl-4-yl)-ethyl]-isoxazol-5-ylimino}-methyl)-piperidin-4-ol

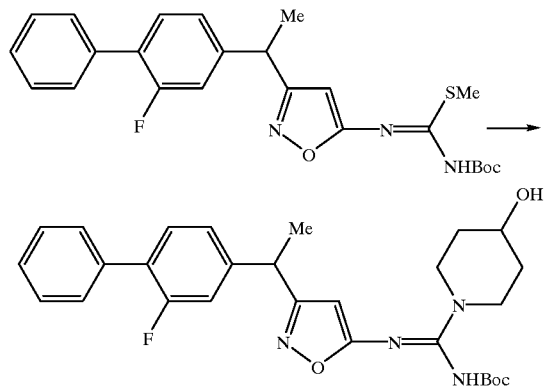

The desired compound was obtained by the same procedure as in Example 1.

¹H-NMR (300 MHz, CDCl₃) δ ppm: 1.43(s, 9H), 1.55–1.68(m, 3H), 1.66(d, 3H, J=7.3 Hz), 1.85–1.99(m, 2H), 3.25–3.40(m, 2H), 3.84–3.99(m, 3H), 4.12(q, 1H, J=7.1 Hz), 5.25(s, 1H), 6.75(br-s, 1H), 7.07–7.16(m, 2H), 7.32–7.46(m, 4H), 7.50–7.54(m, 2H).

Example 120

N-(tert-Butoxycarbonyl)-N'-{3-[1-(2-fluoro-biphenyl-4-yl)-ethyl]-isoxazol-5-yl}-N''-hydroxy-guanidine

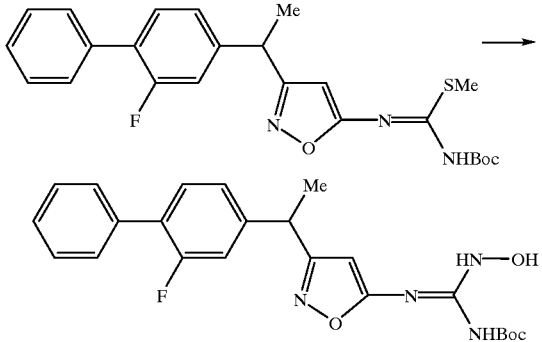

The desired compound was obtained by the same procedure as in Example 1.

¹H-NMR (300 MHz, CDCl₃) δ ppm: 1.51(s, 9H), 1.66(d, 3H, J=7.1 Hz), 4.16(q, 1H, J=7.1 Hz), 5.79(s, 1H), 6.20(br-s, 1H), 7.06–7.14(m, 2H), 7.32–7.46(m, 4H), 7.50–7.54(m, 2H), 7.78(br-s, 1H), 9.89(br-s, 1H).

Example 121

N-(tert-Butoxycarbonyl)-N'-{3-[1-(2-fluoro-biphenyl-4-yl)-ethyl]-isoxazol-5-yl}-N''-methoxy-guanidine

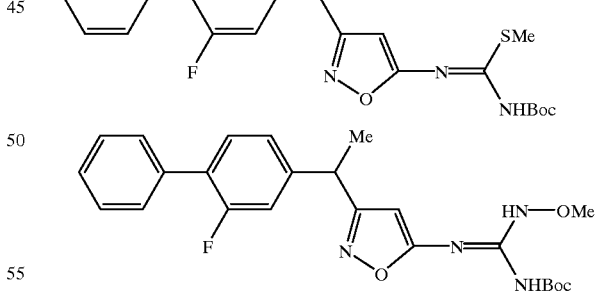

The desired compound was obtained by the same procedure as in Example 1.

¹H-NMR (300 MHz, CDCl₃) δ ppm: 1.51(s, 9H), 1.68(d, 3H, J=7.1 Hz), 3.78(s, 3H), 4.19(q, 1H, J=7.1 Hz), 5.87(s, 1H), 7.08–7.17(m, 2H), 7.32–7.46(m, 4H), 7.50–7.54(m, 2H), 7.70(br-s, 1H), 9.86(br-s, 1H).

Example 122

N-(tert-Butoxycarbonyl)-N'-(2-dimethylaminoethyl)-N"-{3-[1-(2-fluoro-biphenyl-4-yl)-ethyl]-isoxazo-5-yl}-guanidine

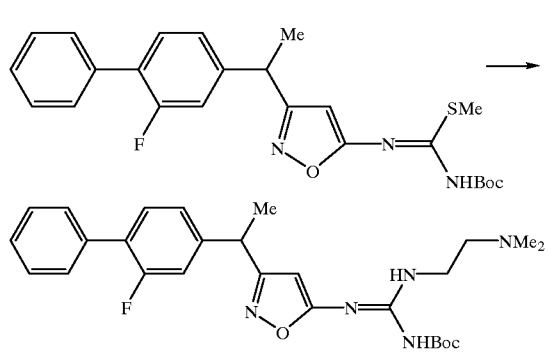

The desired compound was obtained by the same procedure as in Example 1.

¹H-NMR (300 MHz, CDCl₃) δ ppm: 1.49(s, 9H), 1.67(d, 3H, J=7.1 Hz), 2.26(s, 6H), 2.49(t, 2H, J=6.2 Hz), 3.42–3.49 (m, 2H), 4.14(q, 1H, J=7.1 Hz), 5.31(br-s, 1H), 7.07–7.17 (m, 2H), 7.32–7.46(m, 4H), 7.50–7.54(m, 2H), 8.18(br-s, 1H), 8.48(br-s, 1H).

Example 123

N-{3-[1-(2-Fluoro-biphenyl-4-yl)-ethyl]-isoxazol-5-yl}-N'-phenyl-guanidine

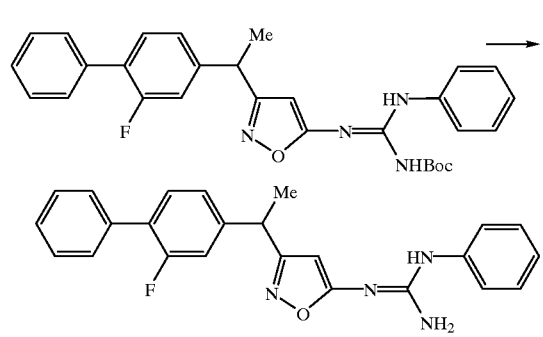

The desired compound was obtained by the same procedure as in Example 48 except for using the compound obtained in Example 115.

¹H-NMR (300 MHz, CDCl₃) δ ppm: 1.64(d, 3H, J=7.1 Hz), 4.14(q, 1H, J=7.1 Hz), 5.18(s, 1H), 5.48(br-s, 2H), 7.05–7.15(m, 2H), 7.23–7.47(m, 3H), 7.32–7.47(m, 6H), 7.51–7.55(m, 3H).

Example 124

N-{3-[1-(2-Fluoro-biphenyl-4-yl)-ethyl]-isoxazol-5-yl}-N'-pyridin-3-yl-guanidine

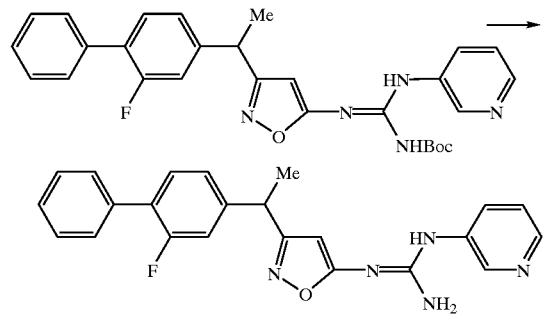

The desired compound was obtained by the same procedure as in Example 48 except for using the compound obtained in Example 116.

¹H-NMR (300 MHz, CDCl₃) δ ppm: 1.64(d, 3H, J=7.1 Hz), 4.14(q, 1H, J=7.1 Hz), 5.33(s, 1H), 5.75(br-s, 2H), 7.04–7.11(m, 2H), 7.13–7.26(m, 1H), 7.31–7.45(m, 5H), 7.49–7.52(m, 2H), 7.90(d, 1H, J=8.3 Hz), 8.28(d, 1H, J=4.2 Hz), 8.46(br-s, 1H).

Example 125

({3-[1-(2-Fluoro-biphenyl-4-yl)-ethyl]-isoxazol-5-ylimino}-thiamorpholin-4-yl-methyl)-amine

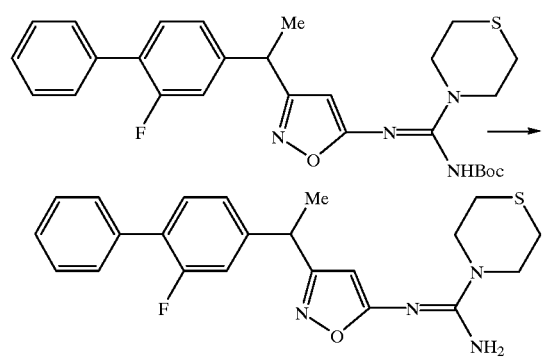

The desired compound was obtained by the same procedure as in Example 48 except for using the compound obtained in Example 117.

¹H-NMR (300 MHz, CDCl₃) δ ppm: 1.65(d, 3H, J=7.1 Hz), 2.62–2.66(m, 4H), 3.80–3.85(m, 4H), 4.14(q, 1H, J=7.1 Hz), 5.24(s, 1H), 5.35(br-s, 1H), 7.07–7.20(m, 2H), 7.32–7.46(m, 4H), 7.50–7.54(m, 2H).

Example 126

1-(Amino-{3-[1-(2-fluoro-biphenyl-4-yl)-ethyl]-isoxazol-5-ylimino}-methyl)-piperidin-4-one

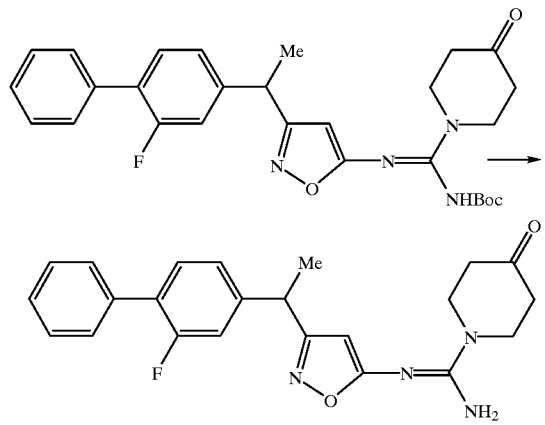

The desired compound was obtained by the same procedure as in Example 48 except for using the compound obtained in Example 118.

$^1$H-NMR (300 MHz, CDCl$_3$) δ ppm: 1.67(d, 3H, J=7.1 Hz), 2.55(t, 4H, J=6.2 Hz), 3.83(t, 4H, J=6.2 Hz), 4.16(q, 1H, J=7.1 Hz), 5.28(s, 1H), 5.47(br-s, 2H), 7.07–7.18(m, 2H), 7.32–7.46(m, 4H), 7.50–7.54(m, 2H).

Example 127

1-(Amino-{3-[1-(2-fluoro-biphenyl-4-yl)-ethyl]-isoxazol-5-ylimino}-methyl)-piperidin-4-ol

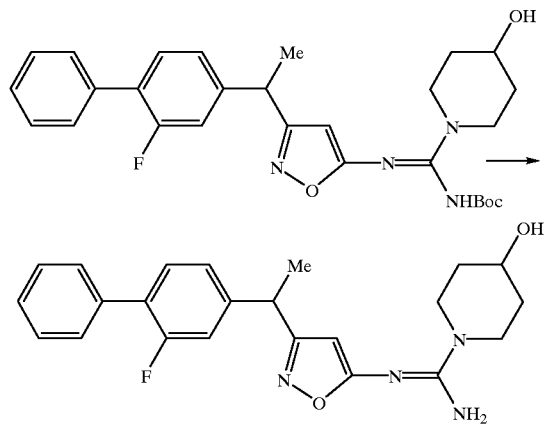

The desired compound was obtained by the same procedure as in Example 48 except for using the compound obtained in Example 119.

$^1$H-NMR (300 MHz, CDCl$_3$) δ ppm: 1.50–1.64(m, 3H), 1.65(d, 3H, J=7.1 Hz), 1.81–1.94(m, 2H), 3.18–3.28(m, 2H), 3.81–3.96(m, 3H), 4.14(q, 1H, J=7.1 Hz), 5.22(s, 1H), 5.34(br-s, 2H), 7.07–7.17(m, 2H), 7.33–7.45(m, 4H), 7.50–7.54(m, 2H).

Example 128

N-{3-[1-(2-Fluoro-biphenyl-4-yl)-ethyl]-isoxazol-5-yl}-N'-hydroxy-guanidine

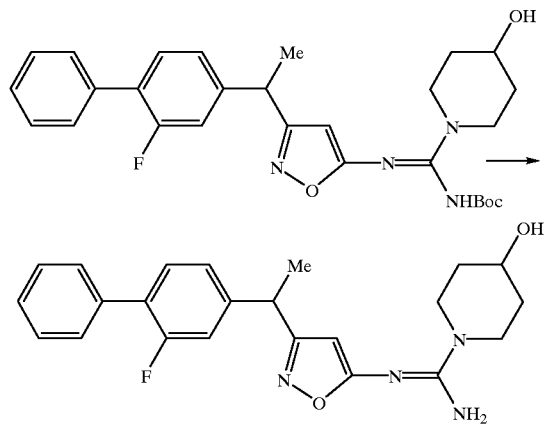

The desired compound was obtained by the same procedure as in Example 48 except for using the compound obtained in Example 120.

$^1$H-NMR (300 MHz, CDCl$_3$) δ ppm: 1.63(d, 3H, J=7.1 Hz), 4.12(q, 1H, J=7.1 Hz), 5.34(s, 1H), 5.59(br-s, 2H), 7.04–7.12(m, 2H), 7.33–7.45(m, 6H), 7.49–7.54(m, 2H).

Example 129

N-{3-[1-(2-Fluoro-biphenyl-4-yl)-ethyl]-isoxazol-5-yl}-N'-methoxy-guanidine

The desired compound was obtained by the same procedure as in Example 48 except for using the compound obtained in Example 121.

$^1$H-NMR (300 MHz, CDCl$_3$) δ ppm: 1.65(d, 3H, J=7.1 Hz), 3.73(s, 3H), 4.14(q, 1H, J=7.1 Hz), 5.32(br-s, 2H), 5.41(s, 1H), 7.06–7.15(m, 2H), 7.32–7.46(m, 4H), 7.50–7.54(m, 2H).

Example 130

N-(2-Dimethylamino-ethyl)-N'-{3-[1-(2-fluoro-biphenyl-4-yl)-ethyl]-isoxazol-5-yl}-guanidine

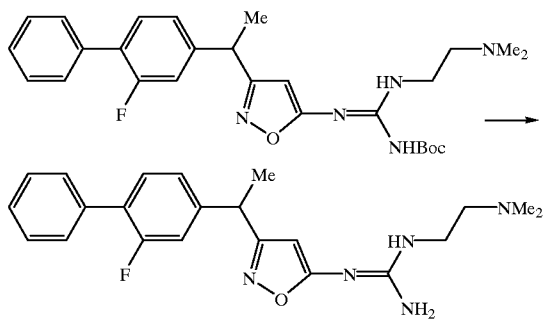

The desired compound was obtained by the same procedure as in Example 48 except for using the compound obtained in Example 122.

$^1$H-NMR (300 MHz, CDCl$_3$) δ ppm: 1.65(d, 3H, J=7.1 Hz), 2.29(s, 6H), 2.50–2.55(m, 2H), 3.26–3.32(m, 2H), 4.14(q, 1H, J=7.1 Hz), 5.19(s, 1H), 5.98(br-s, 1H), 6.34(br-s, 1H), 7.07–7.17(m, 2H), 7.33–7.46(m, 4H), 7.50–7.54(m, 2H).

Example 131

[(3-{1-Methyl-1-[3-(2-phenyl-[1,3]dioxolan-2-yl)-phenyl]-ethyl}-isoxazol-5-ylimino)-morpholin-4-yl-methyl]-amine

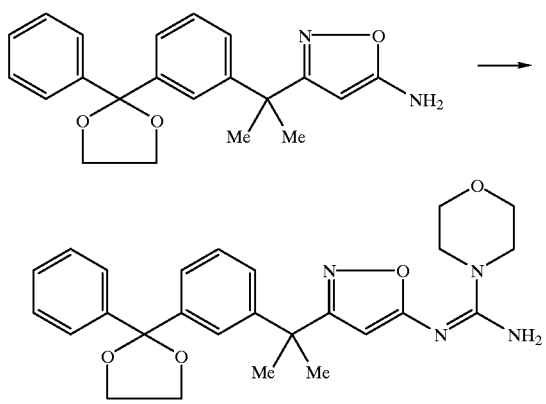

The desired compound was obtained by the same procedure as in Example 54 using the compound obtained in Reference Example 53.

$^1$H-NMR (300 MHz, CDCl$_3$) δ ppm: 1.66(s, 6H), 3.44–3.48(m, 4H), 3.70–3.73(m, 4H), 4.05(s, 4H), 5.07(s, 1H), 5.31(br-s, 2H), 7.20–7.35(m, 6H), 7.47–7.58(m, 3H)

Example 132

(3-{1-[5-(Amino-morpholin-4-yl-methyleneamino)-isoxazol-3-yl]-1-methyl-ethyl}-phenyl)-phenyl-methanone

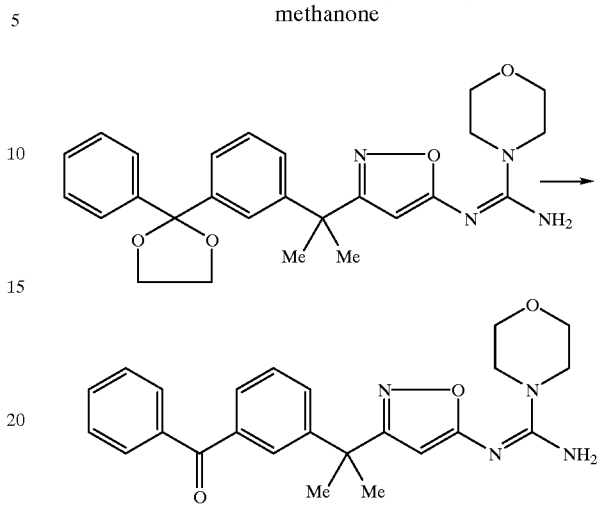

The compound (8.8 mg) obtained in Example 131 was dissolved in 90% aqueous acetic acid solution (2 ml), followed by stirring for 40 hours. The reaction solution was extracted with ethyl acetate, and the extract solution was washed with a saturated aqueous sodium chloride solution, dried over sodium sulfate and thereafter concentrated under reduced pressure. The resulting residue was purified by a silica gel column chromatography to obtain the desired compound (8.3 mg).

$^1$H-NMR (300 MHz, CDCl$_3$) δ ppm: 1.72(s, 6H), 3.46–3.50(m, 4H), 3.70–3.74(m, 4H), 5.14(s, 1H), 5.39(br-r, 2H), 7.35–7.61(m, 6H), 7.76–7.84(m, 3H)

Example 133

(Morpholin-4-yl-{3-[1-(6-phenyl-pyridin-3-yl)-ethyl]-isoxazol-5-ylimino}-methyl)-amine

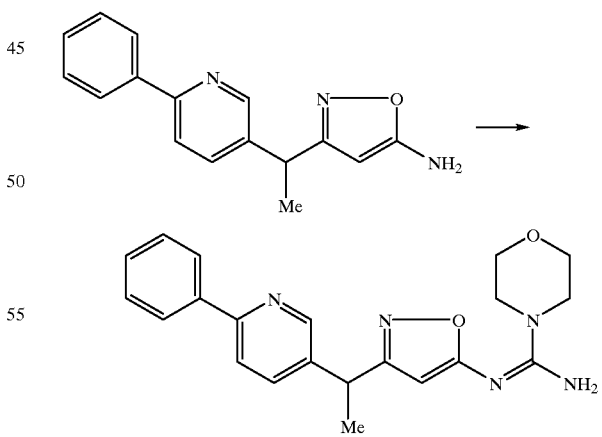

By the same procedure as in Example 54, the desired compound was obtained from the compound obtained in Reference Example 55.

$^1$H-NMR (270 MHz, CDCl$_3$) δ ppm: 1.69(d, 3H, J=7.3 Hz), 3.48(t, 4H, J=5.0 Hz), 3.72(t, 4H, J=5.0 Hz), 4.18(q, 1H, J=7.3 Hz), 5.23(s, 1H), 5.36(br-s, 2H), 7.39–7.50(m, 3H), 7.67(m, 2H), 7.95(dd, 2H, J=8.3, 1.7 Hz), 8.64(s, 1H)

Example 134

(Morpholin-4-yl-{3-[1-(5-phenyl-pyridin-2-yl)-ethyl]-isoxazol-5-ylimino}-methyl)-amine

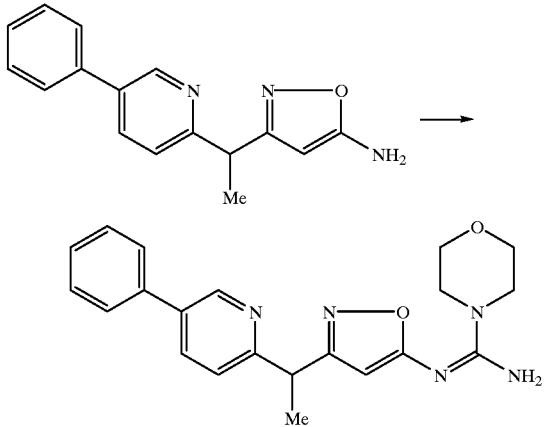

By the same procedure as in Example 54, the desired compound was obtained from the compound obtained in Reference Example 57.

¹H-NMR (270 MHz, CDCl₃) δ ppm: 1.74(d, 3H, J=7.3 Hz), 3.48(t, 4H, J=5.3 Hz), 3.72(t, 4H, J=5.3 Hz), 4.34(q, 1H, J=7.3 Hz), 5.20–5.45(m, 3H), 7.32–7.57(m, 6H), 7.80 (dd, 1H, J=7.9, 2.3 Hz), 8.78(d, 1H, J=2.3 Hz)

Reference Example 1

1-{3-[1-(2-Fluoro-biphenyl-4-yl)-ethyl]-isoxazol-5-yl}-2-methyl-isothiourea

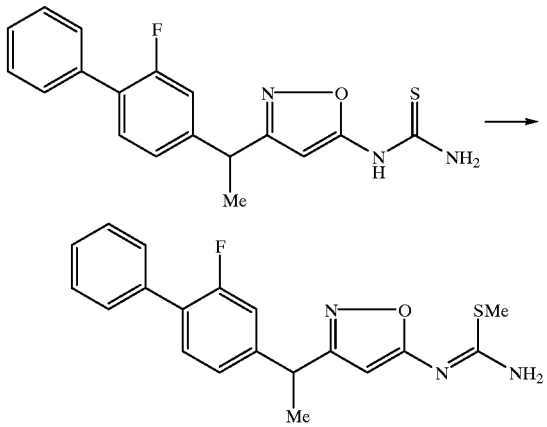

3-[1-(2-Fluoro-biphenyl-4-yl)-ethyl]-isoxazol-5-yl-thiourea (Japanese Patent Unexamined Publication No. 63-152368) (3.03 g) was dissolved in N,N-dimethylformamide (90 ml), followed by adding thereto methyl iodide (1.51 g) and potassium carbonate (0.86 g), and the resulting mixture was stirred at 40° C. for 2 hours. Water was added to the reaction mixture, followed by extraction with ethyl acetate, and the extract solution was washed with water and dried. The solvent was distilled off under reduced pressure and the residue was purified by a silica gel column chromatography to obtain the desired compound (2.67 g).

¹H-NMR (270 MHz, CDCl₃) δ ppm: 1.67(d, 3H, J=7.2 Hz), 2.44(s, 3H), 4.17(q, 1H, J=7.2 Hz), 5.50(s, 1H), 5.92 (br-s, 2H), 7.06–7.15(m, 2H), 7.32–7.54(m, 6H).

Reference Example 2

1-(tert-Butoxycarbonyl)-3-{3-[1-(2-fluoro-biphenyl-4-yl)-ethyl]-isoxazol-5-yl}-2-methyl-isothiourea

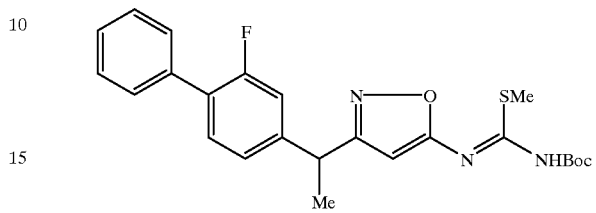

In tetrahydrofuran (80 ml) was suspended sodium hydride (4.22 g, 60% oily), and a solution in tetrahydrofuran (100 ml) of the compound obtained in Reference Example 1 (25.0 g) was added dropwise under ice-cooling, after which a solution of tert-butyl azidoformate ("Organic Syntheses" Coll. Vol. 5, John Wiley and Sons, Inc., New York (1973), p 157) (15.1 g) in tetrahydrofuran (50 ml) was slowly dropped thereinto over a period of 65 minutes, and the resulting mixture was stirred under ice-cooling for 1 hour and then at room temperature overnight. Water was added to the reaction mixture, followed by extraction with diethyl ether, and the extract solution was washed with water and dried. The solvent was distilled off under reduced pressure and the residue was purified by a silica gel column chromatography to obtain the desired compound (21.1 g).

Melting point 124–126° C. (decomp.).

¹H-NMR (270 MHz, CDCl₃) δ ppm: 1.49(s, 9H), 1.68(d, 3H, J=7.1 Hz), 2.37(s, 3H), 4.18(q, 1H, J=7.1 Hz), 5.63(s, 1H), 7.06–7.15(m, 2H), 7.35–7.53(m, 6H), 8.93(br-s, 1H).

IR (KBr) [cm⁻¹]: 3382, 2980, 1750, 1588.

Reference Example 3

3-Benzoyl-1-{3-[1-(2-fluoro-biphenyl-4-yl)-ethyl]-isoxazol-5-yl}-1-methyl-thiourea

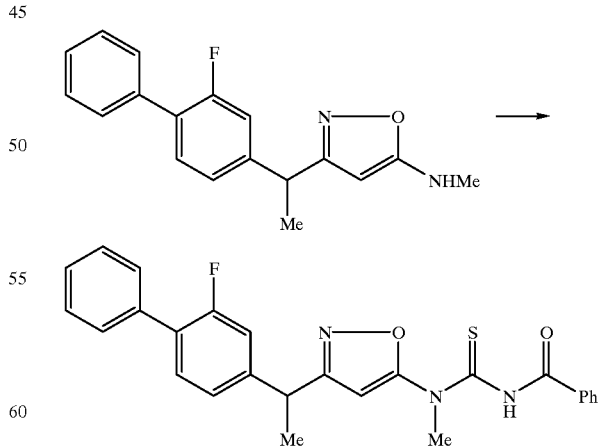

A solution consisting of {3-[1-(2-fluoro-biphenyl-4-yl)-ethyl]-isoxazol-5-yl}-methyl-amine (4.06 g), pyridine (40 ml) and benzoyl isothiocyanate (2.5 g) was stirred overnight at room temperature. The solution was concentrated and the residue was purified by a silica gel column chromatography to obtain the desired compound (5.28 g).

Melting point 115–116° C.

$^1$H-NMR (270 MHz, CDCl$_3$) δ ppm: 1.59(d, 3H, J=7.3 Hz), 3.79(s, 3H), 4.14(q, 1H, J=7.3 Hz), 5.83(s, 1H), 6.92–6.97(m, 2H), 7.16(t, 1H, J=8.2 Hz), 7.34–7.52(m, 8H), 7.68–7.73(m, 2H), 8.79(s, 1H).

IR (KBr) [cm$^{-1}$]: 3440, 3275, 3125, 2980, 1690, 1612, 1515, 1488, 1424, 1360, 1266, 1230, 1168.

Reference Example 4

3-Benzoyl-1-{3-[1-(2-fluoro-biphenyl-4-yl)-ethyl]-isoxazol-5-yl}-1,2-dimethyl-isothiourea

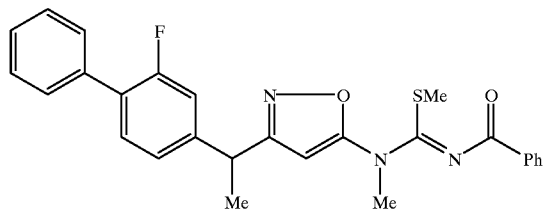

Potassium carbonate (4.1 g) and methyl iodide (1.25 ml) were added to a solution in N,N-dimethylformamide (60 ml) of 5.22 g of the compound obtained in Reference Example 3, and the resulting mixture was stirred at room temperature for 5 hours. The reaction solution was diluted with ethyl acetate and water was added thereto, followed by extraction. The extract was purified by a silica gel column chromatography to obtain the desired compound (4.87 g).

Melting point 124–126° C. (decomp.).

$^1$H-NMR (270 MHz, CDCl$_3$) δ ppm: 1.66(d, 3H, J=7.3 Hz), 2.28(s, 3H), 3.56(s, 3H), 4.19(q, 1H, J=7.3 Hz), 6.06(s, 1H), 7.00–7.10(m, 2H), 7.33–7.52(m, 9H), 9.03(d, 2H, J=7.7 Hz).

Reference Example 5

Ethyl 5-(2-fluoro-biphenyl-4-yl)-2-hydroxy-4-oxo-hex-2-enoate

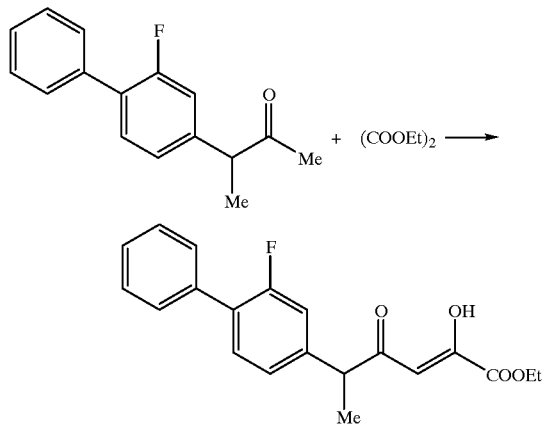

3-(2-Fluoro-biphenyl-4-yl)-butan2-one (Japanese Patent Unexamined Publication No. 54-144347) (116 mg) was dissolved in toluene (2 ml), followed by adding thereto sodium hydride (29 mg, 60% oily), and the mixture was stirred at room temperature for 1 hour. Then, diethyl oxalate (105 mg) was added and the resulting mixture was stirred at 40° C. for 3 hours. Water was added to the reaction mixture, followed by extraction with ethyl acetate, and the extract solution was washed with water and dried. The solvent was distilled off under reduced pressure and the residue was purified by a silica gel column chromatography to obtain the desired compound (163 mg).

$^1$H-NMR (270 MHz, CDCl$_3$) δ ppm: 1.35(t, 3H, J=7.2 Hz), 1.54(d, 3H, J=7.1 Hz), 3.86(q, 1H, J=7.1 Hz), 4.32(q, 2H, J=7.2 Hz), 6.37(s, 1H), 7.04–7.12(m, 2H), 7.31–7.55(m, 7H).

IR (KBr) [cm$^{-1}$]: 2925, 1734, 1636, 1484.

Reference Example 6

Ethyl 5-[1-(2-fluoro-biphenyl-4-yl)-ethyl]-isoxazol-3-carboxylate

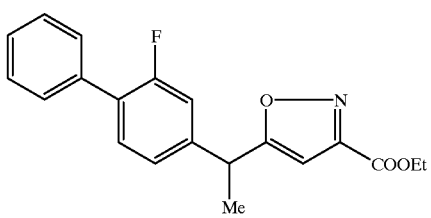

The compound (163 mg) obtained in Reference Example 5 and hydroxylamine hydrochloride (40 mg) were dissolved in ethanol (2 ml) and the resulting solution was stirred at 60° C. for 9 hours. Water was added to the reaction solution, followed by extraction with ethyl acetate, and the extract solution was washed with water and dried. The solvent was distilled off under reduced pressure and the residue was purified by a silica gel column chromatography to obtain the desired compound (143 mg).

$^1$H-NMR (270 MHz, CDCl$_3$) δ ppm: 1.41(t, 3H, J=7.1 Hz), 1.73(d, 3H, J=7.3 Hz), 4.34(q, 1H, J=7.3 Hz), 4.43(q, 2H, J=7.1 Hz), 6.45(s, 1H), 7.02–7.12(m, 2H), 7.33–7.55(m, 6H).

IR (KBr) [cm$^{-1}$]: 2983, 1733, 1625, 1584, 1484, 1418.

Reference Example 7

{5-[1-(2-Fluoro-biphenyl-4-yl)-ethyl]-isoxazol-3-yl}-methanol

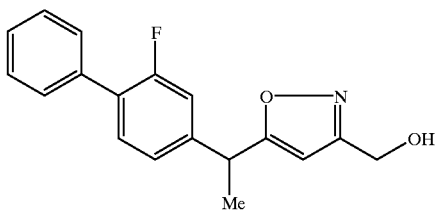

The compound (2.45 g) obtained in Reference Example 6 was dissolved in tetrahydrofuran (20 ml), and lithium aluminum hydride (300 mg) was added at 0° C. and the resulting solution was stirred for 1.5 hours. Water was added to the reaction mixture, followed by extraction with methylene chloride, and the extract solution was washed with water and dried. The solvent was distilled off under reduced pressure and the residue was recrystallized from methylene chloride to obtain the desired compound (2.09 g).

Melting point 127–127.5° C.

$^1$H-NMR (270 MHz, CDCl$_3$) δ ppm: 1.70(d, 3H, J=7.3 Hz), 4.28(q, 1H, J=7.3 Hz), 4.74(s, 2H), 6.09(s, 1H), 7.03–7.13(m, 2H), 7.33–7.55(m, 6H).

IR (KBr) [cm$^{-1}$]: 3308, 1603, 1485, 1418.

Elementary analysis; Calculated: C 72.71, H 5.42, N 4.71 Found: C 72.61, H 5.45, N 4.88

Reference Example 8

3-Bromomethyl-5-[1-(2-fluoro-biphenyl-4-yl)-ethyl]-isoxazole

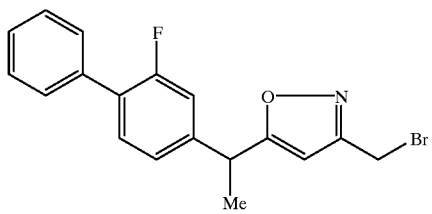

The compound (2.03 g) obtained in Reference Example 7 was dissolved in methylene chloride (80 ml), and carbon tetrabromide (3.40 g) and triphenylphosphine (2.69 g) were added thereto and then the resulting solution was stirred for 1 hour. A saturated aqueous sodium hydrogencarbonate solution was added to the reaction mixture, followed by extraction with methylene chloride, and the extract solution was washed with water and dried. The solvent was distilled off under reduced pressure and the residue was purified by a silica gel column chromatography to obtain the desired compound (6.83 g).

Melting point 102–103° C.

$^1$H-NMR (270 MHz, CDCl$_3$) δ ppm: 1.71(d, 3H, J=7.3 Hz), 4.27(q, 1H, J=7.3 Hz), 4.39(s, 2H), 6.12(d, 1H, J=0.7 Hz), 7.03–7.13(m, 2H), 7.33–7.55(m, 6H).

IR (KBr) [cm$^{-1}$]: 1600, 1484, 1417.

Elementary analysis; Calculated: C 60.02, H 4.20, N 3.89 Found: C 59.86, H 4.17, N 4.04

Reference Example 9

3-Azidomethyl-5-[1-(2-fluoro-biphenyl-4-yl)-ethyl]-isoxazole

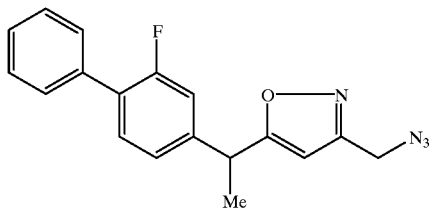

The compound (2.08 g) obtained in Reference Example 8 and sodium azide (749 mg) were dissolved in N,N-dimethylformamide (20 ml) and the resulting solution was stirred at 50° C. for 3 hours. Water was added to the reaction solution, followed by extraction with ethyl acetate, and the extract solution was washed with water and dried. The solvent was distilled off under reduced pressure and the residue was purified by a silica gel column chromatography to obtain the desired compound (1.85 g).

$^1$H-NMR (270 MHz, CDCl$_3$) δ ppm: 1.71(d, 3H, J=7.3 Hz), 4.28(q, 1H, J=7.3 Hz), 4.39(s, 2H), 6.07(s, 1H), 7.02–7.12(m, 2H), 7.33–7.55(m, 6H).

IR (neat) [cm$^{-1}$]: 2978, 2933, 2104, 1596, 1485.

Elementary analysis; Calculated: C 67.07, H 4.69, N 17.38 Found: C 66.93, H 4.78, N 17.56

Reference Example 10

{5-[1-(2-Fluoro-biphenyl-4-yl)-ethyl]-isoxazol-3-ylmethyl}-amine

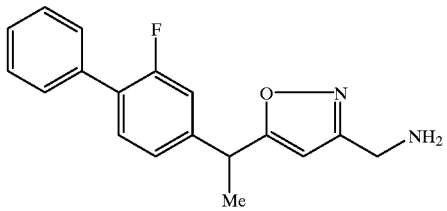

The compound (1.82 g) obtained in Reference Example 9 was dissolved in tetrahydrofuran (15 ml), followed by adding thereto sodium borohydride (641 mg), and the resulting mixture was stirred under reflux. Methanol (3 ml) was added dropwise over a period of 1 hour and stirred for 3 hours, after which the resulting mixture was cooled to room temperature. A 1N aqueous HCl solution (6 ml) was added thereto and separated. The aqueous layer was washed with hexane, adjusted to pH 11 with a 15% aqueous sodium hydroxide solution, and then extracted with methylene chloride, and the extract solution was washed with water and dried. The solvent was distilled off under reduced pressure and the residue was purified by a silica gel column chromatography to obtain the desired compound (1.13 g).

$^1$H-NMR (270 MHz, CDCl$_3$) δ ppm: 1.70(d, 3H, J=7.2 Hz), 3.91(s, 2H), 4.26(q, 1H, J=7.2 Hz), 6.01(s, 1H), 7.03–7.13(m, 2H), 7.33–7.55(m, 6H).

Reference Example 11

N',N''-Di-(tert-butoxycarbonyl)-N,N-dimethyl-guanidine

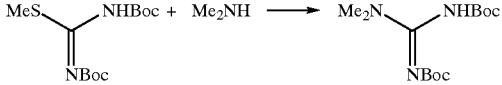

1,3-Di-(tert-butoxycarbonyl)-2-methyl-isothiourea (Japanese Patent Unexamined Publication No. 2-3661) (3.00 g) was dissolved in a 50% aqueous dimethylamine solution (40 ml) and the resulting solution was stirred at room temperature for 18 hours. The solvent was distilled off under reduced pressure and the residue was purified by a silica gel column chromatography to obtain the desired compound (2.58 g).

¹H-NMR (270 MHz, CDCl₃) δ ppm: 1.50(s, 18H), 3.07(s, 6H).

Reference Example 12

(tert-Butoxycarbonyl)-[(tert-butoxycarbonyl)-imino-piperidin-1-yl-methyl]-amine

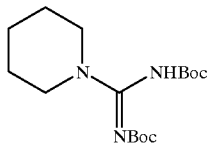

The desired compound was obtained by the same procedure as in Reference Example 11.

¹H-NMR (270 MHz, CDCl₃) δ ppm: 1.49(s, 18H), 1.64 (br-s, 6H), 3.52(br-s, 4H), 10.13(br-s, 1H).

Elementary analysis; Calculated: C 58.69, H 8.93, N 12.83 Found: C 58.46, H 8.86, N 12.79

Reference Example 13

(tert-Butoxycarbonyl)-[(tert-butoxycarbonyl)-imino-morpholin-4-yl-methyl]-amine

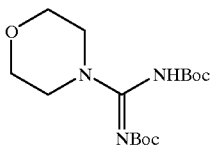

The desired compound was obtained by the same procedure as in Reference Example 11.

¹H-NMR (270 MHz, CDCl₃) δ ppm: 1.48(s, 9H), 1.50(s, 9H), 3.59(br-s, 4H), 3.72–3.76(m, 4H), 10.21(br-s, 1H).

Reference Example 14

1,3-Di-(tert-butoxycarbonyl)-1,2-dimethyl-isothiourea

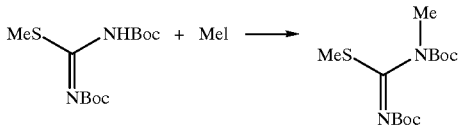

1,3-Di-(tert-butoxycarbonyl)-2-methyl-isothiourea (Japanese Patent Unexamined Publication No. 2-3661) (2.00 g) was dissolved in N,N-dimethylformamide (20 ml), followed by adding thereto 60% sodium hydride (331 mg), and the resulting mixture was stirred at 50° C. for 2 hours. After the mixture was cooled to 0° C., methyl iodide (1.96 g) was added and the resulting mixture was stirred at room temperature for 2 hours. Water was added to the reaction mixture, followed by extraction with ethyl acetate, and the extract solution was washed with water and dried. The solvent was distilled off under reduced pressure and the residue was purified by a silica gel column chromatography to obtain the desired compound (2.07 g).

¹H-NMR (270 MHz, CDCl₃) δ ppm: 1.48(s, 9H), 1.51(s, 9H), 2.39(s, 3H), 3.12(s, 3H).

IR (neat) [cm⁻¹]: 2979, 1720, 1624.

Elementary analysis; Calculated: C 51.29, H 7.95, N 9.20 Found: C 51.06, H 8.08, N 9.31

Reference Example 15

Ethyl [1,3-di-(tert-butoxycarbonyl)-2-methyl-isothioureido]-acetate

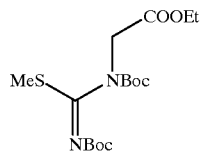

The desired compound was obtained by the same procedure as in Reference Example 14.

¹H-NMR (270 MHz, CDCl₃) δ ppm: 1.29(t, 3H, J=7.1 Hz), 1.48(s, 9H), 1.51(s, 9H), 2.45(s, 3H), 4.22(q, 2H, J=7.1 Hz), 4.30(s, 2H).

IR (neat) [cm⁻¹]: 2981, 1725, 1615, 1369, 1315.

Elementary analysis; Calculated: C 51.05, H 7.50, N 7.44 Found: C 50.76, H 7.56, N 7.50

Reference Example 16

1-{3-[1-(4-Isobutyl-phenyl)-ethyl]-isoxazol-5-yl}-2-methyl-isothiourea

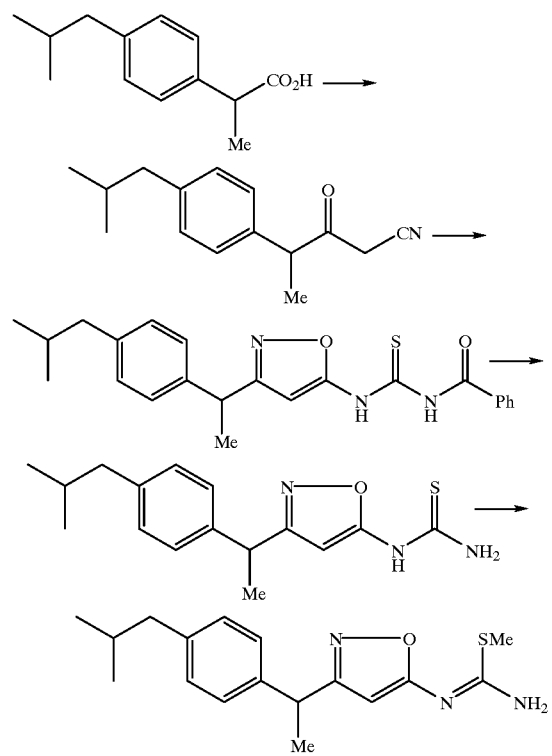

Under a nitrogen atmosphere, 2-(4-isobutylphenyl)-propionic acid (15.0 g) was dissolved in ethanol (200 ml), and conc. sulfuric acid (1 ml) was added, after which the solution was stirred with heating under reflux for 15 hours. The reaction mixture was cooled to room temperature, concentrated under reduced pressure, diluted with ethyl acetate, and thereafter neutralized with a saturated aqueous sodium bicarbonate solution. After extraction with ethyl acetate, the organic layer was dried over sodium sulfate and then concentrated under reduced pressure to obtain ethyl 2-(4-isobutyl-phenyl)-propionate.

Tetrahydrofuran (100 ml) was added to sodium hydride (4.34 g, 60% oily) and then a solution obtained by dissolving the above ester (about 17.0 g) and acetonitrile (7.56 ml) in tetrahydrofuran (150 ml) was added dropwise with heating under reflux over one hour. After stirring with heating under reflux for 6 hours, the resulting mixture was cooled to room temperature and thereto was added a small amount of water, after which the mixture was diluted with ethyl acetate and thereto was added a saturated aqueous sodium bicarbonate solution. After extraction with ethyl acetate, the organic layer was dried over sodium sulfate and then concentrated under reduced pressure. The residue was purified by a recrystallization method from hexane to obtain 4-(4-isobutyl-phenyl)-3-oxo-pentanitrile (10.2 g).

This cyanoketone (10.2 g) was dissolved in ethanol (150 ml) and thereafter pyridine (30 ml) and hydroxylamine hydrochloride (6.17 g) were added, after which the resulting mixture was stirred at room temperature for 24 hours. The reaction mixture was concentrated under reduced pressure, diluted with ethyl acetate, and thereafter neutralized with a saturated aqueous sodium bicarbonate solution, after which the neutralized solution was subjected to extraction with ethyl acetate. The organic layer was dried over sodium sulfate and then concentrated under reduced pressure, to obtain 3-[1-(4-isobutyl-phenyl)-ethyl]-isoxazol-5-yl-amine (11.35 g).

This isoxazol (11.35 g) was dissolved in ethylene dichloride (200 ml) and then benzoyl isothiocyanate (11.9 ml) was added, after which the resulting mixture was stirred at 60° C. for 5 hours. The reaction mixture was concentrated under reduced pressure and a small amount of water was added, after which the resulting mixture was subjected to extraction with ethyl acetate. The organic layer was dried over sodium sulfate and then concentrated under reduced pressure. The residue was isolated by a silica gel column chromatography (hexane/ethyl acetate=2/1) and then purified by a recrystallization method from toluene, to obtain 1-benzoyl-3-{3-[1-(4-isobutyl-phenyl)-ethyl]-isoxazol-5-yl}-thiourea (4.65 g).

This thiourea (4.65 g) was dissolved in tetrahydrofuran (50 ml) and then methanol (50 ml) and potassium carbonate (3.15 g) were added, after which the mixture was stirred at 50° C. for 5 hours. To the reaction mixture was added a small amount of water, and the resulting mixture was subjected to extraction with ethyl acetate. The organic layer was washed with a saturated aqueous sodium chloride solution, then dried over sodium sulfate and thereafter concentrated under reduced pressure, to obtain 3-[1-(4-isobutyl-phenyl)-ethyl]-isoxazol-5-yl-thiourea (15.52 g).

The desired compound was obtained by the same procedure as in Reference Example 1 except for using this thiourea.

$^1$H-NMR (300 MHz, CDCl$_3$) δ ppm: 0.89(d, 6H, J=6.6 Hz), 1.63(d, 3H, J=7.3 Hz), 1.83(m, 1H), 2.43(d, 2H, J=6.1 Hz), 2.44(s, 3H), 4.11(q, 1H, J=7.2 Hz), 5.45(s, 1H), 5.91 (br-s, 2H), 7.06–7.09(m, 2H), 7.17–7.20(m, 2H)

Reference Example 17

1-{3-[1-(6-Methoxy-naphthalen-2-yl)-ethyl]-isoxazol-5-yl}-2-methyl-isothiourea

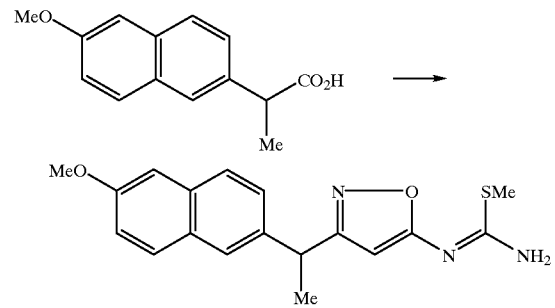

The desired compound was obtained by the same procedure as in Reference Example 16 except for using 2-(6-methoxy-naphthalen-2-yl)-propionic acid.

$^1$H-NMR (300 MHz, CDCl$_3$) δ ppm: 1.72(d, 3H, J=7.2 Hz), 2.42(s, 3H), 3.91(s, 3H), 4.27(q, 1H, J=7.2 Hz), 5.46(s, 1H), 5.90 (br-s, 2H), 7.10–7.15(m, 2H), 7.37(dd, 1H, J=8.4, 1.8 Hz), 7.65–7.71(m, 3H)

Reference Example 18

1-(tert-Butylcarbonyl)-3-{3-[1-(4-isobutyl-phenyl)-ethyl]-isoxazol-5-yl}-2-methyl-isothiourea

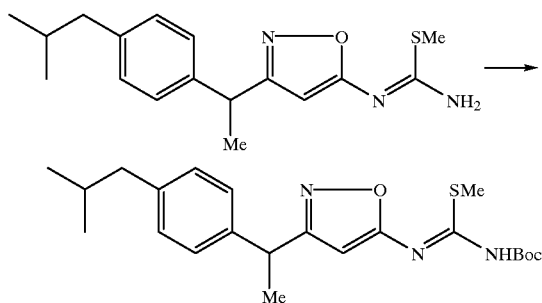

The desired compound was obtained by the same procedure as in Reference Example 2 except for using the compound obtained in Reference Example 16.

$^1$H-NMR (300 MHz, CDCl$_3$) δ ppm: 0.89(d, 6H, J=6.6 Hz), 1.50(s, 9H), 1.65(d, 3H, J=7.3 Hz), 1.84(m, 1H, J=6.6 Hz), 2.36(s, 3H), 2.44(d, 2H, J=7.1 Hz), 4.12(q, 1H, J=7.3 Hz), 5.58(s, 1H), 7.08–7.11(m, 2H), 7.17–7.20(m, 2H), 8.95(br-s, 1H)

Reference Example 19

1-(tert-Butoxycarbonyl)-3-{3-[1-(6-methoxy-naphthalen-2-yl)-ethyl]-isoxazol-5-yl}-2-methyl-isothiourea

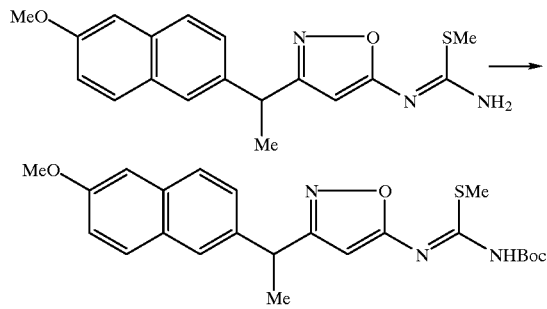

The desired compound was obtained by the same procedure as in Reference Example 2 except for using the compound obtained in Reference Example 17.

$^1$H-NMR (300 MHz, CDCl$_3$) δ ppm: 1.50(s, 9H), 1.74(d, 3H, J=7.2 Hz), 2.34(s, 3H), 3.91(s, 3H), 4.29(q, 1H, J=7.3 Hz), 5.59 (s, 1H), 7.10–7.16(m, 2H), 7.36(dd, 1H, J=8.4, 1.6 Hz), 7.65(s, 1H), 7.68–7.71(m, 2H), 8.95 (br-s, 1H)

Reference Example 20

3-[1-(2-Fluoro-biphenyl-4-yl)-1-methyl-ethyl]-isoxazol-5-ylamine

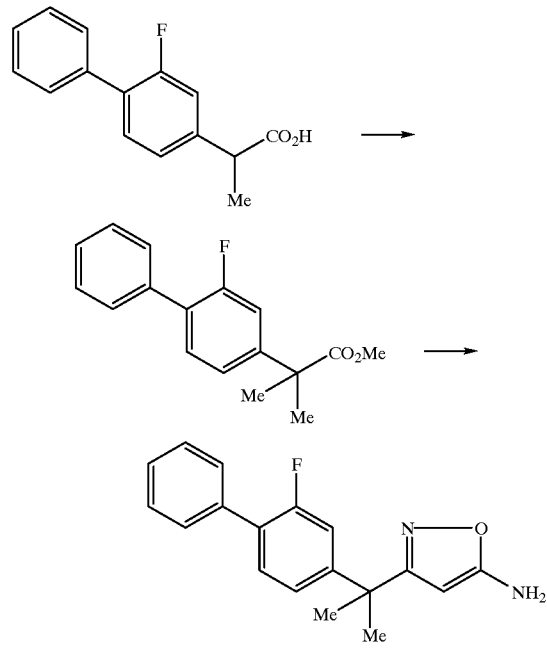

Under a nitrogen atmosphere, 2-(2-fluoro-biphenyl-4-yl)-propionic acid (15.0 g) was dissolved in N,N-dimethylformamide (150 ml) and then sodium hydride (6.14 g, 60% oily) was added, after which the resulting mixture was stirred for one hour. Subsequently, iodomethane (9.5 ml) was added and the mixture was stirred for 12 hours. A small amount of water was added to the reaction mixture and the resulting mixture was then subjected to extraction with ethyl acetate. The organic layer was dried over sodium sulfate and then concentrated under reduced pressure. The residue was purified by a recrystallization method from hexane, to obtain methyl 2-(2-fluoro-biphenyl-4-yl)-2-methyl-propionate (14.2 g).

Tetrahydrofuran (100 ml) was added to sodium hydride (2.70 g, 60% oily), and thereafter, a solution obtained by dissolving the above ester (12.2 g) and acetonitrile (4.66 ml) in tetrahydrofuran (100 ml) was dropwise added with heating under reflux over one hour. The resulting mixture was stirred for 8 hours with heating under reflux and then cooled to room temperature, and a small amount of water was thereafter added thereto, after which the mixture was diluted with ethyl acetate and then a saturated aqueous sodium bicarbonate solution was added. After extraction with ethyl acetate, the organic layer was dried over sodium sulfate and then concentrated under reduced pressure. The residue was purified by a recrystallization method from ethanol, to obtain 4-(2-fluoro-biphenyl-4-yl)-4-methyl-3-oxo-pentanitrile (6.27 g).

This cyanoketone (9.98 g) was dissolved in ethanol (200 ml) and then pyridine (40 ml) and hydroxylamine hydrochloride (2.47 g) were added, after which the resulting mixture was stirred at 50° C. for 5 hours. The reaction mixture was concentrated under reduced pressure, diluted with ethyl acetate, neutralized with a saturated aqueous sodium bicarbonate solution and thereafter subjected to extraction with ethyl acetate. The organic layer was dried over sodium sulfate and then concentrated under reduced pressure. The residue was purified by a recrystallization method from ethanol, to obtain the desired compound (7.00 g).

$^1$H-NMR (300 MHz, CDCl$_3$) δ ppm: 1.69(s, 6H), 4.37 (br-s, 2H), 4.86(s, 1H), 7.10–7.34(m, 2H), 7.32–7.46(m, 4H), 7.50–7.55 (m, 2H)

Reference Example 21

3-[1-Ethoxy-1-(2-fluoro-biphenyl-4-yl)-ethyl]-isoxazol-5-ylamine

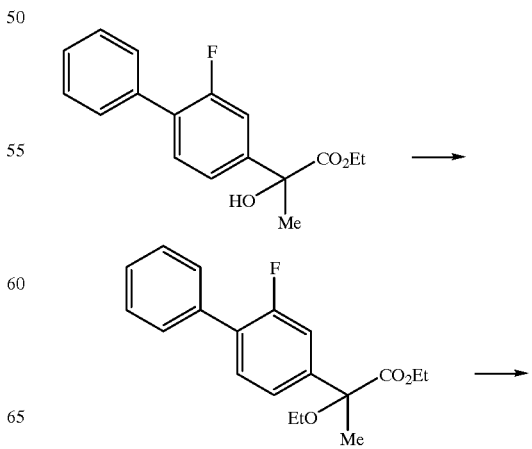

-continued

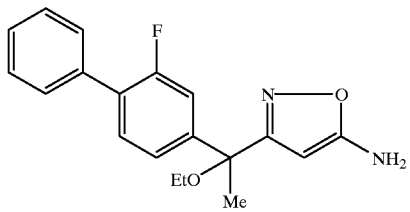

Under a nitrogen atmosphere, ethyl 2-(2-fluoro-biphenyl-4-yl)-2-hydroxy-propionate (Japanese Patent Unexamined Publication No. 52-105,144) (15.0 g) was dissolved in N,N-dimethylformamide (300 ml) and then sodium hydride (4.16 g, 60% oily) was added under ice-cooling, after which the resulting mixture was stirred for one hour. Subsequently, iodoethane (10.4 ml) was added and the resulting mixture was stirred for 12 hours. To the reaction mixture were added a small amount of water and ethanol, and thereafter, the solvent was removed by azeotropic distillation using toluene. To the residue was added ethyl acetate and the resulting mixture was neutralized with a saturated aqueous sodium bicarbonate solution and then subjected to extraction with ethyl acetate. The organic layer was dried over sodium sulfate and then concentrated under reduced pressure to obtain ethyl 2-ethoxy2-(2-fluoro-biphenyl-4-yl)-propionate.

To a mixture of sodium hydride (4.16 g, 60% oily) and tetrahydrofuran (100 ml) was then added dropwise a solution obtained by dissolving the above ester and acetonitrile (5.43 ml) in tetrahydrofuran (200 ml), with heating under reflux over one hour. After stirring with heating under reflux for 4 hours, the mixture was cooled to room temperature, and a small amount of ethanol was added, after which the mixture was diluted with ethyl acetate and then a saturated aqueous sodium bicarbonate solution was added. After extraction with ethyl acetate, the organic layer was dried over sodium sulfate and then concentrated under reduced pressure, to obtain 4-ethoxy-4-(2-fluoro-biphen-yl-4-yl)-3-oxo-pentanitrile which was a cyanoketone derivative.

This cyanoketone was dissolved in ethanol (300 ml) and then pyridine (60 ml) and hydroxylamine hydrochloride (5.42 g) were added, after which the resulting mixture was stirred at 50° C. for 5 hours. The reaction mixture was concentrated under reduced pressure, diluted with ethyl acetate, neutralized with an aqueous sodium bicarbonate solution, and thereafter subjected to extraction with ethyl acetate. The organic layer was dried over sodium sulfate and then concentrated under reduced pressure. The residue was purified by a silica gel column chromatography (hexane/ethyl acetate=3/1) to obtain the desired compound (11.3 g).

$^1$H-NMR (300 MHz, CDCl$_3$) δ ppm: 1.26(t, 3H, J=7.0 Hz), 1.86(s, 3H), 3.35–3.60 (m, 2H), 4.39(br-s, 2H), 5.03(s, 1H), 7.25–7.46(m, 6H), 7.51–7.55(m, 2H)

Reference Example 22

3-[1-(2-Fluoro-biphenyl-4-yl)-cyclopropyl]-isoxazol-5-ylamine

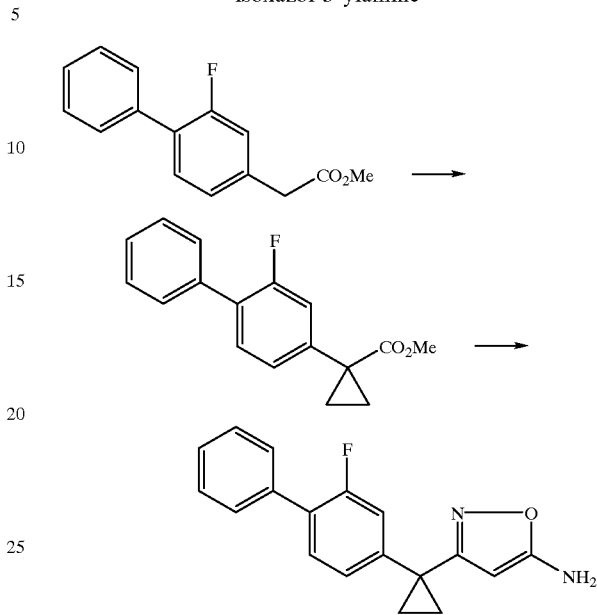

Under a nitrogen atmosphere, methyl (2-fluoro-biphenyl-4-yl)-acetate (5.0 g) was dissolved in tetrahydrofuran (50 ml) and then sodium hydride (8.29 g, 60% oily) was added under ice-cooling, after which the resulting mixture was stirred for 30 minutes. Subsequently, N,N-dimethylformamide (100 ml) was added and then 1,2-dibromoethane (17.6 ml) was added, after which the resulting mixture was stirred for 1.5 hours. To the reaction mixture was added 4 N hydrochloric acid-1,4-dioxane solution (60 ml) and the solution was then neutralized with a saturated aqueous ammonium chloride solution and thereafter subjected to extraction with ethyl acetate. The organic layer was dried over sodium sulfate and then concentrated under reduced pressure. The residue was purified by a silica gel column chromatography (hexane/ethyl acetate=20/1), to obtain methyl 1-(2-fluoro-biphenyl-4-yl)-cyclopropanecarboxylate (4.28 g).

From this ester, the desired compound was obtained by the same procedure as stated in the latter half of Reference Example 20.

$^1$H-NMR (300 MHz, CDCl$_3$) δ ppm: 1.30(q, 2H, J=3.7 Hz), 1.48(q, 2H, J=3.7 Hz), 4.34(br-s, 2H), 4.88(s, 1H), 7.13–7.23(m, 2H), 7.35–7.47(m, 4H), 7.52–7.55(m, 2H)

Reference Example 23

3-(1-Biphenyl-4-yl-ethyl)-isoxazol-5-ylamine

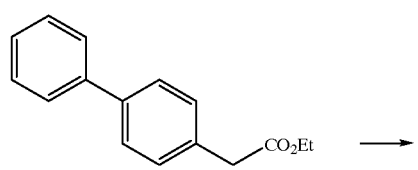

-continued

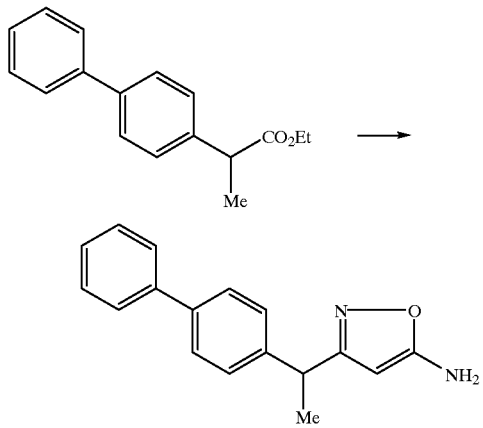

After monomethylation with ethyl 4-biphenylacetoacetate, the desired compound was obtained by the same procedure as stated in the half of Reference Example 20.

$^1$H-NMR (300 MHz, CDCl$_3$) δ ppm: 1.65(d, 3H, J=7.3 Hz), 4.12(q, 1H, J=7.3 Hz), 4.40(s, 2H), 4.92(s, 1H), 7.30–7.45(m, 5H), 7.52–7.59(m, 4H)

Reference Example 24

3-(1-Biphenyl-4-yl-1-methyl-ethyl)-isoxazol-5-ylamine

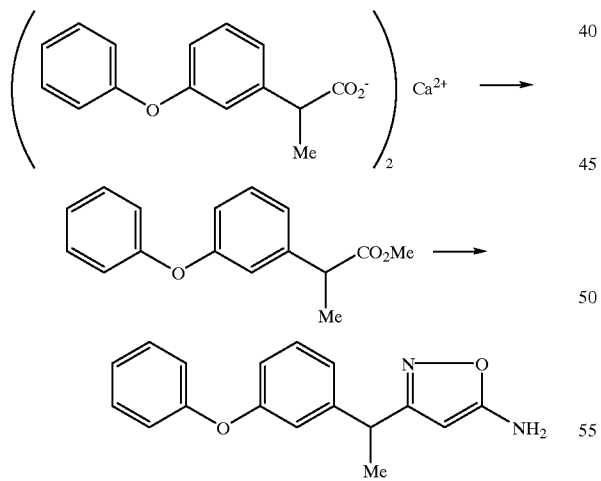

After dimethylation with ethyl 4-biphenylacetoacetate, the desired compound was obtained by the same procedure as stated in the latter half of Reference Example 20.

$^1$H-NMR (300 MHz, CDCl$_3$) δ ppm: 1.70(s, 6H), 4.32(s, 2H), 4.84(s, 1H), 7.33–7.59(m, 9H)

Reference Example 25

3-[1-(3-Phenoxy-phenyl)-ethyl]-isoxazol-5-ylamine

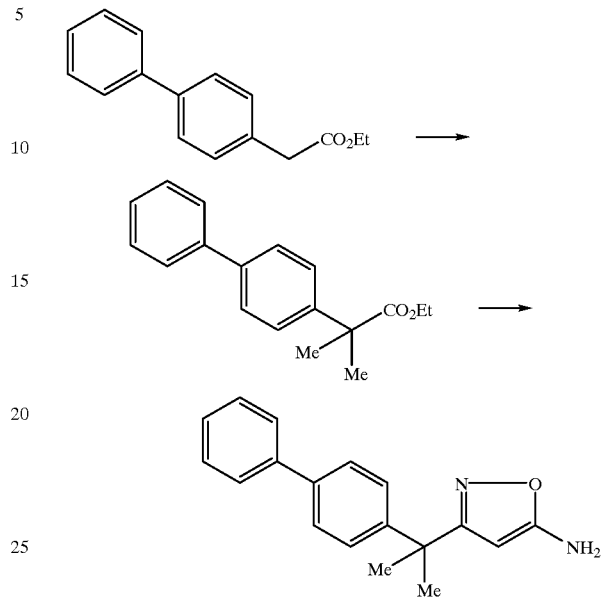

Using calcium 2-(3-phenoxy-phenyl)-propionate, the desired compound was obtained by the same procedure as stated in the latter half of Reference Example 20.

$^1$H-NMR (300 MHz, CDCl$_3$) δ ppm: 1.59(d, 3H, J=7.1 Hz), 4.12(q, IH, J=7.1 Hz), 4.41(br-s, 2H), 4.87(s, 1H), 6.81–6.86(m, 1H), 6.96–7.11(m, 5H), 7.21–7.36(m, 3H)

Reference Example 26

(R)-3-[1-(2-Fluoro-biphenyl-4-yl)-ethyl]-isoxazol-5-ylamine

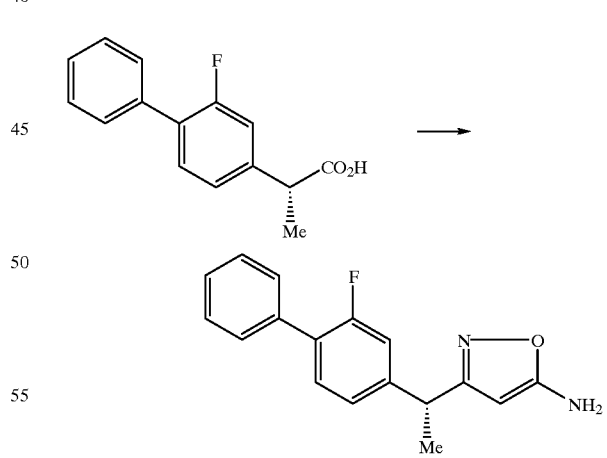

Under a nitrogen atmosphere, tert-butyl cyanoacetate (0.57 ml) was added dropwise to a mixture of tetrahydrofuran (5 ml) and sodium hydride (160 mg, 60% oily) with stirring under ice-cooling. The resulting mixture was stirred for 10 minutes under ice-cooling, then stirred at room temperature for 20 minutes, and again stirred at 0° C. Separately, isobutyl chloroformate (0.26 ml) was added dropwise to a tetrahydrofuran solution (20 ml) of (R)-2-(2- fluoro-biphenyl-4-yl)-propionic acid (449 mg, 93% e.e.) and N-methylmorpholine (0.22 ml) at −15° C. with stirring. After 5 minutes, this solution was added dropwise to the previous mixture. After 20 minutes, this was poured into a saturated aqueous sodium bicarbonate solution and the resulting mixture was subjected to extraction with ethyl acetate. The organic layer was dried over sodium sulfate and then concentrated under reduced pressure. To the viscous residue thus obtained were added hydroxylamine hydrochloride (278 mg) and ethanol (10 ml), and the resulting mixture was stirred for 4 hours with heating under reflux. After cooling to room temperature, ethanol was removed by distillation, and a saturated aqueous sodium bicarbonate solution was added to the residue and the resulting mixture was subjected to extraction with ethyl acetate. The organic layer was dried over sodium sulfate and then concentrated under reduced pressure. The residue was purified by a silica gel column chromatography (hexane/ethyl acetate=3/2), to obtain the desired compound (226 mg, 93% e.e.).

$^1$H-NMR (300 MHz, CDCl$_3$) δ ppm: 1.63(d, 3H, J=7.1 Hz), 4.09(q, 1H, J=7.1 Hz), 4.46(br-s, 2H), 4.91(s, 1H), 7.05–7.18(m, 2H), 7.31–7.47(m, 4H), 7.50–7.76(m, 2H)

Reference Example 27

(S)-3-[1-(2-Fluoro-biphenyl-4-yl)-ethyl]-isoxazol-5-ylamine

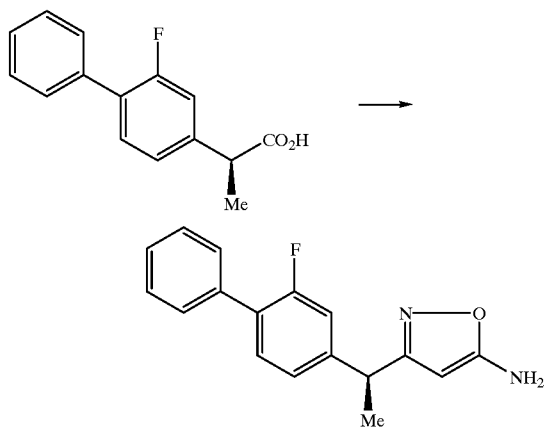

The desired compound was obtained by the same procedure as in Reference Example 26 except for using (S)-2-(2-fluoro-biphenyl-4-yl)-propionic acid.

$^1$H-NMR (300 MHz, CDCl$_3$) δ ppm: 1.61(d, 3H, J=7.1 Hz), 4.08(q, 1H, J=7.1 Hz), 4.55(br-s, 2H), 4.89(s, 1H), 7.05–7.17(m, 2H), 7.31–7.44(m, 4H), 7.50–7.76(m, 2H)

Reference Example 28

3-Biphenyl-4-ylmethyl-isoxazol-5-ylamine

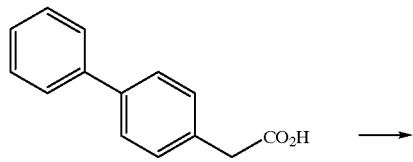

-continued

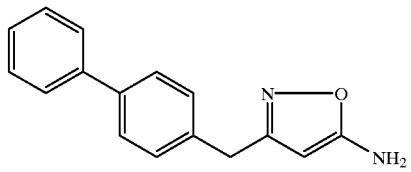

Using 4-biphenyl-acetoacetic acid, the desired compound was obtained by the same procedure as stated in the latter half of Reference Example 20.

$^1$H-NMR (300 MHz, CDCl$_3$) δ ppm: 3.89(s, 2H), 4.36(s, 2H), 4.94(s, 1H), 7.31–7.59(m, 9H)

Reference Example 29

3-[1-(2-Fluoro-2',3',4',5',6'-pentadeuterio-biphenyl-4-yl)-ethyl]-isoxazol-5-ylamine

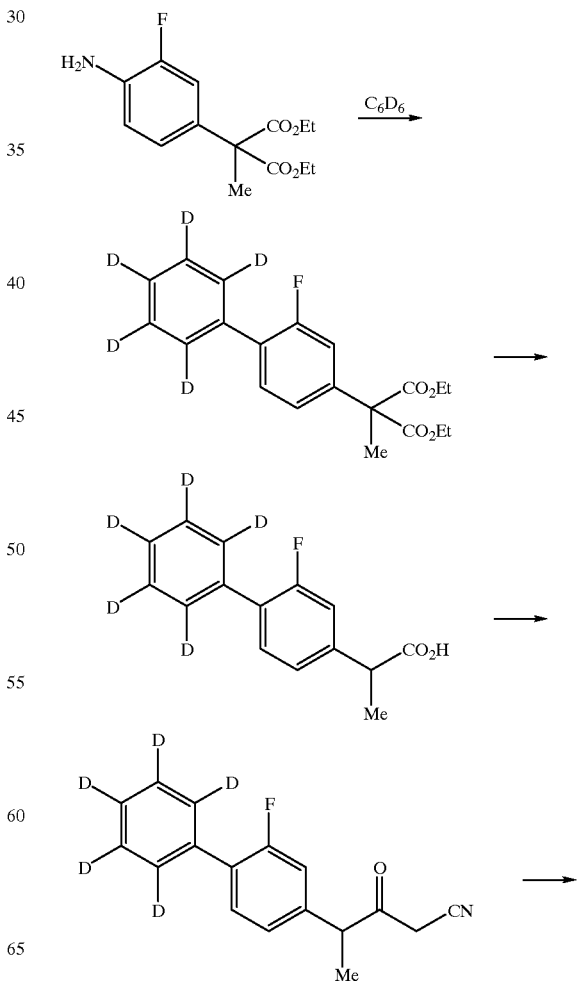

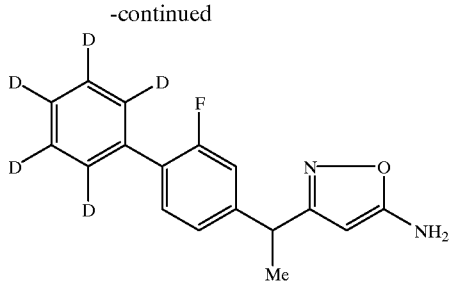

Under a nitrogen atmosphere, benzene deuteride (56 ml) and water (6 ml) were added to sodium nitrite (4.87 g) and the resulting mixture was stirred at 60° C. To this solution wad added dropwise with stirring over 3 hours a solution obtained by dissolving dimethyl 2-(4-amino-3-fluorophenyl)-2-methyl-malonate (Japanese Patent Unexamined Publication No. 2-223,542) (10.0 g) and glacial acetic acid (4.24 g) in benzene deuteride (19 ml). After stirring for 2 hours, the resulting solution was washed with an aqueous sodium sulfate solution and then concentrated under reduced pressure. The residue was dissolved in a 85% aqueous sulfuric acid solution (17.7 ml), and the resulting solution was subjected to extraction with toluene-hexane. It was washed with a 1 N aqueous sodium carbonate solution and then with a saturated aqueous sodium chloride solution and thereafter concentrated under reduced pressure. The residue was purified by a silica gel column chromatography (hexane/ethyl acetate=13/1), to obtain diethyl 2-(2-fluoro-2',3',4', 5',6'-pentadeuterio-biphenyl-4-yl)-2-methyl-malonate (5.99 g).

This ester (5.98 g) was dissolved in ethanol (39 ml) and then a 50% aqueous sodium hydroxide solution (3.42 ml) was added at –15° C., after which the resulting mixture was stirred at room temperature for 6 hours. A small amount of water was added to the reaction mixture and the pH of the solution was adjusted to 8 with 3 N hydrochloric acid, after which the mixture was subjected to extraction with chloroform. The aqueous layer was adjusted to pH 1 and then subjected to extraction with ethyl acetate, after which the organic layer was dried over sodium sulfate and then concentrated under reduced pressure. Glacial acetic acid (4.24 g) was added to the residue and the resulting mixture was heated under reflux for 17 hours. It was cooled under ice-cooling and then water (12 ml) was added, after which the resulting mixture was filtered and the residue was washed with 50% acetic acid, to obtain 2-(2-fluoro-2',3',4', 5',6'-pentadeuterio-biphenyl-4-yl)-propionic acid (3.84 g).

This carboxylic acid (3.84 g) was dissolved in ethanol (20 ml) and then toluene (10 ml) and conc. sulfuric acid (50 mg) were added, after which the resulting mixture was stirred at 60–80° C. for 4 hours. The reaction mixture was diluted with ethyl acetate, then neutralized with sodium carbonate and thereafter subjected to extraction with ethyl acetate. The organic layer was dried over sodium sulfate and then concentrated under reduced pressure, to obtain ethyl 2-(2-fluoro-2',3',4',5',6'-pentadeuterio-biphenyl-4-yl)-propionate (4.26 g).

Tetrahydrofuran (30 ml) was added to sodium hydride (1.11 g, 60% oily), and then to the solution was added dropwise over 40 minutes with heating under reflux a solution obtained by dissolving the above ester (4.26 g) and acetonitrile (1.14 g) in tetrahydrofuran (10 ml). After stirring with heating under reflux for 2 hours, the solution was cooled to room temperature, and then, isopropanol (15 ml) was added, after which the resulting mixture was neutralized with 3 N hydrochloric acid under ice-cooling and then subjected to extraction with chloroform. The organic layer was dried over sodium sulfate and then concentrated under reduced pressure. The residue was dissolved in ethanol (20 ml) and then pyridine (7 ml) and hydroxylamine hydrochloride (2.13 g) were added, after which the resulting mixture was stirred at room temperature for 24 hours. The reaction mixture was concentrated under reduced pressure and then a small amount of water was added, after which the resulting mixture was subjected to extraction with ethyl acetate. The organic layer was dried over sodium sulfate and then concentrated under reduced pressure. The residue was purified by a recrystallization method from chloroform to obtain the desired compound (3.24 g).

$^1$H-NMR (300 MHz, CDCl$_3$) δ ppm: 1.64(d, 3H, J=7.1 Hz), 4.11(q, 1H, J=7.1 Hz), 4.39(br-s, 2H), 4.94(s, 1H), 7.06–7.19(m, 2H), 7.38(t, 1H, J=7.9 Hz)

Reference Example 30

3-[1-(2-Fluoro-2'-methoxy-biphenyl-4-yl)-ethyl]-isoxazol-5-ylamine

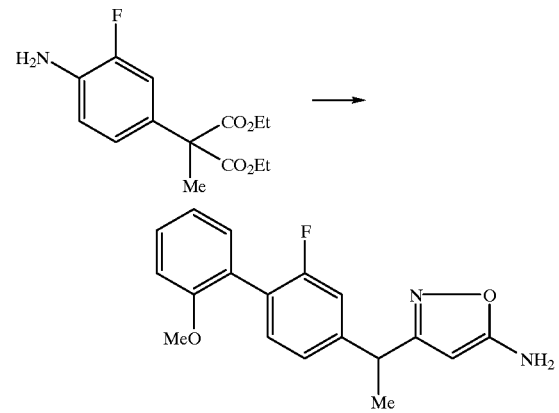

The desired compound was obtained by the same procedure as in Reference Example 29 except for using methoxybenzene.

$^1$H-NMR (300 MHz, CDCl$_3$) δ ppm: 1.64(d, 3H, J=7.1 Hz), 3.81(s, 3H), 4.11(q, 1H, J=7.1 Hz), 4.37(br-s, 2H), 4.95(s, 1H), 6.96–7.13(m, 5H), 7.23–7.48(m, 2H)

Reference Example 31

3-[1-(2'-Fluoro-biphenyl-4-yl)-ethyl]-isoxazol-5-ylamine

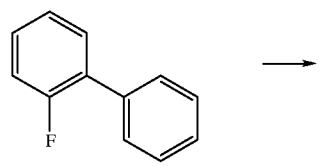

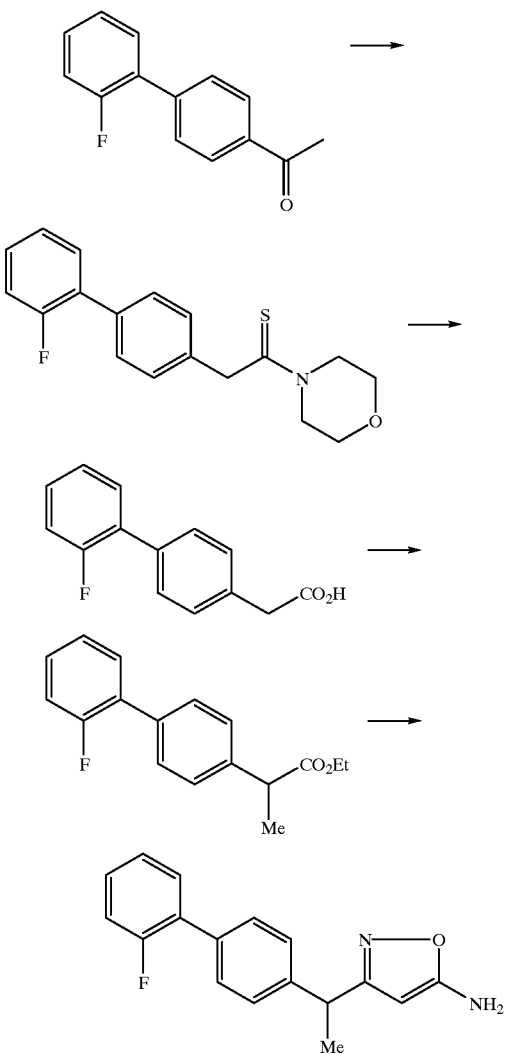

Under a nitrogen atmosphere, methylene chloride (100 ml) was added to aluminum chloride (20.1 g) and then, to thereto was added dropwise at room temperature a solution obtained by dissolving 2-fluorobiphenyl (20.0 g) and acetyl chloride (10.7 ml) in methylene chloride (100 ml). After stirring for 4 hours, a small amount of water was added to the reaction mixture, and then the mixture was subjected to extraction with chloroform. The organic layer was dried over sodium sulfate and then concentrated under reduced pressure. The residue was purified by a recrystallization method from ethanol, to obtain 1-(2'-fluoro-biphenyl-4-yl)-ethanone (17.53 g).

This ketone (17.53 g) was dissolved in morpholine (130 ml) and then sulfur (5.25 g) was added, after which the resulting mixture was stirred with heating under reflux for 10 hours. The mixture was cooled to room temperature and thereafter 1 N hydrochloric acid (500 ml) was added, after which the resulting mixture was subjected to extraction with ethyl acetate. The organic layer was dried over sodium sulfate and then concentrated under reduced pressure. The residue was purified by a recrystallization method from ethanol, to obtain 2-(2'-fluoro-biphenyl-4-yl)-1-morpholin-4-yl-ethanethione (21.69 g).

This compound was dissolved in ethanol (200 ml) and then a 15% aqueous sodium hydroxide solution (50 ml) was added, after which the resulting mixture was stirred with heating under reflux for 4 hours. After cooling to room temperature, the solvent was concentrated under reduced pressure, and diluted hydrochloric acid was added, after which the resulting mixture was subjected to extraction with ethyl acetate. The organic layer was dried over sodium sulfate and then concentrated under reduced pressure. The residue was purified by a recrystallization method from ethanol, to obtain (2'-fluoro-biphenyl-4-yl)-acetic acid (13.46 g).

Diisopropylamine (16.4 ml) was dissolved in tetrahydrofuran (100 ml) and then a hexane solution (30.3 ml, 1.66 M) of n-butyllithium was added under ice-cooling, after which the resulting mixture was stirred for 15 minutes. Subsequently, thereto was added under ice-cooling a solution obtained by dissolving the above carboxylic acid (13.44 g) in tetrahydrofuran (100 ml), and thereafter, hexamethylphosphorus triamide (40 ml) was added, after which the resulting mixture was stirred under ice-cooling for one hour. Further, iodomethane (3.63 ml) was added and the resulting mixture was stirred for 3 hours. To the reaction mixture was added 10% hydrochloric acid (500 ml) and then the solution was subjected to extraction with ethyl acetate. The organic layer was washed with a saturated sodium chloride solution, then dried over sodium sulfate and thereafter concentrated under reduced pressure, to obtain 2-(2'-fluoro-biphenyl-4-yl)-propionic acid (16.64 g).

This carboxylic acid was dissolved in ethanol (100 ml) and conc. sulfuric acid (2 ml) was added to the solution, after which the solution was stirred with heating under reflux for 4 hours. The reaction mixture was diluted with ethyl acetate, neutralized with a saturated aqueous sodium bicarbonate solution, and thereafter subjected to extraction with ethyl acetate. The organic layer was dried over sodium sulfate and then concentrated under reduced pressure. The residue was purified by a silica gel column chromatography (hexane/ethyl acetate=4/1), to obtain ethyl 2-(2'-fluoro-biphenyl-4-yl)-propionate (9.26 g).

Tetrahydrofuran (100 ml) was added to sodium hydride (2.12 g, 60% oily) and thereto was added dropwise with heating under reflux over one hour a solution obtained by dissolving the above ester (9.62 g) and acetonitrile (3.67 ml) in tetrahydrofuran (100 ml). After heating under reflux for 5 hours, the resulting mixture was cooled to room temperature, and then a small amount of water was added, after which the resulting mixture was diluted with ethyl acetate and an aqueous sodium bicarbonate solution was added. After extraction with ethyl acetate, the organic layer was dried over sodium sulfate and then concentrated under reduced pressure. The residue was purified by a silica gel column chromatography (hexane/ethyl acetate=3/1), to obtain 4-(2'-fluoro-biphenyl-4-yl)-3-oxo-pentanitrile (7.33 g).

This cyanoketone was dissolved in ethanol (120 ml) and then pyridine (20 ml) and hydroxylamine hydrochloride (2.86 g) were added, after which the resulting mixture was stirred at 60° C. for 8 hours. The reaction mixture was concentrated under reduced pressure, then diluted with ethyl acetate and thereafter neutralized with an aqueous sodium bicarbonate solution, after which the mixture was subjected to extraction with ethyl acetate. The organic layer was dried over sodium sulfate and then concentrated under reduced pressure. The residue was purified by a silica gel column chromatography (hexane/ethyl acetate=4/1) to obtain the desired compound (6.31 g).

$^1$H-NMR (300 MHz, CDCl$_3$) δ ppm: 1.65(d, 3H, J=7.1 Hz), 4.12(q, 1H, J=7.1 Hz), 4.36(br-s, 2H), 4.92(s, 1H), 7.10–7.53(m, 8H)

Reference Example 32

3-[1-(2-Fluoro-4'-methoxy-biphenyl-4-yl)-ethyl]-isoxazol-5-ylamine

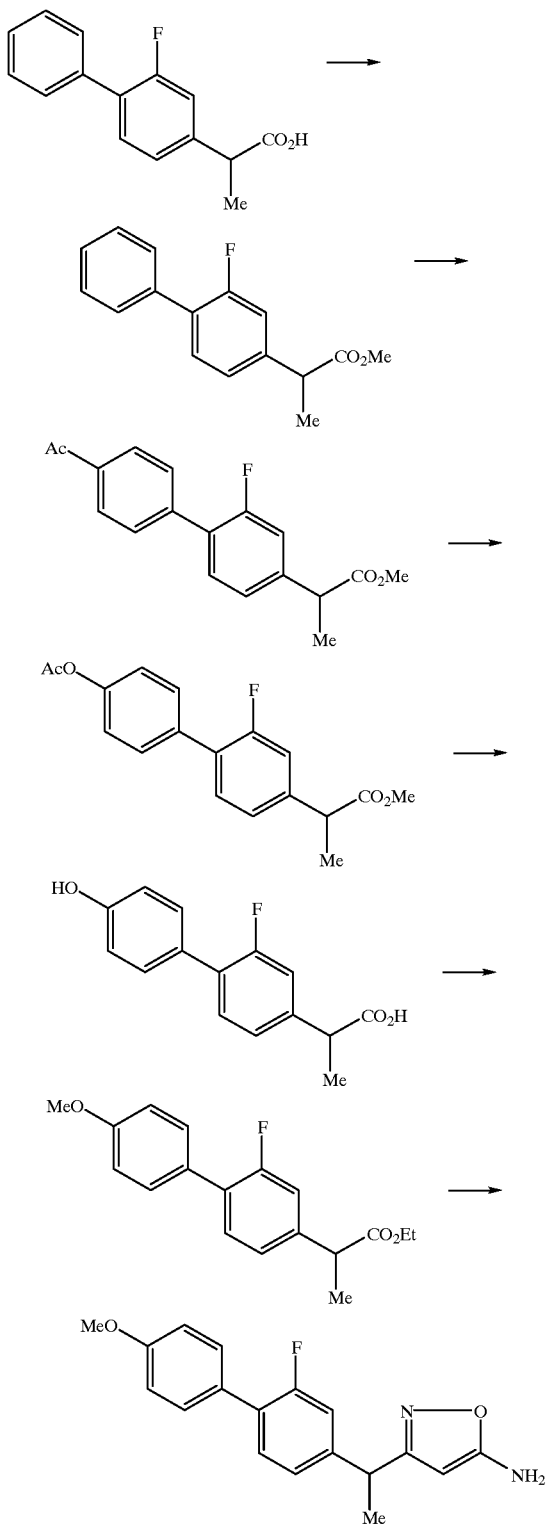

2-(2-Fluoro-biphenyl-4-yl)-propionic acid (104.2 g) was dissolved in methanol (410 ml) and then conc. sulfuric acid (60.2 g) was added, after which the resulting mixture was stirred at 40° C. for 2.5 hours. The mixture was cooled to room temperature, diluted with toluene, then neutralized with a saturated aqueous sodium bicarbonate solution, and thereafter subjected to extraction with ethyl acetate. The organic layer was dried over sodium sulfate and then concentrated under reduced pressure, to obtain methyl 2-(2-fluoro-biphenyl-4-yl)-propionate (110.2 g).

Under a nitrogen atmosphere, ethylene dichloride (700 ml) was added to aluminum chloride (125.1 g) and then 2-fluorobiphenyl (20.0 g) was added. A solution obtained by dissolving acetyl chloride (73.7 g) in ethylene dichloride (300 ml) was dropwise added under ice-cooling over 2 hours. After stirring at 20–30° C. for 2 hours, the temperature was elevated to 40–60° C. and stirring was conducted for 3 hours. After cooling to room temperature, a small amount of water was added to the reaction mixture and then hydrochloric acid was added, after which the resulting mixture was subjected to extraction with ethylene dichloride. The organic layer was dried over sodium sulfate and then concentrated under reduced pressure. The residue was purified by a silica gel column chromatography (hexane/ethyl acetate=10/1→7/1), to obtain methyl 2-(4'-acetyl-2-fluoro-biphenyl-4-yl)-propionate (107.6 g).

This ester (109.6 g) was dissolved in methylene chloride (670 ml) and then m-chloroperbenzoic acid (110.3 g) was added at room temperature, after which the resulting mixture was stirred with heating under reflux for 20 hours. After cooling to room temperature, m-chloroperbenzoic acid was removed by filtration and the residue was washed with a 20% aqueous sodium thiosulfate solution and then with a saturated aqueous sodium bicarbonate solution. The mother liquor was extracted with chloroform, and thereafter, the organic layer was dried over sodium sulfate and then concentrated under reduced pressure. The residue was purified by a recrystallization method from hexane-ethyl acetate (130/1), to obtain methyl 2-(4'-acetoxy-2-fluoro-biphenyl-4-yl)-propionate (97.0 g).

This compound was dissolved in methanol (1,000 ml) and then a 20% aqueous sodium hydroxide solution (200 ml) was added, after which the resulting mixture was stirred at 35° C. for 3 hours. After cooling to room temperature, the solvent was concentrated under reduced pressure, water (1,500 ml) was added and then 4 N hydrochloride acid was added to adjust the pH to 1. The deposit was washed with water and thereafter vacuum dried at 60° C., to obtain 2-(2-fluoro-4'-hydroxy-biphenyl-4-yl)-propionic acid (68.6 g).

This carboxylic acid (67.6 g) was dissolved in acetone (1,300 ml) and then potassium carbonate (100.9 g) and dimethyl sulfate (92.1 g) were added, after which the resulting mixture was stirred with heating under reflux for 5 hours. The reaction mixture was filtered and the filtrate obtained was concentrated under reduced pressure.

To this residue were added methanol (1,000 ml) and then a 20% aqueous sodium hydroxide solution (150 ml), after which the resulting mixture was stirred at 35° C. for 2 hours. After cooling to room temperature, the solvent was concentrated under reduced pressure and then water (1,000 ml) was added, after which 4 N hydrochloric acid was added to adjust the pH to 1 and extraction with chloroform was conducted. The organic layer was dried over sodium sulfate and then concentrated under reduced pressure.

This residue was dissolved in ethanol (300 ml) and then conc. sulfuric acid (34.4 g) was added, after which the resulting mixture was stirred with heating under reflux for 2 hours. The reaction mixture was cooled to room temperature, diluted with toluene, neutralized with a saturated aqueous sodium bicarbonate solution and thereafter subjected to extraction with toluene. The organic layer was dried over sodium sulfate and then concentrated under reduced pressure, to obtain ethyl 2-(2-fluoro-4'-methoxy-biphenyl-4-yl)-propionate (82.9 g).

After tetrahydrofuran (300 ml) was added to sodium hydride (19.7 g, 60% oily), a solution obtained by dissolving the above ester (82.9 g) and acetonitrile (20.3 g) in tetrahydrofuran (100 ml) was added dropwise over 45 minutes thereto. After stirring with heating under reflux for 1.5 hours, the resulting mixture was cooled to room temperature, and isopropanol (50 ml) was added, after which the mixture was neutralized with 3 N hydrochloric acid and then subjected to extraction with chloroform. The organic layer was dried over sodium sulfate and then concentrated under reduced pressure, to obtain 4-(2-fluoro-4'-methoxy-biphenyl-4-yl)-3-oxo-pentanitrile (89.1 g).

After this cyanoketone was dissolved in ethanol (200 ml), pyridine (60 ml) and hydroxylamine hydrochloride (38.1 g) were added, and the resulting mixture was stirred at 70° C. for 4 hours. The reaction mixture was concentrated under reduced pressure, diluted with ethyl acetate, thereafter neutralized with a saturated aqueous sodium bicarbonate solution, and then subjected to extraction with ethyl acetate. The organic layer was dried over sodium sulfate and then concentrated under reduced pressure to obtain the desired compound (79.36 g).

$^1$H-NMR (300 MHz, CDCl$_3$) δ ppm: 1.63(d, 3H, J=7.3 Hz), 3.85(s, 3H), 4.09(q, 1H, J=7.3 Hz), 4.38(br-s, 2H), 4.93(s, 1H), 6.94–7.00(m, 2H), 7.04–7.13(m, 2H), 7.31–7.38(m, 2H), 7.44–7.49(m, 2H)

Reference Example 33

Methyl 2-(9H-carbazol-2-yl)-propionate

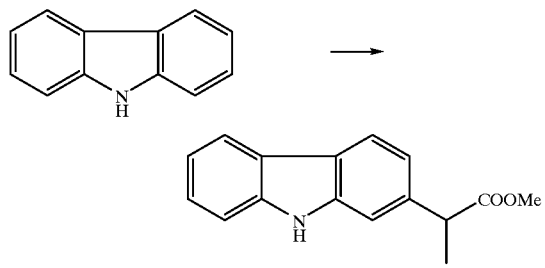

The desired compound was obtained in the same manner as in the known method [P. S. Manchand et al., Heterocycles, 39,833 (1994)] except for using carbazole.

$^1$H-NMR (300 MHz, CDCl$_3$) δ ppm: 1.59(d, 3H, J=7.1 Hz), 3.67(s, 3H), 3.89(q, 1H, J=7.1 Hz), 7.15–7.25(m, 2H), 7.36–7.43(m, 3H), 7.98–8.10(m, 3H)

Reference Example 34

3-[1-(9H-Carbazol-2-yl)-ethyl]-isoxazol-5-ylamine

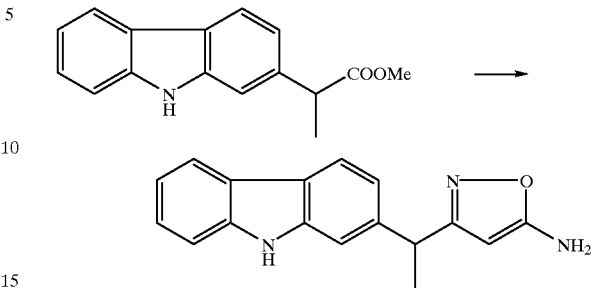

The desired compound was obtained by the same procedure as stated in the latter half of Reference Example 20 except for using the compound obtained in Reference Example 33.

$^1$H-NMR (300 MHz, CDCl$_3$) δ ppm: 1.71(d, 3H, J=7.1 Hz), 4.24(q, 1H, J=7.1 Hz), 4.90(s, 1H), 7.15–7.25(m, 2H), 7.34–7.44(m, 3H), 7.98–8.05(m, 3H)

Reference Example 35

3-(2-Fluoro-biphenyl-4-ylmethyl)-isoxazol-5-ylamine

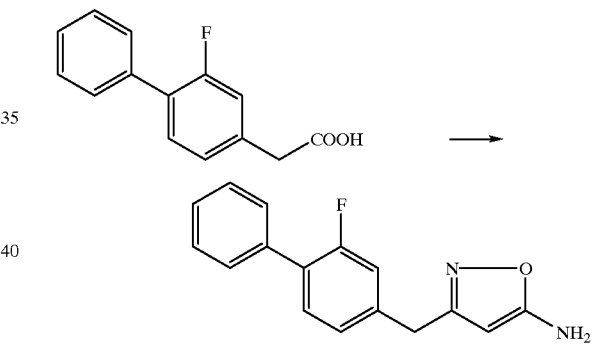

The desired compound was obtained by the same procedure as in Reference Example 26 except for using (2-fluoro-biphenyl-4-yl)-acetic acid.

$^1$H-NMR (270 MHz, CDCl$_3$) δ ppm: 3.88(s, 2H), 4.97(s, 1H), 7.04–7.14(m, 2H), 7.33–7.47(m, 4H), 7.51–7.55(m, 2H)

Reference Example 36

Ethyl 2-(2,3-dihydro-benzo[1,4]dioxin-6-yl)-propionate

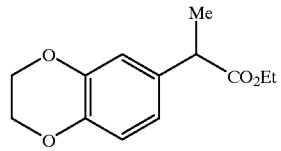

Under a nitrogen atmosphere, 60% sodium hydride (1.13 g) was added to a solution in N,N-dimethylformamide (65 ml) of ethyl 3,4-ethylenedioxyphenylacetate [M. Sasamoto, Chem. Pharm. Bull., 8, 324 (1969)] (6.00 g) in an ice bath. Thereafter, methyl iodide (1.76 ml) was added dropwise and the resulting mixture was stirred under ice-cooling for 4 hours. To the reaction mixture was added 1 N hydrochloric acid and the resulting mixture was subjected to extraction with diethyl ether, after which the extraction solution was washed with water and then dried. The solvent was removed by distillation under reduced pressure and the residue was purified by a silica gel column chromatography to obtain the desired compound (5.57 g).

$^1$H-NMR (270 MHz, CDCl$_3$) δ ppm: 1.22(t, 3H, J=7.3 Hz), 1.44(d, 3H, J=7.3 Hz), 3.59(q, 1H, J=7.3 Hz), 4.05–4.17(m, 2H), 4.24 (s, 4H), 6.74(m, 3H)

Reference Example 37

3-[1-(2,3-Dihydro-benzo[1,4]dioxin-6-yl)-ethyl]-isoxazol-5-ylamine

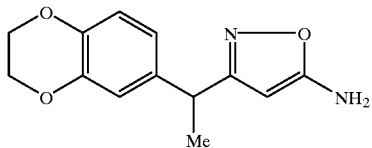

The desired compound was obtained by the same procedure as stated in the latter half of Reference Example 20 except for using the compound obtained in Reference Example 36.

$^1$H-NMR (270 MHz, CDCl$_3$) δ ppm: 1.56(d, 3H, J=7.3 Hz), 3.97(q, 1H, J=7.3 Hz), 4.23(s, 4H), 4.33(br-s, 2H), 4.88(s, 1H), 6.73–6.82(m, 3H)

Reference Example 38

3-[1-(1-Methyl-1H-indol-3-yl)-ethyl]-isoxazol-5-ylamine

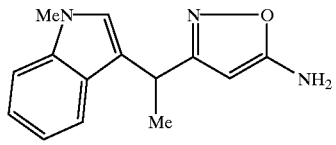

The desired compound was obtained by the same procedure as stated in the latter half of Reference Example 20 except for using ethyl 2-(1-methyl-1H-indol-3-yl)-propionate [L. K. Mehta et al., J. Chem. Soc., Perkin Trans. 2, 1488 (1997)].

$^1$H-NMR (270 MHz, CDCl$_3$) δ ppm: 1.69(d, 3H, J=7.3 Hz), 3.74(s, 3H), 4.26(br-s, 2H), 4.36(q, 1H, J=7.3 Hz), 4.88(s, 1H), 6.91(s, 1H), 7.04–7.29(m, 3H), 7.62(d, 1H, J=7.9 Hz)

Reference Example 39

3-[1-(1H-Indol-3-yl)-ethyl]-isoxazol-5-ylamine

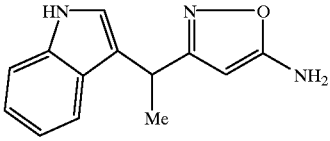

The desired compound was obtained by the same procedure as stated in the latter half of Reference Example 20 except for using ethyl 2-(1H-indol-3-yl)-propionate [M. Julia et al., Bull. Soc. Chim. Fr. 2291 (1966)].

$^1$H-NMR (270 MHz, CDCl$_3$) δ ppm: 1.70(d, 3H, J=7.3 Hz), 4.25(br-s, 2H), 4.37(q, 1H, J=7.3 Hz), 4.87(s, 1H), 7.05–7.21(m, 3H), 7.34(d, 1H, J=8.2 Hz), 7.62(d, 1H, J=7.9 Hz), 8.04(br-s, 1H)

Reference Example 40

Methyl 2-(1-methyl-1H-indol-2-yl)-propionate

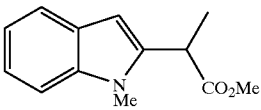

A mixture of 1-methyl-2-(2'-carboxymethoxyvinyl)indole [F. E. Ziegler et al., J. Am. Chem. Soc., 95, 7146 (1973)] (335 mg), 10% palladium/active carbon (50 mg) and tetrahydrofuran (4 ml) was subjected to hydrogenation at room temperature for 30 minutes. The reaction mixture was filtered to remove the catalyst, and thereafter concentrated under reduced pressure, after which the residue was purified by a silica gel column chromatography to obtain the desired compound (168 mg).

$^1$H-NMR (270 MHz, CDCl$_3$) δ ppm: 1.65(d, 3H, J=7.3 Hz), 3.69(s, 3H), 3.72(s, 3H), 3.97(q, 1H, J=7.3 Hz), 6.43(s, 1H), 7.05–7.31(m, 3H), 7.57(d, 1H, J=7.9 Hz)

Reference Example 41

3-[1-(1-Methyl-1H-indol-2-yl)-ethyl]-isoxazol-5-ylamine

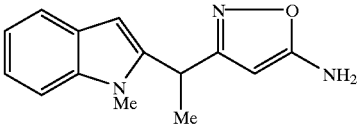

The desired compound was obtained by the same procedure as stated in the latter half of Reference Example 20 except for using the compound obtained in Reference Example 40.

$^1$H-NMR (270 MHz, CDCl$_3$) δ ppm: 1.72(d, 3H, J=7.3 Hz), 3.64(s, 3H), 4.30–4.33 (m, 3H), 4.81(s, 1H), 6.44(s, 1H), 7.05–7.28 (m, 3H), 7.57(d, 1H, J=7.9 Hz)

Reference Example 42

Ethyl 2-benzofuran-5-yl-propionate

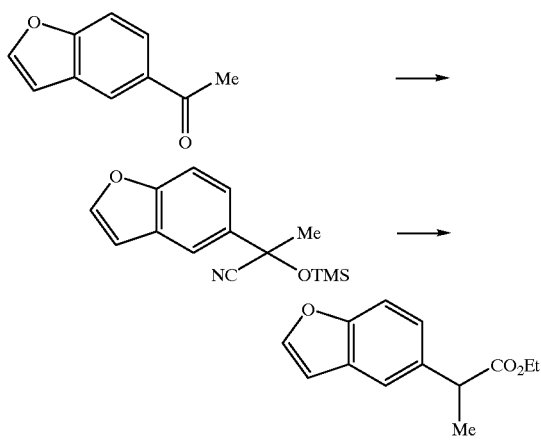

To a solution of 5-benzofurancarbonitrile (Japanese Patent Unexamined Publication No. 9-124,631) (1.30 g) in tetrahydrofuran (5 ml) was added 0.87 M methyl magnesium bromide-tetrahydrofuran solution (21 ml), and the resulting mixture was heated under reflux for 4 hours under a nitrogen atmosphere. The reaction mixture was acidified with conc. sulfuric acid and water was added thereto, after which the resulting mixture was subjected to extraction with diethyl ether. The extract solution was washed with water, dried and then distilled under reduced pressure to remove the solvent. The residue was purified by a silica gel column chromatography to obtain 1-benzofuran-5-yl-ethanone (1.21 g).

$^1$H-NMR (270 MHz, CDCl$_3$) δ ppm: 2.67(s, 3H), 6.86(d, 1H, J=2.3 Hz), 7.55(d, 1H, J=8.9 Hz), 7.70(d, 1H, J=2.3 Hz), 7.97(dd, 1H, J=8.9, 1.7 Hz), 8.26(d, 1H, J=1.7 Hz)

A mixture of 1-benzofuran-5-yl-ethanone (850 mg), trimethylsilyl cyanide (0.85 ml), zinc iodide (34 mg) and chloroform (21 ml) was heated under reflux for 3.5 hours under a nitrogen atmosphere. The solvent was removed by distillation under reduced pressure, and the residue was purified by a silica gel column chromatography to obtain the desired cyano compound (1.21 g).

$^1$H-NMR (270 MHz, CDCl$_3$) δ ppm: 0.18(s, 9H), 1.91(s, 3H), 6.80(m, 1H), 7.45–7.54(m, 2H), 7.67(d, 1H, J=2.0 Hz), 7.81(s, 1H)

To a solution of this cyano compound (1.21 g) in acetic acid (10 ml) was added tin chloride (II) dihydrate and the resulting mixture was stirred at room temperature for 10 minutes, after which conc. hydrochloric acid (20 ml) was added and the mixture was stirred at room temperature overnight. The reaction mixture was further heated and stirred at 100° C. for 2.5 hours and water was added, after which the resulting mixture was subjected to extraction with diethyl ether. The extraction solution was washed with water and dried. The solvent was removed by distillation under reduced pressure and to the residue were added ethanol (4 ml) and conc. sulfuric acid (0.05 ml), after which the resulting mixture was heated and stirred at 80° C. for 2.5 hours. The solvent was removed by distillation under reduced pressure and water was added to the residue, after which the resulting mixture was subjected to extraction with diethyl ether. The extract solution was washed with water and dried. The solvent was removed by distillation under reduced pressure and the residue was purified by a silica gel column chromatography to obtain the desired compound (601 mg).

$^1$H-NMR (270 MHz, CDCl$_3$) δ ppm: 1.20(t, 3H, J=7.3 Hz), 1.54(d, 3H, J=7.3 Hz), 3.80(q, 1H, J=7.3 Hz), 4.05–4.19(m, 2H), 6.74 (d, 1H, J=2.3 Hz), 7.24(d, 1H, J=8.6 Hz), 7.45 (d, 1H, J=8.6 Hz), 7.54(s, 1H), 7.61(d, 1H, J=2.3 Hz)

Reference Example 43

3-(1-Benzofuran-5-yl-ethyl)-isoxazol-5-ylamine

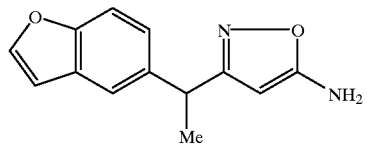

The desired compound was obtained by the same procedure as stated in the latter half of Reference Example 20 except for using the compound obtained in Reference Example 42.

$^1$H-NMR (270 MHz, CDCl$_3$) δ ppm: 1.66(d, 3H, J=7.3 Hz), 4.17(q, 1H, J=7.3 Hz), 4.32(br-s, 2H), 4.86(s, 1H), 6.72(d, 1H, J=2.3 Hz), 7.22(dd, 1H, J=8.6, 1.7 Hz), 7.43 (d, 1H, J=8.6 Hz), 7.51(d, 1H, J=1.7 Hz), 7.60 (d, 1H, J=2.3 Hz)

Reference Example 44

Ethyl 2-benzofuran-6-yl-propionate

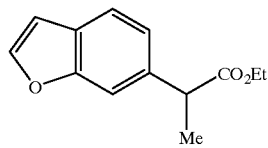

The desired compound was obtained by the same procedure as in Reference Example 42.

$^1$H-NMR (270 MHz, CDCl$_3$) δ ppm: 1.21(t, 3H, J=7.3 Hz), 1.55(d, 3H, J=7.3 Hz), 3.82(q, 1H, J=7.3 Hz), 4.06–4.18(m, 2H), 6.74 (d, 1H, J=2.3 Hz), 7.20(d, 1H, J=7.9 Hz), 7.47 (s, 1H), 7.53(d, 1H, J=7.9 Hz), 7.6(d, 1H, J=2.3 Hz)

Reference Example 45

3-(1-Benzofuran-6-yl-ethyl)-isoxazol-5-ylamine

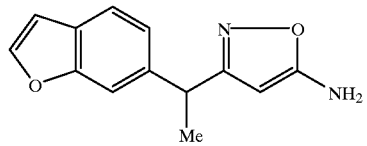

The desired compound was obtained by the same procedure as stated in the latter half of Reference Example 20 except for using the compound obtained in Reference Example 44.

$^1$H-NMR (270 MHz, CDCl$_3$) δ ppm: 1.66(d, 3H, J=7.3 Hz), 4.19(q, 1H, J=7.3 Hz), 4.32(br-s, 2H), 4.87(s, 1H), 6.73(d, 1H, J=2.3 Hz), 7.18(d, 1H, J=8.3 Hz), 7.44(s, 1H), 7.52(d, 1H, J=8.3 Hz), 7.59(d, 1H, J=2.3 Hz)

Reference Example 46

(S)-3-[1-(2-Fluoro-biphenyl-4-yl)-ethyl]-isoxazol-5-ylamine

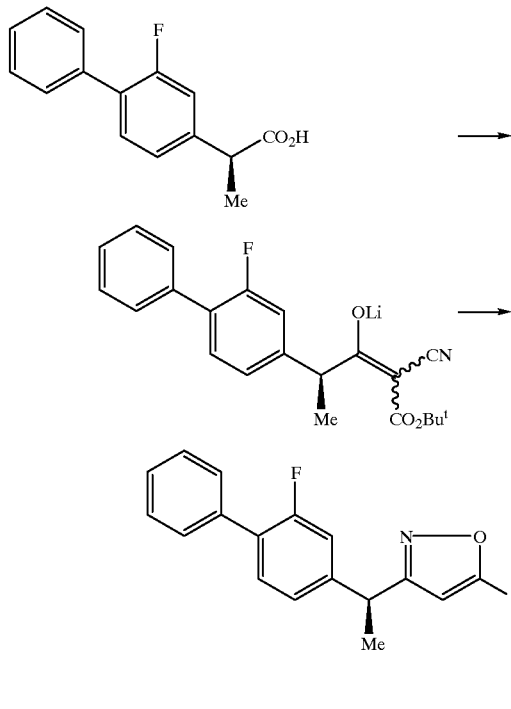

As a different method for producing the compound of Reference Example 27, the following method was carried out: Under a nitrogen atmosphere, a mixture of tetrahydrofuran (73 ml) and lithium amide (1.61 g) was heated to 68° C. and tert-butyl cyanoacetate (11.1 g) was added dropwise. Thereafter, the solution was concentrated until the amount of the contents became 30 g while nitrogen was blown into the mixture, and then cooled to room temperature. Tetrahydrofuran was added thereto to adjust the amount of the contents to 50 g and then the resulting mixture was cooled to −10° C. In a separate reaction vessel, under a nitrogen atmosphere, (S)-2-(2-fluoro-biphenyl-4-yl)-propionic acid (10.1 g, 99% e.e.) and a tetrahydrofuran solution (27 ml) of N-methylmorpholine (5.2 ml) were added dropwise to a tetrahydrofuran solution (27 ml) of isobutyl chloroformate (5.57 g) at −10° C. After 10 minutes, this solution was added dropwise to the previous mixture, and after one hour, water (202 ml) was added, after which the resulting mixture was stirred at room temperature overnight. The crystals precipitated were separated by filtration and dried under reduced pressure to obtain the desired lithium salt (13.4 g).

$^1$H-NMR (300 MHz, d$_6$-DMSO) δ ppm: 1.31(d, 3H, J=6.8 Hz), 1.37(s, 9H), 4.21(q, 1H, J=6.8 Hz), 7.15–7.22(m, 2H), 7.35–7.52(m, 6H).

Na$_2$HPO$_4$ (826 ml) was dissolved in water (11.6 g) and the resulting solution was adjusted to pH 8.0 with 1 N phosphoric acid, after which hydroxylamine hydrochloride (78.1 g) was added thereto. To the resulting mixture was added dropwise a solution of the lithium salt (1.40 g) obtained above in isopropanol (11.7 ml) at 80° C., and the resulting mixture was stirred for one hour, after which the temperature was returned to room temperature and water (27 ml) was added to the mixture to crystallize the desired compound. The crystals were separated by filtration and dried under reduced pressure to obtain the desired amine (875 mg, 98% e.e.).

Reference Example 47

3-(1-Quinolin-3-yl-ethyl)-isoxazol-5-ylamine

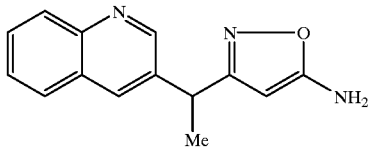

The desired compound was obtained by the same procedure as stated in the latter half of Reference Example 20 except for using 2-quinolin-3-yl-propionic acid methyl ester [T. Sakamoto et al., Heterocycles, 36, 2509(1997)].

$^1$H-NMR (270 MHz, CDCl$_3$) δ ppm: 1.71(d, 3H, J=7.3 Hz), 4.27(q, 1H, J=7.3 Hz), 4.61(br-s, 2H), 4.87(s, 1H), 7.49–7.79(m, 3H), 8.01–8.09(m, 2H), 8.84(d, 1H, J=2.0 Hz).

Reference Example 48

3-(1-Isoquinolin-4-yl-ethyl)-isoxazol-5-ylamine

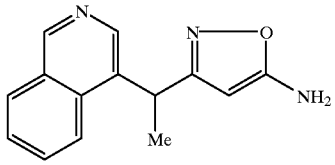

The desired compound was obtained by the same procedure as stated in the latter half of Reference Example 20 except for using 2-isoquinolin-4-yl-propionic acid methyl ester [T. Sakamoto et al., Heterocycles, 36, 2509(1997)].

$^1$H-NMR (270 MHz, CDCl$_3$) δ ppm: 1.81(d, 3H, J=7.3 Hz), 4.52(br-s, 2H), 4.71–4.78(m, 2H), 7.57–7.74(m, 2H), 7.98(d, 1H, J=7.6 Hz), 8.14(d, 1H, J=8.2 Hz), 8.50(s, 1H), 9.16(s, 1H).

Reference Example 49

Biphenyl-4-yl-dimethoxy-acetic acid methyl ester

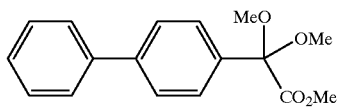

A mixture of biphenyl-4-yl-oxo-acetic acid methyl ester (A. T. Jeffries, et al., J. Org. Chem., 46, 2885(1981)) (10 g), triethyl orthoformate (43 ml), methanol (60 ml) and conc. sulfuric acid (3 ml) was heated under reflux for 8.5 hours under a nitrogen atmosphere. The resulting mixture was poured into a saturated aqueous sodium bicarbonate solution and the resulting mixture was subjected to extraction with diethyl ether. The organic layer was washed with a saturated aqueous sodium chloride solution, then dried over sodium sulfate and thereafter concentrated under reduced pressure, to obtain the desired compound (10.5 g).

$^1$H-NMR (270 MHz, CDCl$_3$) δ ppm: 3.31(s, 6H), 3.75(s, 3H), 7.35–7.47(m, 3H), 7.58–7.69(m, 6H).

Reference Example 50

3-(Biphenyl-4-yl-dimethoxy-methyl)-isoxazol-5-ylamine

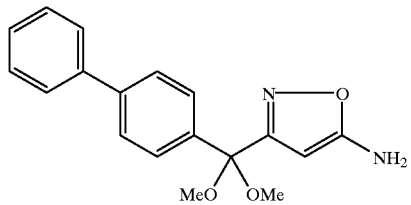

The desired compound was obtained by the same procedure as stated in the latter half of Reference Example 20 except for using the compound obtained in Reference Example 49.

$^1$H-NMR (270 MHz, CDCl$_3$) δ ppm: 3.27(s, 6H), 4.38 (br-s, 2H), 5.02(s, 1H), 7.31–7.46(m, 3H), 7.56–7.67(m, 6H).

Reference Example 51

Dimethoxy-(1-methyl-1H-indol-2-yl)-acetic acid methyl ester

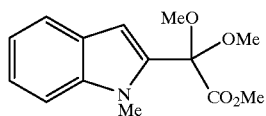

The desired compound was obtained by the same procedure as in Reference Example 49 except for using (1-methyl-1H-indol-2-yl)-oxo-acetic acid methyl ester [F. E. Ziegler, et al., J. Amer. Chem. Soc., 95, 7146(1973)].

$^1$H-NMR (270 MHz, CDCl$_3$) δ ppm: 3.32(s, 6H), 3.77(s, 3H), 3.78(s, 3H), 6.85(s, 1H), 7.10–7.35(m, 3H), 7.63(d, 1H, J=7.9 Hz).

Reference Example 52

3-[Dimethoxy-(1-methyl-1H-indol-2-yl)-methyl]-isoxazol-5-ylamine

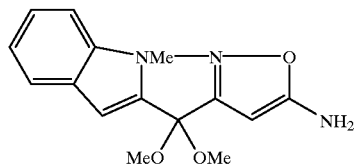

The desired compound was obtained by the same procedure as stated in the latter half of Reference Example 20 except for using the compound obtained in Reference Example 51.

$^1$H-NMR (270 MHz, CDCl$_3$) δ ppm: 3.27(s, 6H), 3.68(s, 3H), 43.8(br-s, 2H), 4.92(s, 1H), 6.86(s, 1H), 7.08–7.31(m, 3H), 7.63(d, 1H, J=7.9 Hz).

Reference Example 53

3-{1-Methyl-1-[3-(2-phenyl-[1,3]dioxolan-2-yl)-phenyl]-ethyl}-isoxazol-5-ylamine

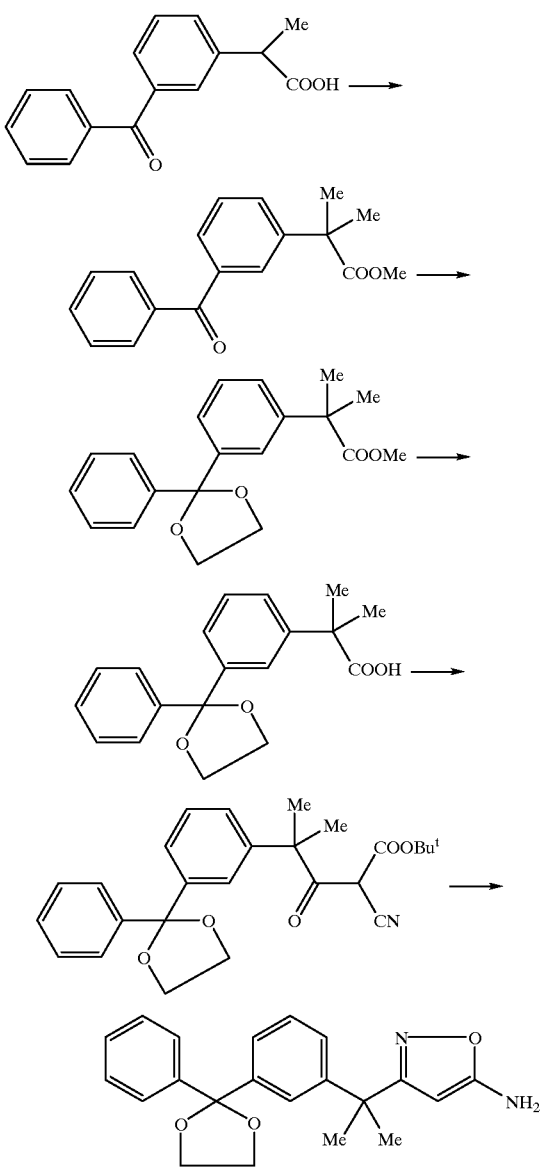

Ketoprofen (10 g) was dissolved in N,N-dimethylformamide (50 ml) under a nitrogen atmosphere. To the solution was added sodium hydride (3.95 g, 60% oily), followed by stirring. Thirty minutes after the stirring, methyliodide (6.1 ml) was added thereto, followed by stirring for 10 hours. To the reaction solution were added an ice water and a saturated agueous sodium hydrogencarbonate solution, followed by extraction with ethyl acetate. The extract solution was washed with a saturated aqueous sodium chloride solution, dried over sodium sulfate and then concentrated under reduced pressure to obtain the residue (12.78 g).

The part of the residue was dissolved in benzene (100 ml), and to the resulting solution were added ethyleneglycol (10 ml) and p-toluenesulfonic acid (10 g), followed by dehydration under reflux for 200 hours. To the resulting solution was added a saturated aqueous sodium hydrogencarbonate, followed by extraction with ethyl acetate. The extract solution was washed with a saturated aqueous sodium chloride, dried over sodium sulfate, and concentrated under reduced pressure to obtain the residue (9.30 g).

The part (1.0 g) of the residue was dissolved in methanol (10 ml), and to the resulting solution was added 10% aqueous potassium hydroxide solution (10 ml), followed by stirring for 10 hours. The reaction solution was concentrated to distill off methanol. To the resulting product was added 2N hydrochloric acid, followed by extraction with ethyl acetate. The extract solution was washed with a saturated aqueous sodium chloride solution, dried over sodium sulfate, and concentrated under reduced pressure to obtain the residue (0.56 g).

On the other hand, tetrahydrofuran (10 ml) was added to sodium hydride (220 mg, 60% oily), and then tert-butyl cyanoacetate (0.76 ml) was added dropwise thereto under ice-cooling under a nitrogen atmosphere. Then, the resulting mixture was stirred under ice-cooling to obtain the sodium salt of tert-butyl cyanoacetate.

On the other hand, a solution of the residue (0.56 g) obtained hereinbefore and N-methylmorphorine (0.24 ml) in tetrahydrofuran (5 ml) was added dropwise to a solution of isopropyl chloroformate (0.26 ml) in tetrahydrofuran (5 ml) under stirring at −15° C. Thirty minutes after the stirring, to the resulting solution was added dropwise the sodium salt of tert-butyl cyanoacetate obtained hereinbefore. One hour after, to the resulting mixture was added a saturated aqueous sodium hydrogencarbonate solution, followed by extraction with ethyl acetate. The extract solution was dried over sodium sulfate, and concentrated under reduced pressure to obtain the biscous residue.

To the residue were added hydroxylamine hydrochloride (500 mg), ethanol (16 ml) and pyridine (4 ml), followed by stirring for 4 hours at 50° C. After the reaction solution was cooled to the room temperature, ethanol was distilled off to obtain the residue. To the residue was added a saturated aqueous sodium hydrogencarbonate solution, followed by extraction with ethyl acetate. The extract was dried over sodium sulfate, and concentrated under reduced pressure to obtain the residue.

The residue was purified by a silica gel column chromatography to obtain the desired compound (37.9 mg).

$^1$H-NMR (300 MHz, CDCl$_3$) δ ppm: 1.66(s, 6H), 4.05(s, 4H), 4.26(br-s, 2H), 4.73(s, 1H), 7.21–7.60(m, 9H)

Reference Example 54

2-(6-Phenyl-pyridin-3-yl)-propionic acid methyl ester

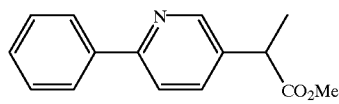

The desired compound was obtained from 5-bromo-2-phenylpyridine (J. W. Tilley, et al., J. Org. Chem., 53,386 (1988)) by the known method described in T. Sakamoto, et al., Heterocycles, 36, 2509 (1993).

$^1$H-NMR (270 MHz, CDCl$_3$) δ ppm: 1.57(d, 3H, J=7.3 Hz), 3.67(s, 3H), 3.80(q, 1H, J=7.3 Hz), 7.41–7.50(m, 3H), 7.71–7.72(m, 2H), 7.97(d, 2H, J=6.6 Hz), 8.61(s, 1H)

Reference Example 55

3-[1-(6-Phenyl-pyridin-3-yl)-ethyl]-isoxazol-5-ylamine

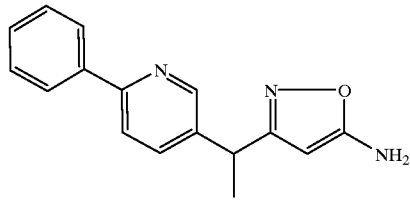

The desired compound was obtained from the compound obtained in Reference Example 54 by the same procedure as that described in the latter half of reference Example 20.

$^1$H-NMR (270 MHz, CDCl$_3$) δ ppm: 1.67(d, 3H, J=7.3 Hz), 4.14(q, 1H, J=7.3 Hz), 4.43(br-s, 2H), 4.91(s, 1H), 7.40–7.49(m, 3H), 7.70(m, 2H), 7.96(dd, 2H, J=8.3, 1.7 Hz), 8.63(s, 1H)

Reference Example 56

2-(5-Phenyl-pyridin-2-yl)-propionic acid methyl ester

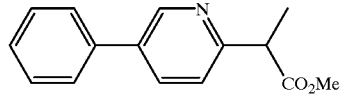

The desired compound was obtained from 2-bromo-5-phenylpyridine (M. G. Knize, et al., Heterocycles, 24, 1815 (1986)) by the known method described in T. Sakamoto, et al., Heterocycles, 36, 2509 (1993).

$^1$H-NMR (270 MHz, CDCl$_3$) δ ppm: 1.61(d, 3H, J=7.3 Hz), 3.72(s, 3H), 4.01(q, 1H, J=7.3 Hz), 7.34–7.59(m, 6H), 7.85 (dd, 1H, J=8.2, 2.3 Hz), 8.78(d, 1H, J=2.3 Hz)

Reference Example 57

3-[1-(5-Phenyl-pyridin-2-yl)-ethyl]-isoxazol-5-ylamine

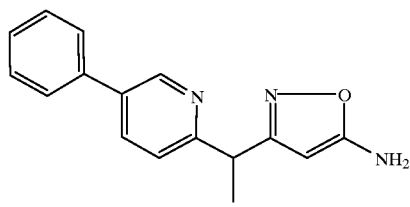

The desired compound was obtained from the compound obtained in Reference Example 56 by the same procedure as that described in the latter half of Reference Example 20.

$^1$H-NMR (270 MHz, CDCl$_3$) δ ppm: 1.71(d, 3H, J=7.3 Hz), 4.30(q, 1H, J=7.3 Hz), 4.39(br-s, 2H), 5.08(s, 1H), 7.32–7.57(m, 6H), 7.81(dd, 1H, J=8.3 Hz, 2.3 Hz), 8.79(d, 1H, J=2.3 Hz).

Test Example 1

Inhibition of Adjuvant-Induced Arthritis

Male SD rats were used as test subjects. Heat-killed Mycobacterium butyricum suspended in liquid paraffin in a concentration of 0.5% was subcutaneously injected into the right hind paw of each rat. After 17 days, animals showing the clear onset of secondary inflammation also in the left hind paw were selected, and each compound of the present invention suspended in a 0.5% methyl cellulose solution was orally administered to these animals for 5 consecutive days. The volume of each hind paw at the completion of the administration was compared with that at the beginning of the administration, and the swelling-inhibitory effect was evaluated by the difference between them. The results are shown in Table 1, Table 2 and Table 3.

TABLE 1

| Compound administered | Oral dose (mg/kg) | Number of animals | Increase of edema volume (ml) | |
|---|---|---|---|---|
| | | | Injected paw | Non-injected paw |
| Control | — | 8 | 0.29 | 0.39 |
| Compound of Example 19 | 25 | 8 | −1.05 | −0.55 |
| Compound of Example 20 | 25 | 9 | −0.63 | −0.40 |
| Indomethacin | 0.5 | 9 | −1.19 | −0.77 |

TABLE 2

| Compound administered | Oral dose (mg/kg) | Number of animals | Increase of edema volume (ml) | |
|---|---|---|---|---|
| | | | Injected paw | Non-injected paw |
| Control | — | 9 | 0.86 | 0.33 |
| Compound of Example 17 | 25 | 9 | −0.01 | −0.24 |
| Compound of Example 18 | 25 | 9 | −0.48 | −0.49 |
| Indomethacin | 0.5 | 9 | −1.51 | −1.05 |

TABLE 3

| Compound administered | Oral dose (mg/kg) | Number of animals | Increase of edema volume (ml) | |
|---|---|---|---|---|
| | | | Injected paw | Non-injected paw |
| Control | — | 10 | 0.01 | 0.00 |
| Compound of Example 87 | 25 | 10 | −0.35 | −0.24 |
| Indomethacin | 0.5 | 10 | −0.45 | −0.40 |

Test Example 2

Inhibition of Allergic Reaction Type III

Male BALB/c mice were used as test subjects. A suspension prepared by suspending sheep red blood cells in physiological saline to a concentration of 20% was intravenously injected into the tail of each mouse, and after 14 days, this procedure was repeated to immunize the animal. After another 5 days, a 100% sheep red blood cell suspension was subcutaneously injected into the right hind paw of each mouse to cause type III allergy, and 3 hours after the injection, the thicknesses of the right and left hind paws were measured. The efficacy of drugs was evaluated by taking the difference between the thicknesses of the right and left hind paws as edema volume. Each compound of the present invention was suspended in a 0.5% methyl cellulose solution and orally administered 24 hours before and 1 hour after the induction of inflammatory reaction. Table 4 shows the edema inhibition rate calculated by comparing the edema volume of a group to which the compound was administered with that of a control group.

TABLE 4

| Compound administered | Oral dose (mg/kg) | Number of animals | Edema inhibition rate (%) |
|---|---|---|---|
| Compound of Example 17 | 10 | 13 | 13.6 |
| Compound of Example 18 | 50 | 13 | 18.4 |
| Levamisole | 50 | 13 | 28.9 |

Test Example 3

Action on Experimental Allergic Encephalomyelitis

The medical effect of a compound was evaluated using experimental allergic encephalomyelitis in mice, which is one of animal models of multiple sclerosis. Experimental allergic encephalomyelitis was caused according to the method described by Bell et al. (J. Immunology, 150: 4085–4092, 1993). Briefly, 200 $\mu$g of a myelin basic protein (prepared from rabbit brain, sigma) mixed with the Freund's complete adjuvant was subcutaneously injected into the thigh of a 8-week older, female (PL×SJL) Fl mouse (Jackson Laboratories, Bar Harbor, Me.). On the sensitization day and 2 days thereafter, 200 ng of pertussis toxin (List Biological Laboratories, Campbell, Calif.) was intraperitoneally injected. The degree of grave-ness of symptom is indicated by score according to the following criterion:

1: tail paralysis
2: mild hind limb weakness
3: hind limb paralysis and/or mild forelimb weakness
4: complete hind limb paralysis and/or moderate to severe forelimb weakness
5: quadriplegia or moribund
6: Death The compound of this invention was suspended in a 0.5% methylcellulose solution and orally administered in a proportion of 0.1 ml/10 g of body weight. The control group was orally administered only a 0.5% methyl cellulose solution. The administration was started from the sensitization day and effected once per day successively for 42 days.

The results obtained are shown in FIG. 1. In the mice in the control group, severe experimental allergic encephalomyelitis was caused and all animals (10 mice) were died owing to neuroparalysis during the test period. On the other hand, in the mice treated with the compound of Example 22 (50 mg/kg), experimental allergic encephalomyelitis was also caused, though the symptom was light, and 3 mice of the 10 mice were died.

As described above, the isoxazole derivatives and the like of the present invention are markedly effective in test systems including animal models of chronic inflammation (e.g. rat adjuvant-induced arthritis, etc.), animal models of immune disorder (e.g. mouse allergic reaction type III, etc.), experimental allergic encephalomyelitis mice (e.g. multiple sclerosis, etc.), etc. Therefore, the isoxazole derivatives and the like of the present invention are clearly effective against chronic inflammation and moreover act on immune disorders responsible for the chronic inflammation. Thus, the isoxazole derivatives and the like of the present invention are effective also against autoimmune diseases such as rheumatoid arthritis and inflammatory diseases.

Preparation Example 1
Production of Tablet

Tablets can be produced by mixing all the ingredients and, if necessary, after subjecting the mixture to granulation, tabletting the same.

|  | Amount (mg/tablet) |
|---|---|
| Compound of Example 85 | 20 |
| Lactose | 70 |
| Corn starch | 17 |
| Low substituted hydroxypropylcellulose | 8 |
| Hydroxypropylcellulose | 4 |
| Magnesium stearate | 1 |
| Total | 120 mg |

Preparation Example 2
Production of Tablet

Tablets can be produced by mixing all the ingredients, and, if necessary, after subjecting the mixture to granulation, tabletting the same.

|  | Amount (mg/tablet) |
|---|---|
| Compound of Example 43 | 20 |
| D-Mannitol | 60 |
| Dibasic calcium phosphate | 25 |
| Carmellose calcium | 8 |
| Hydroxypropylmethylcellulose | 4 |
| Talc | 3 |
| Total | 120 mg |

Preparation Example 3
Production of Capsule

A capsule preparation can be produced by mixing all the ingredients and, if necessary, after granulating the mixture, filling a capsule with the same.

|  | Amount (mg/capsule) |
|---|---|
| Compound of Example 69 | 20 |
| Lactose | 150 |
| Corn starch | 40 |
| Low substituted hydroxypropylcellulose | 8 |
| Magnesium stearate | 2 |
| Total | 220 mg |

Preparation Example 4
Production of Capsule

A capsule preparation can be produced by mixing all the ingredients and, if necessary, after granulating the mixture, filling a capsule with the same.

|  | Amount (mg/capsule) |
|---|---|
| Compound of Example 72 | 20 |
| D-Mannitol | 123.5 |
| Carmellose calcium | 5 |
| Magnesium stearate | 1.5 |
| Total | 150 mg |

Preparation Example 5
Production of Powder

A powder was produced by mixing all the ingredients and, if necessary, granulating the mixture.

|  | Amount (mg/1 g) |
|---|---|
| Compound of Example 74 | 40 |
| Lactose | 750 |
| Corn starch | 200 |
| Magnesium stearate | 10 |
| Total | 1,000 mg |

Preparation Example 6
Production of Powder

A powder can be produced by mixing all the ingredients and, if necessary, granulating the mixture.

|  | Amount (mg/1 g) |
|---|---|
| Compound of Example 107 | 40 |
| D-Mannitol | 700 |
| Corn starch | 200 |
| Magnesium stearate | 10 |
| Total | 1,000 mg |

The isoxazole derivatives and pharmaceutically acceptable salts thereof of the present invention are useful as therapeutic or prophylactic drugs for autoimmune diseases [e.g. rheumatoid arthritis, systemic lupus erythematosus, systemic scleroderma, Sjögren's syndrome, Hashimoto's disease, myasthenia gravis, Basedow's disease, Addison's disease, juvenile diabetes (type I diabetes), autoimmune hemodyscrasias (e.g. hypoplastic anemia, hemolytic anemia, and idiopathic thrombocytopenia, etc.), ulcerative colitis, active chronic hepatitis, glomerular nephritis, interstitial pulmonary fibrosis, multiple sclerosis, etc.] and inflammatory diseases (e.g. osteoarthritis, gout, atopic dermatitis, and psoriasis, etc.).

We claim:

1. An isoxazole compound represented by the formula 1:

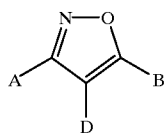

1 wherein D is a hydrogen atom, a halogen atom, a hydroxyl group, a mercapto group, a nitro group, a cyano group, a carboxyl group, a substituted or unsubstituted amino group, a substituted or unsubstituted hydroxylamino group, a substituted or unsubstituted carbamoyl group, a substituted or unsubstituted sulfamoyl group, a sulfo group, —R$^5$, —OR$^5$, —CO$_2$R$^6$, —SR$^7$, —(CO)SR$^7$, —(CS)OR7 or —CS$_2$R7 wherein R$^5$ is a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, a substituted or unsubstituted heterocyclic group, or an acyl group, R$^6$ is a substituted or unsubstituted alkyl group, a substituted or unsubstituted alkenyl group, a substituted or unsubstituted alkynyl group, a substituted or unsubstituted aryl group, or a substituted or unsubstituted heterocyclic group, and R7 is a substituted or unsubstituted alkyl group, or a substituted or unsubstituted aryl group;

one of A and B is a group represented by the formula:

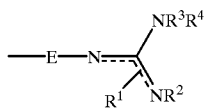

wherein E is a single bond or an alkylene group;

one of the two broken lines represents a double bond together with the solid line, while the other represents a single bond together with the other solid line; R$^1$ is bonded to the nitrogen atom bonded through the single bond represented by the broken line and the solid line; and R$^1$, R$^2$, R$^3$ and R$^4$ are independently a hydrogen atom, a halogen atom, a hydroxyl group, a mercapto group, a nitro group, a cyano group, a carboxyl group, a substituted or unsubstituted amino group, a substituted or unsubstituted hydroxylamino group, a substituted or unsubstituted carbamoyl group, a substituted or unsubstituted sulfamoyl group, a sulfo group, a protecting group for NH group, —R$^5$, —OR$^5$, —CO$_2$R$^6$, —SR$^7$, —(CO)SR$^7$, —(CS)OR$^7$ or —CS$_2$R$^7$ wherein R$^5$, R$^6$ and R$^7$ are as defined above, any two of R$^1$, R$^2$, R$^3$ and R$^4$ may be taken together with the nitrogen atom(s) to form a substituted or unsubstituted heterocyclic ring; and the formula: —NR$^3$R$^4$ may be a group represeted by the following formula: —N=C(NH$_2$)NR$^{43}$R$^{44}$ wherein R$^{43}$ and R$^{44}$ are as defined in (1) or (2)

(1) each represents independently a hydrogen atom; an alkyl group having 1 to 4 carbon atoms; —(CH$_2$)$_n$—COCH$_3$ wherein n represents an integer of 1 to 3; —(CH$_2$)$_n$—CO$_2$R$^{32}$ wherein n is as defined above and R$^{32}$ represents an alkyl group having 1 to 3 carbon atoms; —(CH$_2$)$_n$—CONR$^{33}$R$^{34}$ wherein n is as defined above and R$^{33}$ and R$^{34}$ represent independently hydrogen atoms or alkyl groups having 1 to 3 carbon atoms; —(CH$_2$)$_m$—OR$^{35}$ wherein m represents 2 or 3 and R$^{35}$ represents a hydrogen atom, an alkyl group having 1 to 3 carbon atoms or —(CH$_2$)$_m$—OR$^{36}$ wherein m is as defined above and R$^{36}$ represents a hydrogen atom or an alkyl group having 1 to 3 carbon atoms; —(CH$_2$)$_m$—NR$^{37}$R$^{38}$ wherein m is as defined above and R$^{37}$ and R$^{38}$ represent independently hydrogen atoms or alkyl groups having 1 to 3 carbon atoms, or when taken together with the nitrogen atom, represent pyrrolidine, piperidine, azepane, morpholine or N-methylpiperazine wherein said pyrrolidine, piperidine, azepane, morpholine and N-methylpiperazine may be substituted with one or two methyl groups; a phenyl group; a pyridyl group; a pyrimidinyl group; a pyridazinyl group; a pyrazinyl group; a tetrazolyl group; a benzyl group; a pyridylmethyl group; a pyrimidinylmethyl group; a pyridazinylmethyl group; a pyrazinylmethyl group; a tetrazolylmethyl group; a hydroxyl group; an alkoxy group having 1 to 3 carbon atoms; or —NR$^{39}$R$^{40}$ wherein R$^{39}$ and R$^{40}$ represent independently hydrogen atoms, alkyl groups having 1 to 3 carbon atoms, phenyl groups or pyridyl groups;

(2) when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from alkyl group, amino group, hydroxyl group, alkoxy group and oxo group; and the other of A and B is a group represented by the formula:
—J—G 
wherein G is a substituted or unsubstituted aryl group, or a substituted or unsubstituted heterocyclic group, and J is —C(R$^8$R$^9$)— or —C(=CR$^8$R$^9$)— wherein R$^8$ and R$^9$ are independently a hydrogen atom, a substituted or unsubstituted lower alkoxy group, or a substituted or unsubstituted lower alkyl group. R$^8$ and R$^9$ may be taken together with the carbon atom to form a substituted or unsubstituted hydrocarbon ring, a substituted or unsubstituted 1,3-dioxane, or a substituted or unsubstituted 1,3-dioxalane, or a pharmaceutically acceptable salt thereof.

2. An isoxazole compound or a pharmaceutically acceptable salt thereof according to claim 1, wherein E is a single bond or a lower alkylene.

3. An isoxazole compound or a pharmaceutically acceptable salt thereof according to claim 1, wherein D is a hydrogen atom, a nitro group, a cyano group, a carboxyl group, a substituted or unsubstituted amino group, a substituted or unsubstituted hydroxylamino group, a substituted or unsubstituted carbamoyl group, —R$^5$ or —CO$_2$R$^6$.

4. An isoxazole compound or a pharmaceutically acceptable salt thereof according to claim 3, wherein D is a hydrogen atom, a carboxyl group, —R$^5$ or —CO$_2$R$^6$.

5. An isoxazole compound or a pharmaceutically acceptable salt thereof according to claim 1, wherein R$^1$, R$^2$, R$^3$ and R$^4$ are independently a hydrogen atom, a hydroxyl group, a substituted or unsubstituted amino group, a substituted or unsubstituted hydroxylamino group, a substituted or unsubstituted alkoxy group, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, or a substituted or unsubstituted heterocyclic group; and the formula: —NR$^3$R$^4$ may be a group represented by the following formula: —N=C(NH$_2$)NR$^{43}$R$^{44}$; or any two of R$^1$, R$^2$, R$^3$ and R$^4$ may be taken together with the nitrogen atom(s) to form a substituted or unsubstituted heterocyclic ring.

6. An isoxazole compound or a pharmaceutically acceptable salt thereof according to claim 5, wherein R$^1$, R$^2$, R$^3$ and R$^4$ are independently a hydrogen atom, a hydroxyl group, a substituted or unsubstituted amino group, a substituted or unsubstituted hydroxylamino group, a substituted or unsubstituted alkoxy group, a substituted or unsubstituted alkyl group, a substituted or unsubstituted alkenyl group, a substituted or unsubstituted alkynyl group, or a substituted or unsubstituted cycloalkyl group; and the formula:

—NR³R⁴ may be a group represented by the following formula: —N═C(NH₂)NR⁴³R⁴⁴; or any two of R¹, R², R³ and R⁴ may be taken together with the nitrogen atom(s) to form a substituted or unsubstituted heterocyclic ring.

7. An isoxazole compound or a pharmaceutically acceptable salt thereof according to claim 1, wherein G is a substituted or unsubstituted phenyl group, a substituted or unsubstituted naphthyl group, a substituted or unsubstituted furyl, a substituted or unsubstituted thienyl, a substituted or unsubstituted indolyl, a substituted or unsubstituted isothiazolyl, a substituted or unsubstituted benzothienyl, a substituted or unsubstituted isobenzofuranyl, a substituted or unsubstituted pyrrolyl, a substituted or unsubstituted benzofuryl, a substituted or unsubstituted imidazolyl, a substituted or unsubstituted pyrazolyl, a substituted or unsubstituted isoxazolyl, a substituted or unsubstituted isothiazolyl, a substituted or unsubstituted thiazolyl, a substituted or unsubstituted oxazolyl, a substituted or unsubstituted benzimidazolyl, a substituted or unsubstituted benzothiazolyl, a substituted or unsubstituted benzoxazolyl, a substituted or unsubstituted pyridyl, a substituted or unsubstituted pyrazinyl, a substituted or unsubstituted pyrimidinyl, a substituted or unsubstituted pyridazinyl, a substituted or unsubstituted triazinyl, a substituted or unsubstituted quinolyl, a substituted or unsubstituted isoquinolyl, a substituted or unsubstituted quinazolinyl, a substituted or unsubstituted quinoxalinyl, a substituted or unsubstituted 2,3-dihydrobenzo[1,4]dioxinyl, or a substituted or unsubstituted carbazolyl.

8. An isoxazole compound or a pharmaceutically acceptable salt thereof according to claim 1, which is represented by the formula:

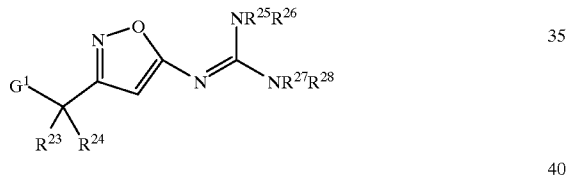

wherein G¹ represents phenyl, biphenyl-4-yl, 3-benzoylphenyl, 4-benzoylphenyl, 1H-indol-2-yl, 1H-indol-3-yl, 1-methyl-1H-indol-2-yl, 1-methyl-1H-indol-3-yl, 2,3-dihydrobenzo(1,4)dioxin-6-yl, 1-benzofuran-5-yl, 1-benzofuran-6-yl, quinolyl, isoquinolyl, phenylpyridyl, phenylpyrimidinyl, phenylpyridazinyl or phenylpyrazinyl wherein said phenyl, biphenyl-4-yl, 3-benzoylphenyl, 4-benzoylphenyl, 1H-indol-2-yl, 1H-indol-3-yl, 1-methyl-1H-indol-2-yl, 1-methyl-1H-indol-3-yl, 2-3-dihydrobenzo [1,4]dioxin-6-yl, 1-benzofuran-5-yl, 1-benzofuran-6-yl, quinolyl, isoquinolyl, phenylpyridyl, phenylpyrimidinyl, phenylpyridazinyl and phenylpyrazinyl may be substituted with one or two groups independently selected from the group consisting of fluorine atom, chlorine atom, bromine atom, acetyl, cyano, —CO₂R²⁹ wherein R²⁹ represented an alkyl group having 1 to 3 carbon atoms and —CONR³⁰R³¹ wherein R³⁰ and R³¹ represent independently hydrogen atoms or alkyl groups having 1 to 3 carbon atoms;

R²³ and R²⁴ represent independently hydrogen atoms, alkyl groups having 1 to 4 carbon atoms, methoxy or ethoxy, or when taken together, from a methylene group; and the formula: ═C(NR²⁵R²⁶)NR²⁷R²⁸ is as defined in the following (1), (2) or (3):

(1) R²⁵ and R²⁶ are as defined in the following (a) or (b) and R²⁷ and R²⁸ are as defined in the following (c) or (d):

(a) each represents independently a hydrogen atom; an alkyl group having 1 to 4 carbon atoms; —(CH₂)ₙ—COCH₃; —(CH₂)ₙ—CO₂R³²; —(CH₂)ₙ—CONR³³R³⁴; —(CH₂)ₘ—OR³⁵; —(CH₂)ₘ—NR³⁷R³⁸; a phenyl; a pyridyl; a pyrimidinyl group; a pyridazinyl group; a pyrazinyl group; a tetrazolyl group; a benzyl group; a pyridylmethyl group; a pyrimidinylmethyl group; a pyridazinylmethyl group; a pyrazinylmethyl group; a tetrazolylmethyl group; a hydroxyl group; an alkoxy group having 1 to 3 carbon atoms; or —NR³⁹R⁴⁰;

(b) when taken together, they form with nitrogen atom a 5- to 7-membered saturated nitrogen-containing heterocyclic group wherein said 5- to 7-membered saturated nitrogen-containing group may be substituted with one or two substituents independently selected from the group consisting of alkyl group; amino group, hydroxyl group, alkoxy group and oxo group;

(c) each represents independently a hydrogen atom; an alkyl group having 1 to 4 carbon atoms; —(CH₂)ₙ—COCH₃ wherein n is as defined above; —(CH₂)ₙ—CO₂R³² wherein n and R³² are as defined above; —(CH₂)ₙ—CONR³³R³⁴ wherein n, R³³ and R³⁴ are as defined above; —(CH₂)ₘ—OR³⁵ wherein m and R³⁵ are as defined above; —(CH₂)ₘ—NR³⁷R³⁸ wherein m, R³⁷ and R³⁸ are as defined above; a phenyl group; a pyridyl group; a pyrimidinyl group; a pyridazinyl group; a pyrazinyl group; a tetrazolyl group; a benzyl group; a pyridylmethyl group; a pyrimidinylmethyl group; a pyridazinylmethyl group; a pyrazinylmethyl group; a tetrazolylmethyl group; a hydroxyl group; an alkoxy group having 1 to 3 carbon atoms; or —NR³⁹R⁴⁰ wherein R³⁹ and R⁴⁰ are as defined above;

(d) when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group;

(2) when taken together, R²⁶ and R²⁷ form with the two nitrogen atoms and the one carbon atom a 5 to 7-membered saturated nitrogen-containing heterocyclic group wherein said 5- to 7-membered nitrogen-containing heterocyclic group may be substituted with one or two substituents independently selected from the group consisting of alkyl group, amino group, hydroxyl group, alkoxy group and oxo group; and R²⁵ and R²⁸ represent independently hydrogen atoms, alkyl groups having 1 to 3 carbon atoms, acetyl or —(CH₂)ₘ—OR³⁶ wherein m is as defined above;

(3) the formula: ═C(NR²⁵R²⁶)NR²⁷R²⁸ is a group represented by the following formula:

wherein R⁴¹ and R⁴² are as defined in the following (a') or (b'); and R⁴³ and R⁴⁴ are as defined in the following (c') or (d'):

(a') each represents independently a hydrogen atom, an alkyl group having 1 to 4 carbon atoms, —(CH₂)ₙ—COCH₃ wherein n is as defined above, —(CH₂)ₙ—CO₂R³² wherein n and R³² are as defined above, —(CH₂)ₙ—CONR³³R³⁴ wherein n, R³³ and R³⁴ are as defined above, —(CH$_2$)$_m$—OR$^{35}$ wherein m and R$^{35}$ are as defined above, —(CH$_2$)$_m$—NR$^{37}$R$^{38}$ wherein m, R$^{37}$ and R$^{38}$ are as defined above, a phenyl group, a pyridyl group, a pyrimidinyl group, a pyridazinyl group, a pyrazinyl group, a tetrazolyl group, a benzyl group, a pyridylmethyl group, a pyrimidinylmethyl group, a pyridazinylmethyl group, a pyrazinylmethyl group, a tetrazolylmethyl group, a hydroxyl group, an alkoxy group having 1 to 3 carbon atoms or —NR$^{39}$R$^{40}$ wherein R$^{39}$ and R$^{40}$ are as defined above;

(b') when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group;

(c') each represents independently a hydrogen atom, an alkyl group having 1 to 4 carbon atoms, —(CH$_2$)$_n$—COCH$_3$ wherein n is as defined above, —(CH$_2$)$_n$—CO$_2$R$^{32}$ wherein n and R$^{32}$ are as defined above, —(CH$_2$)$_n$—CONR$^{33}$R$^{34}$ wherein n, R$^{33}$ and R$^{34}$ are as defined above, —(CH$_2$)$_m$—OR$^{35}$ wherein m and R$^{35}$ are as defined above, —(CH$_2$)$_m$—NR$^{37}$R$^{38}$ wherein m, R$^{37}$ and R$^{38}$ are as defined above, a phenyl group, a pyridyl group, a pyrimidinyl group, a pyridazinyl group, a pyrazinyl group, a tetrazolyl group, a benzyl group, a pyridylmethyl group, a pyrimidinylmethyl group, a pyridazinylmethyl group, a pyrazinylmethyl group, a tetrazolylmethyl group, a hydroxyl group, an alkoxy group having 1 to 3 carbon atoms or —NR$^{39}$R$^{40}$ are as defined above;

(d') when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group; or represented by the formula:

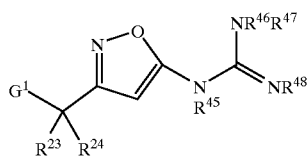

wherein G$^1$, R$^{23}$ and R$^{24}$ are as defined above; the formula: —N(R$^{45}$)C(NR$^{46}$R$^{47}$)=NR$^{48}$ is as defined in the following (1') or (2'):

(1') R$^{45}$ represents an alkyl group having 1 to 3 carbon atoms or an acetyl group; R$^{48}$ represents a hydrogen atom, an alkyl group having 1 to 3 carbon atoms or an acetyl group; and R$^{46}$ and R$^{47}$ are as defined as in the following (a") or (b"):

(a") each represents independently a hydrogen atom, an alkyl group having 1 to 4 carbon atoms, —(CH$_2$)$_n$—COCH$_3$ wherein n is as defined above, —(CH$_2$)$_n$—CO$_2$R$^{32}$ wherein n and R$^{32}$ are as defined above, —(CH$_2$)$_n$—CONR$^{33}$R$^{34}$ wherein n, R$^{33}$ and R$^{34}$ are as defined above, —(CH$_2$)$_m$—OR$^{35}$ wherein m and R$^{35}$ are as defined above, —(CH$_2$)$_m$—NR$^{37}$R$^{38}$ wherein m, R$^{37}$ and R$^{38}$ are as defined above, a phenyl group, a pyridyl group, a pyrimidinyl group, a pyridazinyl group, a pyrazinyl group, a tetrazolyl group, a benzyl group, a pyridylmethyl group, a pyrimidinylmethyl group, a pyridazinylmethyl group, a pyrazinylmethyl group, a tetrazolylmethyl group, a hydroxyl group, an alkoxy group having 1 to 3 carbon atoms or —NR$^{39}$R$^{40}$ wherein R$^{39}$ and R$^{40}$ are as defined above;

(b") when taken together, they form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group;

(2') when taken together, R$^{45}$ and R$^{46}$ form with the nitrogen atom a 5- to 7-membered saturated nitrogen-containing heterocyclic group wherein said 5- to 7-membered saturated nitrogen-containing heterocyclic group may be substituted with one or two substituents independently selected from the group consisting of alkyl group, amino group, hydroxyl group, alkoxy group and oxo group; and R$^{47}$ and R$^{48}$ represent independently alkyl groups having 1 to 3 atoms, acetyl groups or —(CH$_2$)$_m$—OR$^{36}$ wherein m and R$^{36}$ are as defined above.

9. An isoxazole compound or a pharmaceutically acceptable salt thereof according to claim 1, which is represented by the formula:

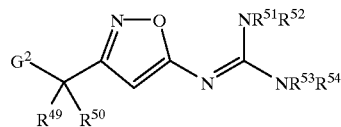

wherein G$^2$ represents 2-fluoro-biphenyl-4-yl, 2'-fluoro-biphenyl-4-yl or 3-benzoyl-phenyl R$^{49}$ represents methyl; R$^{50}$ represents hydrogen, methyl, methoxy or ethoxy; and the formula: =C(NR$^{51}$R$^{52}$)NR$^{53}$R$^{54}$ is as defined in the following (1"), (2") or (3"):

(1") R$^{51}$ and R$^{52}$ are as defined in the following (a'"), (b'") or (c'") and R$^{53}$ and R$^{54}$ are as defined in the following (d'"), (e'") or (f'"):

(a'") each represents independently a hydrogen atom or an alkyl group having 1 to 4 carbon atoms;

(b'") one of them represents a hydrogen atom and the other represents —(CH$_2$)$_n$—COCH$_3$, —(CH$_2$)$_n$—CO$_2$R$^{32}$; —(CH$_2$)$_n$—CONR$^{33}$R$^{34}$, —(CH$_2$)$_m$—OR$^{35}$, or —(CH$_2$)$_m$—NR$^{37}$R$^{38}$;

(c'") when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, and piperidine substituted in the 4-position with an amino group which may be substituted with one or two alkyl groups having 1 to 3 carbon atoms, may be substituted with one or two methyl groups;

(d''') each represents independently a hydrogen atom or an alkyl group having 1 to 4 carbon atoms;

(e''') one of them represents a hydrogen atom and the other represents —$(CH_2)_n$—$COCH_3$ wherein n is as defined above, —$(CH_2)_n$—$CO_2R^{32}$ wherein n and $R^{32}$ are as defined above, —$(CH_2)_n$—$CONR^{33}R^{34}$ wherein n, $R^{33}$ and $R^{34}$ are as defined above, —$(CH_2)_m$—$OR^{35}$ wherein m and $R^{35}$ are as defined above, or —$(CH_2)_m$—$NR^{37}R^{38}$ wherein m, $R^{37}$ and $R^{38}$ are as defined above;

(f''') when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, and piperidine substituted in the 4-position with an amino group which may be substituted with one or two alkyl groups having 1 to 3 carbon atoms, may be substituted with one or two methyl groups;

(2'') the formula: =$C(NR^{51}R^{52})NR^{53}R^{54}$ is a group represented by the following formula:

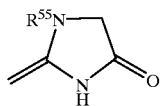

wherein $R^{55}$ represents an alkyl group having 1 to 3 carbon atoms acetyl or —$(CH_2)_m$—$OR^{56}$ wherein m is as defined above and $R^{56}$ represents a hydrogen atom or an alkyl group having 1 to 3 carbon atoms;

(3'') the formula: =$C(NR^{51}R^{52})NR^{53}R^{54}$ is a group represented by the following formula:

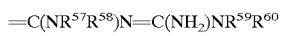

wherein $R^{57}$ and $R^{58}$ are as defined in the following (a''''), (b'''') or (c''''); and $R^{59}$ and $R^{60}$ are as defined in the following (d''''), (e'''') or (f''''):

(a'''') each represents a hydrogen atom or an alkyl group having 1 to 4 carbon atoms;

(b'''') one of them represents a hydrogen atom and the other represents —$(CH_2)_n$—$COCH_3$ wherein n is as defined above, —$(CH_2)_n$—$CO_2R^{32}$ wherein n and $R^{32}$ are as defined above, —$(CH_2)_n$—$CONR^{33}R^{34}$ wherein n, $R^{33}$ and $R^{34}$ are as defined above, —$(CH_2)_m$—$OR^{35}$ wherein m and $R^{35}$ are as defined above, or —$(CH_2)_m$—$NR^{37}R^{38}$ wherein m, $R^{37}$ and $R^{38}$ are as defined above;

(c'''') when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, and piperidine substituted in the 4-position with an amino group which may be substituted with one or two alkyl groups having 1 to 3 carbon atoms, may be substituted with one or two methyl groups;

(d'''') each represents independently a hydrogen atom or an alkyl group having 1 to 4 carbon atoms;

(e'''') one of them represents a hydrogen atom and the other represents —$(CH_2)_n$—$COCH_3$ wherein n is as defined above, —$(CH_2)_n$—$CO_2R^{32}$ wherein n and $R^{32}$ are as defined above, —$(CH_2)_n$—$CONR^{33}R^{34}$ wherein n, $R^{33}$ and $R^{34}$ are as defined above, —$(CH_2)_m$—$OR^{35}$ wherein m and $R^{35}$ are as defined above, or —$(CH_2)_m$—$NR^{37}R^{38}$ wherein m, $R^{37}$ and $R^{38}$ are as defined above;

(f'''') when taken together, they form with the nitrogen atom pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, or piperidine substituted in the 4-position with an amino group which may be substituted with one or two alkyl groups having 1 to 3 carbon atoms wherein said pyrrolidine, azepane, morpholine, thiazoline, piperidin-2-one, piperidin-4-one, thiamorpholine, piperazine which may be substituted in the 4-position with an alkyl group having 1 to 3 carbon atoms, piperidine which may be substituted in the 4-position with an alkoxy group having 1 to 3 carbon atoms, 4-hydroxy-piperidine, and piperidine substituted in the 4-position with an amino group which may be substituted with one or two alkyl groups having 1 to 3 carbon atoms, may be substituted with one or two methyl groups.

10. An isoxazole compound or a pharmaceutically acceptable salt thereof according to claim 1, which is represented by the formula:

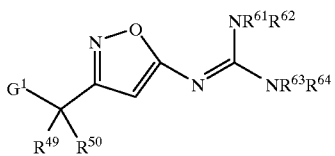

wherein $G^2$ represents 2-fluoro-biphenyl-4-yl, 2'-fluoro-biphenyl-4-yl or 3-benzoyl-phenyl; $R^{49}$ represents methyl; $R^{50}$ represents hydrogen, methyl, methoxy or ethoxy; and the formula: $=C(NR^{61}R^{62})NR^{63}R^{64}$ is as defined in the following (1'''), (2'''), (3'''),:

(1''') $R^{63}$ and $R^{64}$ both represent hydrogen atoms; and $R^{61}$ and $R^{62}$ are as defined in the following (a'), (b'), (c'):
  (a') each represents independently a hydrogen atom or an alkyl group having 1 to 3 carbon atoms;
  (b') one of them represents a hydrogen atom and the other represents $-(CH_2)_n-CO_2R^{32}$; $-(CH_2)_m-OR^{65}$ wherein m is 2 or 3 and $R^{65}$ represents a hydrogen atom or an alkyl group having 1 to 3 carbon atoms; 2-hydroxyethyl or 3-hydroxypropyl; or $-(CH_2)_m-NR^{66}R^{67}$ wherein m is as defined above and $R^{66}$ and $R^{67}$ represents independently hydrogen atoms or alkyl groups having 1 to 3 carbon atoms or, when taken together, form with the nitrogen atom pyrrolidine, piperidine, morpholine, or N-methylpiperazine wherein said pyrrolidine, piperidine, morpholine and N-methylpiperazine may be substituted with one or two methyl groups;
  (c') when taken together, they form with the nitrogen atom pyrrolidine, piperidine, morpholine, or N-methylpiperazine wherein said pyrrolidine, piperidine, morpholine and N-methylpiperazine may be substituted with one or two methyl groups;

(2''') the formula: $=C(NR^{61}R^{62})NR^{63}R^{64}$ is a group represented by the following formula:

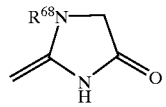

wherein $R^{68}$ represents an alkyl group having 1 to 3 carbon atoms, 2-hydroxyethyl or 3-hydroxypropyl;
  (3''') when taken together, $R^{61}$ and $R^{62}$ form morpholine with the nitrogen atom; and when taken together, $R^{63}$ and $R^{64}$ form amino-morpholin-4-yl-methylene.

11. An isoxazole compound or a pharmaceutically acceptable salt thereof according to claim 1, which is selected from the group consisting of the following compounds:
({3-[1-(2-Fluoro-biphenyl-4-yl)-ethyl]-isoxazol-5-ylimino}-morpholin-4-yl-methyl)-amine;
[{3-[1-(2-Fluoro-biphenyl-4-yl)-ethyl]-isoxazol-5-ylimino}-(4-methyl-piperazin-1-yl)-methyl]-amine;
N-{3-[1-(2-Fluoro-biphenyl-4-yl)-ethyl]-isoxazol-5-yl}-N'-(2-morpholin-4-yl-ethyl)-guanidine;
({3-[1-(2-Fluoro-biphenyl-4-yl)-1-methyl-ethyl]-isoxazol-5-ylimino}-morpholin-4-yl-methyl)-amine;
[{3-[1-(2-Fluoro-biphenyl-4-yl)-1-methyl-ethyl]-isoxazol-5-ylimino}-(4-methyl-piperazin-1-yl)-methyl]-amine;
N-{3-[1-(2-Fluoro-biphenyl-4-yl)-1-methyl-ethyl]-isoxazol-5-yl}-N'-(2-morpholin-4-yl-ethyl)-guanidine;
({3-[1-(2'-Fluoro-biphenyl-4-yl)-ethyl]-isoxazol-5-ylimino}-morpholin-4-yl-methyl)-amine;
[{3-[1-(2'-Fluoro-biphenyl-4-yl)-ethyl]-isoxazol-5-ylimino}-(4-methyl-piperazin-1-yl)-methyl]-amine;
N-{3-[1-(2'-Fluoro-biphenyl-4-yl)-ethyl]-isoxazol-5-yl}-N'-(2-morpholin-4-yl-ethyl)-guanidine;
({3-[1-(2'-Fluoro-biphenyl-4-yl)-1-methyl-ethyl]-isoxazol-5-ylimino}-morpholin-4-yl-methyl)-amine;
[{3-[1-(2'-Fluoro-biphenyl-4-yl)-1-methyl-ethyl]-isoxazol-5-ylimino}-(4-methyl-piperazin-1-yl)-methyl]-amine;
N-{3-[1-(2'-Fluoro-biphenyl-4-yl)-1-methyl-ethyl]-isoxazol-5-yl}-N'-(2-morpholin-4-yl-ethyl)-guanidine;
(3-{1-[5-(Amino-morpholin-4-yl-methyleneamino)-isoxazol-3-yl]-ethyl}-phenyl)-phenyl-methanone;
[3-(1-{5-[Amino-(4-methyl-piperazin-1-yl)-methyleneamino]-isoxazol-3-yl}-ethyl)-phenyl]-phenyl-methanone;
N-{3-[1-(3-Benzoyl-phenyl)-ethyl]-isoxazol-5-yl}-N'-(2-morpholin-4-yl-ethyl)-guanidine;
(3-{1-[5-(Amino-morpholin-4-yl-methyleneamino)-isoxazol-3-yl]-1-methyl-ethyl}-phenyl)-phenyl-methanone;
[3-(1-{5-[Amino-(4-methyl-piperazin-1-yl)-methyleneamino]-isoxazol-3-yl}-1-methyl-ethyl)-phenyl]-phenyl-methane; and
N-{3-[1-(3-Benzoyl-phenyl)-1-methyl-ethyl]-isoxazol-5-yl}-N'-(2-morpholin-4-yl-ethyl)-guanidine.

12. A pharmaceutical composition comprising as an active ingredient an isoxazole compound or a pharmaceutically acceptable salt thereof according to any one of claims 1 to 11, together with a pharmaceutically acceptable carrier.

13. A method for treating autoimmune diseases or inflammatory diseases, which comprises administering an isoxazole compound or a pharmaceutically acceptable salt according to any one of claims 1 to 11 in an effective amount to a human body.

14. A method for treating autoimmune diseases or inflammatory diseases as claimed in claim 13, which comprises administering an amount of the isoxazole compound or a pharmaceutically acceptable salt thereof effective to treat autoimmune disease.

15. A method for treating autoimmune diseases or inflammatory diseases as claimed in claim 13, which comprises administering an amount of the isoxazole compound or a pharmaceutically acceptable salt thereof effective to treat inflammatory disease.

16. A method for treating autoimmune diseases or inflammatory diseases as claimed in claim 13, which comprises administering an amount of the isoxazole compound or a pharmaceutically acceptable salt thereof effective to treat rheumatism.

* * * * *